US009192663B2

(12) United States Patent
Elis et al.

(10) Patent No.: US 9,192,663 B2
(45) Date of Patent: Nov. 24, 2015

(54) ANTIBODIES FOR EPIDERMAL GROWTH FACTOR RECEPTOR 3 (HER3)

(71) Applicant: NOVARTIS AG, Basel (CH)

(72) Inventors: Winfried Elis, Munchen-Pasing (DE); Seth Ettenberg, Melrose, MA (US); Andrew Paul Garner, Arlington, MA (US); Nicole Haubst, Munich (DE); Xizhong Huang, Southborough, MA (US); Christian Carsten Silvester Kunz, Munich (DE); Elizabeth Anne Reisinger Sprague, Concord, MA (US); Qing Sheng, Sharon, MA (US)

(73) Assignee: NOVARTIS AG, Basel (CH)

( * ) Notice: Subject to any disclaimer, the term of this patent is extended or adjusted under 35 U.S.C. 154(b) by 194 days.

(21) Appl. No.: 13/693,330

(22) Filed: Dec. 4, 2012

(65) Prior Publication Data
US 2013/0330324 A1 Dec. 12, 2013

Related U.S. Application Data

(60) Provisional application No. 61/566,890, filed on Dec. 5, 2011.

(51) Int. Cl.
*A61K 39/395* (2006.01)
*C07K 16/00* (2006.01)
*C07K 16/32* (2006.01)
*A61K 45/06* (2006.01)
*A61K 31/4439* (2006.01)
*C07K 16/28* (2006.01)
*A61K 39/00* (2006.01)

(52) U.S. Cl.
CPC .......... *A61K 39/3955* (2013.01); *A61K 31/4439* (2013.01); *A61K 39/39558* (2013.01); *A61K 45/06* (2013.01); *C07K 16/28* (2013.01); *C07K 16/32* (2013.01); *A61K 2039/505* (2013.01); *A61K 2039/507* (2013.01); *C07K 2317/21* (2013.01); *C07K 2317/55* (2013.01); *C07K 2317/73* (2013.01); *C07K 2317/76* (2013.01); *C07K 2317/92* (2013.01)

(58) Field of Classification Search
CPC ................... A61K 2039/505; A61K 39/0011; C12Q 1/6886; G01N 33/57434; G01N 33/574
See application file for complete search history.

(56) References Cited

U.S. PATENT DOCUMENTS

| 6,136,558 | A | 10/2000 | Ballinger et al. | |
|---|---|---|---|---|
| 8,735,551 | B2 * | 5/2014 | Garner et al. | 530/388.1 |
| 8,778,962 | B2 * | 7/2014 | Lane et al. | 514/291 |
| 2008/0124345 | A1 * | 5/2008 | Rothe et al. | 424/174.1 |
| 2008/0214584 | A1 | 9/2008 | Ohta et al. | |
| 2008/0245375 | A1 * | 10/2008 | Trudel | 128/898 |
| 2008/0306057 | A1 * | 12/2008 | Palmer et al. | 514/230.5 |
| 2009/0274693 | A1 | 11/2009 | Gilmer et al. | |
| 2009/0291085 | A1 | 11/2009 | Schoeberl et al. | |
| 2010/0055093 | A1 | 3/2010 | Shepard et al. | |
| 2011/0229493 | A1 | 9/2011 | Jackson et al. | |
| 2012/0014957 | A1 | 1/2012 | Ghayur et al. | |
| 2012/0107234 | A1 | 5/2012 | Pedersen et al. | |
| 2012/0156130 | A1 * | 6/2012 | Hettmann et al. | 424/1.49 |
| 2012/0328623 | A1 * | 12/2012 | Takahashi | 424/139.1 |
| 2013/0273029 | A1 * | 10/2013 | Elis et al. | 424/133.1 |

FOREIGN PATENT DOCUMENTS

| EP | 1414494 | 3/2009 |
|---|---|---|
| WO | 2009/137429 | 11/2009 |
| WO | 2010/127181 | 11/2010 |
| WO | 2011022727 A2 | 2/2011 |
| WO | 2011/076683 | 6/2011 |
| WO | 2011/112953 | 9/2011 |
| WO | 2011/136911 | 11/2011 |
| WO | 2011/144749 | 11/2011 |
| WO | 2011143414 A1 | 11/2011 |
| WO | 2011144749 A1 | 11/2011 |
| WO | 2012/022814 | 2/2012 |
| WO | 2012019024 A2 | 2/2012 |
| WO | 2012031198 A2 | 3/2012 |
| WO | 2012059224 A1 | 5/2012 |
| WO | 2012061558 A2 | 5/2012 |

OTHER PUBLICATIONS

Engelman (Nature, 2009, 9:550-562).*
Dobs et al (Journal of Urology, 2005, 174:1737-1742, abstract).*
Leconte et al (The American Journal of Pathology, 2011, 179:880-889).*
Jin et al (Zhonghua Nan Ke Xue, 2010, 16:1068-75, abstract).*
Wolff et al., Archives of Pathology & Laboratory Medicine, College of american Pathologists, US, 131(1):18-43 (2007).
Chiba, Digestion, 70(2):93-94 (2004).
Nishigaki et al., Digestion, 70(2):95-102 (2004).

(Continued)

*Primary Examiner* — Sean Aeder
*Assistant Examiner* — Julie Wu
(74) *Attorney, Agent, or Firm* — John Prince

(57) ABSTRACT

This invention relates to antibodies or fragments thereof which interact with HER family of receptors, e.g., HER3 receptor. In particular, it relates to antibodies or fragments thereof that recognize a conformational epitope of HER3 receptor comprising residues from both domains 2 and 4 resulting in inhibition of both ligand-dependent and ligand-independent signal transduction; and allow ligand binding (e.g., neuregulin), while preventing ligand-induced activation of signal transduction. These antibodies or fragments can be used to treat a number of diseases or disorders characterized by increased levels of HER3 expression (e.g., esophageal cancer). These antibodies or fragments can be used to treat a number of diseases or disorders characterized by the antibodys or fragments ability to decrease tissue weight (e.g., prostate or uterine weights) or to induce atrophy of tissue (e.g., atrophy of male breast).

8 Claims, 25 Drawing Sheets

(56) References Cited

OTHER PUBLICATIONS

Junttila et al., Cancer Cell, 15(5):429-440 (2009).
Yamamoto et al., Annals of Surgical Oncology, 19(3):757-65 (2012).
Haussler et al., Human Pathology, 30(9):1077-86 (1999).
Nasu et al., Archives of Andrology, 52(3):185-190 (2006).
Peng et al., International Journal of Cancer, 122(6):1303-1310, (2008).
Peng et al., Gastroenterology, 132(4, Suppl. 2):A293 (2007).
Wei et al., International Journal of Oncology, 31(3):493-499 (2007).
Morgan et al., Experimental Cell Research, 315(4):572-582 (2009).
Ohlsson et al., Human Reproduction Update, 16 (2):142-165 (2010).
Ejskjaer et al., Gynecologic and obstetric investigation, 67(2):118-126 (2009).
Haynes et al., Clinical & Exp Pharmacology & Physiology, 32(10):797-804 (2005).
Wang et al., Department of Cancer Endocrinology, 64(2):149-59 (2005).
Gupta et al., Gene Therapy, 10(3):206-12 (2003).
Defrere et al., Human Reproduction, 21(3):810-7 (2006).
Bruner-Tran et al., Fertility & Sterility, 93(8):2519-24 (2010).
Lim et al., Journal of Clinical Investigation, 120(4):1004-15 (2010).
Schaefer et al., A two-in-one antibody against HER3 and EGFR has superior inhibitory activity compared with monospecific antibodies. *Cancer Cell*. Oct. 18, 2011;20(4):472-86.

* cited by examiner

```
 20  SEVCNSQAVC PGTLNCLSVT CDAENQYQTL YKLYERCEVV MCNLEIVLTG HNADLSFLQW IREVTCYVLV AMNEFSTLPL
     ---------- ---------- ---------- ---------- ---------- ---------- ---------- --------
     ...........................................................................  .......
     ---------- ---------- ---------- ---------- ---------- ---------- ---------- ------
     ---------- ---------- ---------- ---------- ---------- ---------- ---------- ------

100  PNLRVVRGTQ VYDGKFAIFV MLNYNTNSSH ALRQLRLTQL TEILSGGVYI EKNDKLCHMD TIDWRDIVRD RDAEIVVKDN
     ---------- ---------                                  - ---------- ---------- ----------
     .......... ......                                      ..........  .........  ..........
     ---------- ------                                                  
     ..........

180  GRSCPPCHEV CKGRCWGPGS EDCQTLTKTI CAPQCNGHCF SPNPNQCCHD ECAGGCSGPQ DTDCFACRHF NDSGACVPRC
     ---------- ---------- ------     ---------- ---------- ---------- ---------- ----------
     ---------- ---------- -----
     ---------- ---------- ---
     ---------- ---------- -

260  PQPLVYNKLT FQLEPNPHTK YQYGGVCVAS CPHNFVVDQT SCVRACPPDK MEVDKNGLKM CEPCGGLCPK ACEGTGSSGSR
     -          ---------- -------               ---------- ---------- ---------- ----------
     -          ---------- -------
                ---------- -------

340  FQTVDSSNID GFVNCTKILG NLDFLITGLN GDPWHKIPAL DPEKLNVFRT VREITGYLNI QSWPPHMHNF SVFSNLTTIG
     -          ---------  ---------- ---------- ---------- ---------- ---------- ----------
                ......... .......... .......... ..........                        ........
                ---------  ---------- ---------- ----------                        ----
                ---------  ---------- ---------- ---------                         ----
                ---------  ---------- ----------                                   ----

420  GRSLYNRGFS LLIMKNLRVT SLGFRSLKEI SAGRIYISAN RQLCYHHSIN WTKVLRGPTE ERLDIKHNRP RRDCVAEGKV
     ---------- -------    ---------- ----------
     ---------- --         ---------- ----------
     ---------- ---        ---------- ----------
     ---------- --         ---------- ----------
     ---------- --         ---------- ----------

500  CDPLCSSGGC WGPGPGQCLS CRNYSRGGVC VTHCNFLNGE PREFAHEAEC FSCHPECQPM EGTATCNGSG SDTCAQCAHF
                           ---------- ---------- ---------- ---------- ---------- ----------
                           ........   ........   ........   ........              -----
                           ----       ----                                         -----
                           ----       -------                                      ----

580  PDGPHCVSSC PHGVLGAKGP IYKYPDVQNE CRPCHENCTQ GCKGPELQDC LGQTLVLIGK TEFRHDS
     ---------- ---------- ---------- ---------- ---------- ---------- --------
     ---------- ---------- ---------- ---------- ---------- ---------- --------
     ---------- ---------- ---------- ---------- ---------- ---------- --------
     ---------- -----                                        - -----  --
     ---------- -----                                           ~~
```

Fig. 4A

MOR0923 treated BT474 xenografts

MOR09823 treated BxPC3 xenografts

G

H

SEQUENCE LISTING

```
<160> NUMBER OF SEQ ID NOS: 497

<210> SEQ ID NO 1
<211> LENGTH: 1342
<212> TYPE: PRT
<213> ORGANISM: Homo sapiens

<400> SEQUENCE: 1

Met Arg Ala Asn Asp Ala Leu Gln Val Leu Gly Leu Leu Phe Ser Leu
1               5                   10                  15

Ala Arg Gly Ser Glu Val Gly Asn Ser Gln Ala Val Cys Pro Gly Thr
            20                  25                  30

Leu Asn Gly Leu Ser Val Thr Gly Asp Ala Glu Asn Gln Tyr Gln Thr
        35                  40                  45

Leu Tyr Lys Leu Tyr Glu Arg Cys Glu Val Val Met Gly Asn Leu Glu
    50                  55                  60

Ile Val Leu Thr Gly His Asn Ala Asp Leu Ser Phe Leu Gln Trp Ile
65                  70                  75                  80

Arg Glu Val Thr Gly Tyr Val Leu Val Ala Met Asn Glu Phe Ser Thr
                85                  90                  95

Leu Pro Leu Pro Asn Leu Arg Val Val Arg Gly Thr Gln Val Tyr Asp
            100                 105                 110

Gly Lys Phe Ala Ile Phe Val Met Leu Asn Tyr Asn Thr Asn Ser Ser
        115                 120                 125

His Ala Leu Arg Gln Leu Arg Leu Thr Gln Leu Thr Glu Ile Leu Ser
    130                 135                 140

Gly Gly Val Tyr Ile Glu Lys Asn Asp Lys Leu Cys His Met Asp Thr
145                 150                 155                 160
```

-continued

```
Ile Asp Trp Arg Asp Ile Val Arg Asp Arg Asp Ala Glu Ile Val Val
            165                 170                 175
Lys Asp Asn Gly Arg Ser Cys Pro Pro Cys His Glu Val Cys Lys Gly
            180                 185                 190
Arg Cys Trp Gly Pro Gly Ser Glu Asp Cys Gln Thr Leu Thr Lys Thr
            195                 200                 205
Ile Cys Ala Pro Gln Cys Asn Gly His Cys Phe Gly Pro Asn Pro Asn
            210                 215                 220
Gln Cys Cys His Asp Glu Cys Ala Gly Gly Cys Ser Gly Pro Gln Asp
225                 230                 235                 240
Thr Asp Cys Phe Ala Cys Arg His Phe Asn Asp Ser Gly Ala Cys Val
            245                 250                 255
Pro Arg Cys Pro Gln Pro Leu Val Tyr Asn Lys Leu Thr Phe Gln Leu
            260                 265                 270
Glu Pro Asn Pro His Thr Lys Tyr Gln Tyr Gly Gly Val Cys Val Ala
            275                 280                 285
Ser Cys Pro His Asn Phe Val Val Asp Gln Thr Ser Cys Val Arg Ala
            290                 295                 300
Cys Pro Pro Asp Lys Met Glu Val Asp Lys Asn Gly Leu Lys Met Cys
305                 310                 315                 320
Glu Pro Cys Gly Gly Leu Cys Pro Lys Ala Cys Glu Gly Thr Gly Ser
                        325                 330                 335
Gly Ser Arg Phe Gln Thr Val Asp Ser Ser Asn Ile Asp Gly Phe Val
            340                 345                 350
Asn Cys Thr Lys Ile Leu Gly Asn Leu Asp Phe Leu Ile Thr Gly Leu
            355                 360                 365
Asn Gly Asp Pro Trp His Lys Ile Pro Ala Leu Asp Pro Glu Lys Leu
            370                 375                 380
Asn Val Phe Arg Thr Val Arg Glu Ile Thr Gly Tyr Leu Asn Ile Gln
385                 390                 395                 400
Ser Trp Pro Pro His Met His Asn Phe Ser Val Phe Ser Asn Leu Thr
                        405                 410                 415
Thr Ile Gly Gly Arg Ser Leu Tyr Asn Arg Gly Phe Ser Leu Leu Ile
                        420                 425                 430
Met Lys Asn Leu Asn Val Thr Ser Leu Gly Phe Arg Ser Leu Lys Glu
            435                 440                 445
Ile Ser Ala Gly Arg Ile Tyr Ile Ser Ala Asn Arg Gln Leu Cys Tyr
            450                 455                 460
His His Ser Leu Asn Trp Thr Lys Val Leu Arg Gly Pro Thr Glu Glu
465                 470                 475                 480
Arg Leu Asp Ile Lys His Asn Arg Pro Arg Arg Asp Cys Val Ala Glu
                        485                 490                 495
Gly Lys Val Cys Asp Pro Leu Cys Ser Ser Gly Gly Cys Trp Gly Pro
            500                 505                 510
Gly Pro Gly Gln Cys Leu Ser Cys Arg Asn Tyr Ser Arg Gly Gly Val
            515                 520                 525
Cys Val Thr His Cys Asn Phe Leu Asn Gly Glu Pro Arg Glu Phe Ala
            530                 535                 540
His Glu Ala Glu Cys Phe Ser Cys His Pro Glu Cys Gln Pro Met Glu
545                 550                 555                 560
Gly Thr Ala Thr Cys Asn Gly Ser Gly Ser Asp Thr Cys Ala Gln Cys
                        565                 570                 575
Ala His Phe Arg Asp Gly Pro His Cys Val Ser Ser Cys Pro His Gly
```

```
              580             585                  590
    Val Leu Gly Ala Lys Gly Pro Ile Tyr Lys Tyr Pro Asp Val Gln Asn
                595             600             605

Glu Cys Arg Pro Cys His Glu Asn Cys Thr Gln Gly Cys Lys Gly Pro
        610             615             620

Glu Leu Gln Asp Cys Leu Gly Gln Thr Leu Val Leu Ile Gly Lys Thr
    625             630             635             640

His Leu Thr Met Ala Leu Thr Val Ile Ala Gly Leu Val Val Ile Phe
                    645             650             655

Met Met Leu Gly Gly Thr Phe Leu Tyr Trp Arg Gly Arg Arg Ile Gln
                    660             665             670

Asn Lys Arg Ala Met Arg Arg Tyr Leu Glu Arg Gly Glu Ser Ile Glu
                675             680             685

Pro Leu Asp Pro Ser Glu Lys Ala Asn Lys Val Leu Ala Arg Ile Phe
                690             695             700

Lys Glu Thr Glu Leu Arg Lys Leu Lys Val Leu Gly Ser Gly Val Phe
    705             710             715             720

Gly Thr Val His Lys Gly Val Trp Ile Pro Glu Gly Glu Ser Ile Lys
                    725             730             735

Ile Pro Val Cys Ile Lys Val Ile Glu Asp Lys Ser Gly Arg Gln Ser
                    740             745             750

Phe Gln Ala Val Thr Asp His Met Leu Ala Ile Gly Ser Leu Asp His
                    755             760             765

Ala His Ile Val Arg Leu Leu Gly Leu Cys Pro Gly Ser Ser Leu Gln
                770             775             780

Leu Val Thr Gln Tyr Leu Pro Leu Gly Ser Leu Leu Asp His Val Arg
    785             790             795             800

Gln His Arg Gly Ala Leu Gly Pro Gln Leu Leu Leu Asn Trp Gly Val
                    805             810             815

Gln Ile Ala Lys Gly Met Tyr Tyr Leu Glu Glu His Gly Met Val His
                820             825             830

Arg Asn Leu Ala Ala Arg Asn Val Leu Leu Lys Ser Pro Ser Gln Val
                835             840             845

Gln Val Ala Asp Phe Gly Val Ala Asp Leu Leu Pro Pro Asp Asp Lys
                850             855             860

Gln Leu Leu Tyr Ser Glu Ala Lys Thr Pro Ile Lys Trp Met Ala Leu
    865             870             875             880

Glu Ser Ile His Phe Gly Lys Tyr Thr His Gln Ser Asp Val Trp Ser
                    885             890             895

Tyr Gly Val Thr Val Trp Glu Leu Met Thr Phe Gly Ala Glu Pro Tyr
                    900             905             910

Ala Gly Leu Arg Leu Ala Glu Val Pro Asp Leu Leu Glu Lys Gly Glu
                915             920             925

Arg Leu Ala Gln Pro Gln Ile Cys Thr Ile Asp Val Tyr Met Val Met
                930             935             940

Val Lys Cys Trp Met Ile Asp Glu Asn Ile Arg Pro Thr Phe Lys Glu
    945             950             955             960

Leu Ala Asn Glu Phe Thr Arg Met Ala Arg Asp Pro Pro Arg Tyr Leu
                    965             970             975

Val Ile Lys Arg Glu Ser Gly Pro Gly Ile Ala Pro Gly Pro Glu Pro
                    980             985             990

His Gly Leu Thr Asn Lys Lys Leu  Glu Glu Val Glu Leu  Glu Pro Glu
                995             1000             1005
```

Leu Asp Leu Asp Leu Asp Leu Glu Ala Glu Glu Asp Asn Leu Ala
       1010                1015                1020

Thr Thr Thr Leu Gly Ser Ala Leu Ser Leu Pro Val Gly Thr Leu
       1025                1030                1035

Asn Arg Pro Arg Gly Ser Gln Ser Leu Leu Ser Pro Ser Ser Gly
       1040                1045                1050

Tyr Met Pro Met Asn Gln Gly Asn Leu Gly Glu Ser Cys Gln Glu
       1055                1060                1065

Ser Ala Val Ser Gly Ser Ser Glu Arg Cys Pro Arg Pro Val Ser
       1070                1075                1080

Leu His Pro Met Pro Arg Gly Cys Leu Ala Ser Glu Ser Ser Glu
       1085                1090                1095

Gly His Val Thr Gly Ser Glu Ala Glu Leu Gln Glu Lys Val Ser
       1100                1105                1110

Met Cys Arg Ser Arg Ser Arg Ser Arg Ser Pro Arg Pro Arg Gly
       1115                1120                1125

Asp Ser Ala Tyr His Ser Gln Arg His Ser Leu Leu Thr Pro Val
       1130                1135                1140

Thr Pro Leu Ser Pro Pro Gly Leu Glu Glu Glu Asp Val Asn Gly
       1145                1150                1155

Tyr Val Met Pro Asp Thr His Leu Lys Gly Thr Pro Ser Ser Arg
       1160                1165                1170

Glu Gly Thr Leu Ser Ser Val Gly Leu Ser Ser Val Leu Gly Thr
       1175                1180                1185

Glu Glu Glu Asp Glu Asp Glu Glu Tyr Glu Tyr Met Asn Arg Arg
       1190                1195                1200

Arg Arg His Ser Pro Pro His Pro Pro Arg Pro Ser Ser Leu Glu
       1205                1210                1215

Glu Leu Gly Tyr Glu Tyr Met Asp Val Gly Ser Asp Leu Ser Ala
       1220                1225                1230

Ser Leu Gly Ser Thr Gln Ser Cys Pro Leu His Pro Val Pro Ile
       1235                1240                1245

Met Pro Thr Ala Gly Thr Thr Pro Asp Glu Asp Tyr Glu Tyr Met
       1250                1255                1260

Asn Arg Gln Arg Asp Gly Gly Gly Pro Gly Gly Asp Tyr Ala Ala
       1265                1270                1275

Met Gly Ala Cys Pro Ala Ser Glu Gln Gly Tyr Glu Glu Met Arg
       1280                1285                1290

Ala Phe Gln Gly Pro Gly His Gln Ala Pro His Val His Tyr Ala
       1295                1300                1305

Arg Leu Lys Thr Leu Arg Ser Leu Glu Ala Thr Asp Ser Ala Phe
       1310                1315                1320

Asp Asn Pro Asp Tyr Trp His Ser Arg Leu Phe Pro Lys Ala Asn
       1325                1330                1335

Ala Gln Arg Thr
       1340

<210> SEQ ID NO 2
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 2

Ser Tyr Ala Met Ser
1               5

<210> SEQ ID NO 3
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Val Thr Gly Ala Val Gly Arg Thr Tyr Tyr Pro Asp Ser Val Lys Gly
1               5                   10                  15

<210> SEQ ID NO 4
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Trp Gly Asp Glu Gly Phe Asp Ile
1               5

<210> SEQ ID NO 5
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Arg Ala Ser Gln Gly Ile Ser Asn Trp Leu Ala
1               5                   10

<210> SEQ ID NO 6
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Gly Ala Ser Ser Leu Gln Ser
1               5

<210> SEQ ID NO 7
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Gln Gln Tyr Ser Ser Phe Pro Thr Thr
```

```
<210> SEQ ID NO 8
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Gly Phe Thr Phe Ser Ser Tyr
1               5

<210> SEQ ID NO 9
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Gly Ala Val Gly Arg
1               5

<210> SEQ ID NO 10
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Trp Gly Asp Glu Gly Phe Asp Ile
1               5

<210> SEQ ID NO 11
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Ser Gln Gly Ile Ser Asn Trp
1               5

<210> SEQ ID NO 12
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Gly Ala Ser
1

<210> SEQ ID NO 13
```

```
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Tyr Ser Ser Phe Pro Thr
1               5

<210> SEQ ID NO 14
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Tyr Ser Ser Phe Pro Thr
                85                  90                  95

Thr Phe Gly Gln Gly Thr Lys Val Glu Ile Lys
            100                 105

<210> SEQ ID NO 15
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Thr Gly Ala Val Gly Arg Thr Tyr Tyr Pro Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Trp Gly Asp Glu Gly Phe Asp Ile Trp Gly Gln Gly Thr Leu Val
            100                 105                 110
```

Thr Val Ser Ser
    115

<210> SEQ ID NO 16
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 16

| | |
|---|---|
| gatatccaga tgacccagag cccgtctagc ctgagcgcga gcgtgggtga tcgtgtgacc | 60 |
| attacctgca gagcgagcca gggtatttct aattggctgg cttggtacca gcagaaacca | 120 |
| ggtaaagcac cgaaactatt aatttatggt gcttcttctt tgcaaagcgg ggtcccgtcc | 180 |
| cgttttagcg gctctggatc cggcactgat tttaccctga ccattagcag cctgcaacct | 240 |
| gaagactttg cggtttatta ttgccagcag tattcttctt ttcctactac ctttggccag | 300 |
| ggtacgaaag ttgaaattaa a | 321 |

<210> SEQ ID NO 17
<211> LENGTH: 348
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 17

| | |
|---|---|
| caggtgcaat tggtggaaag cggcggcggc ctggtgcaac cgggcggcag cctgcgtctg | 60 |
| agctgcgcgg cctccggatt tacctttagc agctatgcga tgagctgggt gcgccaagcc | 120 |
| cctgggaagg gtctcgagtg ggtgagcgtt actggtgctg ttggtcgtac ttattatcct | 180 |
| gattctgtta agggtcgttt taccatttca cgtgataatt cgaaaaacac cctgtatctg | 240 |
| caaatgaaca gcctgcgtgc ggaagatacg gccgtgtatt attgcgcgcg ttggggtgat | 300 |
| gagggttttg atatttgggg ccaaggcacc ctggtgacgg ttagctca | 348 |

<210> SEQ ID NO 18
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Tyr Ser Ser Phe Pro Thr

-continued

```
                    85                  90                  95
Thr Phe Gly Gln Gly Thr Lys Val Glu Ile Lys Arg Thr Val Ala Ala
                100                 105                 110
Pro Ser Val Phe Ile Phe Pro Pro Ser Asp Glu Gln Leu Lys Ser Gly
            115                 120                 125
Thr Ala Ser Val Val Cys Leu Leu Asn Asn Phe Tyr Pro Arg Glu Ala
        130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 19
<211> LENGTH: 446
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

Gln Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Ala Met Ser Trp Val Arg Gln Ala Pro Gly Lys Gly Leu Glu Trp Val
        35                  40                  45
Ser Val Thr Gly Ala Val Gly Arg Thr Tyr Tyr Pro Asp Ser Val Lys
    50                  55                  60
Gly Arg Phe Thr Ile Ser Arg Asp Asn Ser Lys Asn Thr Leu Tyr Leu
65                  70                  75                  80
Gln Met Asn Ser Leu Arg Ala Glu Asp Thr Ala Val Tyr Tyr Cys Ala
                85                  90                  95
Arg Trp Gly Asp Glu Gly Phe Asp Ile Trp Gly Gln Gly Thr Leu Val
                100                 105                 110
Thr Val Ser Ser Ala Ser Thr Lys Gly Pro Ser Val Phe Pro Leu Ala
            115                 120                 125
Pro Ser Ser Lys Ser Thr Ser Gly Gly Thr Ala Ala Leu Gly Cys Leu
        130                 135                 140
Val Lys Asp Tyr Phe Pro Glu Pro Val Thr Val Ser Trp Asn Ser Gly
145                 150                 155                 160
Ala Leu Thr Ser Gly Val His Thr Phe Pro Ala Val Leu Gln Ser Ser
                165                 170                 175
Gly Leu Tyr Ser Leu Ser Ser Val Val Thr Val Pro Ser Ser Ser Leu
            180                 185                 190
Gly Thr Gln Thr Tyr Ile Cys Asn Val Asn His Lys Pro Ser Asn Thr
        195                 200                 205
Lys Val Asp Lys Arg Val Glu Pro Lys Ser Cys Asp Lys Thr His Thr
    210                 215                 220
```

```
Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 20
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Ser Tyr Ala Met Ser
1               5

<210> SEQ ID NO 21
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Val Ile Ser Ala Trp Gly His Val Lys Tyr Tyr Ala Asp Ser Val Lys
1               5                   10                  15

Gly

<210> SEQ ID NO 22
<211> LENGTH: 8
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Trp Gly Asp Glu Gly Phe Asp Ile
1               5

<210> SEQ ID NO 23
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Arg Ala Ser Gln Gly Ile Ser Asn Trp Leu Ala
1               5                   10

<210> SEQ ID NO 24
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Gly Ala Ser Ser Leu Gln Ser
1               5

<210> SEQ ID NO 25
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

Gln Gln Tyr Ser Ser Phe Pro Thr Thr
1               5

<210> SEQ ID NO 26
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Gly Phe Thr Phe Ser Ser Tyr
1               5

<210> SEQ ID NO 27
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic peptide"

<400> SEQUENCE: 27

Ser Ala Trp Gly His Val
1               5

<210> SEQ ID NO 28
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Trp Gly Asp Glu Gly Phe Asp Ile
1               5

<210> SEQ ID NO 29
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Ser Gln Gly Ile Ser Asn Trp
1               5

<210> SEQ ID NO 30
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

Gly Ala Ser
1

<210> SEQ ID NO 31
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Tyr Ser Ser Phe Pro Thr
1               5

<210> SEQ ID NO 32
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 32

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65              70                  75                  80

Glu Asp Phe Ala Val Tyr Tyr Cys Gln Gln Tyr Ser Ser Phe Pro Thr
                85                  90                  95

Thr Phe Gly Gln Gly Thr Lys Val Glu Ile Lys
            100                 105
```

<210> SEQ ID NO 33
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 33

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Ile Ser Ala Trp Gly His Val Lys Tyr Tyr Ala Asp Ser Val
    50                  55                  60

Lys Gly Arg Phe Thr Ile Ser Arg Asp Asn Ser Lys Asn Thr Leu Tyr
65              70                  75                  80

Leu Gln Met Asn Ser Leu Arg Ala Glu Asp Thr Ala Val Tyr Tyr Cys
                85                  90                  95

Ala Arg Trp Gly Asp Glu Gly Phe Asp Ile Trp Gly Gln Gly Thr Leu
            100                 105                 110

Val Thr Val Ser Ser
        115
```

<210> SEQ ID NO 34
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 34
gatatccaga tgacccagag cccgtctagc ctgagcgcga gcgtgggtga tcgtgtgacc    60
attacctgca gagcgagcca gggtatttct aattggctgg cttggtacca gcagaaacca   120
ggtaaagcac cgaaactatt aatttatggt gcttcttctt tgcaaagcgg ggtcccgtcc   180
cgttttagcg gctctggatc cggcactgat tttaccctga ccattagcag cctgcaacct   240
gaagactttg cggtttatta ttgccagcag tattcttctt ttcctactac ctttggccag   300

```
ggtacgaaag ttgaaattaa a                                             321
```

<210> SEQ ID NO 35
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 35

```
caggtgcaat tggtggaaag cggcggcggc ctggtgcaac cgggcggcag cctgcgtctg     60
agctgcgcgg cctccggatt tacctttagc agctatgcga tgagctgggt gcgccaagcc    120
cctgggaagg gtctcgagtg ggtgagcgtt atttctgctt ggggtcatgt taagtattat    180
gctgattctg ttaagggtcg ttttaccatt tcacgtgata attcgaaaaa caccctgtat    240
ctgcaaatga acagcctgcg tgcggaagat acggccgtgt attattgcgc gcgttggggt    300
gatgagggtt ttgatatttg gggccaaggc accctggtga cggttagctc a            351
```

<210> SEQ ID NO 36
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Tyr Ser Ser Phe Pro Thr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 37
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 37

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Ile Ser Ala Trp Gly His Val Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Asp Glu Gly Phe Asp Ile Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

```
Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 38
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 38

Ser Tyr Ala Met Ser
1               5

<210> SEQ ID NO 39
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 39

Ala Ile Asn Ser Gln Gly Lys Ser Thr Tyr Tyr Ala Asp Ser Val Lys
1               5                   10                  15
Gly

<210> SEQ ID NO 40
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 40

Trp Gly Asp Glu Gly Phe Asp Ile
1               5

<210> SEQ ID NO 41
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 41

Arg Ala Ser Gln Gly Ile Ser Asn Trp Leu Ala
1               5                   10
```

```
<210> SEQ ID NO 42
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

Gly Ala Ser Ser Leu Gln Ser
1               5

<210> SEQ ID NO 43
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

Gln Gln Tyr Ser Ser Phe Pro Thr Thr
1               5

<210> SEQ ID NO 44
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Gly Phe Thr Phe Ser Ser Tyr
1               5

<210> SEQ ID NO 45
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Asn Ser Gln Gly Lys Ser
1               5

<210> SEQ ID NO 46
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

Trp Gly Asp Glu Gly Phe Asp Ile
1               5

<210> SEQ ID NO 47
<211> LENGTH: 7
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 47

Ser Gln Gly Ile Ser Asn Trp
1               5

<210> SEQ ID NO 48
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 48

Gly Ala Ser
1

<210> SEQ ID NO 49
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Tyr Ser Ser Phe Pro Thr
1               5

<210> SEQ ID NO 50
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 50

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Tyr Ser Ser Phe Pro Thr
                85                  90                  95

Thr Phe Gly Gln Gly Thr Lys Val Glu Ile Lys
            100                 105

<210> SEQ ID NO 51
<211> LENGTH: 117
<212> TYPE: PRT
```

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 51

```
Gln Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Ala Met Ser Trp Val Arg Gln Ala Pro Gly Lys Gly Leu Glu Trp Val
        35                  40                  45
Ser Ala Ile Asn Ser Gln Gly Lys Ser Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Trp Gly Asp Glu Gly Phe Asp Ile Trp Gly Gln Gly Thr Leu
            100                 105                 110
Val Thr Val Ser Ser
        115
```

<210> SEQ ID NO 52
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 52

```
gatatccaga tgacccagag cccgtctagc ctgagcgcga gcgtgggtga tcgtgtgacc    60
attacctgca gagcgagcca gggtatttct aattggctgg cttggtacca gcagaaacca   120
ggtaaagcac cgaaactatt aatttatggt gcttcttctt tgcaaagcgg ggtcccgtcc   180
cgttttagcg gctctggatc cggcactgat tttaccctga ccattagcag cctgcaacct   240
gaagactttg cggtttatta ttgccagcag tattcttctt ttcctactac ctttggccag   300
ggtacgaaag ttgaaattaa a                                              321
```

<210> SEQ ID NO 53
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 53

```
caggtgcaat tggtggaaag cggcggcggc ctggtgcaac cgggcggcag cctgcgtctg    60
agctgcgcgg cctccggatt taccttttagc agctatgcga tgagctgggt gcgccaagcc   120
cctgggaagg gtctcgagtg ggtgagcgct attaattctc agggtaagtc tacttattat   180
gctgattctg ttaagggtcg ttttaccatt tcacgtgata attcgaaaaa caccctgtat   240
ctgcaaatga acagcctgcg tgcggaagat acggccgtgt attattgcgc gcgttggggt   300
gatgagggtt ttgatatttg gggccaaggc accctggtga cggttagctc a             351
```

<210> SEQ ID NO 54
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 54

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Tyr Ser Ser Phe Pro Thr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 55
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 55

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Asn Ser Gln Gly Lys Ser Thr Tyr Tyr Ala Asp Ser Val
    50                  55                  60

-continued

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Trp Gly Asp Glu Gly Phe Asp Ile Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 56
<211> LENGTH: 5
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"

<400> SEQUENCE: 56

Ser Tyr Ala Met Ser
1               5

<210> SEQ ID NO 57
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 57

Val Ile Asn Pro Ser Gly Asn Phe Thr Asn Tyr Ala Asp Ser Val Lys
1               5                   10                  15

Gly

<210> SEQ ID NO 58
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 58

Trp Gly Asp Glu Gly Phe Asp Ile
1               5

<210> SEQ ID NO 59
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 59

Arg Ala Ser Gln Gly Ile Ser Asn Trp Leu Ala
1               5                   10

<210> SEQ ID NO 60
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 60

Gly Ala Ser Ser Leu Gln Ser
1               5

<210> SEQ ID NO 61
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 61

Gln Gln Tyr Ser Ser Phe Pro Thr Thr
1               5

<210> SEQ ID NO 62
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 62

Gly Phe Thr Phe Ser Ser Tyr
1               5

<210> SEQ ID NO 63
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 63

Asn Pro Ser Gly Asn Phe
1               5

<210> SEQ ID NO 64
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 64

Trp Gly Asp Glu Gly Phe Asp Ile
1               5

<210> SEQ ID NO 65
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 65

Ser Gln Gly Ile Ser Asn Trp
1               5

<210> SEQ ID NO 66
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 66

Gly Ala Ser
```

<210> SEQ ID NO 67
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 67

Tyr Ser Ser Phe Pro Thr
1               5

<210> SEQ ID NO 68
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 68

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Tyr Ser Ser Phe Pro Thr
                85                  90                  95

Thr Phe Gly Gln Gly Thr Lys Val Glu Ile Lys
            100                 105

<210> SEQ ID NO 69
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 69

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Ile Asn Pro Ser Gly Asn Phe Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Asp Glu Gly Phe Asp Ile Trp Gly Gln Gly Thr Leu
            100                 105                 110

Val Thr Val Ser Ser
        115

<210> SEQ ID NO 70
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 70
gatatccaga tgacccagag cccgtctagc ctgagcgcga gcgtgggtga tcgtgtgacc      60
attacctgca gagcgagcca gggtatttct aattggctgg cttggtacca gcagaaacca     120
ggtaaagcac cgaaactatt aatttatggt gcttcttctt tgcaaagcgg ggtcccgtcc     180
cgttttagcg gctctggatc cggcactgat tttaccctga ccattagcag cctgcaacct     240
gaagactttg cggtttatta ttgccagcag tattcttctt ttcctactac ctttggccag     300
ggtacgaaag ttgaaattaa a                                               321

<210> SEQ ID NO 71
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 71
caggtgcaat tggtggaaag cggcggcggc ctggtgcaac cgggcggcag cctgcgtctg      60
agctgcgcgg cctccggatt tacctttagc agctatgcga tgagctgggt gcgccaagcc     120
cctgggaagg gtctcgagtg ggtgagcgtt attaatcctt ctggtaattt tactaattat     180
gctgattctg ttaagggtcg ttttaccatt tcacgtgata attcgaaaaa caccctgtat     240
ctgcaaatga acagcctgcg tgcggaagat acggccgtgt attattgcgc gcgttggggt     300
gatgagggtt ttgatatttg gggccaaggc accctggtga cggttagctc a             351

<210> SEQ ID NO 72
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 72

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

```
Ser Gly Ser Gly Thr Asp Phe Thr Leu Thr Ile Ser Ser Leu Gln Pro
 65                  70                  75                  80

Glu Asp Phe Ala Val Tyr Tyr Cys Gln Gln Tyr Ser Ser Phe Pro Thr
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 73
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 73

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Ile Asn Pro Ser Gly Asn Phe Thr Asn Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Trp Gly Asp Glu Gly Phe Asp Ile Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
```

-continued

```
                195                 200                 205
Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 74
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 74

Ser Tyr Ala Met Ser
1               5

<210> SEQ ID NO 75
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 75

Asn Thr Ser Pro Ile Gly Tyr Thr Tyr Tyr Ala Gly Ser Val Lys Gly
1               5                   10                  15

<210> SEQ ID NO 76
```

```
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 76

Trp Gly Asp Glu Gly Phe Asp Ile
1               5

<210> SEQ ID NO 77
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 77

Arg Ala Ser Gln Gly Ile Ser Asn Trp Leu Ala
1               5                   10

<210> SEQ ID NO 78
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 78

Gly Ala Ser Ser Leu Gln Ser
1               5

<210> SEQ ID NO 79
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 79

Gln Gln Tyr Ser Ser Phe Pro Thr Thr
1               5

<210> SEQ ID NO 80
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 80

Gly Phe Thr Phe Ser Ser Tyr
1               5

<210> SEQ ID NO 81
<211> LENGTH: 5
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 81

Ser Pro Ile Gly Tyr
1               5

<210> SEQ ID NO 82
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 82

Trp Gly Asp Glu Gly Phe Asp Ile
1               5

<210> SEQ ID NO 83
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 83

Ser Gln Gly Ile Ser Asn Trp
1               5

<210> SEQ ID NO 84
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 84

Gly Ala Ser
1

<210> SEQ ID NO 85
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 85

Tyr Ser Ser Phe Pro Thr
1               5

<210> SEQ ID NO 86
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

-continued

<400> SEQUENCE: 86

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Tyr Ser Ser Phe Pro Thr
                85                  90                  95

Thr Phe Gly Gln Gly Thr Lys Val Glu Ile Lys
            100                 105

<210> SEQ ID NO 87
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 87

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Asn Thr Ser Pro Ile Gly Tyr Thr Tyr Tyr Ala Gly Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Trp Gly Asp Glu Gly Phe Asp Ile Trp Gly Gln Gly Thr Leu Val
            100                 105                 110

Thr Val Ser Ser
        115

<210> SEQ ID NO 88
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 88
gatatccaga tgacccagag cccgtctagc ctgagcgcga gcgtgggtga tcgtgtgacc      60
attacctgca gagcgagcca gggtatttct aattggctgg cttggtacca gcagaaacca     120
ggtaaagcac cgaaactatt aatttatggt gcttcttctt tgcaaagcgg ggtcccgtcc     180
cgttttagcg gctctggatc cggcactgat tttaccctga ccattagcag cctgcaacct     240

```
gaagactttg cggtttatta ttgccagcag tattcttctt ttcctactac ctttggccag    300
ggtacgaaag ttgaaattaa a                                              321
```

<210> SEQ ID NO 89
<211> LENGTH: 348
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic polynucleotide"

<400> SEQUENCE: 89

```
caggtgcaat tggtggaaag cggcggcggc ctggtgcaac cgggcggcag cctgcgtctg    60
agctgcgcgg cctccggatt tacctttagc agctatgcga tgagctgggt gcgccaagcc    120
cctgggaagg gtctcgagtg ggtgagcaat acttctccta ttggttatac ttattatgct    180
ggttctgtta agggtcgttt taccatttca cgtgataatt cgaaaaacac cctgtatctg    240
caaatgaaca gcctgcgtgc ggaagatacg gccgtgtatt attgcgcgcg ttggggtgat    300
gagggttttg atatttgggg ccaaggcacc ctggtgacgg ttagctca                 348
```

<210> SEQ ID NO 90
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
       Synthetic polypeptide"

<400> SEQUENCE: 90

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Tyr Ser Ser Phe Pro Thr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Ala
    210

<210> SEQ ID NO 91
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 91

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Asn Thr Ser Pro Ile Gly Tyr Thr Tyr Tyr Ala Gly Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Trp Gly Asp Glu Gly Phe Asp Ile Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser
    210                 215

<210> SEQ ID NO 92
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 92

Ser Tyr Ala Met Ser
1               5

<210> SEQ ID NO 93
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 93

Val Thr Gly Ala Val Gly Arg Ser Thr Tyr Tyr Pro Asp Ser Val Lys
1               5                   10                  15

Gly

<210> SEQ ID NO 94
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 94

Trp Gly Asp Glu Gly Phe Asp Ile
1               5

<210> SEQ ID NO 95
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 95

Arg Ala Ser Gln Gly Ile Ser Asn Trp Leu Ala
1               5                   10

<210> SEQ ID NO 96
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 96

Gly Ala Ser Ser Leu Gln Ser
1               5

<210> SEQ ID NO 97
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 97

Gln Gln Tyr Ser Ser Phe Pro Thr Thr
1               5

<210> SEQ ID NO 98
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 98

Gly Phe Thr Phe Ser Ser Tyr
1               5

<210> SEQ ID NO 99
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 99

Gly Ala Val Gly Arg Ser
1               5

<210> SEQ ID NO 100
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 100

Trp Gly Asp Glu Gly Phe Asp Ile
1               5

<210> SEQ ID NO 101
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 101

Ser Gln Gly Ile Ser Asn Trp
1               5

<210> SEQ ID NO 102
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 102

Gly Ala Ser
1

<210> SEQ ID NO 103
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 103

Tyr Ser Ser Phe Pro Thr

<210> SEQ ID NO 104
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 104

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Phe Pro Thr
                85                  90                  95

Thr Phe Gly Gln Gly Thr Lys Val Glu Ile Lys
            100                 105
```

<210> SEQ ID NO 105
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 105

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Thr Gly Ala Val Gly Arg Ser Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Asp Glu Gly Phe Asp Ile Trp Gly Gln Gly Thr Leu
            100                 105                 110

Val Thr Val Ser Ser
        115
```

<210> SEQ ID NO 106
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic polynucleotide"

<400> SEQUENCE: 106

```
gatatccaga tgacccagag ccccagcagc ctgagcgcca gcgtgggcga cagagtgacc      60
atcacctgtc gggccagcca gggcatcagc aactggctgg cctggtatca gcagaagccc     120
ggcaaggccc ccaagctgct gatctacggc gccagctccc tgcagagcgg cgtgccaagc     180
agattcagcg gcagcggctc cggcaccgac ttcaccctga ccatcagcag cctgcagccc     240
gaggacttcg ccacctacta ctgccagcag tacagcagct cccccaccac cttcggccag     300
ggcaccaagg tggaaatcaa g                                               321
```

<210> SEQ ID NO 107
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 107

```
gaggtgcaat tgctggaaag cggcggaggc ctggtgcagc ctggcggcag cctgagactg      60
tcttgcgccg ccagcggctt caccttcagc agctacgcca tgagctgggt ccgccaggcc     120
cctggcaagg gactggaatg ggtgtccgtg acaggcgccg tgggcagaag cacctactac     180
cccgacagcg tgaagggccg gttcaccatc agccgggaca acagcaagaa caccctgtac     240
ctgcagatga acagcctgcg ggccgaggac accgccgtgt actactgtgc cagatggggc     300
gacgagggct tcgacatctg gggccagggc accctggtca ccgtcagctc a              351
```

<210> SEQ ID NO 108
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 108

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Phe Pro Thr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140
```

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 109
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 109

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Thr Gly Ala Val Gly Arg Ser Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Asp Glu Gly Phe Asp Ile Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys

```
                    275                 280                 285
Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 110
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 110

Ser Tyr Ala Met Ser
1               5

<210> SEQ ID NO 111
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 111

Val Ile Ser Ala Trp Gly His Val Lys Tyr Tyr Ala Asp Ser Val Lys
1               5                   10                  15

Gly

<210> SEQ ID NO 112
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 112

Trp Gly Asp Glu Gly Phe Asp Ile
1               5
```

<210> SEQ ID NO 113
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 113

Arg Ala Ser Gln Gly Ile Ser Asn Trp Leu Ala
1               5                   10

<210> SEQ ID NO 114
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 114

Gly Ala Ser Ser Leu Gln Ser
1               5

<210> SEQ ID NO 115
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 115

Gln Gln Tyr Ser Ser Phe Pro Thr Thr
1               5

<210> SEQ ID NO 116
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 116

Gly Phe Thr Phe Ser Ser Tyr
1               5

<210> SEQ ID NO 117
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 117

Ser Ala Trp Gly His Val
1               5

<210> SEQ ID NO 118
<211> LENGTH: 8
<212> TYPE: PRT

<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 118

Trp Gly Asp Glu Gly Phe Asp Ile
1               5

<210> SEQ ID NO 119
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 119

Ser Gln Gly Ile Ser Asn Trp
1               5

<210> SEQ ID NO 120
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 120

Gly Ala Ser
1

<210> SEQ ID NO 121
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 121

Tyr Ser Ser Phe Pro Thr
1               5

<210> SEQ ID NO 122
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 122

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Phe Pro Thr
                85                  90                  95

Thr Phe Gly Gln Gly Thr Lys Val Glu Ile Lys
            100                 105

<210> SEQ ID NO 123
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 123

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Ile Ser Ala Trp Gly His Val Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Asp Glu Gly Phe Asp Ile Trp Gly Gln Gly Thr Leu
            100                 105                 110

Val Thr Val Ser Ser
        115

<210> SEQ ID NO 124
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 124
gatatccaga tgacccagag ccccagcagc ctgagcgcca gcgtgggcga cagagtgacc    60
atcacctgtc gggccagcca gggcatcagc aactggctgg cctggtatca gcagaagccc   120
ggcaaggccc ccaagctgct gatctacggc gccagctccc tgcagagcgg cgtgccaagc   180
agattcagcg gcagcggctc cggcaccgac ttcaccctga ccatcagcag cctgcagccc   240
gaggacttcg ccacctacta ctgccagcag tacagcagct cccccaccac cttcggccag   300
ggcaccaagg tggaaatcaa g                                             321

<210> SEQ ID NO 125
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 125

```
gaggtgcaat tgctggaaag cggcggaggc ctggtgcagc ctggcggcag cctgagactg      60
tcttgcgccg ccagcggctt caccttcagc agctacgcca tgagctgggt ccgccaggcc     120
cctggcaagg gactggaatg ggtgtccgtg atcagcgcct ggggccacgt gaagtactac     180
gccgacagcg tgaagggccg gttcaccatc agccgggaca acagcaagaa caccctgtac     240
ctgcagatga acagcctgcg ggccgaggac accgccgtgt actactgtgc cagatggggc     300
gacgagggct tcgacatctg gggccagggc accctggtca ccgtcagctc a              351
```

<210> SEQ ID NO 126
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 126

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Phe Pro Thr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 127
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 127

```
Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Ala Met Ser Trp Val Arg Gln Ala Pro Gly Lys Gly Leu Glu Trp Val
        35                  40                  45
Ser Val Ile Ser Ala Trp Gly His Val Lys Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Trp Gly Asp Glu Gly Phe Asp Ile Trp Gly Gln Gly Thr Leu
            100                 105                 110
Val Thr Val Ser Ser Ala Ser Thr Lys Gly Pro Ser Val Phe Pro Leu
        115                 120                 125
Ala Pro Ser Ser Lys Ser Thr Ser Gly Gly Thr Ala Ala Leu Gly Cys
    130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
            180                 185                 190
Leu Gly Thr Gln Thr Tyr Ile Cys Asn Val Asn His Lys Pro Ser Asn
        195                 200                 205
Thr Lys Val Asp Lys Arg Val Glu Pro Lys Ser Cys Asp Lys Thr His
    210                 215                 220
Thr Cys Pro Pro Cys Pro Ala Pro Glu Leu Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser His Glu Asp Pro Glu
            260                 265                 270
Val Lys Phe Asn Trp Tyr Val Asp Gly Val Glu Val His Asn Ala Lys
        275                 280                 285
Thr Lys Pro Arg Glu Glu Gln Tyr Asn Ser Thr Tyr Arg Val Val Ser
    290                 295                 300
Val Leu Thr Val Leu His Gln Asp Trp Leu Asn Gly Lys Glu Tyr Lys
305                 310                 315                 320
Cys Lys Val Ser Asn Lys Ala Leu Pro Ala Pro Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Arg Glu Glu Met Thr Lys Asn Gln Val Ser Leu Thr Cys Leu
        355                 360                 365
Val Lys Gly Phe Tyr Pro Ser Asp Ile Ala Val Glu Trp Glu Ser Asn
    370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
```

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 128
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 128

Ser Tyr Ala Met Ser
1               5

<210> SEQ ID NO 129
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 129

Ala Ile Asn Ser Gln Gly Lys Ser Thr Tyr Tyr Ala Asp Ser Val Lys
1               5                   10                  15

Gly

<210> SEQ ID NO 130
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 130

Trp Gly Asp Glu Gly Phe Asp Ile
1               5

<210> SEQ ID NO 131
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 131

Arg Ala Ser Gln Gly Ile Ser Asn Trp Leu Ala
1               5                   10

<210> SEQ ID NO 132
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 132

Gly Ala Ser Ser Leu Gln Ser
1               5

<210> SEQ ID NO 133
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 133

Gln Gln Tyr Ser Ser Phe Pro Thr Thr
1               5

<210> SEQ ID NO 134
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 134

Gly Phe Thr Phe Ser Ser Tyr
1               5

<210> SEQ ID NO 135
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 135

Asn Ser Gln Gly Lys Ser
1               5

<210> SEQ ID NO 136
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 136

Trp Gly Asp Glu Gly Phe Asp Ile
1               5

<210> SEQ ID NO 137
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 137

Ser Gln Gly Ile Ser Asn Trp
1               5
```

<210> SEQ ID NO 138
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 138

Gly Ala Ser
1

<210> SEQ ID NO 139
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 139

Tyr Ser Ser Phe Pro Thr
1               5

<210> SEQ ID NO 140
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 140

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Phe Pro Thr
                85                  90                  95

Thr Phe Gly Gln Gly Thr Lys Val Glu Ile Lys
            100                 105

<210> SEQ ID NO 141
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 141

Glu Val Gln Leu Leu Glu Ser Gly Gly Gly Leu Val Gln Pro Gly Gly
1               5                   10                  15

```
Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Asn Ser Gln Gly Lys Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Trp Gly Asp Glu Gly Phe Asp Ile Trp Gly Gln Gly Thr Leu
            100                 105                 110

Val Thr Val Ser Ser
        115

<210> SEQ ID NO 142
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 142
gatatccaga tgacccagag ccccagcagc ctgagcgcca gcgtgggcga cagagtgacc      60
atcacctgtc gggccagcca gggcatcagc aactggctgg cctggtatca gcagaagccc     120
ggcaaggccc ccaagctgct gatctacggc gccagctccc tgcagagcgg cgtgccaagc     180
agattcagcg gcagcggctc cggcaccgac ttcaccctga ccatcagcag cctgcagccc     240
gaggacttcg ccacctacta ctgccagcag tacagcagct cccccaccac cttcggccag     300
ggcaccaagg tggaaatcaa g                                               321

<210> SEQ ID NO 143
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 143
gaggtgcaat tgctggaaag cggcggaggc ctggtgcagc ctggcggcag cctgagactg      60
tcttgcgccg ccagcggctt caccttcagc agctacgcca tgagctgggt ccgccaggcc     120
cctggcaagg gactggaatg ggtgtccgcc atcaacagcc agggcaagag cacctactac     180
gccgacagcg tgaagggccg gttcaccatc agccgggaca acagcaagaa caccctgtac     240
ctgcagatga acagcctgcg ggccgaggac accgccgtgt actactgtgc cagatggggc     300
gacgagggct tcgacatctg gggccagggc accctggtca ccgtcagctc a              351

<210> SEQ ID NO 144
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 144

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Phe Pro Thr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 145
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 145

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Asn Ser Gln Gly Lys Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Asp Glu Gly Phe Asp Ile Trp Gly Gln Gly Thr Leu
            100                 105                 110

Val Thr Val Ser Ser Ala Ser Thr Lys Gly Pro Ser Val Phe Pro Leu
        115                 120                 125
```

```
Ala Pro Ser Ser Lys Ser Thr Ser Gly Gly Thr Ala Ala Leu Gly Cys
        130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
                180                 185                 190
Leu Gly Thr Gln Thr Tyr Ile Cys Asn Val Asn His Lys Pro Ser Asn
            195                 200                 205
Thr Lys Val Asp Lys Arg Val Glu Pro Lys Ser Cys Asp Lys Thr His
210                 215                 220
Thr Cys Pro Pro Cys Pro Ala Pro Glu Leu Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser His Glu Asp Pro Glu
                260                 265                 270
Val Lys Phe Asn Trp Tyr Val Asp Gly Val Glu Val His Asn Ala Lys
            275                 280                 285
Thr Lys Pro Arg Glu Glu Gln Tyr Asn Ser Thr Tyr Arg Val Val Ser
290                 295                 300
Val Leu Thr Val Leu His Gln Asp Trp Leu Asn Gly Lys Glu Tyr Lys
305                 310                 315                 320
Cys Lys Val Ser Asn Lys Ala Leu Pro Ala Pro Ile Glu Lys Thr Ile
                325                 330                 335
Ser Lys Ala Lys Gly Gln Pro Arg Glu Pro Gln Val Tyr Thr Leu Pro
                340                 345                 350
Pro Ser Arg Glu Glu Met Thr Lys Asn Gln Val Ser Leu Thr Cys Leu
            355                 360                 365
Val Lys Gly Phe Tyr Pro Ser Asp Ile Ala Val Glu Trp Glu Ser Asn
370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
                420                 425                 430
His Asn His Tyr Thr Gln Lys Ser Leu Ser Leu Ser Pro Gly Lys
            435                 440                 445

<210> SEQ ID NO 146
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 146

Ser Tyr Ala Met Ser
1               5

<210> SEQ ID NO 147
<211> LENGTH: 17
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 147

Ala Ile Ser Ser Gln Gly Lys Ser Thr Tyr Tyr Ala Asp Ser Val Lys
1               5                   10                  15

Gly

<210> SEQ ID NO 148
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 148

Trp Gly Asp Glu Gly Phe Asp Ile
1               5

<210> SEQ ID NO 149
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 149

Arg Ala Ser Gln Gly Ile Ser Asn Trp Leu Ala
1               5                   10

<210> SEQ ID NO 150
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 150

Gly Ala Ser Ser Leu Gln Ser
1               5

<210> SEQ ID NO 151
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 151

Gln Gln Tyr Ser Ser Phe Pro Thr Thr
1               5

<210> SEQ ID NO 152
<211> LENGTH: 7
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 152

Gly Phe Thr Phe Ser Ser Tyr
1               5

<210> SEQ ID NO 153
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 153

Ser Ser Gln Gly Lys Ser
1               5

<210> SEQ ID NO 154
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 154

Trp Gly Asp Glu Gly Phe Asp Ile
1               5

<210> SEQ ID NO 155
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 155

Ser Gln Gly Ile Ser Asn Trp
1               5

<210> SEQ ID NO 156
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 156

Gly Ala Ser
1

<210> SEQ ID NO 157
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 157

Tyr Ser Ser Phe Pro Thr
1               5

<210> SEQ ID NO 158
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 158

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Phe Pro Thr
                85                  90                  95

Thr Phe Gly Gln Gly Thr Lys Val Glu Ile Lys
            100                 105

<210> SEQ ID NO 159
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 159

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Ser Gln Gly Lys Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Asp Glu Gly Phe Asp Ile Trp Gly Gln Gly Thr Leu
            100                 105                 110

Val Thr Val Ser Ser
            115

<210> SEQ ID NO 160
<211> LENGTH: 321
<212> TYPE: DNA

<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 160

```
gatatccaga tgacccagag ccccagcagc ctgagcgcca gcgtgggcga cagagtgacc    60
atcacctgtc gggccagcca gggcatcagc aactggctgg cctggtatca gcagaagccc   120
ggcaaggccc ccaagctgct gatctacggg gccagctccc tgcagagcgg cgtgccaagc   180
agattcagcg gcagcggctc cggcaccgac ttcaccctga ccatcagcag cctgcagccc   240
gaggacttcg ccacctacta ctgccagcag tacagcagct cccccaccac cttcggccag   300
ggcaccaagg tggaaatcaa g                                             321
```

<210> SEQ ID NO 161
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 161

```
gaggtgcaat gctggaaag cggcggaggc ctggtgcagc ctggcggcag cctgagactg    60
tcttgcgccg ccagcggctt caccttcagc agctacgcca tgagctgggt ccgccaggcc   120
cctggcaagg gactggaatg ggtgtccgcc atcagcagcc agggcaagag cacctactac   180
gccgacagcg tgaagggccg gttcaccatc agccgggaca acagcaagaa cacccttgtac  240 ctgcagatga acagcctgcg ggccgaggac accgccgtgt actactgtgc cagatggggc   300
gacgagggct tcgacatctg gggccaggga accctggtca ccgtcagctc a            351
```

<210> SEQ ID NO 162
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 162

```
Asp Ile Gln Met Thr Gln Ser Pro Ser Leu Ser Ala Ser Val Gly
 1               5                  10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Ser Pro Thr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125
```

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 163
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 163

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Ser Gln Gly Lys Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Asp Glu Gly Phe Asp Ile Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255
```

```
Pro Glu Val Thr Cys Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 164
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 164

Ser Tyr Ala Met Ser
1               5

<210> SEQ ID NO 165
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 165

Ala Ile Gly Ser Gln Gly Lys Ser Thr Tyr Tyr Ala Asp Ser Val Lys
1               5                   10                  15

Gly

<210> SEQ ID NO 166
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 166
```

Trp Gly Asp Glu Gly Phe Asp Ile
1               5

<210> SEQ ID NO 167
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 167

Arg Ala Ser Gln Gly Ile Ser Asn Trp Leu Ala
1               5                   10

<210> SEQ ID NO 168
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 168

Gly Ala Ser Ser Leu Gln Ser
1               5

<210> SEQ ID NO 169
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 169

Gln Gln Tyr Ser Ser Phe Pro Thr Thr
1               5

<210> SEQ ID NO 170
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 170

Gly Phe Thr Phe Ser Ser Tyr
1               5

<210> SEQ ID NO 171
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 171

Gly Ser Gln Gly Lys Ser
1               5

```
<210> SEQ ID NO 172
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 172

Trp Gly Asp Glu Gly Phe Asp Ile
1               5

<210> SEQ ID NO 173
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 173

Ser Gln Gly Ile Ser Asn Trp
1               5

<210> SEQ ID NO 174
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 174

Gly Ala Ser
1

<210> SEQ ID NO 175
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 175

Tyr Ser Ser Phe Pro Thr
1               5

<210> SEQ ID NO 176
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 176

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
```

```
                35                  40                  45
Tyr Gly Ala Ser Ser Leu Gln Ser Gly Val Pro Ser Arg Phe Ser Gly
            50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Tyr Ser Ser Phe Pro Thr
                85                  90                  95
Thr Phe Gly Gln Gly Thr Lys Val Glu Ile Lys
            100                 105

<210> SEQ ID NO 177
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 177

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Ala Met Ser Trp Val Arg Gln Ala Pro Gly Lys Gly Leu Glu Trp Val
        35                  40                  45
Ser Ala Ile Gly Ser Gln Gly Lys Ser Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Trp Gly Asp Glu Gly Phe Asp Ile Trp Gly Gln Gly Thr Leu
            100                 105                 110
Val Thr Val Ser Ser
        115

<210> SEQ ID NO 178
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 178
gatatccaga tgacccagag ccccagcagc ctgagcgcca gcgtgggcga cagagtgacc      60
atcacctgtc gggccagcca gggcatcagc aactggctgg cctggtatca gcagaagccc    120
ggcaaggccc ccaagctgct gatctacggc gccagctccc tgcagagcgg cgtgccaagc    180
agattcagcg gcagcggctc cggcaccgac ttcaccctga ccatcagcag cctgcagccc    240
gaggacttcg ccacctacta ctgccagcag tacagcagct cccccaccac cttcggccag    300
ggcaccaagg tggaaatcaa g                                              321

<210> SEQ ID NO 179
<211> LENGTH: 351
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic polynucleotide"

<400> SEQUENCE: 179
gaggtgcaat tgctggaaag cggcggaggc ctggtgcagc ctggcggcag cctgagactg       60
tcttgcgccg ccagcggctt caccttcagc agctacgcca tgagctgggt ccgccaggcc      120
cctggcaagg gactggaatg ggtgtccgcc atcggcagcc agggcaagag cacctactac      180
gccgacagcg tgaagggccg gttcaccatc agccgggaca acagcaagaa caccctgtac      240
ctgcagatga acagcctgcg ggccgaggac accgccgtgt actactgtgc cagatggggc      300
gacgagggct tcgacatctg gggccagggc accctggtca ccgtcagctc a               351

<210> SEQ ID NO 180
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 180
```

Asp Ile Gln Met Thr Gln Ser Pro Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Phe Pro Thr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

```
<210> SEQ ID NO 181
<211> LENGTH: 447
<212> TYPE: PRT
<213> ORGANISM: Artificial Sequence
<220> FEATURE:
```

<221> NAME/KEY: source
<223> OTHER INFORMATION: /note="Description of Artificial Sequence:
      Synthetic polypeptide"

<400> SEQUENCE: 181

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Gly Ser Gln Gly Lys Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Asp Glu Gly Phe Asp Ile Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
```

```
            385                 390                 395                 400
Asp Gly Ser Phe Phe Leu Tyr Ser Lys Leu Thr Val Asp Lys Ser Arg
                    405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
                435                 440                 445
```

<210> SEQ ID NO 182
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 182

```
Ser Tyr Ala Met Ser
1               5
```

<210> SEQ ID NO 183
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 183

```
Ala Ile Ser Asn Gln Gly Lys Ser Thr Tyr Tyr Ala Asp Ser Val Lys
1               5                   10                  15

Gly
```

<210> SEQ ID NO 184
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 184

```
Trp Gly Asp Glu Gly Phe Asp Ile
1               5
```

<210> SEQ ID NO 185
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 185

```
Arg Ala Ser Gln Gly Ile Ser Asn Trp Leu Ala
1               5                   10
```

<210> SEQ ID NO 186
<211> LENGTH: 7
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic peptide"

<400> SEQUENCE: 186

Gly Ala Ser Ser Leu Gln Ser
1               5

<210> SEQ ID NO 187
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 187

Gln Gln Tyr Ser Ser Phe Pro Thr Thr
1               5

<210> SEQ ID NO 188
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 188

Gly Phe Thr Phe Ser Ser Tyr
1               5

<210> SEQ ID NO 189
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 189

Ser Asn Gln Gly Lys Ser
1               5

<210> SEQ ID NO 190
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 190

Trp Gly Asp Glu Gly Phe Asp Ile
1               5

<210> SEQ ID NO 191
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 191

Ser Gln Gly Ile Ser Asn Trp
1               5

<210> SEQ ID NO 192
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 192

Gly Ala Ser
1

<210> SEQ ID NO 193
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 193

Tyr Ser Ser Phe Pro Thr
1               5

<210> SEQ ID NO 194
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 194

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Phe Pro Thr
                85                  90                  95

Thr Phe Gly Gln Gly Thr Lys Val Glu Ile Lys
            100                 105

<210> SEQ ID NO 195
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 195
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Asn Gln Gly Lys Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Asp Glu Gly Phe Asp Ile Trp Gly Gln Gly Thr Leu
            100                 105                 110

Val Thr Val Ser Ser
        115

<210> SEQ ID NO 196
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 196
gatatccaga tgacccagag ccccagcagc ctgagcgcca gcgtgggcga cagagtgacc      60
atcacctgtc gggccagcca gggcatcagc aactggctgg cctggtatca gcagaagccc    120
ggcaaggccc ccaagctgct gatctacggc gccagctccc tgcagagcgg cgtgccaagc    180
agattcagcg gcagcggctc cggcaccgac ttcaccctga ccatcagcag cctgcagccc    240
gaggacttcg ccacctacta ctgccagcag tacagcagct cccccaccac cttcggccag    300
ggcaccaagg tggaaatcaa g                                              321

<210> SEQ ID NO 197
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 197
gaggtgcaat tgctggaaag cggcggaggc ctggtgcagc ctggcggcag cctgagactg      60
tcttgcgccg ccagcggctt caccttcagc agctacgcca tgagctgggt ccgccaggcc    120
cctggcaagg gactggaatg ggtgtccgcc atcagcaacc agggcaagag cacctactac    180
gccgacagcg tgaagggccg gttcaccatc agccgggaca acagcaagaa caccctgtac    240
ctgcagatga acagcctgcg ggccgaggac accgccgtgt actactgtgc cagatggggc    300
gacgagggct tcgacatctg gggccagggc accctggtca ccgtcagctc a             351

<210> SEQ ID NO 198
<211> LENGTH: 214
<212> TYPE: PRT
<213> ORGANISM: Artificial Sequence
<220> FEATURE:

<221> NAME/KEY: source
<223> OTHER INFORMATION: /note="Description of Artificial Sequence:
      Synthetic polypeptide"

<400> SEQUENCE: 198

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Phe Pro Thr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 199
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 199

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Asn Gln Gly Lys Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Asp Glu Gly Phe Asp Ile Trp Gly Gln Gly Thr Leu

```
                    100                 105                 110
Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 200
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 200

Ser Tyr Ala Met Ser
1               5
```

<210> SEQ ID NO 201
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 201

Val Ile Ser Ser Gln Gly Lys Ser Thr Tyr Tyr Ala Asp Ser Val Lys
1               5                   10                  15

Gly

<210> SEQ ID NO 202
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 202

Trp Gly Asp Glu Gly Phe Asp Ile
1               5

<210> SEQ ID NO 203
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 203

Arg Ala Ser Gln Gly Ile Ser Asn Trp Leu Ala
1               5                   10

<210> SEQ ID NO 204
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 204

Gly Ala Ser Ser Leu Gln Ser
1               5

<210> SEQ ID NO 205
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 205

Gln Gln Tyr Ser Ser Phe Pro Thr Thr
1               5

```
<210> SEQ ID NO 206
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 206

Gly Phe Thr Phe Ser Ser Tyr
1               5

<210> SEQ ID NO 207
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 207

Ser Ser Gln Gly Lys Ser
1               5

<210> SEQ ID NO 208
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 208

Trp Gly Asp Glu Gly Phe Asp Ile
1               5

<210> SEQ ID NO 209
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 209

Ser Gln Gly Ile Ser Asn Trp
1               5

<210> SEQ ID NO 210
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 210

Gly Ala Ser
1

<210> SEQ ID NO 211
<211> LENGTH: 6
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 211

Tyr Ser Ser Phe Pro Thr
1               5

<210> SEQ ID NO 212
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 212

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Phe Pro Thr
                85                  90                  95

Thr Phe Gly Gln Gly Thr Lys Val Glu Ile Lys
            100                 105

<210> SEQ ID NO 213
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 213

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Ile Ser Ser Gln Gly Lys Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Asp Glu Gly Phe Asp Ile Trp Gly Gln Gly Thr Leu
            100                 105                 110

Val Thr Val Ser Ser
            115
```

<210> SEQ ID NO 214
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 214

```
gatatccaga tgacccagag ccccagcagc ctgagcgcca gcgtgggcga cagagtgacc      60
atcacctgtc gggccagcca gggcatcagc aactggctgg cctggtatca gcagaagccc     120
ggcaaggccc ccaagctgct gatctacggc gccagctccc tgcagagcgg cgtgccaagc     180
agattcagcg gcagcggctc cggcaccgac ttcaccctga ccatcagcag cctgcagccc     240
gaggacttcg ccacctacta ctgccagcag tacagcagct cccccaccac cttcggccag     300
ggcaccaagg tggaaatcaa g                                                321
```

<210> SEQ ID NO 215
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 215

```
gaggtgcaat gctggaaag cggcggaggc ctggtgcagc ctggcggcag cctgagactg       60
tcttgcgccg ccagcggctt caccttcagc agctacgcca tgagctgggt ccgccaggcc     120
cctggcaagg gactggaatg ggtgtccgtc atcagcagcc agggcaagag cacctactac     180
gccgacagcg tgaagggccg gttcaccatc agccgggaca cagcaagaa caccctgtac     240
ctgcagatga acagcctgcg ggccgaggac accgccgtgt actactgtgc cagatggggc     300
gacgagggct tcgacatctg gggccagggc accctggtca ccgtcagctc a              351
```

<210> SEQ ID NO 216
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 216

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Phe Pro Thr
                85                  90                  95

Thr Phe Gly Gln Gly Thr Lys Val Glu Ile Lys Arg Thr Val Ala Ala
```

```
                100                 105                 110
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
        210

<210> SEQ ID NO 217
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 217

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Ile Ser Ser Gln Gly Lys Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Asp Glu Gly Phe Asp Ile Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240
```

```
Phe Leu Phe Pro Pro Lys Pro Lys Asp Thr Leu Met Ile Ser Arg Thr
            245                 250                 255

Pro Glu Val Thr Cys Val Val Val Asp Val Ser His Glu Asp Pro Glu
        260                 265                 270

Val Lys Phe Asn Trp Tyr Val Asp Gly Val Glu Val His Asn Ala Lys
    275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
                435                 440                 445

<210> SEQ ID NO 218
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 218

Ser Tyr Ala Met Ser
1               5

<210> SEQ ID NO 219
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 219

Val Ile Gly Ser Gln Gly Lys Ser Thr Tyr Tyr Ala Asp Ser Val Lys
1               5                   10                  15

Gly

<210> SEQ ID NO 220
<211> LENGTH: 8
<212> TYPE: PRT
<213> ORGANISM: Artificial Sequence
<220> FEATURE:
<221> NAME/KEY: source
```

<223> OTHER INFORMATION: /note="Description of Artificial Sequence:
      Synthetic peptide"

<400> SEQUENCE: 220

Trp Gly Asp Glu Gly Phe Asp Ile
1               5

<210> SEQ ID NO 221
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 221

Arg Ala Ser Gln Gly Ile Ser Asn Trp Leu Ala
1               5                   10

<210> SEQ ID NO 222
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 222

Gly Ala Ser Ser Leu Gln Ser
1               5

<210> SEQ ID NO 223
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 223

Gln Gln Tyr Ser Ser Phe Pro Thr Thr
1               5

<210> SEQ ID NO 224
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 224

Gly Phe Thr Phe Ser Ser Tyr
1               5

<210> SEQ ID NO 225
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 225

```
Gly Ser Gln Gly Lys Ser
1               5

<210> SEQ ID NO 226
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 226

Trp Gly Asp Glu Gly Phe Asp Ile
1               5

<210> SEQ ID NO 227
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 227

Ser Gln Gly Ile Ser Asn Trp
1               5

<210> SEQ ID NO 228
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 228

Gly Ala Ser
1

<210> SEQ ID NO 229
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 229

Tyr Ser Ser Phe Pro Thr
1               5

<210> SEQ ID NO 230
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 230

Asp Ile Gln Met Thr Gln Ser Pro Ser Ser Leu Ser Ala Ser Val Gly
1               5                   10                  15
```

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Phe Pro Thr
                85                  90                  95

Thr Phe Gly Gln Gly Thr Lys Val Glu Ile Lys
            100                 105

<210> SEQ ID NO 231
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 231

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Ile Gly Ser Gln Gly Lys Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Asp Glu Gly Phe Asp Ile Trp Gly Gln Gly Thr Leu
            100                 105                 110

Val Thr Val Ser Ser
        115

<210> SEQ ID NO 232
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 232
gatatccaga tgacccagag ccccagcagc ctgagcgcca gcgtgggcga cagagtgacc    60
atcacctgtc gggccagcca gggcatcagc aactggctgg cctggtatca gcagaagccc   120
ggcaaggccc ccaagctgct gatctacggc gccagctccc tgcagagcgg cgtgccaagc   180
agattcagcg gcagcggctc cggcaccgac ttcaccctga ccatcagcag cctgcagccc   240
gaggacttcg ccacctacta ctgccagcag tacagcagct cccccaccac cttcggccag   300
ggcaccaagg tggaaatcaa g                                             321

<210> SEQ ID NO 233
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 233

```
gaggtgcaat tgctggaaag cggcggaggc ctggtgcagc ctggcggcag cctgagactg      60
tcttgcgccg ccagcggctt caccttcagc agctacgcca tgagctgggt ccgccaggcc     120
cctggcaagg gactggaatg ggtgtccgtc atcggcagcc agggcaagag cacctactac     180
gccgacagcg tgaagggccg gttcaccatc agccgggaca cagcaagaa caccctgtac     240 ctgcagatga acagcctgcg ggccgaggac accgccgtgt actactgtgc cagatggggc     300
gacgagggct tcgacatctg ggccagggc accctggtca ccgtcagctc a               351
```

<210> SEQ ID NO 234
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 234

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Phe Pro Thr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 235

```
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 235

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Ile Gly Ser Gln Gly Lys Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Asp Glu Gly Phe Asp Ile Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365
```

```
Val Lys Gly Phe Tyr Pro Ser Asp Ile Ala Val Glu Trp Glu Ser Asn
        370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
                420                 425                 430
His Asn His Tyr Thr Gln Lys Ser Leu Ser Leu Ser Pro Gly Lys
            435                 440                 445

<210> SEQ ID NO 236
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 236

Ser Tyr Ala Met Ser
1               5

<210> SEQ ID NO 237
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 237

Ala Ile Asn Ala Gln Gly Lys Ser Thr Tyr Tyr Ala Asp Ser Val Lys
1               5                   10                  15
Gly

<210> SEQ ID NO 238
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 238

Trp Gly Asp Glu Gly Phe Asp Ile
1               5

<210> SEQ ID NO 239
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 239

Arg Ala Ser Gln Gly Ile Ser Asn Trp Leu Ala
1               5                   10

<210> SEQ ID NO 240
```

```
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 240

Gly Ala Ser Ser Leu Gln Ser
1               5

<210> SEQ ID NO 241
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 241

Gln Gln Tyr Ser Ser Phe Pro Thr Thr
1               5

<210> SEQ ID NO 242
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 242

Gly Phe Thr Phe Ser Ser Tyr
1               5

<210> SEQ ID NO 243
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 243

Asn Ala Gln Gly Lys Ser
1               5

<210> SEQ ID NO 244
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 244

Trp Gly Asp Glu Gly Phe Asp Ile
1               5

<210> SEQ ID NO 245
<211> LENGTH: 7
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 245

Ser Gln Gly Ile Ser Asn Trp
1               5

<210> SEQ ID NO 246
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 246

Gly Ala Ser
1

<210> SEQ ID NO 247
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 247

Tyr Ser Ser Phe Pro Thr
1               5

<210> SEQ ID NO 248
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 248

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Phe Pro Thr
                85                  90                  95

Thr Phe Gly Gln Gly Thr Lys Val Glu Ile Lys
            100                 105

<210> SEQ ID NO 249
<211> LENGTH: 117
<212> TYPE: PRT
<213> ORGANISM: Artificial Sequence
<220> FEATURE:
<221> NAME/KEY: source
```

<223> OTHER INFORMATION: /note="Description of Artificial Sequence:
      Synthetic polypeptide"

<400> SEQUENCE: 249

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Asn Ala Gln Gly Lys Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Asp Glu Gly Phe Asp Ile Trp Gly Gln Gly Thr Leu
            100                 105                 110

Val Thr Val Ser Ser
        115

<210> SEQ ID NO 250
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 250
gatatccaga tgacccagag ccccagcagc ctgagcgcca gcgtgggcga cagagtgacc      60
atcacctgtc gggccagcca gggcatcagc aactggctgg cctggtatca gcagaagccc     120
ggcaaggccc ccaagctgct gatctacggc gccagctccc tgcagagcgg cgtgccaagc     180
agattcagcg gcagcggctc cggcaccgac ttcaccctga ccatcagcag cctgcagccc     240
gaggacttcg ccacctacta ctgccagcag tacagcagct cccccaccac cttcggccag     300
ggcaccaagg tggaaatcaa g                                              321

<210> SEQ ID NO 251
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 251
gaggtgcaat tgctggaaag cggcggaggc ctggtgcagc ctggcggcag cctgagactg      60
tcttgcgccg ccagcggctt caccttcagc agctacgcca tgagctgggt ccgccaggcc     120
cctggcaagg gactggaatg ggtgtccgcc atcaacgccc agggcaagag cacctactac     180
gccgacagcg tgaagggccg gttcaccatc agcgggaca cagcaagaa cacccctgtac      240 ctgcagatga acagcctgcg ggccgaggac accgccgtgt actactgtgc cagatggggc     300
gacgagggct tcgacatctg gggccagggc accctggtca ccgtcagctc a              351

<210> SEQ ID NO 252

```
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 252

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Phe Pro Thr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 253
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 253

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Asn Ala Gln Gly Lys Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                 85                  90                  95

Ala Arg Trp Gly Asp Glu Gly Phe Asp Ile Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 254
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 254

Ser Tyr Ala Met Ser
1               5

<210> SEQ ID NO 255
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 255

Ala Ile Asn Thr Gln Gly Lys Ser Thr Tyr Tyr Ala Asp Ser Val Lys
1               5                   10                  15

Gly

<210> SEQ ID NO 256
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 256

Trp Gly Asp Glu Gly Phe Asp Ile
1               5

<210> SEQ ID NO 257
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 257

Arg Ala Ser Gln Gly Ile Ser Asn Trp Leu Ala
1               5                   10

<210> SEQ ID NO 258
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 258

Gly Ala Ser Ser Leu Gln Ser
1               5

<210> SEQ ID NO 259
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 259

Gln Gln Tyr Ser Ser Phe Pro Thr Thr
1               5

<210> SEQ ID NO 260
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 260

Gly Phe Thr Phe Ser Ser Tyr
1               5

<210> SEQ ID NO 261
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 261

Asn Thr Gln Gly Lys Ser
1               5

<210> SEQ ID NO 262
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 262

Trp Gly Asp Glu Gly Phe Asp Ile
1               5

<210> SEQ ID NO 263
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 263

Ser Gln Gly Ile Ser Asn Trp
1               5

<210> SEQ ID NO 264
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 264

Gly Ala Ser
1

```
<210> SEQ ID NO 265
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 265

Tyr Ser Ser Phe Pro Thr
1               5

<210> SEQ ID NO 266
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 266

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Phe Pro Thr
                85                  90                  95

Thr Phe Gly Gln Gly Thr Lys Val Glu Ile Lys
            100                 105

<210> SEQ ID NO 267
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 267

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Asn Thr Gln Gly Lys Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Asp Glu Gly Phe Asp Ile Trp Gly Gln Gly Thr Leu
            100                 105                 110
```

<210> SEQ ID NO 268
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 268

```
gatatccaga tgacccagag ccccagcagc ctgagcgcca gcgtgggcga cagagtgacc    60
atcacctgtc gggccagcca gggcatcagc aactggctgg cctggtatca gcagaagccc   120
ggcaaggccc ccaagctgct gatctacggc gccagctccc tgcagagcgg cgtgccaagc   180
agattcagcg gcagcggctc cggcaccgac ttcaccctga ccatcagcag cctgcagccc   240
gaggacttcg ccacctacta ctgccagcag tacagcagct tccccaccac cttcggccag   300
ggcaccaagg tggaaatcaa g                                             321
```

<210> SEQ ID NO 269
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 269

```
gaggtgcaat tgctggaaag cggcggaggc ctggtgcagc ctggcggcag cctgagactg    60
tcttgcgccg ccagcggctt caccttcagc agctacgcca tgagctgggt ccgccaggcc   120
cctggcaagg gactggaatg ggtgtccgcc atcaacaccc agggcaagag cacctactac   180
gccgacagcg tgaagggccg gttcaccatc agccgggaca acagcaagaa caccctgtac   240
ctgcagatga acagcctgcg ggccgaggac accgccgtgt actactgtgc cagatggggc   300
gacgagggct tcgacatctg gggccagggc accctggtca ccgtcagctc a            351
```

<210> SEQ ID NO 270
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 270

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

Glu Asp Phe Ala Thr Tyr Tyr Cys Gln Gln Tyr Ser Ser Phe Pro Thr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
        210

<210> SEQ ID NO 271
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 271

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Asn Thr Gln Gly Lys Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Asp Glu Gly Phe Asp Ile Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
            130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Arg Val Glu Pro Lys Ser Cys Asp Lys Thr His

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser His Glu Asp Pro Glu
        260                 265                 270

Val Lys Phe Asn Trp Tyr Val Asp Gly Val Glu Val His Asn Ala Lys
    275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 272
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 272

Ser Tyr Ala Met Ser
1               5

<210> SEQ ID NO 273
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 273

Val Thr Gly Ala Val Gly Ser Ser Thr Tyr Tyr Pro Asp Ser Val Lys
1               5                   10                  15

Gly

<210> SEQ ID NO 274
<211> LENGTH: 8

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 274

Trp Gly Asp Glu Gly Phe Asp Ile
1               5

<210> SEQ ID NO 275
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 275

Arg Ala Ser Gln Gly Ile Ser Asn Trp Leu Ala
1               5                   10

<210> SEQ ID NO 276
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 276

Gly Ala Ser Ser Leu Gln Ser
1               5

<210> SEQ ID NO 277
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 277

Gln Gln Tyr Ser Ser Phe Pro Thr Thr
1               5

<210> SEQ ID NO 278
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 278

Gly Phe Thr Phe Ser Ser Tyr
1               5

<210> SEQ ID NO 279
<211> LENGTH: 6
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"

<400> SEQUENCE: 279

Gly Ala Val Gly Ser Ser
1               5

<210> SEQ ID NO 280
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 280

Trp Gly Asp Glu Gly Phe Asp Ile
1               5

<210> SEQ ID NO 281
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 281

Ser Gln Gly Ile Ser Asn Trp
1               5

<210> SEQ ID NO 282
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 282

Gly Ala Ser
1

<210> SEQ ID NO 283
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 283

Tyr Ser Ser Phe Pro Thr
1               5

<210> SEQ ID NO 284
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 284
```

```
Asp Ile Gln Met Thr Gln Ser Pro Ser Ser Leu Ser Ala Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65              70                  75                  80

Glu Asp Phe Ala Thr Tyr Tyr Cys Gln Gln Tyr Ser Ser Phe Pro Thr
                85                  90                  95

Thr Phe Gly Gln Gly Thr Lys Val Glu Ile Lys
            100                 105
```

<210> SEQ ID NO 285
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 285

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Thr Gly Ala Val Gly Ser Ser Thr Tyr Tyr Pro Asp Ser Val
50                  55                  60

Lys Gly Arg Phe Thr Ile Ser Arg Asp Asn Ser Lys Asn Thr Leu Tyr
65              70                  75                  80

Leu Gln Met Asn Ser Leu Arg Ala Glu Asp Thr Ala Val Tyr Tyr Cys
                85                  90                  95

Ala Arg Trp Gly Asp Glu Gly Phe Asp Ile Trp Gly Gln Gly Thr Leu
            100                 105                 110

Val Thr Val Ser Ser
        115
```

<210> SEQ ID NO 286
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 286

| | | | | | |
|---|---|---|---|---|---|
| gatatccaga | tgacccagag | ccccagcagc | ctgagcgcca | gcgtgggcga | cagagtgacc | 60 |
| atcacctgtc | gggccagcca | gggcatcagc | aactggctgg | cctggtatca | gcagaagccc | 120 |
| ggcaaggccc | ccaagctgct | gatctacggc | gccagctccc | tgcagagcgg | cgtgccaagc | 180 |
| agattcagcg | gcagcggctc | cggcaccgac | ttcaccctga | ccatcagcag | cctgcagccc | 240 |
| gaggacttcg | ccacctacta | ctgccagcag | tacagcagct | tccccaccac | cttcggccag | 300 | ggcaccaagg tggaaatcaa g                                               321

<210> SEQ ID NO 287
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 287
gaggtgcaat tgctggaaag cggcggaggc ctggtgcagc ctggcggcag cctgagactg      60
tcttgcgccg ccagcggctt caccttcagc agctacgcca tgagctgggt ccgccaggcc     120
cctggcaagg gactggaatg ggtgtccgtg acaggcgccg tgggcagcag cacctactac     180
cccgacagcg tgaagggccg gttcaccatc agccgggaca cagcaagaa cacctgtac      240 ctgcagatga acagcctgcg ggccgaggac accgccgtgt actactgtgc cagatggggc     300
gacgagggct tcgacatctg ggccagggc accctggtca ccgtcagctc a               351

<210> SEQ ID NO 288
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 288

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Phe Pro Thr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 289
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 289

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Thr Gly Ala Val Gly Ser Ser Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Asp Glu Gly Phe Asp Ile Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350
```

```
Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
        435                 440                 445

<210> SEQ ID NO 290
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 290

Ser Tyr Ala Met Ser
1               5

<210> SEQ ID NO 291
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 291

Val Thr Gly Ala Val Gly Gly Ser Thr Tyr Tyr Pro Asp Ser Val Lys
1               5                   10                  15
Gly

<210> SEQ ID NO 292
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 292

Trp Gly Asp Glu Gly Phe Asp Ile
1               5

<210> SEQ ID NO 293
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 293

Arg Ala Ser Gln Gly Ile Ser Asn Trp Leu Ala
```

<210> SEQ ID NO 294
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 294

Gly Ala Ser Ser Leu Gln Ser
1               5

<210> SEQ ID NO 295
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 295

Gln Gln Tyr Ser Ser Phe Pro Thr Thr
1               5

<210> SEQ ID NO 296
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 296

Gly Phe Thr Phe Ser Ser Tyr
1               5

<210> SEQ ID NO 297
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 297

Gly Ala Val Gly Gly Ser
1               5

<210> SEQ ID NO 298
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 298

Trp Gly Asp Glu Gly Phe Asp Ile
1               5

<210> SEQ ID NO 299

```
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 299

Ser Gln Gly Ile Ser Asn Trp
1               5

<210> SEQ ID NO 300
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 300

Gly Ala Ser
1

<210> SEQ ID NO 301
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 301

Tyr Ser Ser Phe Pro Thr
1               5

<210> SEQ ID NO 302
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 302

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Phe Pro Thr
                85                  90                  95

Thr Phe Gly Gln Gly Thr Lys Val Glu Ile Lys
            100                 105

<210> SEQ ID NO 303
<211> LENGTH: 117
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 303

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Thr Gly Ala Val Gly Gly Ser Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Asp Glu Gly Phe Asp Ile Trp Gly Gln Gly Thr Leu
            100                 105                 110

Val Thr Val Ser Ser
        115

<210> SEQ ID NO 304
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 304
gatatccaga tgacccagag ccccagcagc ctgagcgcca gcgtgggcga cagagtgacc      60
atcacctgtc gggccagcca gggcatcagc aactggctgg cctggtatca gcagaagccc    120
ggcaaggccc ccaagctgct gatctacggc gccagctccc tgcagagcgg cgtgccaagc    180
agattcagcg gcagcggctc cggcaccgac ttcaccctga ccatcagcag cctgcagccc    240
gaggacttcg ccacctacta ctgccagcag tacagcagct cccccaccac cttcggccag    300
ggcaccaagg tggaaatcaa g                                              321

<210> SEQ ID NO 305
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 305
gaggtgcaat tgctggaaag cggcggaggc ctggtgcagc ctggcggcag cctgagactg      60
tcttgcgccg ccagcggctt caccttcagc agctacgcca tgagctgggt ccgccaggcc    120
cctggcaagg gactggaatg ggtgtccgtg acaggcgccg tgggcggaag cacctactac    180
cccgacagcg tgaagggccg gttcaccatc agccgggaca acagcaagaa caccctgtac    240
ctgcagatga acagcctgcg ggccgaggac accgccgtgt actactgtgc cagatggggc    300
```
gacgagggct tcgacatctg gggccagggc accctggtca ccgtcagctc a    351

<210> SEQ ID NO 306
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 306

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Phe Pro Thr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 307
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 307

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Thr Gly Ala Val Gly Ser Thr Tyr Tyr Pro Asp Ser Val
50                  55                  60

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Trp Gly Asp Glu Gly Phe Asp Ile Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Arg Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 308
<211> LENGTH: 5
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 308

Ser Tyr Ala Met Ser
1               5

<210> SEQ ID NO 309
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 309

Val Thr Gly Ala Val Gly Lys Ser Thr Tyr Tyr Pro Asp Ser Val Lys
1               5                   10                  15

Gly

<210> SEQ ID NO 310
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 310

Trp Gly Asp Glu Gly Phe Asp Ile
1               5

<210> SEQ ID NO 311
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 311

Arg Ala Ser Gln Gly Ile Ser Asn Trp Leu Ala
1               5                   10

<210> SEQ ID NO 312
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 312

Gly Ala Ser Ser Leu Gln Ser
1               5

<210> SEQ ID NO 313
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
```

-continued

Synthetic peptide"

<400> SEQUENCE: 313

Gln Gln Tyr Ser Ser Phe Pro Thr Thr
1               5

<210> SEQ ID NO 314
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 314

Gly Phe Thr Phe Ser Ser Tyr
1               5

<210> SEQ ID NO 315
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 315

Gly Ala Val Gly Lys Ser
1               5

<210> SEQ ID NO 316
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 316

Trp Gly Asp Glu Gly Phe Asp Ile
1               5

<210> SEQ ID NO 317
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 317

Ser Gln Gly Ile Ser Asn Trp
1               5

<210> SEQ ID NO 318
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 318

```
Gly Ala Ser
  1
```

<210> SEQ ID NO 319
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 319

```
Tyr Ser Ser Phe Pro Thr
  1               5
```

<210> SEQ ID NO 320
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 320

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Ser Asn Trp
                 20                  25                  30

Leu Ala Trp Tyr Gln Gln Lys Pro Gly Lys Ala Pro Lys Leu Leu Ile
             35                  40                  45

Tyr Gly Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ser Ser Phe Pro Thr
                 85                  90                  95

Thr Phe Gly Gln Gly Thr Lys Val Glu Ile Lys
                100                 105
```

<210> SEQ ID NO 321
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 321

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
                 20                  25                  30

Ala Met Ser Trp Val Arg Gln Ala Pro Gly Lys Gly Leu Glu Trp Val
             35                  40                  45

Ser Val Thr Gly Ala Val Gly Lys Ser Thr Tyr Tyr Pro Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
```

```
            85                  90                  95
Ala Arg Trp Gly Asp Glu Gly Phe Asp Ile Trp Gly Gln Gly Thr Leu
            100                 105                 110

Val Thr Val Ser Ser
        115

<210> SEQ ID NO 322
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 322
gatatccaga tgacccagag ccccagcagc ctgagcgcca gcgtgggcga cagagtgacc     60
atcacctgtc gggccagcca gggcatcagc aactggctgg cctggtatca gcagaagccc    120
ggcaaggccc ccaagctgct gatctacggc gccagctccc tgcagagcgg cgtgccaagc    180
agattcagcg gcagcggctc cggcaccgac ttcaccctga ccatcagcag cctgcagccc    240
gaggacttcg ccacctacta ctgccagcag tacagcagct cccccaccac cttcggccag    300
ggcaccaagg tggaaatcaa g                                              321

<210> SEQ ID NO 323
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 323
gaggtgcaat tgctggaaag cggcggaggc ctggtgcagc ctggcggcag cctgagactg     60
tcttgcgccg ccagcggctt caccttcagc agctacgcca tgagctgggt ccgccaggcc    120
cctggcaagg gactggaatg ggtgtccgtg acaggcgccg tgggcaaaag cacctactac    180
cccgacagcg tgaagggccg gttcaccatc agccgggaca cagcaagaa caccctgtac    240 ctgcagatga acagcctgcg ggccgaggac accgccgtgt actactgtgc cagatggggc    300
gacgagggct cgacatctg gggccagggc accctggtca ccgtcagctc a              351

<210> SEQ ID NO 324
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 324

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60
```

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ser Ser Phe Pro Thr
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 325
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 325

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Thr Gly Ala Val Gly Lys Ser Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Asp Glu Gly Phe Asp Ile Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

```
Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 326
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 326

Ser Tyr Ala Met Ser
1               5

<210> SEQ ID NO 327
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 327

Val Thr Gly Ala Val Gly Arg Thr Tyr Tyr Pro Asp Ser Val Lys Gly
1               5                   10                  15
```

```
<210> SEQ ID NO 328
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 328

Trp Gly Asp Glu Gly Phe Asp Ile
1               5

<210> SEQ ID NO 329
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 329

Arg Ala Ser Gln Gly Ile Ser Asn Trp Leu Ala
1               5                   10

<210> SEQ ID NO 330
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 330

Gly Ala Ser Ser Leu Gln Ser
1               5

<210> SEQ ID NO 331
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 331

Gln Gln Tyr Ser Ser Phe Pro Thr Thr
1               5

<210> SEQ ID NO 332
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 332

Gly Phe Thr Phe Ser Ser Tyr
1               5

<210> SEQ ID NO 333
<211> LENGTH: 6
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 333

Gly Ala Val Gly Arg Thr
1               5

<210> SEQ ID NO 334
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 334

Trp Gly Asp Glu Gly Phe Asp Ile
1               5

<210> SEQ ID NO 335
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 335

Ser Gln Gly Ile Ser Asn Trp
1               5

<210> SEQ ID NO 336
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 336

Gly Ala Ser
1

<210> SEQ ID NO 337
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 337

Tyr Ser Ser Phe Pro Thr
1               5

<210> SEQ ID NO 338
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 338

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Phe Pro Thr
                85                  90                  95

Thr Phe Gly Gln Gly Thr Lys Val Glu Ile Lys
            100                 105

<210> SEQ ID NO 339
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 339

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Thr Gly Ala Val Gly Arg Thr Tyr Tyr Pro Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Trp Gly Asp Glu Gly Phe Asp Ile Trp Gly Gln Gly Thr Leu Val
            100                 105                 110

Thr Val Ser Ser
        115

<210> SEQ ID NO 340
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 340
gatatccaga tgacccagag ccccagcagc ctgagcgcca gcgtgggcga cagagtgacc        60
atcacctgtc gggccagcca gggcatcagc aactggctgg cctggtatca gcagaagccc       120
ggcaaggccc ccaagctgct gatctacggc gccagctccc tgcagagcgg cgtgccaagc       180
agattcagcg gcagcggctc cggcaccgac ttcaccctga ccatcagcag cctgcagccc       240

```
gaggacttcg ccacctacta ctgccagcag tacagcagct tccccaccac cttcggccag    300
ggcaccaagg tggaaatcaa g                                              321
```

<210> SEQ ID NO 341
<211> LENGTH: 348
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 341

```
gaggtgcaat tgctggaaag cggcggaggc ctggtgcagc ctggcggcag cctgagactg     60
tcttgcgccg ccagcggctt caccttcagc agctacgcca tgagctgggt ccgccaggcc    120
cctggcaagg gactggaatg ggtgtccgtg acaggcgccg tgggcagaac ctactacccc    180
gacagcgtga aggccggtt caccatcagc cgggacaaca gcaagaacac cctgtacctg    240
cagatgaaca gcctgcgggc cgaggacacc gccgtgtact actgtgccag atggggcgac    300
gagggcttcg acatctgggg ccagggcacc ctggtcaccg tcagctca                348
```

<210> SEQ ID NO 342
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 342

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Phe Pro Thr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

Phe Asn Arg Gly Glu Cys
    210

<210> SEQ ID NO 343
<211> LENGTH: 446
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 343

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Thr Gly Ala Val Gly Arg Thr Tyr Tyr Pro Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Trp Gly Asp Glu Gly Phe Asp Ile Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

```
Lys Ala Lys Gly Gln Pro Arg Glu Pro Gln Val Tyr Thr Leu Pro Pro
                340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys
                435                 440                 445

<210> SEQ ID NO 344
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 344

Ser Tyr Ala Met Ser
1               5

<210> SEQ ID NO 345
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 345

Val Ile Asn Gly Leu Gly Tyr Thr Thr Phe Tyr Ala Asp Ser Val Lys
1               5                   10                  15

Gly

<210> SEQ ID NO 346
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 346

Trp Gly Asp Glu Gly Phe Asp Ile
1               5

<210> SEQ ID NO 347
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 347
```

Arg Ala Ser Gln Gly Ile Ser Asn Trp Leu Ala
1               5                   10

<210> SEQ ID NO 348
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 348

Gly Ala Ser Ser Leu Gln Ser
1               5

<210> SEQ ID NO 349
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 349

Gln Gln Tyr Ser Ser Phe Pro Thr Thr
1               5

<210> SEQ ID NO 350
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 350

Gly Phe Thr Phe Ser Ser Tyr
1               5

<210> SEQ ID NO 351
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 351

Asn Gly Leu Gly Tyr Thr
1               5

<210> SEQ ID NO 352
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 352

Trp Gly Asp Glu Gly Phe Asp Ile
1               5

<210> SEQ ID NO 353
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 353

Ser Gln Gly Ile Ser Asn Trp
1               5

<210> SEQ ID NO 354
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 354

Gly Ala Ser
1

<210> SEQ ID NO 355
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 355

Tyr Ser Ser Phe Pro Thr
1               5

<210> SEQ ID NO 356
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 356

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Tyr Ser Ser Phe Pro Thr
                85                  90                  95

Thr Phe Gly Gln Gly Thr Lys Val Glu Ile Lys
            100                 105

<210> SEQ ID NO 357
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 357

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Ile Asn Gly Leu Gly Tyr Thr Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Asp Glu Gly Phe Asp Ile Trp Gly Gln Gly Thr Leu
            100                 105                 110

Val Thr Val Ser Ser
        115

<210> SEQ ID NO 358
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 358
gatatccaga tgacccagag cccgtctagc ctgagcgcga gcgtgggtga tcgtgtgacc       60
attacctgca gagcgagcca gggtatttct aattggctgg cttggtacca gcagaaacca      120
ggtaaagcac cgaaactatt aatttatggt gcttcttctt tgcaaagcgg ggtcccgtcc      180
cgttttagcg gctctggatc cggcactgat tttaccctga ccattagcag cctgcaacct      240
gaagactttg cggtttatta ttgccagcag tattcttctt ttcctactac ctttggccag      300
ggtacgaaag ttgaaattaa a                                                321

<210> SEQ ID NO 359
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 359
caggtgcaat tggtggaaag cggcggcggc ctggtgcaac cgggcggcag cctgcgtctg       60
agctgcgcgg cctccggatt tacctttagc agctatgcga tgagctgggt gcgccaagcc      120
cctgggaagg gtctcgagtg ggtgagcgtt attaatggtc ttggttatac tactttttat      180
gctgattctg ttaagggtcg ttttaccatt tcacgtgata attcgaaaaa caccctgtat      240

```
ctgcaaatga acagcctgcg tgcggaagat acggccgtgt attattgcgc gcgttggggt    300
gatgagggtt ttgatatttg gggccaaggc accctggtga cggttagctc a            351
```

<210> SEQ ID NO 360
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 360

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Tyr Ser Ser Phe Pro Thr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 361
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 361

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

```
Ser Val Ile Asn Gly Leu Gly Tyr Thr Thr Phe Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Trp Gly Asp Gly Phe Asp Ile Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Arg Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 362
<211> LENGTH: 5
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 362

Ser Tyr Ala Met Ser
1               5

<210> SEQ ID NO 363
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 363

Gly Thr Gly Pro Tyr Gly Gly Thr Tyr Tyr Pro Asp Ser Val Lys Gly
1               5                   10                  15

<210> SEQ ID NO 364
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 364

Trp Gly Asp Glu Gly Phe Asp Ile
1               5

<210> SEQ ID NO 365
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 365

Arg Ala Ser Gln Gly Ile Ser Asn Trp Leu Ala
1               5                   10

<210> SEQ ID NO 366
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 366

Gly Ala Ser Ser Leu Gln Ser
1               5

<210> SEQ ID NO 367
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic peptide"

<400> SEQUENCE: 367

Gln Gln Tyr Ser Ser Phe Pro Thr Thr
1               5

<210> SEQ ID NO 368
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 368

Gly Phe Thr Phe Ser Ser Tyr
1               5

<210> SEQ ID NO 369
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 369

Gly Pro Tyr Gly Gly
1               5

<210> SEQ ID NO 370
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 370

Trp Gly Asp Glu Gly Phe Asp Ile
1               5

<210> SEQ ID NO 371
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 371

Ser Gln Gly Ile Ser Asn Trp
1               5

<210> SEQ ID NO 372
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 372

Gly Ala Ser
1

<210> SEQ ID NO 373
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 373

Tyr Ser Ser Phe Pro Thr
1               5

<210> SEQ ID NO 374
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 374

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Tyr Ser Ser Phe Pro Thr
                85                  90                  95

Thr Phe Gly Gln Gly Thr Lys Val Glu Ile Lys
            100                 105

<210> SEQ ID NO 375
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 375

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Thr Gly Pro Tyr Gly Gly Thr Tyr Tyr Pro Asp Ser Val Lys
50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala 85                 90                  95
Arg Trp Gly Asp Glu Gly Phe Asp Ile Trp Gly Gln Gly Thr Leu Val
            100                 105                 110

Thr Val Ser Ser
        115

<210> SEQ ID NO 376
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 376
gatatccaga tgacccagag cccgtctagc ctgagcgcga gcgtgggtga tcgtgtgacc      60
attacctgca gcgcagccca gggtatttct aattggctgg cttggtacca gcagaaacca     120
ggtaaagcac cgaaactatt aatttatggt gcttcttctt tgcaaagcgg ggtcccgtcc     180
cgttttagcg gctctggatc cggcactgat tttaccctga ccattagcag cctgcaacct     240
gaagactttg cggtttatta ttgccagcag tattcttctt ttcctactac ctttggccag     300
ggtacgaaag ttgaaattaa a                                                321

<210> SEQ ID NO 377
<211> LENGTH: 348
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 377
caggtgcaat tggtggaaag cggcggcggc ctggtgcaac cgggcggcag cctgcgtctg      60
agctgcgcgg cctccggatt tacctttagc agctatgcga tgagctgggt gcgccaagcc     120
cctgggaagg gtctcgagtg ggtgagcggt actggtcctt atggtggtac ttattatcct     180
gattctgtta agggtcgttt taccatttca cgtgataatt cgaaaaacac cctgtatctg     240
caaatgaaca gcctgcgtgc ggaagatacg gccgtgtatt attgcgcgcg ttggggtgat     300
gagggttttg atatttgggg ccaaggcacc ctggtgacgg ttagctca                  348

<210> SEQ ID NO 378
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 378

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

```
Ser Gly Ser Gly Thr Asp Phe Thr Leu Thr Ile Ser Ser Leu Gln Pro
 65                  70                  75                  80

Glu Asp Phe Ala Val Tyr Tyr Cys Gln Gln Tyr Ser Ser Phe Pro Thr
             85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
    195                 200                 205

Phe Asn Arg Gly Glu Cys
    210

<210> SEQ ID NO 379
<211> LENGTH: 446
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 379

Gln Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Gly Thr Gly Pro Tyr Gly Gly Thr Tyr Tyr Pro Asp Ser Val Lys
     50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
             85                  90                  95

Arg Trp Gly Asp Glu Gly Phe Asp Ile Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
        180                 185                 190
```

```
Gly Thr Gln Thr Tyr Ile Cys Asn Val Asn His Lys Pro Ser Asn Thr
            195                 200                 205

Lys Val Asp Lys Arg Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Arg Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
435                 440                 445

<210> SEQ ID NO 380
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 380

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Val Thr Gly Ala Val Gly Arg Ser Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Asp Glu Gly Phe Asp Ile
```

<210> SEQ ID NO 381
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 381

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Val Thr Gly Ala Val Gly Arg Ser Thr Tyr Tyr Pro Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Trp Gly Asp Glu Gly Phe Asp Ile
            100                 105

<210> SEQ ID NO 382
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 382

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Ile Arg Gln Ala Pro Gly Lys Gly Leu Glu Trp Val
            35                  40                  45

Ser Val Thr Gly Ala Val Gly Arg Ser Thr Tyr Tyr Pro Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Asp Glu Gly Phe Asp Ile
            100                 105

<210> SEQ ID NO 383
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 383

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Thr Gly Lys Gly Leu Glu Trp Val
            35                  40                  45

Ser Val Thr Gly Ala Val Gly Arg Ser Thr Tyr Tyr Pro Asp Ser Val
    50                  55                  60

Lys Gly Arg Phe Thr Ile Ser Arg Glu Asn Ala Lys Asn Ser Leu Tyr
65                  70                  75                  80

Leu Gln Met Asn Ser Leu Arg Ala Gly Asp Thr Ala Val Tyr Tyr Cys
                85                  90                  95

Ala Arg Trp Gly Asp Glu Gly Phe Asp Ile
            100                 105

<210> SEQ ID NO 384
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 384

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Gly Val Thr Gly Ala Val Gly Arg Ser Thr Tyr Tyr Pro Asp Ser Val
    50                  55                  60

Lys Gly Arg Phe Thr Ile Ser Arg Asp Asp Ser Lys Asn Thr Leu Tyr
65                  70                  75                  80

Leu Gln Met Asn Ser Leu Lys Thr Glu Asp Thr Ala Val Tyr Tyr Cys
                85                  90                  95

Thr Thr Trp Gly Asp Glu Gly Phe Asp Ile
            100                 105

<210> SEQ ID NO 385
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 385

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Val Thr Gly Ala Val Gly Arg Ser Thr Tyr Tyr Pro Asp Ser Val
    50                  55                  60

```
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr His Cys
                 85                  90                  95

Ala Arg Trp Gly Asp Glu Gly Phe Asp Ile
            100                 105

<210> SEQ ID NO 386
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 386

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Val Thr Gly Ala Val Gly Arg Ser Thr Tyr Tyr Pro Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Trp Gly Asp Glu Gly Phe Asp Ile
            100                 105

<210> SEQ ID NO 387
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 387

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Val Thr Gly Ala Val Gly Arg Ser Thr Tyr Tyr Pro Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Trp Gly Asp Glu Gly Phe Asp Ile
            100                 105

<210> SEQ ID NO 388
<211> LENGTH: 106
<212> TYPE: PRT
```

<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 388

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Val Thr Gly Ala Val Gly Arg Ser Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Trp Gly Asp Glu Gly Phe Asp Ile
            100                 105

<210> SEQ ID NO 389
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 389

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Val Thr Gly Ala Val Gly Arg Ser Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Asp Glu Gly Phe Asp Ile
            100                 105

<210> SEQ ID NO 390
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 390

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

```
Ala Met Ser Trp Val Arg Gln Ala Pro Gly Lys Gly Leu Glu Trp Val
            35                  40                  45

Ala Val Thr Gly Ala Val Gly Arg Ser Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Trp Gly Asp Glu Gly Phe Asp Ile
            100                 105

<210> SEQ ID NO 391
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 391

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ala Val Thr Gly Ala Val Gly Arg Ser Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Asp Glu Gly Phe Asp Ile
            100                 105

<210> SEQ ID NO 392
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 392

Glu Val Gln Leu Val Glu Ser Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Val Thr Gly Ala Val Gly Arg Ser Thr Tyr Tyr Pro Asp Ser Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Ala Glu Asp Thr Ala Leu Tyr Tyr Cys
                85                  90                  95
```

Ala Lys Trp Gly Asp Glu Gly Phe Asp Ile
            100                 105

<210> SEQ ID NO 393
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 393

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Thr Gly Ala Val Gly Arg Ser Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Trp Gly Asp Glu Gly Phe Asp Ile
            100                 105

<210> SEQ ID NO 394
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 394

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Ser Ser Tyr
            20                  25                  30

Ala Met Ser Trp Phe Arg Gln Ala Pro Gly Lys Gly Leu Glu Trp Val
        35                  40                  45

Gly Val Thr Gly Ala Val Gly Arg Ser Thr Tyr Tyr Pro Asp Ser Val
    50                  55                  60

Lys Gly Arg Phe Thr Ile Ser Arg Asp Gly Ser Lys Ser Ile Ala Tyr
65                  70                  75                  80

Leu Gln Met Asn Ser Leu Lys Thr Glu Asp Thr Ala Val Tyr Tyr Cys
                85                  90                  95

Thr Arg Trp Gly Asp Glu Gly Phe Asp Ile
            100                 105

<210> SEQ ID NO 395
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 395

Glu Val Gln Leu Val Glu Thr Gly Gly Gly Leu Ile Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Thr Gly Ala Val Gly Arg Ser Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Asp Glu Gly Phe Asp Ile
            100                 105

<210> SEQ ID NO 396
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 396

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Tyr Val
        35                  40                  45

Ser Val Thr Gly Ala Val Gly Arg Ser Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Gly Ser Leu Arg Ala Glu Asp Met Ala Val Tyr Tyr Cys
                85                  90                  95

Ala Arg Trp Gly Asp Glu Gly Phe Asp Ile
            100                 105

<210> SEQ ID NO 397
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 397

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Thr Gly Ala Val Gly Arg Ser Thr Tyr Tyr Pro Asp Ser Val
    50                  55                  60

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Trp Gly Asp Glu Gly Phe Asp Ile
            100                 105
```

<210> SEQ ID NO 398
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 398

```
Glu Val Gln Leu Val Glu Ser Gly Gly Gly Leu Val Gln Pro Gly Gly
 1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Gly Val Thr Gly Ala Val Gly Arg Ser Thr Tyr Tyr Pro Asp Ser Val
 50                  55                  60

Lys Gly Arg Phe Thr Ile Ser Arg Asp Asp Ser Lys Asn Ser Leu Tyr
 65                  70                  75                  80

Leu Gln Met Asn Ser Leu Lys Thr Glu Asp Thr Ala Val Tyr Tyr Cys
                 85                  90                  95

Ala Arg Trp Gly Asp Glu Gly Phe Asp Ile
            100                 105
```

<210> SEQ ID NO 399
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 399

```
Glu Val Gln Leu Val Glu Ser Gly Gly Gly Leu Val Gln Pro Gly Gly
 1               5                   10                  15

Ser Leu Lys Leu Ser Cys Ala Ala Ser Gly Phe Thr Phe Ser Ser Tyr
                20                  25                  30

Ala Met Ser Trp Val Arg Gln Ala Ser Gly Lys Gly Leu Glu Trp Val
            35                  40                  45

Gly Val Thr Gly Ala Val Gly Arg Ser Thr Tyr Tyr Pro Asp Ser Val
 50                  55                  60

Lys Gly Arg Phe Thr Ile Ser Arg Asp Asp Ser Lys Asn Thr Ala Tyr
 65                  70                  75                  80

Leu Gln Met Asn Ser Leu Lys Thr Glu Asp Thr Ala Val Tyr Tyr Cys
                 85                  90                  95

Thr Arg Trp Gly Asp Glu Gly Phe Asp Ile
            100                 105
```

<210> SEQ ID NO 400
<211> LENGTH: 106

<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 400

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Val Trp Val
        35                  40                  45

Ser Val Thr Gly Ala Val Gly Arg Ser Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Asp Glu Gly Phe Asp Ile
            100                 105
```

<210> SEQ ID NO 401
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 401

```
Glu Val Gln Leu Val Glu Ser Arg Gly Val Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Thr Gly Ala Val Gly Arg Ser Thr Tyr Tyr Pro Asp Ser Val
    50                  55                  60

Lys Gly Arg Phe Thr Ile Ser Arg Asp Asn Ser Lys Asn Thr Leu His
65                  70                  75                  80

Leu Gln Met Asn Ser Leu Arg Ala Glu Asp Thr Ala Val Tyr Tyr Cys
                85                  90                  95

Lys Lys Trp Gly Asp Glu Gly Phe Asp Ile
            100                 105
```

<210> SEQ ID NO 402
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 402

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
```

```
                20                  25                  30

Ala Met Ser Trp Val Arg Gln Ala Pro Gly Lys Gly Leu Glu Trp Val
            35                  40                  45

Ala Ala Ile Asn Ser Gln Gly Lys Ser Thr Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Asp Glu Gly Phe Asp Ile
            100                 105

<210> SEQ ID NO 403
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 403

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ala Ile Asn Ser Gln Gly Lys Ser Thr Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Trp Gly Asp Glu Gly Phe Asp Ile
            100                 105

<210> SEQ ID NO 404
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 404

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Ile Arg Gln Ala Pro Gly Lys Gly Leu Glu Trp Val
            35                  40                  45

Ser Ala Ile Asn Ser Gln Gly Lys Ser Thr Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95
```

Ala Arg Trp Gly Asp Glu Gly Phe Asp Ile
            100                 105

<210> SEQ ID NO 405
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 405

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Thr Gly Lys Gly Leu Glu Trp Val
        35                  40                  45

Ser Ala Ile Asn Ser Gln Gly Lys Ser Thr Tyr Tyr Ala Asp Ser Val
    50                  55                  60

Lys Gly Arg Phe Thr Ile Ser Arg Glu Asn Ala Lys Asn Ser Leu Tyr
65                  70                  75                  80

Leu Gln Met Asn Ser Leu Arg Ala Gly Asp Thr Ala Val Tyr Tyr Cys
                85                  90                  95

Ala Arg Trp Gly Asp Glu Gly Phe Asp Ile
            100                 105

<210> SEQ ID NO 406
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 406

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Gly Ala Ile Asn Ser Gln Gly Lys Ser Thr Tyr Tyr Ala Asp Ser Val
    50                  55                  60

Lys Gly Arg Phe Thr Ile Ser Arg Asp Asp Ser Lys Asn Thr Leu Tyr
65                  70                  75                  80

Leu Gln Met Asn Ser Leu Lys Thr Glu Asp Thr Ala Val Tyr Tyr Cys
                85                  90                  95

Thr Thr Trp Gly Asp Glu Gly Phe Asp Ile
            100                 105

<210> SEQ ID NO 407
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

-continued

<400> SEQUENCE: 407

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Asn Ser Gln Gly Lys Ser Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr His Cys
                85                  90                  95

Ala Arg Trp Gly Asp Glu Gly Phe Asp Ile
            100                 105

<210> SEQ ID NO 408
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 408

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Asn Ser Gln Gly Lys Ser Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Asp Glu Gly Phe Asp Ile
            100                 105

<210> SEQ ID NO 409
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 409

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Asn Ser Gln Gly Lys Ser Thr Tyr Tyr Ala Asp Ser Val

```
            50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Trp Gly Asp Glu Gly Phe Asp Ile
            100                 105
```

<210> SEQ ID NO 410
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 410

```
Gln Val Gln Leu Val Glu Ser Gly Gly Val Val Gln Pro Gly Arg
 1               5                  10                  15

Ser Leu Arg Leu Ser Cys Ala Ala Ser Gly Phe Thr Phe Ser Ser Tyr
                 20                  25                  30

Ala Met Ser Trp Val Arg Gln Ala Pro Gly Lys Gly Leu Glu Trp Val
             35                  40                  45

Ala Ala Ile Asn Ser Gln Gly Lys Ser Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Trp Gly Asp Glu Gly Phe Asp Ile
            100                 105
```

<210> SEQ ID NO 411
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 411

```
Gln Val Gln Leu Val Glu Ser Gly Gly Val Val Gln Pro Gly Arg
 1               5                  10                  15

Ser Leu Arg Leu Ser Cys Ala Ala Ser Gly Phe Thr Phe Ser Ser Tyr
                 20                  25                  30

Ala Met Ser Trp Val Arg Gln Ala Pro Gly Lys Gly Leu Glu Trp Val
             35                  40                  45

Ala Ala Ile Asn Ser Gln Gly Lys Ser Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Trp Gly Asp Glu Gly Phe Asp Ile
            100                 105
```

<210> SEQ ID NO 412

-continued

<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 412

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Ala Ile Asn Ser Gln Gly Lys Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Trp Gly Asp Glu Gly Phe Asp Ile
            100                 105

<210> SEQ ID NO 413
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 413

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Ala Ile Asn Ser Gln Gly Lys Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Asp Glu Gly Phe Asp Ile
            100                 105

<210> SEQ ID NO 414
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 414

Glu Val Gln Leu Val Glu Ser Gly Gly Val Val Val Gln Pro Gly Gly
1               5                   10                  15

```
Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Asn Ser Gln Gly Lys Ser Thr Tyr Tyr Ala Asp Ser Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Thr Glu Asp Thr Ala Leu Tyr Tyr Cys
                85                  90                  95

Ala Lys Trp Gly Asp Glu Gly Phe Asp Ile
            100                 105
```

<210> SEQ ID NO 415
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 415

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Asn Ser Gln Gly Lys Ser Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Trp Gly Asp Glu Gly Phe Asp Ile
            100                 105
```

<210> SEQ ID NO 416
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 416

```
Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Ser Ser Tyr
            20                  25                  30

Ala Met Ser Trp Phe Arg Gln Ala Pro Gly Lys Gly Leu Glu Trp Val
        35                  40                  45

Gly Ala Ile Asn Ser Gln Gly Lys Ser Thr Tyr Tyr Ala Asp Ser Val
    50                  55                  60

Lys Gly Arg Phe Thr Ile Ser Arg Asp Gly Ser Lys Ser Ile Ala Tyr
65                  70                  75                  80

Leu Gln Met Asn Ser Leu Lys Thr Glu Asp Thr Ala Val Tyr Tyr Cys
```

```
                    85                  90                  95

Thr Arg Trp Gly Asp Glu Gly Phe Asp Ile
            100                 105

<210> SEQ ID NO 417
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 417

Glu Val Gln Leu Val Glu Thr Gly Gly Gly Leu Ile Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Asn Ser Gln Gly Lys Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Asp Glu Gly Phe Asp Ile
            100                 105

<210> SEQ ID NO 418
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 418

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Tyr Val
        35                  40                  45

Ser Ala Ile Asn Ser Gln Gly Lys Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Gly Ser Leu Arg Ala Glu Asp Met Ala Val Tyr Tyr Cys
                85                  90                  95

Ala Arg Trp Gly Asp Glu Gly Phe Asp Ile
            100                 105

<210> SEQ ID NO 419
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
```

-continued

Synthetic polypeptide"

<400> SEQUENCE: 419

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Asn Ser Gln Gly Lys Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Asp Glu Gly Phe Asp Ile
            100                 105

<210> SEQ ID NO 420
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 420

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Gly Ala Ile Asn Ser Gln Gly Lys Ser Thr Tyr Tyr Ala Asp Ser Val
    50                  55                  60

Lys Gly Arg Phe Thr Ile Ser Arg Asp Asp Ser Lys Asn Ser Leu Tyr
65                  70                  75                  80

Leu Gln Met Asn Ser Leu Lys Thr Glu Asp Thr Ala Val Tyr Tyr Cys
                85                  90                  95

Ala Arg Trp Gly Asp Glu Gly Phe Asp Ile
            100                 105

<210> SEQ ID NO 421
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 421

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Ala Ser Gly Lys Gly Leu Glu Trp Val
        35                  40                  45

```
Gly Ala Ile Asn Ser Gln Gly Lys Ser Thr Tyr Tyr Ala Asp Ser Val
        50                  55                  60

Lys Gly Arg Phe Thr Ile Ser Arg Asp Asp Ser Lys Asn Thr Ala Tyr
 65                  70                  75                  80

Leu Gln Met Asn Ser Leu Lys Thr Glu Asp Thr Ala Val Tyr Tyr Cys
                85                  90                  95

Thr Arg Trp Gly Asp Glu Gly Phe Asp Ile
            100                 105
```

<210> SEQ ID NO 422
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 422

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Val Trp Val
            35                  40                  45

Ser Ala Ile Asn Ser Gln Gly Lys Ser Thr Tyr Tyr Ala Asp Ser Val
        50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Trp Gly Asp Glu Gly Phe Asp Ile
            100                 105
```

<210> SEQ ID NO 423
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 423

```
Glu Val Gln Leu Val Glu Ser Arg Gly Val Leu Val Gln Pro Gly Gly
 1               5                  10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Asn Ser Gln Gly Lys Ser Thr Tyr Tyr Ala Asp Ser Val
        50                  55                  60

Lys Gly Arg Phe Thr Ile Ser Arg Asp Asn Ser Lys Asn Thr Leu His
 65                  70                  75                  80

Leu Gln Met Asn Ser Leu Arg Ala Glu Asp Thr Ala Val Tyr Tyr Cys
                85                  90                  95

Lys Lys Trp Gly Asp Glu Gly Phe Asp Ile
            100                 105
```

```
<210> SEQ ID NO 424
<211> LENGTH: 97
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 424
```

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Phe Pro Thr
                85                  90                  95

Thr

```
<210> SEQ ID NO 425
<211> LENGTH: 97
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 425
```

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Phe Pro Thr
                85                  90                  95

Thr

```
<210> SEQ ID NO 426
<211> LENGTH: 97
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 426
```

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Asn Trp

```
                    20                  25                  30

Leu Ala Trp Tyr Gln Gln Lys Pro Gly Lys Ala Pro Lys Leu Leu Ile
            35                  40                  45

Tyr Gly Ala Ser Ser Leu Gln Ser Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Tyr Ser Ser Phe Pro Thr
                85                  90                  95

Thr
```

<210> SEQ ID NO 427
<211> LENGTH: 97
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 427

```
Asp Ile Gln Met Thr Gln Ser Pro Ser Ser Leu Ser Ala Ser Val Gly
 1                   5                  10                  15

Asp Arg Val Thr Ile Thr Cys Arg Ala Ser Gln Gly Ile Ser Asn Trp
                20                  25                  30

Leu Ala Trp Tyr Gln Gln Lys Pro Gly Lys Ala Pro Lys Leu Leu Ile
            35                  40                  45

Tyr Gly Ala Ser Ser Leu Gln Ser Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Tyr Ser Ser Phe Pro Thr
                85                  90                  95

Thr
```

<210> SEQ ID NO 428
<211> LENGTH: 97
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 428

```
Asp Ile Gln Met Thr Gln Ser Pro Ser Ser Leu Ser Ala Ser Val Gly
 1                   5                  10                  15

Asp Arg Val Thr Ile Thr Cys Arg Ala Ser Gln Gly Ile Ser Asn Trp
                20                  25                  30

Leu Ala Trp Tyr Gln Gln Lys Pro Gly Lys Val Pro Lys Leu Leu Ile
            35                  40                  45

Tyr Gly Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Gln Tyr Ser Ser Phe Pro Thr
                85                  90                  95

Thr
```

<210> SEQ ID NO 429
<211> LENGTH: 97
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 429

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Arg Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Ser Ser Phe Pro Thr
                85                  90                  95

Thr

<210> SEQ ID NO 430
<211> LENGTH: 97
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 430

Asn Ile Gln Met Thr Gln Ser Pro Ser Ala Met Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Phe Gln Gln Lys Pro Gly Lys Val Pro Lys His Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Ser Ser Phe Pro Thr
                85                  90                  95

Thr

<210> SEQ ID NO 431
<211> LENGTH: 97
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 431

Asp Ile Gln Met Thr Gln Ser Pro Ser Ser Leu Ser Ala Ser Val Gly
1               5                   10                  15

-continued

Asp Arg Val Thr Ile Thr Cys Arg Ala Ser Gln Gly Ile Ser Asn Trp
            20                  25                  30

Leu Ala Trp Phe Gln Gln Lys Pro Gly Lys Ala Pro Lys Ser Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Phe Pro Thr
                85                  90                  95

Thr

<210> SEQ ID NO 432
<211> LENGTH: 97
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 432

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Glu Lys Ala Pro Lys Ser Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Phe Pro Thr
                85                  90                  95

Thr

<210> SEQ ID NO 433
<211> LENGTH: 97
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 433

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Phe Pro Thr
                85                  90                  95

<210> SEQ ID NO 434
<211> LENGTH: 97
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 434

```
Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Phe Pro Thr
                85                  90                  95

Thr
```

<210> SEQ ID NO 435
<211> LENGTH: 97
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 435

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Phe Pro Thr
                85                  90                  95

Thr
```

<210> SEQ ID NO 436
<211> LENGTH: 97
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 436

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Asn Trp
                20                  25                  30

Leu Ala Trp Tyr Gln Gln Lys Pro Gly Lys Ala Pro Lys Leu Leu Ile
            35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Phe Pro Thr
                85                  90                  95

Thr

<210> SEQ ID NO 437
<211> LENGTH: 97
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 437

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Asn Trp
                20                  25                  30

Leu Ala Trp Tyr Gln Gln Lys Pro Gly Lys Ala Pro Lys Leu Leu Ile
            35                  40                  45

Tyr Gly Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Ser Ser Phe Pro Thr
                85                  90                  95

Thr

<210> SEQ ID NO 438
<211> LENGTH: 97
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 438

Ala Ile Arg Met Thr Gln Ser Pro Phe Ser Leu Ser Ala Ser Val Gly
1               5                   10                  15

Asp Arg Val Thr Ile Thr Cys Arg Ala Ser Gln Gly Ile Ser Asn Trp
                20                  25                  30

Leu Ala Trp Tyr Gln Gln Lys Pro Ala Lys Ala Pro Lys Leu Phe Ile
            35                  40                  45

Tyr Gly Ala Ser Ser Leu Gln Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Ser Ser Phe Pro Thr
                85                  90                  95

Thr

<210> SEQ ID NO 439
<211> LENGTH: 97
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 439

Ala Ile Arg Met Thr Gln Ser Pro Ser Ser Phe Ser Ala Ser Thr Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Cys Leu Gln Ser
65                  70                  75                  80

Glu Asp Phe Ala Thr Tyr Tyr Cys Gln Gln Tyr Ser Ser Phe Pro Thr
                85                  90                  95

Thr

<210> SEQ ID NO 440
<211> LENGTH: 97
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 440

Val Ile Trp Met Thr Gln Ser Pro Ser Leu Leu Ser Ala Ser Thr Gly
1               5                   10                  15

Asp Arg Val Thr Ile Ser Cys Arg Ala Ser Gln Gly Ile Ser Asn Trp
            20                  25                  30

Leu Ala Trp Tyr Gln Gln Lys Pro Gly Lys Ala Pro Glu Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Cys Leu Gln Ser
65                  70                  75                  80

Glu Asp Phe Ala Thr Tyr Tyr Cys Gln Gln Tyr Ser Ser Phe Pro Thr
                85                  90                  95

Thr

<210> SEQ ID NO 441
<211> LENGTH: 97
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 441

```
Ala Ile Gln Met Thr Gln Ser Pro Ser Leu Ser Ala Ser Val Gly
1               5                   10                  15

Asp Arg Val Thr Ile Thr Cys Arg Ala Ser Gln Gly Ile Ser Asn Trp
                20                  25                  30

Leu Ala Trp Tyr Gln Gln Lys Pro Gly Lys Ala Pro Lys Leu Leu Ile
            35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Phe Pro Thr
                85                  90                  95

Thr
```

<210> SEQ ID NO 442
<211> LENGTH: 97
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 442

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Gly Ile Ser Asn Trp
                20                  25                  30

Leu Ala Trp Tyr Gln Gln Lys Pro Gly Lys Ala Pro Lys Leu Leu Ile
            35                  40                  45

Tyr Gly Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Ser Ser Phe Pro Thr
                85                  90                  95

Thr
```

<210> SEQ ID NO 443
<211> LENGTH: 97
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 443

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
                20                  25                  30

Leu Ala Trp Tyr Gln Gln Lys Pro Gly Lys Ala Pro Lys Leu Leu Ile
            35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
```

65                  70                  75                  80

Glu Asp Phe Ala Thr Tyr Tyr Cys Gln Gln Tyr Ser Ser Phe Pro Thr
                85                  90                  95

Thr

<210> SEQ ID NO 444
<211> LENGTH: 97
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 444

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
                20                  25                  30

Leu Ala Trp Tyr Gln Gln Lys Pro Gly Lys Ala Pro Lys Leu Leu Ile
            35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Phe Pro Thr
                85                  90                  95

Thr

<210> SEQ ID NO 445
<211> LENGTH: 97
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 445

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
                20                  25                  30

Leu Ala Trp Tyr Gln Gln Lys Pro Gly Lys Ala Pro Lys Leu Leu Ile
            35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Ser Ser Phe Pro Thr
                85                  90                  95

Thr

<210> SEQ ID NO 446
<211> LENGTH: 97
<212> TYPE: PRT
<213> ORGANISM: Artificial Sequence
<220> FEATURE:
<221> NAME/KEY: source
<223> OTHER INFORMATION: /note="Description of Artificial Sequence:

<400> SEQUENCE: 446

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Ser Ser Phe Pro Thr
                85                  90                  95

Thr

<210> SEQ ID NO 447
<211> LENGTH: 97
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 447

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Val Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Tyr Ser Ser Phe Pro Thr
                85                  90                  95

Thr

<210> SEQ ID NO 448
<211> LENGTH: 97
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 448

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Arg Leu Ile
        35                  40                  45

Tyr Gly Ala Ser Ser Leu Gln Ser Gly Val Pro Ser Arg Phe Ser Gly
    50                  55                  60

-continued

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Ser Ser Phe Pro Thr
                85                  90                  95

Thr

<210> SEQ ID NO 449
<211> LENGTH: 97
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 449

Asn Ile Gln Met Thr Gln Ser Pro Ser Ala Met Ser Ala Ser Val Gly
1               5                   10                  15

Asp Arg Val Thr Ile Thr Cys Arg Ala Ser Gln Gly Ile Ser Asn Trp
                20                  25                  30

Leu Ala Trp Phe Gln Gln Lys Pro Gly Lys Val Pro Lys His Leu Ile
            35                  40                  45

Tyr Gly Ala Ser Ser Leu Gln Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Ser Ser Phe Pro Thr
                85                  90                  95

Thr

<210> SEQ ID NO 450
<211> LENGTH: 97
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 450

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
                20                  25                  30

Leu Ala Trp Phe Gln Gln Lys Pro Gly Lys Ala Pro Lys Ser Leu Ile
            35                  40                  45

Tyr Gly Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Phe Pro Thr
                85                  90                  95

Thr

<210> SEQ ID NO 451
<211> LENGTH: 97
<212> TYPE: PRT
<213> ORGANISM: Artificial Sequence
<220> FEATURE:

<221> NAME/KEY: source
<223> OTHER INFORMATION: /note="Description of Artificial Sequence:
      Synthetic polypeptide"

<400> SEQUENCE: 451

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Glu Lys Ala Pro Lys Ser Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Phe Pro Thr
                85                  90                  95

Thr
```

<210> SEQ ID NO 452
<211> LENGTH: 97
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 452

```
Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Phe Pro Thr
                85                  90                  95

Thr
```

<210> SEQ ID NO 453
<211> LENGTH: 97
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 453

```
Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45
```

```
Tyr Gly Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ser Ser Phe Pro Thr
                 85                  90                  95

Thr
```

<210> SEQ ID NO 454
<211> LENGTH: 97
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 454

```
Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Ile Ser Asn Trp
                 20                  25                  30

Leu Ala Trp Tyr Gln Gln Lys Pro Gly Lys Ala Pro Lys Leu Leu Ile
             35                  40                  45

Tyr Gly Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ser Ser Phe Pro Thr
                 85                  90                  95

Thr
```

<210> SEQ ID NO 455
<211> LENGTH: 97
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 455

```
Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Ile Ser Asn Trp
                 20                  25                  30

Leu Ala Trp Tyr Gln Gln Lys Pro Gly Lys Ala Pro Lys Leu Leu Ile
             35                  40                  45

Tyr Gly Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ser Ser Phe Pro Thr
                 85                  90                  95

Thr
```

<210> SEQ ID NO 456
<211> LENGTH: 97
<212> TYPE: PRT

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 456

```
Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Ser Ser Phe Pro Thr
                85                  90                  95

Thr
```

<210> SEQ ID NO 457
<211> LENGTH: 97
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 457

```
Ala Ile Arg Met Thr Gln Ser Pro Phe Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Ala Lys Ala Pro Lys Leu Phe Ile
        35                  40                  45

Tyr Gly Ala Ser Ser Leu Gln Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Ser Ser Phe Pro Thr
                85                  90                  95

Thr
```

<210> SEQ ID NO 458
<211> LENGTH: 97
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 458

```
Ala Ile Arg Met Thr Gln Ser Pro Ser Ser Phe Ser Ala Ser Thr Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
```

```
                 35                  40                  45
Tyr Gly Ala Ser Ser Leu Gln Ser Gly Val Pro Ser Arg Phe Ser Gly
             50                  55                  60
Ser Gly Ser Gly Thr Asp Phe Thr Leu Thr Ile Ser Cys Leu Gln Ser
 65                  70                  75                  80
Glu Asp Phe Ala Thr Tyr Tyr Cys Gln Gln Tyr Ser Ser Phe Pro Thr
                 85                  90                  95

Thr

<210> SEQ ID NO 459
<211> LENGTH: 97
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 459

Val Ile Trp Met Thr Gln Ser Pro Ser Leu Ser Ala Ser Thr Gly
 1               5                  10                  15
Asp Arg Val Thr Ile Ser Cys Arg Ala Ser Gln Gly Ile Ser Asn Trp
             20                  25                  30
Leu Ala Trp Tyr Gln Gln Lys Pro Gly Lys Ala Pro Glu Leu Leu Ile
         35                  40                  45
Tyr Gly Ala Ser Ser Leu Gln Ser Gly Val Pro Ser Arg Phe Ser Gly
             50                  55                  60
Ser Gly Ser Gly Thr Asp Phe Thr Leu Thr Ile Ser Cys Leu Gln Ser
 65                  70                  75                  80
Glu Asp Phe Ala Thr Tyr Tyr Cys Gln Gln Tyr Ser Ser Phe Pro Thr
                 85                  90                  95

Thr

<210> SEQ ID NO 460
<211> LENGTH: 97
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 460

Ala Ile Gln Met Thr Gln Ser Pro Ser Ser Leu Ser Ala Ser Val Gly
 1               5                  10                  15
Asp Arg Val Thr Ile Thr Cys Arg Ala Ser Gln Gly Ile Ser Asn Trp
             20                  25                  30
Leu Ala Trp Tyr Gln Gln Lys Pro Gly Lys Ala Pro Lys Leu Leu Ile
         35                  40                  45
Tyr Gly Ala Ser Ser Leu Gln Ser Gly Val Pro Ser Arg Phe Ser Gly
             50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Tyr Ser Ser Phe Pro Thr
                 85                  90                  95

Thr

<210> SEQ ID NO 461
```

<211> LENGTH: 97
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 461

Asp Ile Gln Met Thr Gln Ser Pro Ser Thr Leu Ser Ala Ser Val Gly
1               5                   10                  15
Asp Arg Val Thr Ile Thr Cys Arg Ala Ser Gln Gly Ile Ser Asn Trp
            20                  25                  30
Leu Ala Trp Tyr Gln Gln Lys Pro Gly Lys Ala Pro Lys Leu Leu Ile
        35                  40                  45
Tyr Gly Ala Ser Ser Leu Gln Ser Gly Val Pro Ser Arg Phe Ser Gly
    50                  55                  60
Ser Gly Ser Gly Thr Glu Phe Thr Leu Thr Ile Ser Ser Leu Gln Pro
65                  70                  75                  80
Asp Asp Phe Ala Thr Tyr Tyr Cys Gln Gln Tyr Ser Ser Phe Pro Thr
                85                  90                  95
Thr

<210> SEQ ID NO 462
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 462

Trp Gly Gln Gly Thr Leu Val Thr Val Ser Ser
1               5                   10

<210> SEQ ID NO 463
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 463

Trp Gly Arg Gly Thr Leu Val Thr Val Ser Ser
1               5                   10

<210> SEQ ID NO 464
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 464

Trp Gly Gln Gly Thr Met Val Thr Val Ser Ser
1               5                   10

<210> SEQ ID NO 465
<211> LENGTH: 11
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 465

Trp Gly Gln Gly Thr Leu Val Thr Val Ser Ser
1               5                   10

<210> SEQ ID NO 466
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 466

Trp Gly Gln Gly Thr Leu Val Thr Val Ser Ser
1               5                   10

<210> SEQ ID NO 467
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 467

Trp Gly Gln Gly Thr Thr Val Thr Val Ser Ser
1               5                   10

<210> SEQ ID NO 468
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 468

Phe Gly Gln Gly Thr Lys Val Glu Ile Lys
1               5                   10

<210> SEQ ID NO 469
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 469

Phe Gly Gln Gly Thr Lys Leu Glu Ile Lys
1               5                   10

<210> SEQ ID NO 470
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
```

-continued

Synthetic peptide"

<400> SEQUENCE: 470

Phe Gly Pro Gly Thr Lys Val Asp Ile Lys
1               5                   10

<210> SEQ ID NO 471
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 471

Phe Gly Gly Gly Thr Lys Val Glu Ile Lys
1               5                   10

<210> SEQ ID NO 472
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 472

Phe Gly Gln Gly Thr Arg Leu Glu Ile Lys
1               5                   10

<210> SEQ ID NO 473
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 473

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Gly Val Thr Gly Ala Val Gly Arg Ser Thr Tyr Tyr Pro Asp Ser Val
    50                  55                  60

Lys Gly Arg Phe Thr Ile Ser Arg Asp Asp Ser Lys Asn Thr Leu Tyr
65                  70                  75                  80

Leu Gln Met Asn Ser Leu Lys Thr Glu Asp Thr Ala Val Tyr Tyr Cys
                85                  90                  95

Thr Thr Trp Gly Asp Glu Gly Phe Asp Ile Trp Gly Gln Gly Thr Leu
            100                 105                 110

Val Thr Val Ser Ser
        115

<210> SEQ ID NO 474
<211> LENGTH: 117
<212> TYPE: PRT
<213> ORGANISM: Artificial Sequence
<220> FEATURE:

<221> NAME/KEY: source
<223> OTHER INFORMATION: /note="Description of Artificial Sequence:
      Synthetic polypeptide"

<400> SEQUENCE: 474

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Gly Val Thr Gly Ala Val Gly Arg Ser Thr Tyr Tyr Pro Asp Ser Val
    50                  55                  60

Lys Gly Arg Phe Thr Ile Ser Arg Asp Asp Ser Lys Asn Thr Leu Tyr
65                  70                  75                  80

Leu Gln Met Asn Ser Leu Lys Thr Glu Asp Thr Ala Val Tyr Tyr Cys
                85                  90                  95

Thr Thr Trp Gly Asp Glu Gly Phe Asp Ile Trp Gly Gln Gly Thr Met
            100                 105                 110

Val Thr Val Ser Ser
        115

<210> SEQ ID NO 475
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 475

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Gly Ala Ile Asn Ser Gln Gly Lys Ser Thr Tyr Tyr Ala Asp Ser Val
    50                  55                  60

Lys Gly Arg Phe Thr Ile Ser Arg Asp Asp Ser Lys Asn Thr Leu Tyr
65                  70                  75                  80

Leu Gln Met Asn Ser Leu Lys Thr Glu Asp Thr Ala Val Tyr Tyr Cys
                85                  90                  95

Thr Thr Trp Gly Asp Glu Gly Phe Asp Ile Trp Gly Gln Gly Thr Leu
            100                 105                 110

Val Thr Val Ser Ser
        115

<210> SEQ ID NO 476
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 476

Glu Val Gln Leu Val Glu Ser Gly Gly Gly Leu Val Lys Pro Gly Gly

```
1               5                   10                  15
Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Gly Ala Ile Asn Ser Gln Gly Lys Ser Thr Tyr Tyr Ala Asp Ser Val
            50                  55                  60

Lys Gly Arg Phe Thr Ile Ser Arg Asp Ser Lys Asn Thr Leu Tyr
65                  70                  75                  80

Leu Gln Met Asn Ser Leu Lys Thr Glu Asp Thr Ala Val Tyr Tyr Cys
                85                  90                  95

Thr Thr Trp Gly Asp Glu Gly Phe Asp Ile Trp Gly Gln Gly Thr Met
            100                 105                 110

Val Thr Val Ser Ser
        115
```

<210> SEQ ID NO 477
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 477

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
            35                  40                  45

Tyr Gly Ala Ser Ser Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Phe Pro Thr
                85                  90                  95

Thr Phe Gly Gln Gly Thr Lys Val Glu Ile Lys
            100                 105
```

<210> SEQ ID NO 478
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 478

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
            35                  40                  45

Tyr Gly Ala Ser Ser Leu Gln Ser Gly Val Pro Ser Arg Phe Ser Gly
            50                  55                  60
```

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Phe Pro Thr
                85                  90                  95

Thr Phe Gly Gly Gly Thr Lys Val Glu Ile Lys
            100                 105

<210> SEQ ID NO 479
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 479

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Val Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Tyr Ser Ser Phe Pro Thr
                85                  90                  95

Thr Phe Gly Gly Gly Thr Lys Val Glu Ile Lys
            100                 105

<210> SEQ ID NO 480
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 480

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Val Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Tyr Ser Ser Phe Pro Thr
                85                  90                  95

Thr Phe Gly Gln Gly Thr Lys Val Glu Ile Lys
            100                 105

<210> SEQ ID NO 481
<211> LENGTH: 117

<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 481

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Gly Val Thr Gly Ala Val Gly Arg Ser Thr Tyr Tyr Pro Asp Ser Val
    50                  55                  60

Lys Gly Arg Phe Thr Ile Ser Arg Asp Asp Ser Lys Asn Thr Leu Tyr
65                  70                  75                  80

Leu Gln Met Asn Ser Leu Lys Thr Glu Asp Thr Ala Val Tyr Tyr Cys
                85                  90                  95

Thr Thr Trp Gly Asp Glu Gly Phe Asp Ile Trp Gly Gln Gly Thr Met
            100                 105                 110

Val Thr Val Ser Ser
        115

<210> SEQ ID NO 482
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 482

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Arg Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Ser Ser Phe Pro Thr
                85                  90                  95

Thr Phe Gly Gly Gly Thr Lys Val Glu Ile Lys
            100                 105

<210> SEQ ID NO 483
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 483

Gln Val Gln Leu Val Glu Ser Gly Gly Gly Val Val Gln Pro Gly Arg

```
                1               5                   10                  15
Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
                35                  40                  45

Ala Val Thr Gly Ala Val Gly Arg Ser Thr Tyr Tyr Pro Asp Ser Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Trp Gly Asp Glu Gly Phe Asp Ile Trp Gly Gln Gly Thr Leu
                100                 105                 110

Val Thr Val Ser Ser
            115
```

<210> SEQ ID NO 484
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 484

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
                20                  25                  30

Leu Ala Trp Phe Gln Gln Lys Pro Gly Lys Ala Pro Lys Ser Leu Ile
                35                  40                  45

Tyr Gly Ala Ser Ser Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Phe Pro Thr
                85                  90                  95

Thr Phe Gly Gln Gly Thr Lys Leu Glu Ile Lys
                100                 105
```

<210> SEQ ID NO 485
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 485

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
                35                  40                  45

Ala Val Thr Gly Ala Val Gly Arg Ser Thr Tyr Tyr Pro Asp Ser Val
            50                  55                  60
```

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Trp Gly Asp Glu Gly Phe Asp Ile Trp Gly Arg Gly Thr Leu
            100                 105                 110

Val Thr Val Ser Ser
            115

<210> SEQ ID NO 486
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 486

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Phe Gln Gln Lys Pro Gly Lys Ala Pro Lys Ser Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Phe Pro Thr
                85                  90                  95

Thr Phe Gly Gln Gly Thr Lys Leu Glu Ile Lys
            100                 105

<210> SEQ ID NO 487
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 487

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Asn Ser Gln Gly Lys Ser Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr His Cys
                85                  90                  95

Ala Arg Trp Gly Asp Glu Gly Phe Asp Ile Trp Gly Gln Gly Thr Leu
            100                 105                 110

Val Thr Val Ser Ser
        115

<210> SEQ ID NO 488
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 488

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Glu Lys Ala Pro Lys Ser Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Phe Pro Thr
                85                  90                  95

Thr Phe Gly Pro Gly Thr Lys Val Asp Ile Lys
            100                 105

<210> SEQ ID NO 489
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 489

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Ala Ile Asn Ser Gln Gly Lys Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Asp Glu Gly Phe Asp Ile Trp Gly Arg Gly Thr Leu
            100                 105                 110

Val Thr Val Ser Ser
        115

<210> SEQ ID NO 490
<211> LENGTH: 107
<212> TYPE: PRT
<213> ORGANISM: Artificial Sequence
<220> FEATURE:
<221> NAME/KEY: source

```
<223> OTHER INFORMATION: /note="Description of Artificial Sequence:
      Synthetic polypeptide"

<400> SEQUENCE: 490

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Val Pro Lys Leu Leu Ile
        35                  40                  45

Tyr Gly Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Tyr Ser Ser Phe Pro Thr
                85                  90                  95

Thr Phe Gly Gln Gly Thr Lys Val Glu Ile Lys
            100                 105

<210> SEQ ID NO 491
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 491

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Ala Ile Asn Ser Gln Gly Lys Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Asp Glu Gly Phe Asp Ile Trp Gly Gln Gly Thr Met
            100                 105                 110

Val Thr Val Ser Ser
        115

<210> SEQ ID NO 492
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 492

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30
```

```
Leu Ala Trp Tyr Gln Gln Lys Pro Gly Lys Val Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Tyr Ser Ser Phe Pro Thr
                85                  90                  95

Thr Phe Gly Gln Gly Thr Lys Leu Glu Ile Lys
                100                 105

<210> SEQ ID NO 493
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(30)
<223> OTHER INFORMATION: Any amino acid
<220> FEATURE:
<221> NAME/KEY: MOD_RES
<222> LOCATION: (36)..(49)
<223> OTHER INFORMATION: Any amino acid
<220> FEATURE:
<221> NAME/KEY: MOD_RES
<222> LOCATION: (67)..(98)
<223> OTHER INFORMATION: Any amino acid
<220> FEATURE:
<221> NAME/KEY: MOD_RES
<222> LOCATION: (107)..(117)
<223> OTHER INFORMATION: Any amino acid

<400> SEQUENCE: 493

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Ser Tyr
            20                  25                  30

Ala Met Ser Xaa Xaa Xaa Xaa Xaa Xaa Xaa Xaa Xaa Xaa Xaa Xaa Xaa
        35                  40                  45

Xaa Ala Ile Asn Ser Gln Gly Lys Ser Thr Tyr Tyr Ala Asp Ser Val
    50                  55                  60

Lys Gly Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Trp Gly Asp Glu Gly Phe Asp Ile Xaa Xaa Xaa Xaa Xaa Xaa
                100                 105                 110

Xaa Xaa Xaa Xaa Xaa
        115

<210> SEQ ID NO 494
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
```

```
<222> LOCATION: (1)..(23)
<223> OTHER INFORMATION: Any amino acid
<220> FEATURE:
<221> NAME/KEY: MOD_RES
<222> LOCATION: (35)..(49)
<223> OTHER INFORMATION: Any amino acid
<220> FEATURE:
<221> NAME/KEY: MOD_RES
<222> LOCATION: (57)..(88)
<223> OTHER INFORMATION: Any amino acid
<220> FEATURE:
<221> NAME/KEY: MOD_RES
<222> LOCATION: (98)..(107)
<223> OTHER INFORMATION: Any amino acid

<400> SEQUENCE: 494

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Arg Ala Ser Gln Gly Ile Ser Asn Trp
            20                  25                  30

Leu Ala Xaa Xaa Xaa Xaa Xaa Xaa Xaa Xaa Xaa Xaa Xaa Xaa
        35                  40                  45

Xaa Gly Ala Ser Ser Leu Gln Ser Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Gln Gln Tyr Ser Ser Phe Pro Thr
                85                  90                  95

Thr Xaa Xaa Xaa Xaa Xaa Xaa Xaa Xaa Xaa Xaa
            100                 105

<210> SEQ ID NO 495
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 495

His His His His His His
1               5

<210> SEQ ID NO 496
<211> LENGTH: 18
<212> TYPE: PRT
<213> ORGANISM: Homo sapiens

<400> SEQUENCE: 496

Thr Phe Gln Leu Glu Pro Asn Pro His Thr Lys Tyr Gln Tyr Gly Gly
1               5                   10                  15

Val Cys

<210> SEQ ID NO 497
<211> LENGTH: 627
<212> TYPE: PRT
<213> ORGANISM: Homo sapiens

<400> SEQUENCE: 497

Ser Glu Val Gly Asn Ser Gln Ala Val Cys Pro Gly Thr Leu Asn Gly
1               5                   10                  15

Leu Ser Val Thr Gly Asp Ala Glu Asn Gln Tyr Gln Thr Leu Tyr Lys
            20                  25                  30
```

-continued

Leu Tyr Glu Arg Cys Glu Val Met Gly Asn Leu Glu Ile Val Leu
         35                  40                 45

Thr Gly His Asn Ala Asp Leu Ser Phe Leu Gln Trp Ile Arg Glu Val
 50                  55                  60

Thr Gly Tyr Val Leu Val Ala Met Asn Glu Phe Ser Thr Leu Pro Leu
 65                  70                  75                  80

Pro Asn Leu Arg Val Val Arg Gly Thr Gln Val Tyr Asp Gly Lys Phe
                 85                  90                  95

Ala Ile Phe Val Met Leu Asn Tyr Asn Thr Asn Ser Ser His Ala Leu
                100                 105                 110

Arg Gln Leu Arg Leu Thr Gln Leu Thr Glu Ile Leu Ser Gly Gly Val
             115                 120                 125

Tyr Ile Glu Lys Asn Asp Lys Leu Cys His Met Asp Thr Ile Asp Trp
         130                 135                 140

Arg Asp Ile Val Arg Asp Arg Asp Ala Glu Ile Val Val Lys Asp Asn
145                 150                 155                 160

Gly Arg Ser Cys Pro Pro Cys His Glu Val Cys Lys Gly Arg Cys Trp
                 165                 170                 175

Gly Pro Gly Ser Glu Asp Cys Gln Thr Leu Thr Lys Thr Ile Cys Ala
             180                 185                 190

Pro Gln Cys Asn Gly His Cys Phe Gly Pro Asn Pro Asn Gln Cys Cys
         195                 200                 205

His Asp Glu Cys Ala Gly Gly Cys Ser Gly Pro Gln Asp Thr Asp Cys
         210                 215                 220

Phe Ala Cys Arg His Phe Asn Asp Ser Gly Ala Cys Val Pro Arg Cys
225                 230                 235                 240

Pro Gln Pro Leu Val Tyr Asn Lys Leu Thr Phe Gln Leu Glu Pro Asn
                 245                 250                 255

Pro His Thr Lys Tyr Gln Tyr Gly Gly Val Cys Val Ala Ser Cys Pro
             260                 265                 270

His Asn Phe Val Val Asp Gln Thr Ser Cys Val Arg Ala Cys Pro Pro
         275                 280                 285

Asp Lys Met Glu Val Asp Lys Asn Gly Leu Lys Met Cys Glu Pro Cys
         290                 295                 300

Gly Gly Leu Cys Pro Lys Ala Cys Glu Gly Thr Gly Ser Gly Ser Arg
305                 310                 315                 320

Phe Gln Thr Val Asp Ser Ser Asn Ile Asp Gly Phe Val Asn Cys Thr
                 325                 330                 335

Lys Ile Leu Gly Asn Leu Asp Phe Leu Ile Thr Gly Leu Asn Gly Asp
             340                 345                 350

Pro Trp His Lys Ile Pro Ala Leu Asp Pro Glu Lys Leu Asn Val Phe
         355                 360                 365

Arg Thr Val Arg Glu Ile Thr Gly Tyr Leu Asn Ile Gln Ser Trp Pro
370                 375                 380

Pro His Met His Asn Phe Ser Val Phe Ser Asn Leu Thr Thr Ile Gly
385                 390                 395                 400

Gly Arg Ser Leu Tyr Asn Arg Gly Phe Ser Leu Leu Ile Met Lys Asn
                 405                 410                 415

Leu Asn Val Thr Ser Leu Gly Phe Arg Ser Leu Lys Glu Ile Ser Ala
             420                 425                 430

Gly Arg Ile Tyr Ile Ser Ala Asn Arg Gln Leu Cys Tyr His His Ser
         435                 440                 445

-continued

```
Leu Asn Trp Thr Lys Val Leu Arg Gly Pro Thr Glu Glu Arg Leu Asp
    450                 455                 460
Ile Lys His Asn Arg Pro Arg Arg Asp Cys Val Ala Glu Gly Lys Val
465                 470                 475                 480
Cys Asp Pro Leu Cys Ser Ser Gly Gly Cys Trp Gly Pro Gly Pro Gly
                485                 490                 495
Gln Cys Leu Ser Cys Arg Asn Tyr Ser Arg Gly Gly Val Cys Val Thr
            500                 505                 510
His Cys Asn Phe Leu Asn Gly Glu Pro Arg Glu Phe Ala His Glu Ala
        515                 520                 525
Glu Cys Phe Ser Cys His Pro Glu Cys Gln Pro Met Glu Gly Thr Ala
    530                 535                 540
Thr Cys Asn Gly Ser Gly Ser Asp Thr Cys Ala Gln Cys Ala His Phe
545                 550                 555                 560
Arg Asp Gly Pro His Cys Val Ser Ser Cys Pro His Gly Val Leu Gly
                565                 570                 575
Ala Lys Gly Pro Ile Tyr Lys Tyr Pro Asp Val Gln Asn Glu Cys Arg
            580                 585                 590
Pro Cys His Glu Asn Cys Thr Gln Gly Cys Lys Gly Pro Glu Leu Gln
        595                 600                 605
Asp Cys Leu Gly Gln Thr Leu Val Leu Ile Gly Lys Thr Glu Phe Arg
    610                 615                 620
His Asp Ser
625
```

ANTIBODIES FOR EPIDERMAL GROWTH FACTOR RECEPTOR 3 (HER3)

RELATED APPLICATIONS

This application claims priority to U.S. Provisional Application No. 61/566,890 filed on Dec. 5, 2011, the contents of which are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Mar. 29, 2013, is named PAT054912-US-NP_SL.txt and is 390,734 bytes in size.

FIELD OF THE INVENTION

This invention relates generally to antibodies or fragments thereof which interact with HER family of receptors, e.g., HER3 receptor. In particular, it relates to antibodies or fragments thereof that recognize a conformational epitope of HER3 receptor comprising residues from both domains 2 and 4 resulting in inhibition of both ligand-dependent and ligand-independent signal transduction; and allow ligand binding (e.g., neuregulin), whilst preventing ligand-induced activation of signal transduction. These antibodies or fragments can be used to treat a number of diseases or disorders characterized by increased levels of HER3 expression (e.g., esophageal cancer). These antibodies or fragments can be used to treat a number of diseases or disorders characterized by the antibodys or fragments ability to decrease tissue weight (e.g., prostate or uterine weights) or to induce atrophy of tissue (e.g., atrophy of male breast).

BACKGROUND OF THE INVENTION

The human epidermal growth factor receptor 3 (ErbB3, also known as HER3) is a receptor protein tyrosine kinase and belongs to the epidermal growth factor receptor (EGFR) subfamily of receptor protein tyrosine kinases, which also includes EGFR (HER1, ErbB1), HER2 (ErbB2, Neu), and HER4 (ErbB4) (Plowman et al., (1990) Proc. Natl. Acad. Sci. U.S.A. 87:4905-4909; Kraus et al., (1989) Proc. Natl. Acad. Sci. U.S.A. 86:9193-9197; and Kraus et al., (1993) Proc. Natl. Acad. Sci. U.S.A. 90:2900-2904). Like the prototypical epidermal growth factor receptor, the transmembrane receptor HER3 consists of an extracellular ligand-binding domain (ECD), a dimerization domain within the ECD, a transmembrane domain, an intracellular protein tyrosine kinase-like domain (TKD) and a C-terminal phosphorylation domain. Unlike the other HER family members, the kinase domain of HER3 displays very low intrinsic kinase activity.

The ligands neuregulin 1 (NRG) or neuregulin 2 bind to the extracellular domain of HER3 and activate receptor-mediated signaling pathway by promoting dimerization with other dimerization partners such as HER2. Heterodimerization results in activation and transphosphorylation of HER3's intracellular domain and is a means not only for signal diversification but also signal amplification. In addition, HER3 heterodimerization can also occur in the absence of activating ligands and this is commonly termed ligand-independent HER3 activation. For example, when HER2 is expressed at high levels as a result of gene amplification (e.g. in breast, lung, ovarian or gastric cancer) spontaneous HER2/HER3 dimers can be formed. In this situation the HER2/HER3 is considered the most active ErbB signaling dimer and is therefore highly transforming.

Increased HER3 has been found in several types of cancer such as breast, lung, gastrointestinal and pancreatic cancers. Interestingly, a correlation between the expression of HER2/HER3 and the progression from a non-invasive to an invasive stage has been shown (Alimandi et al., (1995) Oncogene 10:1813-1821; DeFazio et al., (2000) Cancer 87:487-498; Naidu et al., (1988) Br. J. Cancer 78:1385-1390). Accordingly, agents that interfere with HER3 mediated signaling are needed.

SUMMARY OF THE INVENTION

The invention is based on the discovery of antigen binding proteins (e.g., antibodies or fragments thereof) that bind to a conformational epitope of HER3 receptor comprising amino acid residues within domain 2 and domain 4 of HER3. This binding of the antibodies or fragments thereof with domain 2 and domain 4 stabilizes the HER3 receptor in an inactive or closed conformation such that HER3 activation is inhibited. Surprisingly, binding of the antibodies or fragments thereof with this conformational epitope blocks both ligand-dependent (e.g. neuregulin) and ligand-independent HER3 signaling pathways. Furthermore, antibody mediated inhibition of ligand induced signaling occurs without blocking ligand binding (i.e. both ligand and antibody can bind HER3) presumably because HER3 cannot undergo the conformational rearrangements required for activation. Also disclosed are methods for using the antibodies or fragments thereof to treat a number of diseases or disorders characterized by increased expression of HER3; and disease or disorders characterized by the antibodies or fragments ability to decrease tissue weight (e.g., prostate or uterine weights) or to induce atrophy of tissue (e.g., atrophy of male breast).

Accordingly, in one aspect, the invention pertains to a method of treating a disorder characterized by increased levels of HER3 expression in an esophageal tract comprising: selecting patient suffering from increased levels of HER3 expression in an esophageal tract; and administering an antibody or fragment thereof that specifically binds to a HER3 receptor, such that the antibody or fragment thereof binds to a conformational epitope comprising amino acid residues within domain 2 and domain 4 of the HER3 receptor and blocks both ligand-dependent and ligand-independent signal transduction, thereby treating the disorder. In one embodiment, the disorder is selected from the group consisting of esophageal cancer and Barretts esophageal cancer.

In another aspect, the invention pertains to a method of treating gastric cancer comprising: selecting a patient suffering from gastric cancer; and administering an antibody or fragment thereof that specifically binds to a HER3 receptor, such that the antibody or fragment thereof binds to a conformational epitope comprising amino acid residues within domain 2 and domain 4 of the HER3 receptor and blocks both ligand-dependent and ligand-independent signal transduction, thereby treating gastric cancer.

In another aspect, the invention pertains to a method of treating head and neck cancer comprising selecting a patient suffering from cancer the head and neck; and administering an antibody or fragment thereof that specifically binds to a HER3 receptor, such that the antibody or fragment thereof binds to a conformational epitope comprising amino acid residues within domain 2 and domain 4 of the HER3 receptor and blocks both ligand-dependent and ligand-independent signal transduction, thereby treating head and neck cancer.

In another aspect, the invention pertains to a method of treating benign prostate hyperplasia comprising: selecting a patient suffering from benign prostate hyperplasia; and administering an antibody or fragment thereof that specifically binds to a HER3 receptor, such that the antibody or fragment thereof binds to a conformational epitope comprising amino acid residues within domain 2 and domain 4 of the HER3 receptor and blocks both ligand-dependent and ligand-independent signal transduction, thereby treating benign prostate hyperplasia.

In yet another aspect, the invention pertains to a method of treating gynecomastia, comprising: selecting a patient suffering from gynecomastia; and administering an antibody or fragment thereof that specifically binds to a HER3 receptor, such that the antibody or fragment thereof binds to a conformational epitope comprising amino acid residues within domain 2 and domain 4 of the HER3 receptor and blocks both ligand-dependent and ligand-independent signal transduction, thereby treating gynecomastia.

In yet another aspect, the invention pertains to a method of treating endometiosis comprising: selecting a patient suffering from endometiosis; and administering an antibody or fragment thereof that specifically binds to a HER3 receptor, such that the antibody or fragment thereof binds to a conformational epitope comprising amino acid residues within domain 2 and domain 4 of the HER3 receptor and blocks both ligand-dependent and ligand-independent signal transduction, thereby treating endometiosis.

In one embodiment, the antibody or fragment thereof is administered by a route selected from the group consisting of oral, subcutaneous, intraperitoneal, intramuscular, intracerebroventricular, intraparenchymal, intrathecal, intracranial, buccal, mucosal, nasal, and rectal administration. In one embodiment, the antibody or fragment thereof is formulated into a pharmaceutical composition comprising a physiologically acceptable carrier, excipient, or diluent. In another embodiment, the pharmaceutical composition comprises an additional therapeutic agent. In one embodiment, the additional therapeutic agent is selected from the group consisting of an HER1 inhibitor, a HER2 inhibitor, a HER3 inhibitor, a HER4 inhibitor, an mTOR inhibitor and a PI3 Kinase inhibitor. In one embodiment, the additional therapeutic agent is a HER1 inhibitor selected from the group consisting of Matuzumab (EMD72000), Erbitux®/Cetuximab, Vectibix®/Panitumumab, mAb 806, Nimotuzumab, Iressa®/Gefitinib, CI-1033 (PD183805), Lapatinib (GW-572016), Tykerb®/Lapatinib Ditosylate, Tarceva®/Erlotinib HCL (OSI-774), PKI-166, and Tovok®; a HER2 inhibitor selected from the group consisting of Pertuzumab, Trastuzumab, MM-111, neratinib, lapatinib or lapatinib ditosylate/Tykerb®; a HER3 inhibitor selected from the group consisting of, MM-121, MM-111, IB4C3, 2DID12 (U3 Pharma AG), AMG888 (Amgen), AV-203 (Aveo), MEHD7945A (Genentech), MOR10703 (Novartis) and small molecules that inhibit HER3; and a HER4 inhibitor. In one embodiment, the additional therapeutic agent is an mTOR inhibitor selected from the group consisting of Temsirolimus/Torisel®, ridaforolimus/Deforolimus, AP23573, MK8669, everolimus/Affinitor®. In one embodiment, the additional therapeutic agent is a PI3 Kinase inhibitor selected from the group consisting of GDC 0941, BEZ235, BMK120 and BYL719.

In another aspect, the invention pertains to use of an antibody or fragment thereof that specifically binds to a HER3 receptor, such that the antibody or fragment thereof binds to a conformational epitope comprising amino acid residues within domain 2 and domain 4 of the HER3 receptor and blocks both ligand-dependent and ligand-independent signal transduction for the manufacture of a medicament for the treatment of an esophageal disorder, or gastric cancer, or head and neck cancer, or benign prostatic hyperplasia (BPH), or gynecomastia, or endometriosis.

DETAILED DESCRIPTION OF THE INVENTION

Definitions

Figure 1:
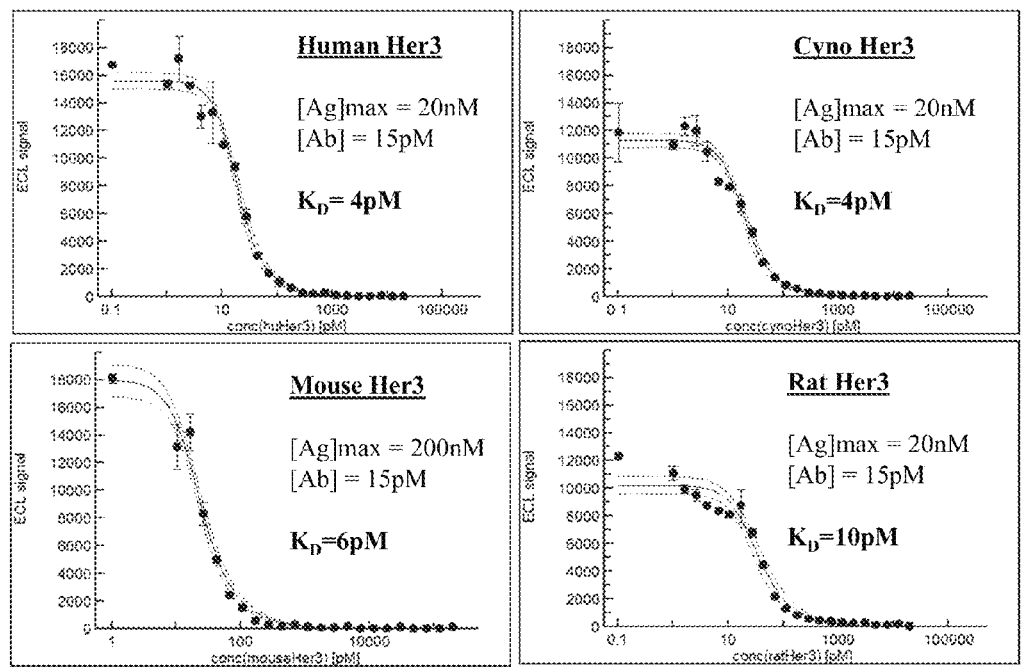
FIG. 1: Representative MOR10701 SET curves obtained with human, mouse, rat and cyno HER3

In order that the present invention may be more readily understood, certain terms are first defined. Additional definitions are set forth throughout the detailed description.

The phrase "signal transduction" or "signaling activity" as used herein refers to a biochemical causal relationship generally initiated by a protein-protein interaction such as binding of a growth factor to a receptor, resulting in transmission of a signal from one portion of a cell to another portion of a cell. For HER3, the transmission involves specific phosphorylation of one or more tyrosine, serine, or threonine residues on one or more proteins in the series of reactions causing signal transduction. Penultimate processes typically include nuclear events, resulting in a change in gene expression.

A "HER receptor" is a receptor protein tyrosine kinase which belongs to the HER receptor family and includes EGFR, HER2, HER3 and HER4 receptors and other members of this family to be identified in the future. The HER receptor will generally comprise an extracellular domain, which may bind an HER ligand; a lipophilic transmembrane domain; a conserved intracellular tyrosine kinase domain; and a carboxyl-terminal signaling domain harboring several tyrosine residues which can be phosphorylated. Preferably the HER receptor is native sequence human HER receptor.

The terms "HER1," "ErbB1," "epidermal growth factor receptor" and "EGFR" are used interchangeably herein and refer to EGFR as disclosed, for example, in Carpenter et al. Ann. Rev. Biochem. 56:881-914 (1987), including naturally occurring mutant forms thereof (e.g. a deletion mutant EGFR as in Humphrey et al., (1990) PNAS (USA) 87:4207-4211). erbB1 refers to the gene encoding the EGFR protein product.

The terms "HER2" and "ErbB2" and are used interchangeably herein and refer to human HER2 protein described, for example, in Semba et al., (1985) PNAS (USA) 82:6497-6501 and Yamamoto et al. (1986) Nature 319:230-234 (Genebank accession number X03363). The term "erbB2" refers to the gene encoding human ErbB2 and "neu" refers to the gene encoding rat p185$^{neu}$.

The terms "HER4" and "ErbB4" herein refer to the receptor polypeptide as disclosed, for example, in EP Pat Appln No 599,274; Plowman et al., (1993) Proc. Natl. Acad. Sci. USA, 90:1746-1750; and Plowman et al., (1993) Nature, 366:473-475, including isoforms thereof, e.g., as disclosed in WO99/19488, published Apr. 22, 1999.

The term "HER3" or "HER3 receptor" also known as "ErbB3" as used herein refers to mammalian HER3 protein and "her3" or "erbB3" refers to mammalian her3 gene. The preferred HER3 protein is human HER3 protein present in the cell membrane of a cell. The human her3 gene is described in U.S. Pat. No. 5,480,968 and Plowman et al., (1990) Proc. Natl. Acad. Sci. USA, 87:4905-4909.

Human HER3 as defined in Accession No. NP_001973 (human), and represented below as SEQ ID NO: 1. All nomenclature is for full length, immature HER3 (amino acids 1-1342). The immature HER3 is cleaved between positions 19 and 20, resulting in the mature HER3 protein (20-1342 amino acids).

(SEQ ID NO: 1)

```
mrandalqvl gllfslargs evgnsqavcp gtlnglsvtg daenqyqtly klyercevvm gnleivltgh nadlsflqwi revtgyvlva mnefstlplp nlrvvrgtqv ydgkfaifvm lnyntnssha lrqlrltqlt eilsggvyie kndklchmdt idwrdivrdr daeivvkdng rscppchevc kgrcwgpgse dcqtltktic apqcnghcfg pnpnqcchde caggcsgpqd tdcfacrhfn dsgacvprcp qplyynklif qlepnphtky qyggvcvasc phnfvvdqts cvracppdkm evdknglkmc epcgglcpka cegtgsgsrf qtvdssnidg fvnctkilgn ldflitglng dpwhkipald peklnyfrtv reitgylniq swpphmhnfs vfsnittigg rslynrgfsl limknlnvts lgfrslkeis agriyisanr qlcyhhslnw tkvlrgptee rldikhnrpr rdcvaegkvc dplcssggcw gpgpgqclsc rnysrggvcv thcnflngep refaheaecf schpecqpme gtatcngsgs dtcaqcahfr dgphcvsscp hgvlgakgpi ykypdvqnec rpchenctqg ckgpelqdcl gqtivligkt hltmaltvia glvvifmmlg gtflywrgrr iqnkramrry lergesiepl dpsekankvl arifketelr klkvlgsgvf gtvhkgvwip egesikipvc ikviedksgr qsfqavtdhm laigsldhah ivrllglcpg sslqlvtqyl plgslldhvr qhrgalgpql llnwgvqiak gmyyleehgm vhrnlaarnv llkspsqvqv adfgvadllp pddkqllyse aktpikwmal esihfgkyth qsdvwsygvt vwelmtfgae pyaglrlaev pdllekgerl aqpqictidv ymvmvkcwmi denirptfke laneftrmar dpprylvikr esgpgiapgp ephgltnkkl eevelepeld ldldleaeed
```

```
-continued
nlatttlgsa lslpvgtlnr prgsqsllsp ssgympmnqg nlgescqesa vsgssercpr pvslhpmprg clasessegh vtgseaelqe kvsmcrsrsr srsprprgds ayhsqrhsll tpvtplsppg leeedvngyv mpdthlkgtp ssregtlssv glssvlgtee ededeeyeym nrrrrhspph pprpssleel gyeymdvgsd lsaslgstqs cplhpvpimp tagttpdedy eymnrqrdgg gpggdyaamg acpaseqgye emrafqgpgh qaphvhyarl ktlrsleatd safdnpdywh srlfpkanaq rt
```

The term "HER ligand" as used herein refers to polypeptides which bind and activate HER receptors such as HER1, HER2, HER3 and HER4. Examples of HER ligands include, but are not limited to neuregulin 1 (NRG), neuregulin 2, neuregulin 3, neuregulin 4, betacellulin, heparin-binding epidermal growth factor, epiregulin, epidermal growth factor, amphiregulin, and transforming growth factor alpha. The term includes biologically active fragments and/or variants of a naturally occurring polypeptide.

The term "HER3 ligand" as used herein refers to polypeptides which bind and activate HER3. Examples of HER3 ligands include, but are not limited to neuregulin 1 (NRG) and neuregulin 2, betacellulin, heparin-binding epidermal growth factor, and epiregulin. The term includes biologically active fragments and/or variants of a naturally occurring polypeptide.

The "HER-HER protein complex" is a noncovalently associated oligomer containing a HER co-receptors in any combination (e.g., HER1-HER2, HER1-HER3, HER1-HER4, HER2-HER3, HER3-HER4, and the like). This complex can form when a cell expressing both of these receptors is exposed to a HER ligand e.g., NRG, or when a HER receptor is active or overexpressed.

The "HER2-HER3 protein complex" is a noncovalently associated oligomer containing HER2 receptor and the HER3 receptor. This complex can form when a cell expressing both of these receptors is exposed to a HER3 ligand e.g., NRG or when HER2 is active/overexpressed The phrase "HER3 activity" or "HER3 activation" as used herein refers to an increase in oligomerization (e.g. an increase in HER3 containing complexes), HER3 phosphorylation, conformational rearrangements (for example those induced by ligands), and HER3 mediated downstream signaling.

The term "stabilization" or "stabilized" used in the context of HER3 refers to an antibody or fragment thereof that directly maintains (locks, tethers, holds, preferentially binds, favors) the inactive state or conformation of HER3 without blocking ligand binding to HER3, such that ligand binding is no longer able to activate HER3. Assays described in the Examples can be used to measure ligand binding to a stabilized HER3 receptor, e.g., Biacore assay.

The term "ligand-dependent signaling" as used herein refers to the activation of HER (e.g., HER3) via ligand. HER3 activation is evidenced by increased oligomerization (e.g. heterodimerization) and/or HER3 phosphorylation such that downstream signaling pathways (e.g. PI3K) are activated. The antibody or fragment thereof can statistically significantly reduce the amount of phosphorylated HER3 in a stimulated cell exposed to the antigen binding protein (e.g., an antibody) relative to an untreated (control) cell, as measured using the assays described in the Examples. The cell which expresses HER3 can be a naturally occurring cell line (e.g. MCF7) or can be recombinantly produced by introducing nucleic acids encoding HER3 protein into a host cell. Cell stimulation can occur either via the exogenous addition of an activating HER3 ligand or by the endogenous expression of an activating ligand.

The antibody or fragment thereof which "reduces neregulin-induced HER3 activation in a cell" is one which statistically significantly reduces HER3 tyrosine phosphorylation relative to an untreated (control) cell, as measured using the assays described in the Examples. This can be determined based on HER3 phosphotyrosine levels following exposure of HER3 to NRG and the antibody of interest. The cell which expresses HER3 protein can be a naturally occurring cell or cell line (e.g. MCF7) or can be recombinantly produced.

The term "ligand-independent signaling" as used herein refers to cellular HER3 activity (e.g phosphorylation) in the absence of a requirement for ligand binding. For example, ligand-independent HER3 activation can be a result of HER2 overexpression or activating mutations in HER3 heterodimer partners such as EGFR and HER2. The antibody or fragment thereof can statistically significantly reduce the amount of phosphorylated HER3 in a cell exposed to the antigen binding protein (e.g., an antibody) relative to an untreated (control) cell. The cell which expresses HER3 can be a naturally occurring cell line (e.g. SK-Br-3) or can be recombinantly produced by introducing nucleic acids encoding HER3 protein into a host cell.

The term "blocks" as used herein refers to stopping or preventing an interaction or a process, e.g., stopping ligand-dependent or ligand-independent signaling.

The term "recognize" as used herein refers to an antibody or fragment thereof that finds and interacts (e.g., binds) with its conformational epitope.

The phrase "concurrently binds" as used herein refers to a HER ligand that can bind to a ligand binding site on the HER receptor along with the HER antibody. This means that both the antibody and antibody can bind to the HER receptor together. For the sake of illustration only, the HER3 ligand NRG, can bind to the HER3 receptor along with the HER3 antibody. Assay to measure concurrent binding of the ligand and antibody are described in the Examples section (e.g., Biacore).

The term "fails" as used herein refers to an antibody or fragment thereof that does not do a particular event. For example, an antibody or fragment thereof that "fails to activate signal transduction" is one that does not trigger signal transduction; an antibody or fragment thereof that "fails to induce a conformational change" is one that does not cause a structural alteration in the HER receptor; an antibody or fragment thereof that stabilizes the HER receptor in an inactive state such that the HER receptor "fails to dimerize" is one that does not form protein-protein complexes.

The term "antibody" as used herein refers to whole antibodies that interact with (e.g., by binding, steric hindrance, stabilizing/destabilizing, spatial distribution) an HER3 epitope and inhibit signal transduction. A naturally occurring "antibody" is a glycoprotein comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and $V_L$ regions can be further subdivided into regions of hypervariability, termed complementarity determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system. The term "antibody" includes for example, monoclonal antibodies, human antibodies, humanized antibodies, camelised antibodies, chimeric antibodies, single-chain Fvs (scFv), disulfide-linked Fvs (sdFv), Fab fragments, F (ab') fragments, and anti-idiotypic (anti-Id) antibodies (including, e.g., anti-Id antibodies to antibodies of the invention), and epitope-binding fragments of any of the above. The antibodies can be of any isotype (e.g., IgG, IgE, IgM, IgD, IgA and IgY), class (e.g., IgG1, IgG2, IgG3, IgG4, IgA1 and IgA2) or subclass.

Both the light and heavy chains are divided into regions of structural and functional homology. The terms "constant" and "variable" are used functionally. In this regard, it will be appreciated that the variable domains of both the light (VL) and heavy (VH) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention the numbering of the constant region domains increases as they become more distal from the antigen binding site or amino-terminus of the antibody. The N-terminus is a variable region and at the C-terminus is a constant region; the CH3 and CL domains actually comprise the carboxy-terminus of the heavy and light chain, respectively.

The phrase "antibody fragment", as used herein, refers to one or more portions of an antibody that retain the ability to specifically interact with (e.g., by binding, steric hindrance, stabilizing/destabilizing, spatial distribution) an HER3 epitope and inhibit signal transduction. Examples of binding fragments include, but are not limited to, a Fab fragment, a monovalent fragment consisting of the VL, VH, CL and CH1 domains; a F(ab)$_2$ fragment, a bivalent fragment comprising two Fab fragments linked by a disulfide bridge at the hinge region; a Fd fragment consisting of the VH and CH1 domains; a Fv fragment consisting of the VL and VH domains of a single arm of an antibody; a dAb fragment (Ward et al., (1989) Nature 341:544-546), which consists of a VH domain; and an isolated complementarity determining region (CDR).

Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al., (1988) Science 242:423-426; and Huston et al., (1988) Proc. Natl. Acad. Sci. 85:5879-5883). Such single chain antibodies are also intended to be encompassed within the term "antibody fragment". These antibody fragments are obtained using conventional techniques known to those of skill in the art, and the fragments are screened for utility in the same manner as are intact antibodies.

Antibody fragments can also be incorporated into single domain antibodies, maxibodies, minibodies, intrabodies, diabodies, triabodies, tetrabodies, v-NAR and bis-scFv (see, e.g., Hollinger and Hudson, (2005) Nature Biotechnology 23:1126-1136). Antibody fragments can be grafted into scaffolds based on polypeptides such as Fibronectin type III (Fn3) (see U.S. Pat. No. 6,703,199, which describes fibronectin polypeptide monobodies).

Antibody fragments can be incorporated into single chain molecules comprising a pair of tandem Fv segments (VH-CH1-VH-CH1) which, together with complementary light chain polypeptides, form a pair of antigen binding regions (Zapata et al., (1995) Protein Eng. 8:1057-1062; and U.S. Pat. No. 5,641,870).

The term "epitope" includes any protein determinant capable of specific binding to an immunoglobulin or otherwise interacting with a molecule. Epitopic determinants generally consist of chemically active surface groupings of molecules such as amino acids or carbohydrate or sugar side chains and can have specific three-dimensional structural characteristics, as well as specific charge characteristics. An epitope may be "linear" or "conformational."

The term "linear epitope" refers to an epitope with all of the points of interaction between the protein and the interacting molecule (such as an antibody) occur linearly along the primary amino acid sequence of the protein (continuous). Once a desired epitope on an antigen is determined, it is possible to generate antibodies to that epitope, e.g., using the techniques described in the present invention. Alternatively, during the discovery process, the generation and characterization of antibodies may elucidate information about desirable epitopes. From this information, it is then possible to competitively screen antibodies for binding to the same epitope. An approach to achieve this is to conduct cross-competition studies to find antibodies that competitively bind with one another, e.g., the antibodies compete for binding to the antigen. A high throughput process for "binning" antibodies based upon their cross-competition is described in International Patent Application No. WO 2003/48731. As will be appreciated by one of skill in the art, practically anything to which an antibody can specifically bind could be an epitope. An epitope can comprises those residues to which the antibody binds.

The term "conformational epitope" refers to an epitope in which discontinuous amino acids that come together in three dimensional conformation. In a conformational epitope, the points of interaction occur across amino acid residues on the protein that are separated from one another. In one embodiment, the epitope is that described in Examples of this specification. In one embodiment, the conformational epitope is defined by (i) HER3 amino acid residues 265-277 and 315 (of domain 2) and (ii) HER3 amino acid residues 571, 582-584, 596-597, 600-602, 609-615 (of domain 4) of SEQ ID NO: 1, or a subset thereof. As will be appreciated by one of skill in the art, the space that is occupied by a residue or side chain that creates the shape of a molecule helps to determine what an epitope is.

Generally, antibodies specific for a particular target antigen will preferentially recognize an epitope on the target antigen in a complex mixture of proteins and/or macromolecules.

Regions of a given polypeptide that include an epitope can be identified using any number of epitope mapping techniques, well known in the art. See, e.g., Epitope Mapping Protocols in Methods in Molecular Biology, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al., (1984) Proc. Natl. Acad. Sci. USA 8:3998-4002; Geysen et al., (1985) Proc. Natl. Acad. Sci. USA 82:78-182; Geysen et al., (1986) Mol. Immunol. 23:709-715. Similarly, conformational epitopes are readily identified by determining spatial conformation of amino acids such as by, e.g., hydrogen/deuterium exchange, x-ray crystallography and two-dimensional nuclear magnetic resonance. See, e.g., Epitope Mapping Protocols, supra. Antigenic regions of proteins can also be identified using standard antigenicity and hydropathy plots, such as those calculated using, e.g., the Omiga version 1.0 software program available from the Oxford Molecular Group. This computer program employs the Hopp/Woods method, Hopp et al., (1981) Proc. Natl. Acad. Sci. USA 78:3824-3828; for determining antigenicity profiles, and the Kyte-Doolittle technique, Kyte et al., (1982) J. Mol. Biol. 157:105-132; for hydropathy plots.

The term "paratope" as used herein refers to the general structure of a binding region that determines binding to an epitope. This structure influences whether or not and in what manner the binding region might bind to an epitope. Paratope can refer to an antigenic site of an antibody that is responsible for an antibody or fragment thereof, to bind to an antigenic determinant. Paratope also refers to the idiotope of the antibody, and the complementary determining region (CDR) region that binds to the epitope. In one embodiment, the paratope is the region of the antibody that binds to the conformational epitope comprising (i) HER3 amino acid residues 265-277 and 315 (of domain 2), and (ii) HER3 amino acid residues 571, 582-584, 596-597, 600-602, 609-615 (of domain 4) of SEQ ID NO: 1, or a subset thereof. In one embodiment, the paratope is the region of the antibody that comprises the CDR sequences. In one embodiment, the paratope comprises the sequences listed in Table 1. In one embodiment, the paratope comprises at least one amino acid residue that binds with HER3 residues: Asn266, Lys267, Leu268, Thr269, Gln271, Glu273, Pro274, Asn275, Pro276, His277, Asn315, Asp571, Pro583, His584, Ala596, Lys597 (residues of SEQ ID NO: 1). In one embodiment, the paratope comprises at least one amino acid residue that binds with HER3 residues: Tyr265, Lys267, Leu268, Phe270, Gly582, Pro583, Lys597, Ile600, Lys602, Glu609, Arg611, Pro612, Cys613, His614, Glu615 (residues of SEQ ID NO: 1). As will be appreciated by one of skill in the art, the paratope of any antibody, or variant thereof, can be determined in the manner set forth by the present application.

The phrases "monoclonal antibody" or "monoclonal antibody composition" as used herein refers to polypeptides, including antibodies, antibody fragments, bispecific antibodies, etc. that have substantially identical to amino acid sequence or are derived from the same genetic source. This term also includes preparations of antibody molecules of single molecular composition. A monoclonal antibody composition displays a single binding specificity and affinity for a particular epitope.

The phrase "human antibody", as used herein, includes antibodies having variable regions in which both the framework and CDR regions are derived from sequences of human origin. Furthermore, if the antibody contains a constant region, the constant region also is derived from such human sequences, e.g., human germline sequences, or mutated versions of human germline sequences or antibody containing consensus framework sequences derived from human framework sequences analysis, for example, as described in Knappik et al., (2000) J Mol Biol 296:57-86). The structures and locations of immunoglobulin variable domains, e.g., CDRs, may be defined using well known numbering schemes, e.g., the Kabat numbering scheme, the Chothia numbering scheme, or a combination of Kabat and Chothia (see, e.g., Sequences of Proteins of Immunological Interest, U.S. Department of Health and Human Services (1991), eds. Kabat et al.; Lazikani et al., (1997) J. Mol. Bio. 273:927-948); Kabat et al., (1991) Sequences of Proteins of Immunological Interest, 5th edit., NIH Publication no. 91-3242 U.S. Department of Health and Human Services; Chothia et al., (1987) J. Mol. Biol. 196:901-917; Chothia et al., (1989) Nature 342: 877-883; and Al-Lazikani et al., (1997) J. Mol. Biol. 273:927-948.

The human antibodies of the invention may include amino acid residues not encoded by human sequences (e.g., mutations introduced by random or site-specific mutagenesis in vitro or by somatic mutation in vivo, or a conservative substitution to promote stability or manufacturing).

The phrase "human monoclonal antibody" as used herein refers to antibodies displaying a single binding specificity which have variable regions in which both the framework and CDR regions are derived from human sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

The phrase "recombinant human antibody", as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the human antibody, e.g., from a transfectoma, antibodies isolated from a recombinant, combinatorial human antibody library, and antibodies prepared, expressed, created or isolated by any other means that involve splicing of all or a portion of a human immunoglobulin gene, sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

Specific binding between two entities means a binding with an equilibrium constant ($K_A$) ($k_{on}/k_{off}$) of at least $10^2$ $M^{-1}$, at least $5\times10^2 M^{-1}$, at least $10^3 M^{-1}$, at least $5\times10^3 M^{-1}$, at least $10^4 M^{-1}$ at least $5\times10^4 M^{-1}$, at least $10^5 M^{-1}$, at least $5\times10^5 M^{-1}$, at least $10^6 M^{-1}$, at least $5\times10^6 M^{-1}$, at least $10^7$ $M^{-1}$, at least $5\times10^7 M^{-1}$, at least $10^8 M^{-1}$, at least $5\times10^8 M^{-1}$, at least $10^9 M^{-1}$, at least $5\times10^9 M^{-1}$, at least $10^{10} M^{-1}$, at least $5\times10^{10} M^{-1}$, at least $10^{11} M^{-1}$, at least $5\times10^{11} M^{-1}$, at least $10^{12} M^{-1}$, at least $5\times10^{12} M^{-1}$, at least $10^{13} M^{-1}$, at least $5 \times 10^{13}$ M$^{-1}$, at least $10^{14}$M$^{-1}$, at least $5 \times 10^{14}$M$^{-1}$, at least $10^{15}$M$^{-1}$, or at least $5 \times 10^{15}$M$^{-1}$.

The phrase "specifically (or selectively) binds" to an antibody (e.g., a HER3 binding antibody) refers to a binding reaction that is determinative of the presence of a cognate antigen (e.g., a human HER3) in a heterogeneous population of proteins and other biologics. In addition to the equilibrium constant ($K_A$) noted above, an HER3 binding antibody of the invention typically also has a dissociation rate constant ($K_D$) ($k_{off}/k_{on}$) of less than $5 \times 10^{-2}$M, less than $10^{-2}$M, less than $5 \times 10^{-3}$M, less than $10^{-3}$M, less than $5 \times 10^{-4}$M, less than $10^{-4}$M, less than $5 \times 10^{-5}$M, less than $10^{-5}$M, less than $5 \times 10^{-6}$M, less than $10^{-6}$M, less than $5 \times 10^{-7}$M, less than $10^{-7}$M, less than $5 \times 10^{-8}$M, less than $10^{-8}$M, less than $5 \times 10^{-9}$M, less than $10^{-9}$M, less than $5 \times 10^{-10}$M, less than $10^{-10}$M, less than $5 \times 10^{-11}$M, less than $10^{-11}$M, less than $5 \times 10^{-12}$M, less than $10^{-12}$M, less than $5 \times 10^{-13}$M, less than $10^{-13}$M, less than $5 \times 10^{-14}$M, less than $10^{-14}$M, less than $5 \times 10^{-15}$M, or less than $10^{-15}$M or lower, and binds to HER3 with an affinity that is at least two-fold greater than its affinity for binding to a non-specific antigen (e.g., HSA).

In one embodiment, the antibody or fragment thereof has dissociation constant ($K_d$) of less than 3000 pM, less than 2500 pM, less than 2000 pM, less than 1500 pM, less than 1000 pM, less than 750 pM, less than 500 pM, less than 250 pM, less than 200 pM, less than 150 pM, less than 100 pM, less than 75 pM, less than 10 pM, less than 1 pM as assessed using a method described herein or known to one of skill in the art (e.g., a BIAcore assay, ELISA, FACS, SET) (Biacore International AB, Uppsala, Sweden). The term "$K_{asso}$," or "$K_a$", as used herein, refers to the association rate of a particular antibody-antigen interaction, whereas the term "$K_{dis}$" or "$K_d$," as used herein, refers to the dissociation rate of a particular antibody-antigen interaction. The term "$K_D$", as used herein, refers to the dissociation constant, which is obtained from the ratio of $K_d$ to $K_a$ (i.e. $K_d/K_a$) and is expressed as a molar concentration (M). $K_D$ values for antibodies can be determined using methods well established in the art. A method for determining the $K_D$ of an antibody is by using surface plasmon resonance, or using a biosensor system such as a Biacore® system.

The term "affinity" as used herein refers to the strength of interaction between antibody and antigen at single antigenic sites. Within each antigenic site, the variable region of the antibody "arm" interacts through weak non-covalent forces with antigen at numerous sites; the more interactions, the stronger the affinity.

The term "avidity" as used herein refers to an informative measure of the overall stability or strength of the antibody-antigen complex. It is controlled by three major factors: antibody epitope affinity; the valence of both the antigen and antibody; and the structural arrangement of the interacting parts. Ultimately these factors define the specificity of the antibody, that is, the likelihood that the particular antibody is binding to a precise antigen epitope.

The term "valency" as used herein refers to the number of potential target binding sites in a polypeptide. Each target binding site specifically binds one target molecule or specific site (i.e, epitope) on a target molecule. When a polypeptide comprises more than one target binding site, each target binding site may specifically bind the same or different molecules (e.g., may bind to different molecules, e.g., different antigens, or different epitopes on the same molecule).

The phrase "antagonist antibody" as used herein refers to an antibody that binds with HER3 and neutralizes the biological activity of HER3 signaling, e.g., reduces, decreases and/or inhibits HER3 induced signaling activity, e.g., in a phospho-HER3 or phospho-Akt assay. Examples of assays are described in more details in the examples below. Accordingly, an antibody that "inhibits" one or more of these HER3 functional properties (e.g., biochemical, immunochemical, cellular, physiological or other biological activities, or the like) as determined according to methodologies known to the art and described herein, will be understood to relate to a statistically significant decrease in the particular activity relative to that seen in the absence of the antibody (e.g., or when a control antibody of irrelevant specificity is present). An antibody that inhibits HER3 activity effects such a statistically significant decrease by at least 10% of the measured parameter, by at least 50%, 80% or 90%, and in certain embodiments an antibody of the invention may inhibit greater than 95%, 98% or 99% of HER3 functional activity as evidenced by a reduction in the level of cellular HER3 phosphorylation.

The phrase "isolated antibody" refers to an antibody that is substantially free of other antibodies having different antigenic specificities (e.g., an isolated antibody that specifically binds HER3 is substantially free of antibodies that specifically bind antigens other than HER3). An isolated antibody that specifically binds HER3 may, however, have cross-reactivity to other antigens. Moreover, an isolated antibody may be substantially free of other cellular material and/or chemicals.

The phrase "conservatively modified variant" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

For polypeptide sequences, "conservatively modified variants" include individual substitutions, deletions or additions to a polypeptide sequence which result in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. The following eight groups contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). In some embodiments, the term "conservative sequence modifications" are used to refer to amino acid modifications that do not significantly affect or alter the binding characteristics of the antibody containing the amino acid sequence.

The terms "cross-compete" and "cross-competing" are used interchangeably herein to mean the ability of an antibody or other binding agent to interfere with the binding of other antibodies or binding agents to HER3 in a standard competitive binding assay.

The ability or extent to which an antibody or other binding agent is able to interfere with the binding of another antibody or binding molecule to HER3, and therefore whether it can be said to cross-compete according to the invention, can be determined using standard competition binding assays. One suitable assay involves the use of the Biacore technology (e.g. by using the BIAcore 3000 instrument (Biacore, Uppsala, Sweden)), which can measure the extent of interactions using surface plasmon resonance technology. Another assay for measuring cross-competing uses an ELISA-based approach.

The term "optimized" as used herein refers to a nucleotide sequence has been altered to encode an amino acid sequence using codons that are preferred in the production cell or organism, generally a eukaryotic cell, for example, a cell of *Pichia*, a cell of *Trichoderma*, a Chinese Hamster Ovary cell (CHO) or a human cell. The optimized nucleotide sequence is engineered to retain completely or as much as possible the amino acid sequence originally encoded by the starting nucleotide sequence, which is also known as the "parental" sequence.

Standard assays to evaluate the binding ability of the antibodies toward HER3 of various species are known in the art, including for example, ELISAs, western blots and RIAs. Suitable assays are described in detail in the Examples. The binding kinetics (e.g., binding affinity) of the antibodies also can be assessed by standard assays known in the art, such as by Biacore analysis, or FACS relative affinity (Scatchard). Assays to evaluate the effects of the antibodies on functional properties of HER3 (e.g., receptor binding assays, modulating the Her pathway) are described in further detail in the Examples.

The phrases "percent identical" or "percent identity," in the context of two or more nucleic acids or polypeptide sequences, refers to two or more sequences or subsequences that are the same. Two sequences are "substantially identical" if two sequences have a specified percentage of amino acid residues or nucleotides that are the same (i.e., 60% identity, optionally 65%, 70%, 75%, 80%, 85%, 90%, 95%, or 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200 or more amino acids) in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman, (1970) Adv. Appl. Math. 2:482c, by the homology alignment algorithm of Needleman and Wunsch, (1970) J. Mol. Biol. 48:443, by the search for similarity method of Pearson and Lipman, (1988) Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Brent et al., (2003) Current Protocols in Molecular Biology).

Two examples of algorithms that are suitable for determining percent sequence identity and sequence similarity are the BLAST and BLAST 2.0 algorithms, which are described in Altschul et al., (1977) Nuc. Acids Res. 25:3389-3402; and Altschul et al., (1990) J. Mol. Biol. 215:403-410, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff, (1989) Proc. Natl. Acad. Sci. USA 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul, (1993) Proc. Natl. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The percent identity between two amino acid sequences can also be determined using the algorithm of E. Meyers and W. Miller, (1988) Comput. Appl. Biosci. 4:11-17) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (1970) J. Mol. Biol. 48:444-453) algorithm which has been incorporated into the GAP program in the GCG software package (available at www.gcg.com), using either a Blossom 62 matrix or a PAM250 matrix, and a gap weight of 16, 14, 12, 10, 8, 6, or 4 and a length weight of 1, 2, 3, 4, 5, or 6.

Other than percentage of sequence identity noted above, another indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The phrase "nucleic acid" is used herein interchangeably with the term "polynucleotide" and refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, as detailed below, degenerate codon substitutions may be achieved by generating sequences in which the third position of one or more selected (or all) codons is substituted with mixed-base and/or deoxyinosine residues (Batzer et al., (1991) Nucleic Acid Res. 19:5081; Ohtsuka et al., (1985) J. Biol. Chem. 260:2605-2608; and Rossolini et al., (1994) Mol. Cell. Probes 8:91-98).

The phrase "operably linked" refers to a functional relationship between two or more polynucleotide (e.g., DNA) segments. Typically, it refers to the functional relationship of a transcriptional regulatory sequence to a transcribed sequence. For example, a promoter or enhancer sequence is operably linked to a coding sequence if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

The terms "polypeptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Unless otherwise indicated, a particular polypeptide sequence also implicitly encompasses conservatively modified variants thereof.

The term "subject" includes human and non-human animals. Non-human animals include all vertebrates, e.g., mammals and non-mammals, such as non-human primates, sheep, dog, cow, chickens, amphibians, and reptiles. Except when noted, the terms "patient" or "subject" are used herein interchangeably.

The term "anti-cancer agent" means any agent that can be used to treat a cell proliferative disorder such as cancer, including cytotoxic agents, chemotherapeutic agents, radiotherapy and radiotherapeutic agents, targeted anti-cancer agents, and immunotherapeutic agents.

"Tumor" refers to neoplastic cell growth and proliferation, whether malignant or benign, and all pre-cancerous and cancerous cells and tissues.

The term "anti-tumor activity" means a reduction in the rate of tumor cell proliferation, viability, or metastatic activity. A possible way of showing anti-tumor activity is show a decline in growth rate of abnormal cells that arises during therapy or tumor size stability or reduction. Such activity can be assessed using accepted in vitro or in vivo tumor models, including but not limited to xenograft models, allograft models, MMTV models, and other known models known in the art to investigate anti-tumor activity.

The term "malignancy" refers to a non-benign tumor or a cancer. As used herein, the term "cancer" includes a malignancy characterized by deregulated or uncontrolled cell growth. Exemplary cancers include: carcinomas, sarcomas, leukemias, and lymphomas. The term "cancer" includes primary malignant tumors (e.g., those whose cells have not migrated to sites in the subject's body other than the site of the original tumor) and secondary malignant tumors (e.g., those arising from metastasis, the migration of tumor cells to secondary sites that are different from the site of the original tumor).

Various aspects of the invention are described in further detail in the following sections and subsections.

Structure and Mechanism of Activation of the HER Receptors

All four HER receptors have an extracellular ligand-binding domain, a single trans-membrane domain and a cytoplasmic tyrosine kinase-containing domain. The intracellular tyrosine kinase domain of HER receptors is highly conserved, although the kinase domain of HER3 contains substitutions of critical amino acids and therefore lacks kinase activity (Guy et al., (1994): PNAS 91, 8132-8136). Ligand-induced dimerisation of the HER receptors induces activation of the kinase, receptor transphosphorylation on tyrosine residues in the C-terminal tail, followed by recruitment and activation of intracellular signalling effectors (Yarden and Sliwkowski, (2001) Nature Rev 2, 127-137; Jorissen et al., (2003) Exp Cell Res 284, 31-53.

The crystal structures of the extracellular domains of HERs have provided some insight into the process of ligand-induced receptor activation (Schlessinger, (2002) Cell 110, 669-672). The extracellular domain of each HER receptor consists of four subdomains: Subdomain I and III cooperate in forming the ligand-binding site, whereas subdomain II (and perhaps also subdomain IV) participates in receptor dimerisation via direct receptor-receptor interactions. In the structures of ligand-bound HER1, a β hairpin (termed the dimerisation loop) in subdomain II interacts with the dimerisation loop of the partner receptor, mediating receptor dimerisation (Garrett et al, (2002) Cell 110, 763-773; Ogiso et al., (2002) Cell 110, 775-787). In contrast, in the structures of the inactive HER1, HER3 and HER4, the dimerisation loop is engaged in intramolecular interactions with subdomain IV, which prevents receptor dimerisation in the absence of ligand (Cho and Leahy, (2002) Science 297, 1330-1333; Ferguson et al., (2003) Mol Cell 12, 541-552; Bouyan et al., (2005) PNAS102, 15024-15029). The structure of HER2 is unique among the HERs. In the absence of a ligand, HER2 has a conformation that resembles the ligand-activated state of HER1 with a protruding dimerisation loop, available to interact with other HER receptors (Cho et al., (2003) Nature 421, 756-760; Garrett et al., (2003) Mol Cell 11, 495-505). This may explain the enhanced heterodimerisation capacity of HER2.

Although the HER receptor crystal structures provide a model for HER receptor homo- and heterodimerisation, the background for the prevalence of some HER homo- and heterodimers over others (Franklin et al., (2004) Cancer Cell 5, 317-328) as well as the conformational role of each of the domain in receptor dimerisation and autoinhibition (Burgess et al., (2003) Mol Cell 12, 541-552; Mattoon et al., (2004) PNAS101, 923-928) remains somewhat unclear. As described below, the HER3 X-ray crystal structure provides more insights.

HER3 Structure and Conformational Epitopes

A conformational epitope to which antigen binding proteins, e.g., anti-HER3 antibodies bind is provided herein. For the first time, the three dimensional structure of a truncated form (residues 20-640) of the extracellular domain of HER3 complexed with an antibody have been shown. The HER3-MOR09823 Fab complex and the HER3-MOR09825 have been determined at 3.2 Å and 3.4 Å resolution, respectively, and shown in FIG. 5A. The disclosure herein also shows for the first time an antibody or fragment thereof that binds to an inactive state of HER3 and stabilizes the receptor in the inactive state. The antibodies of the invention also permit concurrent binding of a HER3 ligand, such as neuregulin with the HER3 receptor.

Although not bound to provide a theory, one possible model for the mechanism of action is that HER3 typically exists in an inactive (closed, tethered) or active (open) state. Ligand binding induces a conformational change such that HER3 exists in the active (open) state which is capable of binding heterodimer partners resulting in activation in downstream signaling. Antibodies such as MOR09823 bind the inactive (tethered) state of HER3 but do not block the ligand binding site. Antibodies such as MOR09823 inhibit HER3 by preventing the ligand induced structural rearrangements required for HER3 to transition to the active conformation, thereby preventing signal transduction. In one embodiment, the antibodies of the invention or fragments thereof bind the inactive (tethered) state of HER3 but do not block the ligand binding site. In another embodiment, the antibodies or fragments thereof inhibit HER3 by preventing the ligand-induced structural rearrangements required for HER3 to transition to the active conformation, thereby preventing signal transduction. In another embodiment, the antibody or fragment thereof stabilizes (directly maintains, locks, tethers, holds, preferentially binds, or favors) HER3 receptor in the inactive state or conformation. In one embodiment, the inactive HER3 receptor may be susceptible to preferential internalization or degradation such that it leads to loss of cell surface HER3 receptors. The biological data presented in the Examples section supports these embodiments.

The crystals of HER3 may be prepared by expressing a nucleotide sequence encoding HER3 or a variant thereof in a suitable host cell, and then crystallising the purified protein(s) in the presence of the relevant HER3 targeted Fab. Preferably the HER3 polypeptide contains the extracellular domain (amino acids 20 to 640 of the human polypeptide or a truncated version thereof, preferably comprising amino acids 20-640) but lacks the transmembrane and intracellular domains.

HER3 polypeptides may also be produced as fusion proteins, for example to aid in extraction and purification. Examples of fusion protein partners include glutathione-S-transferase (GST), histidine (HIS), hexahistidine (6HIS) (SEQ ID NO: 495), GAL4 (DNA binding and/or transcriptional activation domains) and beta-galactosidase. It may also be convenient to include a proteolytic cleavage site between the fusion protein partner and the protein sequence of interest to allow removal of fusion protein sequences.

After expression, the proteins may be purified and/or concentrated, for example by immobilised metal affinity chromatography, ion-exchange chromatography, and/or gel filtration.

The protein(s) may be crystallised using techniques described herein. Commonly, in a crystallisation process, a drop containing the protein solution is mixed with the crystallisation buffer and allowed to equilibrate in a sealed container. Equilibration may be achieved by known techniques such as the "hanging drop" or the "sitting drop" method. In these methods, the drop is hung above or sitting beside a much larger reservoir of crystallization buffer and equilibration is reached through vapor diffusion. Alternatively, equilibration may occur by other methods, for example under oil, through a semi-permeable membrane, or by free-interface diffusion (See e.g., Chayen et al., (2008) Nature Methods 5, 147-153.

Once the crystals have been obtained, the structure may be solved by known X-ray diffraction techniques. Many techniques use chemically modified crystals, such as those modified by heavy atom derivatization to approximate phases. In practice, a crystal is soaked in a solution containing heavy metal atom salts, or organometallic compounds, e.g., lead chloride, gold thiomalate, thimerosal or uranyl acetate, which can diffuse through the crystal and bind to the surface of the protein. The location(s) of the bound heavy metal atom(s) can then be determined by X-ray diffraction analysis of the soaked crystal. The patterns obtained on diffraction of a monochromatic beam of X-rays by the atoms (scattering centres) of the crystal can be solved by mathematical equations to give mathematical coordinates. The diffraction data are used to calculate an electron density map of the repeating unit of the crystal. Another method of obtaining phase information is using a technique known as molecular replacement. In this method, rotational and translational alogrithms are applied to a search model derived from a related structure, resulting in an approximate orientation for the protein of interest (See Rossmann, (1990) Acta Crystals A 46, 73-82). The electron density maps are used to establish the positions of the individual atoms within the unit cell of the crystal (Blundel et al., (1976) Protein Crystallography, Academic Press).

The present disclosure describes for the first time, the three-dimensional structure of HER3 and a Fab of an anti-HER3 antibody. The approximate domain boundaries of extracellular domain of HER3 are as follows; domain 1: amino acids 20-207; domain 2: amino acids 208-328; domain 3: amino acids 329-498; and domain 4: amino acids 499-642. The three-dimensional structure of HER3 and the antibody also allows the identification of target binding sites for potential HER3 modulators. Preferred target binding sites are those involved in the activation of HER3. In one embodiment, the target binding site is located within domain 2 and domain 4 of HER3. Thus an antibody or fragment thereof which binds to either domain 2 or domain 4, and preferably to both domains can modulate HER3 activation by either preventing the domains from dissociation from each other or by modifying the relative positions of the domains. Thus binding an antibody or fragment thereof to amino acid residues within domain 2 or domain 4 may cause the protein to adopt a conformation that prevents activation. The disclosure herein also shows for the first time an antibody or fragment thereof that can concurrently bind with a HER3 ligand, such as neuregulin.

In some embodiments, the antibody or fragment thereof recognize a specific conformational state of HER3 such that the antibody or fragment thereof prevents HER3 from interacting with a co-receptor (including, but not limited to, HER1, HER2 and HER4). In some embodiments, the antibody or fragment thereof prevents HER3 from interacting with a co-receptor by stabilizing the HER3 receptor in an inactive or closed state. In one embodiment, the antibody or fragment thereof stabilizes the HER3 receptor by binding to amino acid residues within domain 2 and domain 4 of HER3. In this inactive state, the dimerization loop located within domain 2 is not exposed and therefore unavailable for dimerization with other co-receptors (including, but not limited to, HER1, HER2 and HER4). In some embodiments, the antibody or fragment thereof binds to human HER3 protein having a conformational epitope comprising (i) HER3 amino acid residues 265-277 and 315 (of domain 2) and (ii) HER3 amino acid residues 571, 582-584, 596-597, 600-602, 609-615 (of domain 4) of SEQ ID NO: 1, or a subset thereof. In some embodiments, the antibody or fragment thereof binds to amino acids within or overlapping amino acid residues 265-277 and 315 (of domain 2) and (ii) HER3 amino acid residues 571, 582-584, 596-597, 600-602, 609-615 (of domain 4) of SEQ ID NO: 1. In some embodiments, the antibody or fragment thereof binds to amino acids within (and/or amino acid sequences consisting of) amino acids 265-277 and 315 (of domain 2) and (ii) HER3 amino acid residues 571, 582-584, 596-597, 600-602, 609-615 (of domain 4) of SEQ ID NO: 1, or a subset thereof. In some embodiments, the antibody or fragment thereof binds to the conformational epitope such that it restricts the mobility of domain 2 and domain 4, stabilizing it in an inactive or closed conformation. The failure to form the active conformation results in failure to activate signal transduction. In some embodiments, the antibody or fragment thereof binds to the conformational epitope such that it occludes the dimerization loop within domain 2, thereby rendering it unavailable for receptor-receptor interaction. The failure to form homo- or heterodimers results in failure to activate signal transduction.

In another aspect, the antibody or fragment thereof binds a conformational epitope of HER receptor, such as a HER3 receptor. In one embodiment, the antibody or fragment thereof stabilizes the HER3 receptor in the inactive state. In another embodiment, the antibody or fragment thereof binds to the active state of the HER3 receptor and drives it into the inactive state as the inactive state. Thus, the antibody or fragment thereof can bind to either the active or inactive state of HER3, but favors the formation of the inactive state and drives the active state of HER3 into the inactive state, resulting in a failure to activate signal transduction.

In another aspect, the antibody or fragment thereof binds a conformational epitope of HER receptor, such as a HER3 receptor where binding of the antibody or fragment thereof stabilizes the HER3 receptor in an inactive state such that the HER3 receptor fails to dimerize with a co-receptor to form a receptor-receptor complex. The failure to form a receptor-receptor complex prevents activation of both ligand-dependent and ligand-independent signal transduction.

In another aspect, the antibody or fragment thereof binds a conformational epitope of HER receptor such as a HER3 receptor, where binding of the antibody or fragment thereof to the HER3 receptor allows dimerization with a co-receptor to form an inactive receptor-receptor complex. The formation of the inactive receptor-receptor complex prevents activation of ligand-independent signal transduction. For example, in ligand-independent signal transduction, HER3 may exists in an inactive state, however the overexpression of HER2 causes HER2-HER3 complex formation, however these resulting complexes are inactive and prevent activation of ligand-independent signal transduction.

The depicted structure also allows one to identify specific core HER3 amino acid residues for the interaction interface of an antibody or fragment thereof (e.g., MOR09823) with HER3. This was defined as residues that are within 5 Å of the MOR09823 protein VH chain. The core residues are as follows: Asn266, Lys267, Leu268, Thr269, Gln271, Glu273, Pro274, Asn275, Pro276, His277, Asn315, Asp571, Pro583, His584, Ala596, Lys597 (residues of SEQ ID NO: 1).

The structures can also used to identify boundary HER3 amino acid residues for the interaction interface with an antibody or fragment thereof (e.g., MOR09823). These residues can be HER3 residues that were 5-8 Å from the MOR09823 protein VH chain. The boundary residues are as follows: Pro262, Val264, Tyr265, Phe270, Leu272, Thr278, Lys314, Gly316, Glu321, Asn566, Ser568, Gly569, Ser570, Thr572, Arg580, Asp581, Gly582, Gly595, Gly598, Ile600 (residues of SEQ ID NO: 1).

The depicted structure also allows one to identify specific core HER3 amino acid residues for the interaction interface of an antibody or fragment thereof (e.g., MOR09823) with HER3. This was defined as residues that are within 5 Å of the MOR09823 protein VL chain. The core residues are as follows: Tyr265, Lys267, Leu268, Phe270, Gly582, Pro583, Lys597, Ile600, Lys602, Glu609, Arg611, Pro612, Cys613, His614, Glu615 (residues of SEQ ID NO: 1).

The structures were also used to identify boundary HER3 amino acid residues for the interaction interface with an antibody or fragment thereof (e.g., MOR09823). These residues were HER3 residues that were 5-8 Å from the MOR09823 protein VL chain. The boundary residues are as follows: Asn266, Thr269, Asp571, Arg580, Asp581, His584, Pro590, Ala596, Pro599, Tyr601, Tyr603, Asp605, Gln607, Cys610, Asn616, Cys617, Cys621, Gly623, Pro624 (residues of SEQ ID NO: 1).

As can be seen in Tables 11 and 12 (MOR09823) and Tables 13 and 14 (MOR09825), respectively, the heavy chain is mainly involved in the antigen binding protein's binding to amino acid residues within domain 2 of the epitope with fewer interactions with amino acid residues of domain 4, while the light chain is mainly involved with binding to amino acid residues within domain 4 of the epitope with fewer interactions with amino acid residues within domain 2.

As such, one of skill in the art, given the present teachings, can predict which residues and areas of the antigen binding proteins can be varied without unduly interfering with the antigen binding protein's ability to bind to HER3.

Core interaction interface amino acids were determined as being all amino acid residues with at least one atom less than or equal to 5 Å from the HER3 partner protein. 5 Å was chosen as the core region cutoff distance to allow for atoms within a van der Waals radius plus a possible water-mediated hydrogen bond. Boundary interaction interface amino acids were determined as all amino acid residues with at least one atom less than or equal to 8 Å from the HER3 partner protein but not included in the core interaction list.

In some embodiments, any antigen binding protein that binds to, covers, or prevents MOR09823 from interacting with any of the above residues can be employed to bind to or neutralize HER3. In some embodiments, the antibodies or fragments thereof binds to or interacts with at least one of the following HER3 residues (SEQ ID NO: 1): Asn266, Lys267, Leu268, Thr269, Gln271, Glu273, Pro274, Asn275, Pro276, His277, Asn315, Asp571, Pro583, His584, Ala596, Lys597. In some embodiments, the antibodies and fragments thereof binds to or interacts with at least one of the following HER3 residues (SEQ ID NO: 1): Tyr265, Lys267, Leu268, Phe270, Gly582, Pro583, Lys597, Ile600, Lys602, Glu609, Arg611, Pro612, Cys613, His614, Glu615. In some embodiments, the antibodies or fragments thereof binds to or interacts with at least one of the following HER3 residues (SEQ ID NO: 1): Asn266, Lys267, Leu268, Thr269, Gln271, Glu273, Pro274, Asn275, Pro276, His277, Asn315, Asp571, Pro583, His584, Ala596, Lys597, Tyr265, Lys267, Leu268, Phe270, Gly582, Pro583, Lys597, Ile600, Lys602, Glu609, Arg611, Pro612, Cys613, His614, Glu615. In some embodiments, the antibodies or fragments thereof binds to or interacts with a combination of the following HER3 residues (SEQ ID NO: 1): Asn266, Lys267, Leu268, Thr269, Gln271, Glu273, Pro274, Asn275, Pro276, His277, Asn315, Asp571, Pro583, His584, Ala596, Lys597, Tyr265, Lys267, Leu268, Phe270, Gly582, Pro583, Lys597, Ile600, Lys602, Glu609, Arg611, Pro612, Cys613, His614, Glu615. In some embodiments, the antibodies or fragments thereof binds to or interacts with all of the following HER3 residues (SEQ ID NO: 1): Asn266, Lys267, Leu268, Thr269, Gln271, Glu273, Pro274, Asn275, Pro276, His277, Asn315, Asp571, Pro583, His584, Ala596, Lys597, Tyr265, Lys267, Leu268, Phe270, Gly582, Pro583, Lys597, Ile600, Lys602, Glu609, Arg611, Pro612, Cys613, His614, Glu615. In some embodiments, the antibody or fragment thereof is within 5 angstroms of one or more of the above residues. In some embodiments, the antibody or fragment thereof is 5 to 8 angstroms from one or more of the above residues. In some embodiments, the antibody or fragment thereof interacts, blocks, or is within 8 angstroms of 1, 2, 3, 4, 5, 6, 7, 8, 9, 10, 11, 12, 13, 14, 15, 20, 25, 30, 35, 40, 45, or 50 of the above residues.

The availability of 3D structures for the HER3 and the complex of HER3:MOR09823, for example, provides the framework to explore other HER3 antibodies in more detail. The 3D structure of HER3 allows the epitopes for monoclonal antibodies to be mapped and their mode of action inferred, since some inhibit, some stimulate and others have no effect on cell growth. The conformational epitope for MOR09823 has been located to the domains 2 and 4 of HER3. The availability of the 3D structures of this receptor will facilitate the determination of the precise mechanism of action of these inhibitory agents and the design of new approaches to interfering with HER3 receptor function. In one embodiment, the antibodies of the invention bind to the same conformational epitope as MOR09823.

In some embodiments, the conformational epitope bound by any of the antibodies listed in Table 1 is especially useful. In certain embodiments, a HER3 conformational epitope can be utilized to isolate antibodies of fragments thereof that bind to HER3. In certain embodiments, a HER3 conformational epitope can be utilized to generate antibodies or fragments thereof which bind to HER3. In certain embodiments, a HER3 conformational epitope can be utilized as an immunogen to generate antibodies of fragments thereof that bind to the HER3 conformational epitope. In certain embodiments, a HER3 conformational epitope can be administered to an animal, and antibodies that bind to HER3 can subsequently be obtained from the animal.

In some embodiments, the domain(s)/region(s) containing residues that are in contact with or are buried by an antibody can be identified by mutating specific residues in HER3 (e.g., a wild-type antigen) and determining whether antibody or fragment thereof can bind the mutated or variant HER3 protein or measure changes of affinity from wild-type. By making a number of individual mutations, residues that play a direct role in binding or that are in sufficiently close proximity to the antibody such that a mutation can affect binding between the antibody and antigen can be identified. From a knowledge of these amino acids, the domain(s) or region(s) of the antigen (HER3) that contain residues in contact with the antibody or covered by the antibody can be elucidated. Mutagenesis using known techniques such as alanine-scanning can help define functionally relevant epitopes. Mutagenesis utilizing an arginine/glutamic acid scanning protocol can also be employed (see, e.g., Nanevicz et al., (1995), J. Biol. Chem. 270(37):21619-21625 and Zupnick et al., (2006), J. Biol. Chem. 281(29):20464-20473). In general, arginine and glutamic acids are substituted (typically individually) for an amino acid in the wild-type polypeptide because these amino acids are charged and bulky and thus have the potential to disrupt binding between an antigen binding protein and an antigen in the region of the antigen where the mutation is introduced. Arginines that exist in the wild-type antigen are replaced with glutamic acid. A variety of such individual mutants can be obtained and the collected binding results analyzed to determine what residues affect binding. A series of mutant HER3 antigens can be created, with each mutant antigen having a single mutation. Binding of each mutant HER3 antigen with various HER3 antibodies or fragments thereof can be measured and compared to the ability of the selected an antibody or fragments thereof to bind wild-type HER3 (SEQ ID NO: 1).

An alteration (for example a reduction or increase) in binding between an antibody or fragment thereof and a mutant or variant HER3 as used herein means that there is a change in binding affinity (e.g., as measured by known methods such as Biacore testing or the bead based assay described below in the examples), $EC_{50}$, and/or a change (for example a reduction) in the total binding capacity of the antigen binding protein (for example, as evidenced by a decrease in $B_{max}$ in a plot of antigen binding protein concentration versus antigen concentration). A significant alteration in binding indicates that the mutated residue is involved in binding to the antibody or fragment thereof.

In some embodiments, a significant reduction in binding means that the binding affinity, $EC_{50}$, and/or capacity between an antibody or fragments thereof and a mutant HER3 antigen is reduced by greater than 10%, greater than 20%, greater than 40%, greater than 50%, greater than 55%, greater than 60%, greater than 65%, greater than 70%, greater than 75%, greater than 80%, greater than 85%, greater than 90% or greater than 95% relative to binding between the an antibody or fragment thereof and a wild type HER3 (e.g., SEQ ID NO: 1).

In some embodiments, binding of an antibody or fragments thereof is significantly reduced or increased for a mutant HER3 protein having one or more (e.g., 1, 2, 3, 4, 5, 6, 7, 8, 9, 10, or more) mutations as compared to a wild-type HER3 protein (e.g., SEQ ID NO: 1).

Although the variant forms are referenced with respect to the wild-type sequence shown in SEQ ID NO: 1, it will be appreciated that in an allelic or splice variants of HER3 the amino acids could differ. Antibodies or fragments thereof showing significantly altered binding (e.g., lower or higher binding) for such allelic forms of HER3 are also contemplated.

In addition to the general structural aspects of antibodies, the more specific interaction between the paratope and the epitope may be examined through structural approaches. In one embodiment, the structure of the CDRs contribute to a paratope, through which an antibody is able to bind to an epitope. The shape of such a paratope may be determined in a number of ways. Traditional structural examination approaches can be used, such as NMR or x-ray crystallography. These approaches can examine the shape of the paratope alone, or while it is bound to the epitope. Alternatively, molecular models may be generated in silico. A structure can be generated through homology modeling, aided with a commercial package, such as InsightII modeling package from Accelrys (San Diego, Calif.). Briefly, one can use the sequence of the antibody to be examined to search against a database of proteins of known structures, such as the Protein Data Bank. After one identifies homologous proteins with known structures, these homologous proteins are used as modeling templates. Each of the possible templates can be aligned, thus producing structure based sequence alignments among the templates. The sequence of the antibody with the unknown structure can then be aligned with these templates to generate a molecular model for the antibody with the unknown structure. As will be appreciated by one of skill in the art, there are many alternative methods for generating such structures in silico, any of which may be used. For instance, a process similar to the one described in Hardman et al., issued U.S. Pat. No. 5,958,708 employing QUANTA (Polygen Corp., Waltham, Mass.) and CHARM (Brooks et al., (1983), J. Comp. Chem. 4:187) may be used (hereby incorporated in its entirety by reference).

Not only is the shape of the paratope important in determining whether and how well a possible paratope will bind to an epitope, but the interaction itself, between the epitope and the paratope is a source of great information in the design of variant antibodies. As appreciated by one of skill in the art, there are a variety of ways in which this interaction can be studied. One way is to use the structural model generated, perhaps as described above, and then to use a program such as InsightII (Accelrys, San Diego, Calif.), which has a docking module, which, among other things, is capable of performing a Monte Carlo search on the conformational and orientational spaces between the paratope and its epitope. The result is that one is able to estimate where and how the epitope interacts with the paratope. In one embodiment, only a fragment, or variant, of the epitope is used to assist in determining the relevant interactions. In one embodiment, the entire epitope is used in the modeling of the interaction between the paratope and the epitope.

Through the use of these modelled structures, one is able to predict which residues are the most important in the interaction between the epitope and the paratope. Thus, in one embodiment, one is able to readily select which residues to change in order to alter the binding characteristics of the antibody. For instance, it may be apparent from the docking models that the side chains of certain residues in the paratope may sterically hinder the binding of the epitope, thus altering these residues to residues with smaller side chains may be beneficial. One can determine this in many ways. For example, one may simply look at the two models and estimate interactions based on functional groups and proximity. Alternatively, one may perform repeated pairings of epitope and paratope, as described above, in order to obtain more favorable energy interactions. One can also determine these interactions for a variety of variants of the antibody to determine alternative ways in which the antibody may bind to the epitope. One can also combine the various models to determine how one should alter the structure of the antibodies in order to obtain an antibody with the particular characteristics that are desired.

The models determined above can be tested through various techniques. For example, the interaction energy can determined with the programs discussed above in order to determine which of the variants to further examine. Also, coulumbic and van der Waals interactions are used to determine the interaction energies of the epitope and the variant paratopes. Also site directed mutagenesis is used to see if predicted changes in antibody structure actually result in the desired changes in binding characteristics. Alternatively, changes may be made to the epitope to verify that the models are correct or to determine general binding themes that may be occurring between the paratope and the epitope.

As will be appreciated by one of skill in the art, while these models will provide the guidance necessary to make the antibodies and variants thereof of the present embodiments, it may still be desirable to perform routine testing of the in silico models, perhaps through in vitro studies. In addition, as will be apparent to one of skill in the art, any modification may also have additional side effects on the activity of the antibody. For instance, while any alteration predicted to result in greater binding, may induce greater binding, it may also cause other structural changes which might reduce or alter the activity of the antibody. The determination of whether or not this is the case is routine in the art and can be achieved in many ways. For example, the activity can be tested through an ELISA test. Alternatively, the samples can be tested through the use of a surface plasmon resonance device.

HER3 Antibodies

The present invention provides antibodies that recognize a conformational epitope of HER3. The invention is based on the surprising finding that a class of antibodies against HER3, block both ligand-dependent and ligand-independent HER3 signal transduction pathways. A class of antibodies that bind to the particular conformation epitope of HER3 is disclosed in Table 1. In one embodiment, the antibodies inhibit both ligand-dependent and ligand-independent HER3 signalling. In another embodiment, the antibodies bind to HER3 and do not block HER ligand binding to the ligand binding site (i.e. both ligand and antibody can bind HER3 concurrently).

The present invention provides antibodies that specifically bind a HER3 protein (e.g., human and/or cynomologus HER3), said antibodies comprising a VH domain having an amino acid sequence of SEQ ID NO: 15, 33, 51, 69, 87, 105, 123, 141, 159, 177, 195, 213, 231, 249, 267, 285, 303, 321, 339, 357, and 375. The present invention provides antibodies that specifically bind a HER3 protein (e.g., human and/or cynomologus HER3), said antibodies comprising a VL domain having an amino acid sequence of SEQ ID NO: 14, 32, 50, 68, 86, 104, 122, 140, 158, 176, 194, 212, 230, 248, 266, 284, 302, 320, 338, 356, and 374. The present invention also provides antibodies that specifically bind to a HER3 protein (e.g., human and/or cynomologus HER3), said antibodies comprising a VH CDR having an amino acid sequence of any one of the VH CDRs listed in Table 1, infra. In particular, the invention provides antibodies that specifically bind to a HER3 protein (e.g., human and/or cynomologus HER3), said antibodies comprising (or alternatively, consisting of) one, two, three, four, five or more VH CDRs having an amino acid sequence of any of the VH CDRs listed in Table 1, infra.

Other antibodies of the invention include amino acids that have been mutated, yet have at least 60, 70, 80, 90, 95, or 98 percent identity in the CDR regions with the CDR regions depicted in the sequences described in Table 1. In some embodiments, it includes mutant amino acid sequences wherein no more than 1, 2, 3, 4 or 5 amino acids have been mutated in the CDR regions when compared with the CDR regions depicted in the sequence described Table 1, while still maintaining their specificity for the original antibody's epitope Other antibodies of the invention include amino acids that have been mutated, yet have at least 60, 70, 80, 90, 95, or 98 percent identity in the framework regions with the framework regions depicted in the sequences described in Table 1. In some embodiments, it includes mutant amino acid sequences wherein no more than 1, 2, 3, 4, 5, 6, or 7 amino acids have been mutated in the framework regions when compared with the framework regions depicted in the sequence described Table 1, while still maintaining their specificity for the original antibody's epitope. The present invention also provides nucleic acid sequences that encode VH, VL, the full length heavy chain, and the full length light chain of the antibodies that specifically bind to a HER3 protein (e.g., human and/or cynomologus HER3).

The HER3 antibodies of the invention bind to the conformational epitope of HER3 comprising amino acid residues from domain 2 and domain 4 of HER3.

TABLE 1

Examples of HER3 Antibodies of the Present Invention

| SEQ ID NUMBER | Ab region | |
|---|---|---|
| MOR09823 | | |
| SEQ ID NO: 2 (Kabat) | HCDR1 | SYAMS |
| SEQ ID NO: 3 (Kabat) | HCDR2 | VTGAVGRTYYPDSVKG |
| SEQ ID NO: 4 (Kabat) | HCDR3 | WGDEGFDI |
| SEQ ID NO: 5 (Kabat) | LCDR1 | RASQGISNWLA |
| SEQ ID NO: 6 (Kabat) | LCDR2 | GASSLQS |
| SEQ ID NO: 7 (Kabat) | LCDR3 | QQYSSFPTT |
| SEQ ID NO: 8 (Chothia) | HCDR1 | GFTFSSY |
| SEQ ID NO: 9 (Chothia) | HCDR2 | GAVGR |
| SEQ ID NO: 10 (Chothia) | HCDR3 | WGDEGFDI |
| SEQ ID NO: 11 (Chothia) | LCDR1 | SQGISNW |
| SEQ ID NO: 12 (Chothia) | LCDR2 | GAS |
| SEQ ID NO: (Chothia) 13 | LCDR3 | YSSFPT |
| SEQ ID NO: 14 | VL | DIQMTQSPSSLSASVGDRVTITCRASQGISNWLAWYQQKPGKAPKLLIYG ASSLQSGVPSRFSGSGSGTDFILTISSLQPEDFAVYYCQQESSEPTIFGQ GTKVEIK |
| SEQ ID NO: 15 | VH | QVQLVESGGGLVQPGGSLRLSCAASGFTFSSYAMSWVRQAPGKGLEWVSV TGAVGRTYYPDSVKGRFTISRDNSKNTLYLQMNSLRAEDTAVYYCARWGD EGFDIWGQGTLVTVSS |
| SEQ ID NO: 16 | DNA VL | GATATCCAGATGACCCAGAGCCCGTCTAGCCTGAGCGCGAGCGTGGGTGATCGTG TGACCATTACCTGCAGAGCGAGCCAGGGTATTTCTAATTGGCTGGCTTGGTACCA GCAGAAACCAGGTAAAGCACCGAAACTATTAATTTATGGTGCTTCTTCTTTGCAA AGCGGGGTCCCGTCCCGTTTTAGCGGCTCTGGATCCGGCACTGATTTTACCCTGA CCATTAGCAGCCTGCAACCTGAAGACTTTGCGGTTTATTATTGCCAGCAGTATTC TTCTTTTCCTACTACCTTTGGCCAGGGTACGAAAGTTGAAATTAAA |
| SEQ ID NO: 17 | DNA VH | CAGGTGCAATTGGTGGAAAGCGGCGGCGGCCTGGTGCAACCGGGCGGCAGCCTGC GTCTGAGCTGCGCGGCCTCCGGATTTACCTTTAGCAGCTATGCGATGAGCTGGGT GCGCCAAGCCCCTGGGAAGGGTCTCGAGTGGGTGAGCGTTACTGGTGCTGTTGGT CGTACTTATTATCCTGATTCTGTTAAGGGTCGTTTTACCATTTCACGTGATAATT CGAAAAACACCCTGTATCTGCAAATGAACAGCCTGCGTGCGGAAGATACGGCCGT GTATTATTGCGCGCGTTGGGGTGATGAGGGTTTTGATATTTGGGGCCAAGGCACC CTGGTGACGGTTAGCTCA |

TABLE 1-continued

Examples of HER3 Antibodies of the Present Invention

| SEQ ID NUMBER | Ab region | |
|---|---|---|
| SEQ ID NO: 18 | Light Kappa | DIQMTQSPSSLSASVGDRVTITCRASQGISNWLAWYQQKPGKAPKLLIYG ASSLQSGVPSRFSGSGSGTDFTLTISSLQPEDFAVYYCQQYSSFPTTFGQ GTKVEIKRTVAAPSVFIFPPSDEQLKSGTASVVCLLNNFYPREAKVQWKV DNALQSGNSQESVTEQDSKDSTYSLSSTLTLSKADYEKHKVYACEVTHQG LSSPVTKSFNRGEC |
| SEQ ID NO: 19 | Heavy IgG1 | QVQLVESGGGLVQPGGSLRLSCAASGFTFSSYAMSWVRQAPGKGLEWVSV TGAVGRTYYPDSVKGRFTISRDNSKNTLYLQMNSLRAEDTAVYYCARWGD EGFDIWGQGTLVTVSSASTKGPSVFPLAPSSKSTSGGTAALGCLVKDYFP EPVTVSWNSGALTSGVHTFPAVLQSSGLYSLSSVVTVPSSSLGTQTYICN VNHKPSNTKVDKRVEPKSCDKTHTCPPCPAPELLGGPSVFLFPPKPKDTL MISRTPEVTCVVVDVSHEDPEVKFNWYVDGVEVHNAKTKPREEQYNSTYR VVSVLTVLHQDWLNGKEYKCKVSNKALPAPIEKTISKAKGQPREPQVYTL PPSREEMTKNQVSLTCLVKGFYPSDIAVEWESNGQPENNYKTTPPVLDSD GSFFLYSKLTVDKSRWQQGNVFSCSVMHEALHNHYTQKSLSLSPGK |
| MOR09824 | | |
| SEQ ID NO: 20 (Kabat) | HCDR1 | SYAMS |
| SEQ ID NO: 21 (Kabat) | HCDR2 | VISAWGHVKYYADSVKG |
| SEQ ID NO: 22 (Kabat) | HCDR3 | WGDEGFDI |
| SEQ ID NO: 23 (Kabat) | LCDR1 | RASQGISNWLA |
| SEQ ID NO: 24 (Kabat) | LCDR2 | GASSLQS |
| SEQ ID NO: 25 (Kabat) | LCDR3 | QQYSSFPTT |
| SEQ ID NO: 26 (Chothia) | HCDR1 | GFTFSSY |
| SEQ ID NO: 27 (Chothia) | HCDR2 | SAWGHV |
| SEQ ID NO: 28 (Chothia) | HCDR3 | WGDEGFDI |
| SEQ ID NO: 29 (Chothia) | LCDR1 | SQGISNW |
| SEQ ID NO: 30 (Chothia) | LCDR2 | GAS |
| SEQ ID NO: 31 (Chothia) | LCDR3 | YSSFPT |
| SEQ ID NO: 32 | VL | DIQMTQSPSSLSASVGDRVTITCRASQGISNWLAWYQQKPGKAPKLLIYG ASSLQSGVPSRFSGSGSGTDFTLTISSLQPEDFAVYYCQQYSSEPTTFGQ GTKVEIK |
| SEQ ID NO: 33 | VH | QVQLVESGGGLVQPGGSLRLSCAASGFTFSSYAMSWVRQAPGKGLEWVSV ISAWGHVKYYADSVKGRFTISRDNSKNTLYLQMNSLRAEDTAVYYCARWG DEGFDIWGQGTLVTVSS |
| SEQ ID NO: 34 | DNA VL | GATATCCAGATGACCCAGAGCCCGTCTAGCCTGAGCGCGAGCGTGGGTGATCGTG TGACCATTACCTGCAGAGCGAGCCAGGGTATTTCTAATTGGCTGGCTTGGTACCA GCAGAAACCAGGTAAAGCACCGAAACTATTAATTTATGGTGCTTCTTCTTTGCAA AGCGGGGTCCCGTCCCGTTTTAGCGGCTCTGGATCCGGCACTGATTTTACCCTGA CCATTAGCAGCCTGCAACCTGAAGACTTTGCCGGTTTATTATTGCCAGCAGTATTC TTCTTTTCCTACTACCTTTGGCCAGGGTACGAAAGTTGAAATTAAA |
| SEQ ID NO: 35 | DNA VH | CAGGTGCAATTGGTGGAAAGCGGCGGCGGCGGCCTGGTGCAACCGGGCGGCAGCCTGC GTCTGAGCTGCGCGGCCTCCGGATTTACCTTTAGCAGCTATGCGATGAGCTGGGT GCGCCAAGCCCCTGGGAAGGGTCTCGAGTGGGTGAGCGTTATTTCTGCTTGGGGT CATGTTAAGTATTATGCTGATTCTGTTAAGGGTCGTTTTACCATTTCACGTGATA ATTCGAAAAACACCCTGTATCTGCAAATGAACAGCCTGCGTGCGGAAGATACGGC CGTGTATTATTGCGCGCGTTGGGGTGATGAGGGTTTTGATATTTGGGGCCAAGGC ACCCTGGTGACGGTTAGCTCA |
| SEQ ID NO: 36 | Light Kappa | DIQMTQSPSSLSASVGDRVTITCRASQGISNWLAWYQQKPGKAPKLLIYG ASSLQSGVPSRFSGSGSGTDFTLTISSLQPEDFAVYYCQQYSSFPTTFGQ GTKVEIKRTVAAPSVFIFPPSDEQLKSGTASVVCLLNNFYPREAKVQWKV DNALQSGNSQESVTEQDSKDSTASLSSTLTLSKADYEKHKVYACEVTHQG LSSPVTKSFNRGEC |
| SEQ ID NO: 37 | Heavy IgG1 | QVQLVESGGGLVQPGGSLRLSCAASGFTFSSYAMSWVRQAPGKGLEWVSV ISAWGHVKYYADSVKGRFTISRDNSKNTLYLQMNSLRAEDTAVYYCARWG DEGFDIWGQGTLVTVSSASTKGPSVFPLAPSSKSTSGGTAALGCLVKDYF PEPVTVSWNSGALTSGVHTFPAVLQSSGLYSLSSVVTVPSSSLGTQTYIC |

TABLE 1-continued

Examples of HER3 Antibodies of the Present Invention

| SEQ ID NUMBER | Ab region | |
|---|---|---|
| | | NVNHKPSNTKVDKRVEPKSCDKTHTCPPCPAPELLGGPSVFLFPPKPKDT LMISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYT LPPSREEMTKNQVSLTCLVKGFYPSDIAVEWESNGQPENNYKTTPPVLDS DGSFFLYSKLTVDKSRWQQGNVFSCSVMHEALHNHYTQKSLSLSPGK |
| MOR09825 | | |
| SEQ ID NO: 38 (Kabat) | HCDR1 | SYAMS |
| SEQ ID NO: 39 (Kabat) | HCDR2 | AINSQGKSTYYADSVKG |
| SEQ ID NO: 40 (Kabat) | HCDR3 | WGDEGFDI |
| SEQ ID NO: 41 (Kabat) | LCDR1 | RASQGISNWLA |
| SEQ ID NO: 42 (Kabat) | LCDR2 | GASSLQS |
| SEQ ID NO: 43 (Kabat) | LCDR3 | QQYSSFPTT |
| SEQ ID NO: 44 (Chothia) | HCDR1 | GFTFSSY |
| SEQ ID NO: 45 (Chothia) | HCDR2 | NSQGKS |
| SEQ ID NO: 46 (Chothia) | HCDR3 | WGDEGFDI |
| SEQ ID NO: 47 (Chothia) | LCDR1 | SQGISNW |
| SEQ ID NO: 48 (Chothia) | LCDR2 | GAS |
| SEQ ID NO: 49 (Chothia) | LCDR3 | YSSFPT |
| SEQ ID NO: 50 | VL | DIQMTQSPSSLSASVGDRVTITCRASQGISNWLAWYQQKPGKAPKLLIYG ASSLQSGVPSRFSGSGSGTDFTLTISSLQPEDFAVYYCQQYSSEPTTFGQ GTKVEIK |
| SEQ ID NO: 51 | VH | QVQLVESGGGLVQPGGSLRLSCAASGETFSSYAMSWVRQAPGKGLEWVSA INSQGKSTYYADSVKGRFTISRDNSKNTLYLQMNSTRAEDTAVYYCARWG DEGFDIWGQGTLVTVSS |
| SEQ ID NO: 52 | DNA VL | GATATCCAGATGACCCAGAGCCCGTCTAGCCTGAGCGCGAGCGTGGGTGATCGTG TGACCATTACCTGCAGAGCGAGCCAGGGTATTTCTAATTGGCTGGCTTGGTACCA GCAGAAACCAGGTAAAGCACCGAAACTATTAATTTATGGTGCTTCTTCTTTGCAA AGCGGGGTCCCGTCCCGTTTTAGCGGCTCTGGATCCGGCACTGATTTTACCCTGA CCATTAGCAGCCTGCAACCTGAAGACTTTGCGGTTTATTATTGCCAGCAGTATTC TTCTTTTCCTACTACCTTTGGCCAGGGTACGAAAGTTGAAATTAAA |
| SEQ ID NO: 53 | DNA VH | CAGGTGCAATTGGTGGAAAGCGGCGGCGGCCTGGTGCAACCGGGCGGCAGCCTGC GTCTGAGCTGCGCGGCCTCCGGATTTACCTTTAGCAGCTATGCGATGAGCTGGGT GCGCCAAGCCCCTGGGAAGGGTCTCGAGTGGGTGAGCGCTATTAATTCTCAGGGT AAGTCTACTTATTATGCTGATTCTGTTAAGGGTCGTTTTACCATTTCACGTGATA ATTCGAAAAACACCCTGTATCTGCAAATGAACAGCCTGCGTGCGGAAGATACGGC CGTGTATTATTGCGCGCGTTGGGGTGATGAGGGTTTTGATATTTGGGGCCAAGGC ACCCTGGTGACGGTTAGCTCA |
| SEQ ID NO: 54 | Light Kappa | DIQMTQSPSSLSASVGDRVTITCRASQGISNWLAWYQQKPGKAPKLLIYG ASSLQSGVPSRFSGSGSGTDFTLTISSLQPEDFAVYYCQQYSSEPTTFGQ GTKVEIKRTVAAPSVFIFPPSDEQLKSGTASVVCLLNNFYPREAKVQWKV DNALQSGNSQESVTEQDSKDSTYSLSSTLTLSKADYEKHKVYACEVTHQG LSSPVTKSFNRGEC |
| SEQ ID NO: 55 | Heavy IgG1 | QVQLVESGGGLVQPGGSLRLSCAASGFTFSSYAMSWVRQAPGKGLEWVSA INSQGKSTYYADSVKGRFTISRDNSKNTLYLQMNSLRAEDTAVYYCARWG DEGFDIWGQGTLVTVSSASTKGPSVFPLAPSSKSTSGGTAALGCLVKDYF PEPVTVSWNSGALTSGVHTFPAVLQSSGLYSLSSVVTVPSSSLGTQTYIC NVNHKPSNTKVDKRVEPKSCDKTHTCPPCPAPELLGGPSVFLFPPKPKDT LMISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYT LPPSREEMTKNQVSLTCLVKGFYPSDIAVEWESNGQPENNYKTTPPVLDS DGSFFLYSKLTVDKSRWQQGNVFSCSVMHEALHNHYTQKSLSLSPGK |
| MOR09974 | | |
| SEQ ID NO: 56 (Kabat) | HCDR1 | SYAMS |
| SEQ ID NO: 57 (Kabat) | HCDR2 | VINPSGNFTNYADSVKG |

TABLE 1-continued

Examples of HER3 Antibodies of the Present Invention

| SEQ ID NUMBER | Ab region | |
|---|---|---|
| SEQ ID NO: 58 (Kabat) | HCDR3 | WGDEGFDI |
| SEQ ID NO: 59 (Kabat) | LCDR1 | RASQGISNWLA |
| SEQ ID NO: 60 (Kabat) | LCDR2 | GASSLQS |
| SEQ ID NO: 61 (Kabat) | LCDR3 | QQYSSFPTT |
| SEQ ID NO: 62 (Chothia) | HCDR1 | GFTFSSY |
| SEQ ID NO: 63 (Chothia) | HCDR2 | NPSGNF |
| SEQ ID NO: 64 (Chothia) | HCDR3 | WGDEGFDI |
| SEQ ID NO: 65 (Chothia) | LCDR1 | SQGISNW |
| SEQ ID NO: 66 (Chothia) | LCDR2 | GAS |
| SEQ ID NO: 67 (Chothia) | LCDR3 | YSSFPT |
| SEQ ID NO: 68 | VL | DIQMTQSPSSLSASVGDRVTITCRASQGISNWLAWYQQKPGKAPKLLIYG ASSLQSGVPSRFSGSGSGTDFTLTISSLQPEDFAVYYCQQYSSFPTTFGQ GTKVEIK |
| SEQ ID NO: 69 | VH | QVQLVESGGGLVQPGGSLRLSCAASGFTFSSYAMSWVRQAPGKGLEWVSV INPSGNFTNYADSVKGRFTISRDNSKNTLYLQMNSLRAEDTAVYYCARWG DEGFDIWGQGTLVTVSS |
| SEQ ID NO: 70 | DNA VL | GATATCCAGATGACCCAGAGCCCGTCTAGCCTGAGCGCGAGCGTGGGTGATCGTG TGACCATTACCTGCAGAGCGAGCCAGGGTATTTCTAATTGGCTGGCTTGGTACCA GCAGAAACCAGGTAAAGCACCGAAACTATTAATTTATGGTGCTTCTTCTTTGCAA AGCGGGGTCCCGTCCCGTTTTAGCGGCTCTGGATCCGGCACTGATTTTACCCTGA CCATTAGCAGCCTGCAACCTGAAGACTTTGCGGTTTATTATTGCCAGCAGTATTC TTCTTTTCCTACTACCTTTGGCCAGGGTACGAAAGTTGAAATTAAA |
| SEQ ID NO: 71 | DNA VH | CAGGTGCAATTGGTGGAAAGCGGCGGCGGCCTGGTGCAACCGGGCGGCAGCCTGC GTCTGAGCTGCGCGGCCTCCGGATTTACCTTTAGCAGCTATGCGATGAGCTGGGT GCGCCAAGCCCCTGGGAAGGGTCTCGAGTGGGTGAGCGTTATTAATCCTTCTGGT AATTTTACTAATTATGCTGATTCTGTTAAGGGTCGTTTTACCATTTCACGTGATA ATTCGAAAAACACCCTGTATCTGCAAATGAACAGCCTGCGTGCGGAAGATACGGC CGTGTATTATTGCGCGCGTTGGGGTGATGAGGGTTTTGATATTTGGGGCCAAGGC ACCCTGGTGACGGTTAGCTCA |
| SEQ ID NO: 72 | Light Kappa | DIQMTQSPSSLSASVGDRVTITCRASQGISNWLAWYQQKPGKAPKLLIYG ASSLQSGVPSRFSGSGSGTDFTLTISSLQPEDFAVYYCQQYSSFPTTFGQ GTKVEIKRTVAAPSVFIFPPSDEQLKSGTASVVCLLNNFYPREAKVQWKV DNALQSGNSQESVTEQDSKDSTYSLSSTLTLSKADYEKHKVYACEVTHQG LSSPVTKSFNRGEC |
| SEQ ID NO: 73 | Heavy IgG1 | QVQLVESGGGLVQPGGSLRLSCAASGFTFSSYAMSWVRQAPGKGLEWVSV INPSGNFTNYADSVKGRFTISRDNSKNTLYLQMNSLRAEDTAVYYCARWG DEGFDIWGQGTLVTVSSASTKGPSVFPLAPSSKSTSGGTAALGCLVKDYF PEPVTVSWNSGALTSGVHTFPAVLQSSGLYSLSSVVTVPSSSLGTQTYIC NVNHKPSNTKVDKRVEPKSCDKTHTCPPCPAPELLGGPSVFLFPPKPKDT LMISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYT LPPSREEMTKNQVSLTCLVKGFYPSDIAVEWESNGQPENNYKTTPPVLDS DGSFFLYSKLTVDKSRWQQGNVFSCSVMHEALHNHYTQKSLSLSPGK |
| MOR10452 | | |
| SEQ ID NO: 74 (Kabat) | HCDR1 | SYAMS |
| SEQ ID NO: 75 (Kabat) | HCDR2 | NTSPIGYTYYAGSVKG |
| SEQ ID NO: 76 (Kabat) | HCDR3 | WGDEGFDI |
| SEQ ID NO: 77 (Kabat) | LCDR1 | RASQGISNWLA |
| SEQ ID NO: 78 (Kabat) | LCDR2 | GASSLQS |
| SEQ ID NO: 79 (Kabat) | LCDR3 | QQYSSFPTT |
| SEQ ID NO: 80 (Chothia) | HCDR1 | GFTFSSY |
| SEQ ID NO: 81 (Chothia) | HCDR2 | SPIGY |

TABLE 1-continued

Examples of HER3 Antibodies of the Present Invention

| SEQ ID NUMBER | Ab region | |
|---|---|---|
| SEQ ID NO: 82 (Chothia) | HCDR3 | WGDEGFDI |
| SEQ ID NO: 83 (Chothia) | LCDR1 | SQGISNW |
| SEQ ID NO: 84 (Chothia) | LCDR2 | GAS |
| SEQ ID NO: 85 (Chothia) | LCDR3 | YSSFPT |
| SEQ ID NO: 86 | VL | DIQMTQSPSSLSASVGDRVTITCRASQGISNWLAWYQQKPGKAPKLLIYG ASSLQSGVPSRFSGSGSGTDFTLTISSLQPEDFAVYYCQQYSSFPTTFGQ GTKVEIK |
| SEQ ID NO: 87 | VH | QVQLVESGGGLVQPGGSLRLSCAASGFTFSSYAMSWVRQAPGKGLEWVSN TSPIGYTYYAGSVKGRFTISRDNSKNTLYLQMNSLRAEDTAVYYCARWGD EGFDIWGQGTLVTVSS |
| SEQ ID NO: 88 | DNA VL | GATATCCAGATGACCCAGAGCCCGTCTAGCCTGAGCGCGAGCGTGGGTGATCGTG TGACCATTACCTGCAGAGCGAGCCAGGGTATTTCTAATTGGCTGGCTTGGTACCA GCAGAAACCAGGTAAAGCACCGAAACTATTAATTTATGGTGCTTCTTCTTTGCAA AGCGGGGTCCCGTCCCGTTTTAGCGGCTCTGGATCCGGCACTGATTTTACCCTGA CCATTAGCAGCCTGCAACCTGAAGACTTTGCGGTTTATTATTGCCAGCAGTATTC TTCTTTTCCTACTACCTTTGGCCAGGGTACGAAAGTTGAAATTAAA |
| SEQ ID NO: 89 | DNA VH | CAGGTGCAATTGGTGGAAAGCGGCGGCGGCCTGGTGCAACCGGGCGGCAGCCTGC GTCTGAGCTGCGCGGCCTCCGGATTTACCTTTAGCAGCTATGCGATGAGCTGGGT GCGCCAAGCCCCTGGGAAGGGTCTCGAGTGGGTGAGCAATACTTCTCCTATTGGT TATACTTATTATGCTGGTTCTGTTAAGGGTCGTTTTACCATTTCACGTGATAATT CGAAAAACACCCTGTATCTGCAAATGAACAGCCTGCGTGCGGAAGATACGGCCGT GTATTATTGCGCGCGTTGGGGTGATGAGGGTTTTGATATTTGGGGCCAAGGCACC CTGGTGACGGTTAGCTCA |
| SEQ ID NO: 90 | Light Kappa | DIQMTQSPSSLSASVGDRVTITCRASQGISNWLAWYQQKPGKAPKLLIYG ASSLQSGVPSRFSGSGSGTDFTLTISSLQPEDFAVYYCQQYSSFPTTFGQ GTKVEIKRTVAAPSVFIFPPSDEQLKSGTASVVCLLNNFYPREAKVQWKV DNALQSGNSQESVTEQDSKDSTYSLSSTLTLSKADYEKHKVYACEVTHQG LSSPVTKSFNRGEA |
| SEQ ID NO: 91 | Heavy Chain (only VH and CH1 domains) | QVQLVESGGGLVQPGGSLRLSCAASGFTFSSYAMSWVRQAPGKGLEWVSN TSPIGYTYYAGSVKGRFTISRDNSKNTLYLQMNSLRAEDTAVYYCARWGD EGFDIWGQGTLVTVSSASTKGPSVFPLAPSSKSTSGGTAALGCLVKDYFP EPVTVSWNSGALTSGVHTFPAVLQSSGLYSLSSVVTVPSSSLGTQTYICN VNHKPSNTKVDKKVEPKS |
| MOR10701 | | |
| SEQ ID NO: 92 (Kabat) | HCDR1 | SYAMS |
| SEQ ID NO: 93 (Kabat) | HCDR2 | VTGAVGRSTYYPDSVKG |
| SEQ ID NO: 94 (Kabat) | HCDR3 | WGDEGFDI |
| SEQ ID NO: 95 (Kabat) | LCDR1 | RASQGISNWLA |
| SEQ ID NO: 96 (Kabat) | LCDR2 | GASSLQS |
| SEQ ID NO: 97 (Kabat) | LCDR3 | QQYSSFPTT |
| SEQ ID NO: 98 (Chothia) | HCDR1 | GFTFSSY |
| SEQ ID NO: 99 (Chothia) | HCDR2 | GAVGRS |
| SEQ ID NO: 100 (Chothia) | HCDR3 | WGDEGFDI |
| SEQ ID NO: 101 (Chothia) | LCDR1 | SQGISNW |
| SEQ ID NO: 102 (Chothia) | LCDR2 | GAS |
| SEQ ID NO: 103 (Chothia) | LCDR3 | YSSFPT |
| SEQ ID NO: 104 | VL | DIQMTQSPSSLSASVGDRVTITCRASQGISNWLAWYQQKPGKAPKLLIYG ASSLQSGVPSRFSGSGSGTDFTLTISSLQPEDFATYYCQQYSSFPTTFGQ GTKVEIK |
| SEQ ID NO: 105 | VH | EVQLLESGGGLVQPGGSLRLSCAASGFTFSSYAMSWVRQAPGKGLEWVSV TGAVGRSTYYPDSVKGRFTISRDNSKNTLYLQMNSLRAEDTAVYYCARWG DEGFDIWGQGTLVTVSS |

TABLE 1-continued

Examples of HER3 Antibodies of the Present Invention

| SEQ ID NUMBER | Ab region | |
|---|---|---|
| SEQ ID NO: 106 | DNA VL | GATATCCAGATGACCCAGAGCCCCAGCAGCCTGAGCGCCAGCGTGGGCGACAGAG<br>TGACCATCACCTGTCGGGCCAGCCAGGGCATCAGCAACTGGCTGGCCTGGTATCA<br>GCAGAAGCCCGGCAAGGCCCCCAAGCTGCTGATCTACGGCGCCAGCTCCCTGCAG<br>AGCGGCGTGCCAAGCAGATTCAGCGGCAGCGGCTCCGGCACCGACTTCACCCTGA<br>CCATCAGCAGCCTGCAGCCCGAGGACTTCGCCACCTACTACTGCCAGCAGTACAG<br>CAGCTTCCCCACCACCTTCGGCCAGGGCACCAAGGTGGAAATCAAG |
| SEQ ID NO: 107 | DNA VH | GAGGTGCAATTGCTGGAAAGCGGCGGAGGCCTGGTGCAGCCTGGCGGCAGCCTGA<br>GACTGTCTTGCGCCGCCAGCGGCTTCACCTTCAGCAGCTACGCCATGAGCTGGGT<br>CCGCCAGGCCCCTGGCAAGGGACTGGAATGGGTGTCCGTGACAGGCGCCGTGGGC<br>AGAAGCACCTACTACCCCGACAGCGTGAAGGGCCGGTTCACCATCAGCCGGGACA<br>ACAGCAAGAACACCCTGTACCTGCAGATGAACAGCCTGCGGGCCGAGGACACCGC<br>CGTGTACTACTGTGCCAGATGGGGCGACGAGGGCTTCGACATCTGGGGCCAGGGC<br>ACCCTGGTCACCGTCAGCTCA |
| SEQ ID NO: 108 | Light Kappa | DIQMTQSPSSLSASVGDRVTITCRASQGISNWLAWYQQKPGKAPKLLIYG<br>ASSLQSGVPSRFSGSGSGTDFTLTISSLQPEDFATYYCQQYSSFPTTFGQ<br>GTKVEIKRTVAAPSVFIFPPSDEQLKSGTASVVCLLNNFYPREAKVQWKV<br>DNALQSGNSQESVTEQDSKDSTYSLSSTLTLSKADYEKHKVYACEVTHQG<br>LSSPVTKSFNRGEC |
| SEQ ID NO: 109 | Heavy IgG1 | EVQLLESGGGLVQPGGSLRLSCAASGFTFSSYAMSWVRQAPGKGLEWVSV<br>TGAVGRSTYYPDSVKGRFTISRDNSKNTLYLQMNSLRAEDTAVYYCARWG<br>DEGFDIWGQGTLVTVSSASTKGPSVFPLAPSSKSTSGGTAALGCLVKDYF<br>PEPVTVSWNSGALTSGVHTFPAVLQSSGLYSLSSVVTVPSSSLGTQTYIC<br>NVNHKPSNTKVDKRVEPKSCDKTHTCPPCPAPELLGGPSVFLFPPKPKDT<br>LMISRTPEVTCVVVDVSHEDPEVKFNWYVDGVEVHNAKTKPREEQYNSTY<br>RVVSVLTVLHQDWLNGKEYKCKVSNKALPAPIEKTISKAKGQPREPQVYT<br>LPPSREEMTKNQVSLTCLVKGFYPSDIAVEWESNGQPENNYKTTPPVLDS<br>DGSFFLYSKLTVDKSRWQQGNVFSCSVMHEALHNHYTQKSLSLSPGK |
| MOR10702 | | |
| SEQ ID NO: 110 (Kabat) | HCDR1 | SYAMS |
| SEQ ID NO: 111 (Kabat) | HCDR2 | VISAWGHVKYYADSVKG |
| SEQ ID NO: 112 (Kabat) | HCDR3 | WGDEGFDI |
| SEQ ID NO: 113 (Kabat) | LCDR1 | RASQGISNWLA |
| SEQ ID NO: 114 (Kabat) | LCDR2 | GASSLQS |
| SEQ ID NO: 115 (Kabat) | LCDR3 | QQYSSFPTT |
| SEQ ID NO: 116 (Chothia) | HCDR1 | GFTFSSY |
| SEQ ID NO: 117 (Chothia) | HCDR2 | SAWGHV |
| SEQ ID NO: 118 (Chothia) | HCDR3 | WGDEGFDI |
| SEQ ID NO: 119 (Chothia) | LCDR1 | SQGISNW |
| SEQ ID NO: 120 (Chothia) | LCDR2 | GAS |
| SEQ ID NO: 121 (Chothia) | LCDR3 | YSSFPT |
| SEQ ID NO: 122 | VL | DIQMTQSPSSLSASVGDRVTITCRASQGISNWLAWYQQKPGKAPKLLIYG<br>ASSLQSGVPSRFSGSGSGTDFTLTISSLQPEDFATYYCQQYSSFPTTFGQ<br>GTKVEIK |
| SEQ ID NO: 123 | VH | EVQLLESGGGLVQPGGSLRLSCAASGFTFSSYAMSWVRQAPGKGLEWVSV<br>ISAWGHVKYYADSVKGRFTISRDNSKNTLYLQMNSLRAEDTAVYYCARWG<br>DEGFDIWGQGTLVTVSS |
| SEQ ID NO: 124 | DNA VL | GATATCCAGATGACCCAGAGCCCCAGCAGCCTGAGCGCCAGCGTGGGCGACAGAG<br>TGACCATCACCTGTCGGGCCAGCCAGGGCATCAGCAACTGGCTGGCCTGGTATCA<br>GCAGAAGCCCGGCAAGGCCCCCAAGCTGCTGATCTACGGCGCCAGCTCCCTGCAG<br>AGCGGCGTGCCAAGCAGATTCAGCGGCAGCGGCTCCGGCACCGACTTCACCCTGA<br>CCATCAGCAGCCTGCAGCCCGAGGACTTCGCCACCTACTACTGCCAGCAGTACAG<br>CAGCTTCCCCACCACCTTCGGCCAGGGCACCAAGGTGGAAATCAAG |
| SEQ ID NO: 125 | DNA VH | GAGGTGCAATTGCTGGAAAGCGGCGGAGGCCTGGTGCAGCCTGGCGGCAGCCTGA<br>GACTGTCTTGCGCCGCCAGCGGCTTCACCTTCAGCAGCTACGCCATGAGCTGGGT<br>CCGCCAGGCCCCTGGCAAGGGACTGGAATGGGTGTCCGTGATCAGCGCCTGGGGC |

TABLE 1-continued

Examples of HER3 Antibodies of the Present Invention

| SEQ ID NUMBER | Ab region | |
|---|---|---|
| | | CACGTGAAGTACTACGCCGACAGCGTGAAGGGCCGGTTCACCATCAGCCGGGACA<br>ACAGCAAGAACACCCTGTACCTGCAGATGAACAGCCTGCGGGCCGAGGACACCGC<br>CGTGTACTACTGTGCCAGATGGGGCGACGAGGGCTTCGACATCTGGGGCCAGGGC<br>ACCCTGGTCACCGTCAGCTCA |
| SEQ ID NO: 126 | Light Kappa | DIQMTQSPSSLSASVGDRVTITCRASQGISNWLAWYQQKPGKAPKLLIYG<br>ASSLQSGVPSRFSGSGSGTDFTLTISSLQPEDFATYYCQQYSSFPTTFGQ<br>GTKVEIKRTVAAPSVFIFPPSDEQLKSGTASVVCLINNFYPREAKVQWKV<br>DNALQSGNSQESVTEQDSKDSTYSLSSTLTLSKADYEKHKVYACEVTHQG<br>LSSPVTKSFNRGEC |
| SEQ ID NO: 127 | Heavy IgG1 | EVQLLESGGGLVQPGGSLRLSCAASGFTFSSYAMSWVRQAPGKGLEWVSV<br>ISAWGHVKYYADSVKGRFTISRDNSKNTLYLQMNSLRAEDTAVYYCARWG<br>DEGFDIWGQGTLVTVSSASTKGPSVFPLAPSSKSTSGGTAALGCLVKDYF<br>PEPVTVSWNSGALTSGVHTFPAVLQSSGLYSLSSVVTVPSSSLGTQTYIC<br>NVNHKPSNTKVDKRVEPKSCDKTHTCPPCPAPELLGGPSVFLFPPKPKDT<br>LMISRTPEVTCVVVDVSHEDPEVKFNWYVDGVEVHNAKTKPREEQYNSTY<br>RVVSVLTVLHQDWLNGKEYKCKVSNKALPAPIEKTISKAKGQPREPQVYT<br>LPPSREEMTKNQVSLTCLVKGFYPSDIAVEWESNGQPENNYKTTPPVLDS<br>DGSFFLYSKLTVDKSRWQQGNVFSCSVMHEALHNHYTQKSLSLSPGK |
| MOR10703 | | |
| SEQ ID NO: 128 (Kabat) | HCDR1 | SYAMS |
| SEQ ID NO: 129 (Kabat) | HCDR2 | AINSQGKSTYYADSVKG |
| SEQ ID NO: 130 (Kabat) | HCDR3 | WGDEGFDI |
| SEQ ID NO: 131 (Kabat) | LCDR1 | RASQGISNWLA |
| SEQ ID NO: 132 (Kabat) | LCDR2 | GASSLQS |
| SEQ ID NO: 133 (Kabat) | LCDR3 | QQYSSFPTT |
| SEQ ID NO: 134 (Chothia) | HCDR1 | GFTFSSY |
| SEQ ID NO: 135 (Chothia) | HCDR2 | NSQGKS |
| SEQ ID NO: 136 (Chothia) | HCDR3 | WGDEGFDI |
| SEQ ID NO: 137 (Chothia) | LCDR1 | SQGISNW |
| SEQ ID NO: 138 (Chothia) | LCDR2 | GAS |
| SEQ ID NO: 139 (Chothia) | LCDR3 | YSSFPT |
| SEQ ID NO: 140 | VL | DIQMTQSPSSLSASVGDRVTITCRASQGISNWLAWYQQKPGKAPKLLIYG<br>ASSLQSGVPSRFSGSGSGTDFTLTISSLQPEDFATYYCQQYSSFPTTFGQ<br>GTKVEIK |
| SEQ ID NO: 141 | VH | EVQLLESGGGLVQPGGSLRLSCAASGETFSSYAMSWVRQAPGKGLEWVSA<br>INSQGKSTYYADSVKGRFTISRDNSKNTLYLQMNSLRAEDTAVYYCARWG<br>DEGFDIWGQGTLVTVSS |
| SEQ ID NO: 142 | DNA VL | GATATCCAGATGACCCAGAGCCCCAGCAGCCTGAGCGCCAGCGTGGGCGACAGAG<br>TGACCATCACCTGTCGGGCCAGCCAGGGCATCAGCAACTGGCTGGCCTGGTATCA<br>GCAGAAGCCCGGCAAGGCCCCCAAGCTGCTGATCTACGGCGCCAGCTCCCTGCAG<br>AGCGGCGTGCCAAGCAGATTCAGCGGCAGCGGCTCCGGCACCGACTTCACCCTGA<br>CCATCAGCAGCCTGCAGCCCGAGGACTTCGCCACCTACTACTGCCAGCAGTACAG<br>CAGCTTCCCCACCACCTTCGGCCAGGGCACCAAGGTGGAAATCAAG |
| SEQ ID NO: 143 | DNA VH | GAGGTGCAATTGCTGGAAAGCGGCGGAGGCCTGGTGCAGCCTGGCGGCAGCCTGA<br>GACTGTCTTGCGCCGCCAGCGGCTTCACCTTCAGCAGCTACGCCATGAGCTGGGT<br>CCGCCAGGCCCCTGGCAAGGGACTGGAATGGGTGTCCGCCATCAACAGCCAGGGC<br>AAGAGCACCTACTACGCCGACAGCGTGAAGGGCCGGTTCACCATCAGCCGGGACA<br>ACAGCAAGAACACCCTGTACCTGCAGATGAACAGCCTGCGGGCCGAGGACACCGC<br>CGTGTACTACTGTGCCAGATGGGGCGACGAGGGCTTCGACATCTGGGGCCAGGGC<br>ACCCTGGTCACCGTCAGCTCA |
| SEQ ID NO: 144 | Light Kappa | DIQMTQSPSSLSASVGDRVTITCRASQGISNWLAWYQQKPGKAPKLLIYG<br>ASSLQSGVPSRFSGSGSGTDFTLTISSLQPEDFATYYCQQYSSFPTTFGQ<br>GTKVEIKRTVAAPSVFIFPPSDEQLKSGTASVVCLINNFYPREAKVQWKV<br>DNALQSGNSQESVTEQDSKDSTYSLSSTLTLSKADYEKHKVYACEVTHQG<br>LSSPVTKSFNRGEC |

TABLE 1-continued

Examples of HER3 Antibodies of the Present Invention

| SEQ ID NUMBER | Ab region | |
|---|---|---|
| SEQ ID NO: 145 | Heavy IgG1 | EVQLLESGGGLVQPGGSLRLSCAASGFTFSSYAMSWVRQAPGKGLEWVSA<br>INSQGKSTYYADSVKGRFTISRDNSKNTLYLQMNSTRAEDTAVYYCARWG<br>DEGFDIWGQGTLVTVSSASTKGPSVFPLAPSSKSTSGGTAALGCLVKDYF<br>PEPVTVSWNSGALTSGVHTFPAVLQSSGLYSLSSVVTVPSSSLGTQTYIC<br>NVNHKPSNTKVDKRVEPKSCDKTHTCPPCPAPELLGGPSVFLFPPKPKDT<br>LMISRTPEVTCVVVDVSHEDPEVKFNWYVDGVEVHNAKTKPREEQYNSTY<br>RVVSVLTVLHQDWLNGKEYKCKVSNKALPAPIEKTISKAKGQPREPQVYT<br>LPPSREEMTKNQVSLTCLVKGFYPSDIAVEWESNGQPENNYKTTPPVLDS<br>DGSFFLYSKLTVDKSRWQQGNVFSCSVMHEALHNHYTQKSLSLSPGK |
| MOR10703 N52S | | |
| SEQ ID NO: 146 (Kabat) | HCDR1 | SYAMS |
| SEQ ID NO: 147 (Kabat) | HCDR2 | AISSQGKSTYYADSVKG |
| SEQ ID NO: 148 (Kabat) | HCDR3 | WGDEGFDI |
| SEQ ID NO: 149 (Kabat) | LCDR1 | RASQGISNWLA |
| SEQ ID NO: 150 (Kabat) | LCDR2 | GASSLQS |
| SEQ ID NO: 151 (Kabat) | LCDR3 | QQYSSFPTT |
| SEQ ID NO: 152 (Chothia) | HCDR1 | GFTFSSY |
| SEQ ID NO: 153 (Chothia) | HCDR2 | SSQGKS |
| SEQ ID NO: 154 (Chothia) | HCDR3 | WGDEGFDI |
| SEQ ID NO: 155 (Chothia) | LCDR1 | SQGISNW |
| SEQ ID NO: 156 (Chothia) | LCDR2 | GAS |
| SEQ ID NO: 157 (Chothia) | LCDR3 | YSSFPT |
| SEQ ID NO: 158 | VL | DIQMTQSPSSLSASVGDRVTITCRASQGISNWLAWYQQKPGKAPkLLIYGASSLQ<br>SGVPSRFSGSGSGTDFTLTISSLQPEDFATYYCQQYSSFPTTFGQGTKVEIK |
| SEQ ID NO: 159 | VH | EVQLLESGGGLVQPGGSLRLSCAASGFTFSSYAMSWVRQAPGKGLEWVSAISSQG<br>KSTYYADSVKGRFTISRDNSKNTLYLQMNSLRAEDTAVYYCARWGDEGFDIWGQG<br>TLVTVSS |
| SEQ ID NO: 160 | DNA VL | GATATCCAGATGACCCAGAGCCCCAGCAGCCTGAGCGCCAGCGTGGGCGACAGAG<br>TGACCATCACCTGTCGGGCCAGCCAGGGCATCAGCAACTGGCTGGCCTGGTATCA<br>GCAGAAGCCCGGCAAGGCCCCCAAGCTGCTGATCTACGGCGCCAGCTCCCTGCAG<br>AGCGGCGTGCCAAGCAGATTCAGCGGCAGCGGCTCCGGCACCGACTTCACCCTGA<br>CCATCAGCAGCCTGCAGCCCGAGGACTTCGCCACCTACTACTGCCAGCAGTACAG<br>CAGCTTCCCCACCACCTTCGGCCAGGGCACCAAGGTGGAAATCAAG |
| SEQ ID NO: 161 | DNA VH | GAGGTGCAATTGCTGGAAAGCGGCGGAGGCCTGGTGCAGCCTGGCGGCAGCCTGA<br>GACTGTCTTGCGCCGCCAGCGGCTTCACCTTCAGCAGCTACGCCATGAGCTGGGT<br>CCGCCAGGCCCCTGGCAAGGGACTGGAATGGGTGTCCGCCATCAGCAGCCAGGGC<br>AAGAGCACCTACTACGCCGACAGCGTGAAGGGCCGGTTCACCATCAGCCGGGACA<br>ACAGCAAGAACACCCTGTACCTGCAGATGAACAGCCTGCGGGCCGAGGACACCGC<br>CGTGTACTACTGTGCCAGATGGGGCGACGAGGGCTTCGACATCTGGGGCCAGGGC<br>ACCCTGGTCACCGTCAGCTCA |
| SEQ ID NO: 162 | Light Kappa | DIQMTQSPSSLSASVGDRVTITCRASQGISNWLAWYQQKPGKAPKLLIYGASSLQ<br>SGVPSRFSGSGSGTDFTLTISSLQPEDFATYYCQQYSSFPTTFGQGTKVEIKRTV<br>AAPSVFIFPPSDEQLKSGTASVVCLLNNFYPREAKVQWEVDNALQSGNSQESVTE<br>QDSKDSTYSLSSTLTLSKADYEKHKVYACEVTHQGLSSPVTKSFNRGEC |
| SEQ ID NO: 163 | Heavy IgG1 | EVQLLESGGGLVQPGGSLRLSCAASGFTFSSYAMSWVRQAPGKGLEWVSAISSQG<br>KSTYYADSVKGRFTISRDNSKNTLYLQMNSLRAEDTAVYYCARWGDEGFDIWGQG<br>TLVTVSSASTKGPSVFPLAPSSKSTSGGTAALGCLVKDYFPEPVTVSWNSGALTS<br>GVHTFPAVLQSSGLYSLSSVVTVPSSSLGTQTYICNVNHKPSNTKVDKRVEPKSC<br>DKTHTCPPCPAPELLGGPSVFLFPPKPKDTLMISRTPEVTCVVVDVSHEDPEVEF<br>NWYVDGVEVHNAKTKPREEQYNSTYRVVSVLTVLHQDWLNGKEYKCKVSNKALPA<br>PIEKTISKAKGQPREPQVYTLPPSREEMTKNQVSLTCLVKGFYPSDIAVEWESNG<br>QPENNYKTTPPVLDSDGSFFLYSKLTVDKSRWQQGNVFSCSVMHEALHNHYTQKS<br>LSLSPGK |

TABLE 1-continued

Examples of HER3 Antibodies of the Present Invention

| SEQ ID NUMBER | Ab region | |
|---|---|---|
| MOR10703 N52G | | |
| SEQ ID NO: 164 (Kabat) | HCDR1 | SYAMS |
| SEQ ID NO: 165 (Kabat) | HCDR2 | AIGSQGKSTYYADSVKG |
| SEQ ID NO: 166 (Kabat) | HCDR3 | WGDEGFDI |
| SEQ ID NO: 167 (Kabat) | LCDR1 | RASQGISNWLA |
| SEQ ID NO: 168 (Kabat) | LCDR2 | GASSLQS |
| SEQ ID NO: 169 (Kabat) | LCDR3 | QQYSSFPTT |
| SEQ ID NO: 170 (Chothia) | HCDR1 | GFTFSSY |
| SEQ ID NO: 171 (Chothia) | HCDR2 | GSQGKS |
| SEQ ID NO: 172 (Chothia) | HCDR3 | WGDEGFDI |
| SEQ ID NO: 173 (Chothia) | LCDR1 | SQGISNW |
| SEQ ID NO: 174 (Chothia) | LCDR2 | GAS |
| SEQ ID NO: 175 (Chothia) | LCDR3 | YSSFPT |
| SEQ ID NO: 176 | VL | DIQMTQSPSSLSASVGDRVTITCRASQGISNWLAWYQQKPGKAPELLIYGASSLQ SGVPSRFSGSGSGTDFTLTISSLQPEDFATYYCQQYSSFPTTFGQGTKVEIK |
| SEQ ID NO: 177 | VH | EVQLLESGGGLVQPGGSLRLSCAASGFTFSSYAMSWVRQAPGKGLEWVSAIGSQG KSTYYADSVKGRFTISRDNSENTLYLQMNSLRAEDTAVYYCARWGDEGFDIWGQG TLVTVSS |
| SEQ ID NO: 178 | DNA VL | GATATCCAGATGACCCAGAGCCCCAGCAGCCTGAGCGCCAGCGTGGGCGACAGAG TGACCATCACCTGTCGGGCCAGCCAGGGCATCAGCAACTGGCTGGCCTGGTATCA GCAGAAGCCCGGCAAGGCCCCCAAGCTGCTGATCTACGGCGCCAGCTCCCTGCAG AGCGGCGTGCCAAGCAGATTCAGCGGCAGCGGCTCCGGCACCGACTTCACCCTGA CCATCAGCAGCCTGCAGCCCGAGGACTTCGCCACCTACTACTGCCAGCAGTACAG CAGCTTCCCCACCACCTTCGGCCAGGGCACCAAGGTGGAAATCAAG |
| SEQ ID NO: 179 | DNA VH | GAGGTGCAATTGCTGGAAAGCGGCGGAGGCCTGGTGCAGCCTGGCGGCAGCCTGA GACTGTCTTGCGCCGCCAGCGGCTTCACCTTCAGCAGCTACGCCATGAGCTGGGT CCGCCAGGCCCCTGGCAAGGGACTGGAATGGGTGTCCGCCATCGGCAGCCAGGGC AAGAGCACCTACTACGCCGACAGCGTGAAGGGCCGGTTCACCATCAGCCGGGACA ACAGCAAGAACACCCTGTACCTGCAGATGAACAGCCTGCGGGCCGAGGACACCGC CGTGTACTACTGTGCCAGATGGGGCGACGAGGGCTTCGACATCTGGGGCCAGGGC ACCCTGGTCACCGTCAGCTCA |
| SEQ ID NO: 180 | Light Kappa | DIQMTQSPSSLSASVGDRVTITCRASQGISNWLAWYQQKPGKAPKLLIYGASSLQ SGVPSRFSGSGSGTDFTLTISSLQPEDFATYYCQQYSSFPTTFGQGTKVEIKRTV AAPSVFIFPPSDEQLKSGTASVVCLLNNFYPREAKVQWKVDNALQSGNSQESVTE QDSKDSTYSLSSTLTLSKADYEKHKVYACEVTHQGLSSPVTKSFNRGEC |
| SEQ ID NO: 181 | Heavy IgG1 | EVQLLESGGGLVQPGGSLRLSCAASGFTFSSYAMSWVRQAPGKGLEWVSAIGSQG KSTYYADSVKGRFTISRDNSKNTLYLQMNSLRAEDTAVYYCARWGDEGFDIWGQG TLVTVSSASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDKRVEPKSC DKTHTCPPCPAPELLGGPSVFLFPPKPKDTLMISRTPEVTCVVVDVSHEDPEVKF NWYVDGVEVHNAKTKPREEQYNSTYRVVSVLTVLHQDWLNGKEYKCKVSNKALPA PIEKTISKAKGQPREPQVYTLPPSREEMTKNQVSLTCLVKGFYPSDIAVEWESNG QPENNYKTTPPVLDSDGSFFLYSKLTVDKSRWQQGNVFSCSVMHEALHNHYTQKS LSLSPGK |
| MOR10703 N52S_S52aN | | |
| SEQ ID NO: 182 (Kabat) | HCDR1 | SYAMS |
| SEQ ID NO: 183 (Kabat) | HCDR2 | AISNQGKSTYYADSVKG |
| SEQ ID NO: 184 (Kabat) | HCDR3 | WGDEGFDI |
| SEQ ID NO: 185 (Kabat) | LCDR1 | RASQGISNWLA |
| SEQ ID NO: 186 (Kabat) | LCDR2 | GASSLQS |
| SEQ ID NO: 187 (Kabat) | LCDR3 | QQYSSFPTT |

TABLE 1-continued

Examples of HER3 Antibodies of the Present Invention

| SEQ ID NUMBER | | Ab region | |
|---|---|---|---|
| SEQ ID NO: 188 (Chothia) | | HCDR1 | GFTFSSY |
| SEQ ID NO: 189 (Chothia) | | HCDR2 | SNQGKS |
| SEQ ID NO: 190 (Chothia) | | HCDR3 | WGDEGFDI |
| SEQ ID NO: 191 (Chothia) | | LCDR1 | SQGISNW |
| SEQ ID NO: 192 (Chothia) | | LCDR2 | GAS |
| SEQ ID NO: 193 (Chothia) | | LCDR3 | YSSFPT |
| SEQ ID NO: 194 | | VL | DIQMTQSPSSLSASVGDRVTITCRASQGISNWLAWYQQKPGKAPKLLIYGASSLQ SGVPSRFSGSGSGTDFTLTISSLQPEDFATYYCQQYSSFPTTFGQGTKVEIK |
| SEQ ID NO: 195 | | VH | EVQLLESGGGLVQPGGSLRLSCAASGFTFSSYAMSWVRQAPGKGLEWVSAISNQG KSTYYADSVKGRFTISRDNSKNTLYLQMNSLRAEDTAVYYCARWGDEGFDIWGQG TLVTVSS |
| SEQ ID NO: 196 | | DNA VL | GATATCCAGATGACCCAGAGCCCCAGCAGCCTGAGCGCCAGCGTGGGCGACAGAG TGACCATCACCTGTCGGGCCAGCCAGGGCATCAGCAACTGGCTGGCCTGGTATCA GCAGAAGCCCGGCAAGGCCCCCAAGCTGCTGATCTACGGCGCCAGCTCCCTGCAG AGCGGCGTGCCAAGCAGATTCAGCGGCAGCGGCTCCGGCACCGACTTCACCCTGA CCATCAGCAGCCTGCAGCCCGAGGACTTCGCCACCTACTACTGCCAGCAGTACAG CAGCTTCCCCACCACCTTCGGCCAGGGCACCAAGGTGGAAATCAAG |
| SEQ ID NO: 197 | | DNA VH | GAGGTGCAATTGCTGGAAAGCGGCGGAGGCCTGGTGCAGCCTGGCGGCAGCCTGA GACTGTCTTGCGCCGCCAGCGGCTTCACCTTCAGCAGCTACGCCATGAGCTGGGT CCGCCAGGCCCCTGGCAAGGGACTGGAATGGGTGTCCGCCATCAGCAACCAGGGC AAGAGCACCTACTACGCCGACAGCGTGAAGGGCCGGTTCACCATCAGCCGGGACA ACAGCAAGAACACCCTGTACCTGCAGATGAACAGCCTGCGGGCCGAGGACACCGC CGTGTACTACTGTGCCAGATGGGGCGACGAGGGCTTCGACATCTGGGGCCAGGGC ACCCTGGTCACCGTCAGCTCA |
| SEQ ID NO: 198 | | Light Kappa | DIQMTQSPSSLSASVGDRVTITCRASQGISNWLAWYQQKPGKAPKLLIYGASSLQ SGVPSRFSGSGSGTDFTLTISSLQPEDFATYYCQQYSSFPTTFGQGTKVEIKRTV AAPSVFIFPPSDEQLKSGTASVVCLLNNFYPREAKVQWKVDNALQSGNSQESVTE QDSKDSTYSLSSTLTLSKADYEKHKVYACEVTHQGLSSPVTKSFNRGEC |
| SEQ ID NO: 199 | | Heavy IgG1 | EVQLLESGGGLVQPGGSLRLSCAASGFTFSSYAMSWVRQAPGKGLEWVSAISNQG KSTYYADSVKGRFTISRDNSKNTLYLQMNSLRAEDTAVYYCARWGDEGFDIWGQG TLVTVSSASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDKRVEPKSC DKTHTCPPCPAPELLGGPSVFLFPPKPKDTLMISRTPEVTCVVVDVSHEDPEVKF NWYVDGVEVHNAKTKPREEQYNSTYRVVSVLTVLHQDWLNGKEYKCKVSNKALPA PIEKTISKAKGQPREPQVYTLPPSREEMTKNQVSLTCLVKGFYPSDIAVEWESNG QPENNYKTTPPVLDSDGSFFLYSKLTVDKSRWQQGNVFSCSVMHEALHNHYTQKS LSLSPGK |
| MOR10703 A50V_N52S | | | |
| SEQ ID NO: 200 (Kabat) | | HCDR1 | SYAMS |
| SEQ ID NO: 201 (Kabat) | | HCDR2 | VISSQGKSTYYADSVKG |
| SEQ ID NO: 202 (Kabat) | | HCDR3 | WGDEGFDI |
| SEQ ID NO: 203 (Kabat) | | LCDR1 | RASQGISNWLA |
| SEQ ID NO: 204 (Kabat) | | LCDR2 | GASSLQS |
| SEQ ID NO: 205 (Kabat) | | LCDR3 | QQYSSFPTT |
| SEQ ID NO: 206 (Chothia) | | HCDR1 | GFTFSSY |
| SEQ ID NO: 207 (Chothia) | | HCDR2 | SSQGKS |
| SEQ ID NO: 208 (Chothia) | | HCDR3 | WGDEGFDI |
| SEQ ID NO: 209 (Chothia) | | LCDR1 | SQGISNW |
| SEQ ID NO: 210 (Chothia) | | LCDR2 | GAS |
| SEQ ID NO: 211 (Chothia) | | LCDR3 | YSSFPT |

TABLE 1-continued

Examples of HER3 Antibodies of the Present Invention

| SEQ ID NUMBER | Ab region | |
|---|---|---|
| SEQ ID NO: 212 | VL | DIQMTQSPSSLSASVGDRVTITCRASQGISNWLAWYQQKPGKAPKLLIYGASSLQ SGVPSRFSGSGSGTDFTLTISSLQPEDFATYYCQQYSSFPTTFGQGTKVEIK |
| SEQ ID NO: 213 | VH | EVQLLESGGGLVQPGGSLRLSCAASGFTFSSYAMSWVRQAPGRGLEWVSVISSQG KSTYYADSVKGRFTISRDNSKNTLYLQMNSLRAEDTAVYYCARWGDEGFDIWGQG TLVTVSS |
| SEQ ID NO: 214 | DNA VL | GATATCCAGATGACCCAGAGCCCCAGCAGCCTGAGCGCCAGCGTGGGCGACAGAG TGACCATCACCTGTCGGGCCAGCCAGGGCATCAGCAACTGGCTGGCCTGGTATCA GCAGAAGCCCGGCAAGGCCCCCAAGCTGCTGATCTACGGCGCCAGCTCCCTGCAG AGCGGCGTGCCAAGCAGATTCAGCGGCAGCGGCTCCGGCACCGACTTCACCCTGA CCATCAGCAGCCTGCAGCCCGAGGACTTCGCCACCTACTACTGCCAGCAGTACAG CAGCTTCCCCACCACCTTCGGCCAGGGCACCAAGGTGGAAATCAAG |
| SEQ ID NO: 215 | DNA VH | GAGGTGCAATTGCTGGAAAGCGGCGGAGGCCTGGTGCAGCCTGGCGGCAGCCTGA GACTGTCTTGCGCCGCCAGCGGCTTCACCTTCAGCAGCTACGCCATGAGCTGGGT CCGCCAGGCCCCTGGCAAGGGACTGGAATGGGTGTCCGTCATCAGCAGCCAGGGC AAGAGCACCTACTACGCCGACAGCGTGAAGGGCCGGTTCACCATCAGCCGGGACA ACAGCAAGAACACCCTGTACCTGCAGATGAACAGCCTGCGGGCCGAGGACACCGC CGTGTACTACTGTGCCAGATGGGGCGACGAGGGCTTCGACATCTGGGGCCAGGGC ACCCTGGTCACCGTCAGCTCA |
| SEQ ID NO: 216 | Light Kappa | DIQMTQSPSSLSASVGDRVTITCRASQGISNWLAWYQQKPGKAPKLLIYGASSLQ SGVPSRFSGSGSGTDFTLTISSLQPEDFATYYCQQYSSFPTTFGQGTKVEIKRTV AAPSVFIFPPSDEQLKSGTASVVCLLNNFYPREAKVQWKVDNALQSGNSQESVTE QDSKDSTYSLSSTLTLSKADYEKHKVYACEVTHQGLSSPVTKSFNRGEC |
| SEQ ID NO: 217 | Heavy IgG1 | EVQLLESGGGLVQPGGSLRLSCAASGFTFSSYAMSWVRQAPGKGLEWVSVISSQG KSTYYADSVKGRFTISRDNSKNTLYLQMNSLRAEDTAVYYCARWGDEGFDIWGQG TLVTVSSASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDKRVEPKSC DKTHTCPPCPAPELLGGPSVFLFPPKPKDTLMISRTPEVTCVVVDVSHEDPEVKF NWYVDGVEVHNAKTKPREEQYNSTYRVVSVLTVLHQDWLNGKEYKCKVSNKALPA PIEKTISKAKGQPREPQVYTLPPSREEMTKNQVSLTCLVKGFYPSDIAVEWESNG QPENNYKTTPPVLDSDGSFFLYSKLTVDKSRWQQGNVFSCSVMHEALHNHYTQKS LSLSPGK |
| MOR10703 A50V_N52G | | |
| SEQ ID NO: 218 (Kabat) | HCDR1 | SYAMS |
| SEQ ID NO: 219 (Kabat) | HCDR2 | VIGSQGKSTYYADSVKG |
| SEQ ID NO: 220 (Kabat) | HCDR3 | WGDEGFDI |
| SEQ ID NO: 221 (Kabat) | LCDR1 | RASQGISNWLA |
| SEQ ID NO: 222 (Kabat) | LCDR2 | GASSLQS |
| SEQ ID NO: 223 (Kabat) | LCDR3 | QQYSSFPTT |
| SEQ ID NO: 224 (Chothia) | HCDR1 | GFTFSSY |
| SEQ ID NO: 225 (Chothia) | HCDR2 | GSQGKS |
| SEQ ID NO: 226 (Chothia) | HCDR3 | WGDEGFDI |
| SEQ ID NO: 227 (Chothia) | LCDR1 | SQGISNW |
| SEQ ID NO: 228 (Chothia) | LCDR2 | GAS |
| SEQ ID NO: 229 (Chothia) | LCDR3 | YSSFPT |
| SEQ ID NO: 230 | VL | DIQMTQSPSSLSASVGDRVTITCRASQGISNWLAWYQQKPGKAPKLLIYGASSLQ SGVPSRFSGSGSGTDFTLTISSLQPEDFATYYCQQYSSFPTTFGQGTKVEIK |
| SEQ ID NO: 231 | VH | EVQLLESGGGLVQPGGSLRLSCAASGFTFSSYAMSWVRQAPGKGLEWVSVIGSQG KSTYYADSVKGRFTISRDNSKNTLYLQMNSLRAEDTAVYYCARWGDEGFDIWGQG TLVTVSS |
| SEQ ID NO: 232 | DNA VL | GATATCCAGATGACCCAGAGCCCCAGCAGCCTGAGCGCCAGCGTGGGCGACAGAG TGACCATCACCTGTCGGGCCAGCCAGGGCATCAGCAACTGGCTGGCCTGGTATCA GCAGAAGCCCGGCAAGGCCCCCAAGCTGCTGATCTACGGCGCCAGCTCCCTGCAG AGCGGCGTGCCAAGCAGATTCAGCGGCAGCGGCTCCGGCACCGACTTCACCCTGA CCATCAGCAGCCTGCAGCCCGAGGACTTCGCCACCTACTACTGCCAGCAGTACAG CAGCTTCCCCACCACCTTCGGCCAGGGCACCAAGGTGGAAATCAAG |

TABLE 1-continued

Examples of HER3 Antibodies of the Present Invention

| SEQ ID NUMBER | Ab region | |
|---|---|---|
| SEQ ID NO: 233 | DNA VH | GAGGTGCAATTGCTGGAAAGCGGCGGAGGCCTGGTGCAGCCTGGCGGCAGCCTGA<br>GACTGTCTTGCGCCGCCAGCGGCTTCACCTTCAGCAGCTACGCCATGAGCTGGGT<br>CCGCCAGGCCCCTGGCAAGGGACTGGAATGGGTGTCCGTCATCGGCAGCCAGGGC<br>AAGAGCACCTACTACGCCGACAGCGTGAAGGGCCGGTTCACCATCAGCCGGGACA<br>ACAGCAAGAACACCCTGTACCTGCAGATGAACAGCCTGCGGGCCGAGGACACCGC<br>CGTGTACTACTGTGCCAGATGGGGCGACGAGGGCTTCGACATCTGGGGCCAGGGC<br>ACCCTGGTCACCGTCAGCTCA |
| SEQ ID NO: 234 | Light Kappa | DIQMTQSPSSLSASVGDRVTITCRASQGISNWLAWYQQKPGKAPKLLIYGASSLQ<br>SGVPSRFSGSGSGTDFTLTISSLQPEDFATYYCQQYSSFPTTFGQGTKVEIKRTV<br>AAPSVFIFPPSDEQLKSGTASVVCLLNNFYPREAKVQWKVDNALQSGNSQESVTE<br>QDSKDSTYSLSSTLTLSKADYEKHKVYACEVTHQGLSSPVTKSFNRGEC |
| SEQ ID NO: 235 | Heavy IgG1 | EVQLLESGGGLVQPGGSLRLSCAASGFTFSSYAMSWVRQAPGKGLEWVSVIGSQG<br>KSTYYADSVKGRFTISRDNSKNTLYLQMNSLRAEDTAVYYCARWGDEGFDIWGQG<br>TLVTVSSASTKGPSVFPLAPSSKSTSGGTAALGCLVKDYFPEPVTVSWNSGALTS<br>GVHTFPAVLQSSGLYSLSSVVTVPSSSLGTQTYICNVNHKPSNTKVDKRVEPKSC<br>DKTHTCPPCPAPELLGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALPA<br>PIEKTISKAKGQPREPQVYTLPPSREEMTKNQVSLTCLVKGFYPSDIAVEWESNG<br>QPENNYKTTPPVLDSDGSFFLYSKLTVDKSRWQQGNVFSCSVMHEALHNHYTQKS<br>LSLSPGK |
| MOR10703 S52aA | | |
| SEQ ID NO: 236 (Kabat) | HCDR1 | SYAMS |
| SEQ ID NO: 237 (Kabat) | HCDR2 | AINAQGKSTYYADSVKG |
| SEQ ID NO: 238 (Kabat) | HCDR3 | WGDEGFDI |
| SEQ ID NO: 239 (Kabat) | LCDR1 | RASQGISNWLA |
| SEQ ID NO: 240 (Kabat) | LCDR2 | GASSLQS |
| SEQ ID NO: 241 (Kabat) | LCDR3 | QQYSSFPTT |
| SEQ ID NO: 242 (Chothia) | HCDR1 | GFTFSSY |
| SEQ ID NO: 243 (Chothia) | HCDR2 | NAQGKS |
| SEQ ID NO: 244 (Chothia) | HCDR3 | WGDEGFDI |
| SEQ ID NO: 245 (Chothia) | LCDR1 | SQGISNW |
| SEQ ID NO: 246 (Chothia) | LCDR2 | GAS |
| SEQ ID NO: 247 (Chothia) | LCDR3 | YSSFPT |
| SEQ ID NO: 248 | VL | DIQMTQSPSSLSASVGDRVTITCRASQGISNWLAWYQQKPGKAPKLLIYGASSLQ<br>SGVPSRFSGSGSGTDFTLTISSLQPEDFATYYCQQYSSFPTTFGQGTKVEIK |
| SEQ ID NO: 249 | VH | EVQLLESGGGLVQPGGSLRLSCAASGFTFSSYAMSWVRQAPGKGLEWVSAINAQG<br>KSTYYADSVKGRFTISRDNSKNTLYLQMNSLRAEDTAVYYCARWGDEGFDIWGQG<br>TLVTVSS |
| SEQ ID NO: 250 | DNA VL | GATATCCAGATGACCCAGAGCCCCAGCAGCCTGAGCGCCAGCGTGGGCGACAGAG<br>TGACCATCACCTGTCGGGCCAGCCAGGGCATCAGCAACTGGCTGGCCTGGTATCA<br>GCAGAAGCCCGGCAAGGCCCCCAAGCTGCTGATCTACGGCGCCAGCTCCCTGCAG<br>AGCGGCGTGCCAAGCAGATTCAGCGGCAGCGGCTCCGGCACCGACTTCACCCTGA<br>CCATCAGCAGCCTGCAGCCCGAGGACTTCGCCACCTACTACTGCCAGCAGTACAG<br>CAGCTTCCCCACCACCTTCGGCCAGGGCACCAAGGTGGAAATCAAG |
| SEQ ID NO: 251 | DNA VH | GAGGTGCAATTGCTGGAAAGCGGCGGAGGCCTGGTGCAGCCTGGCGGCAGCCTGA<br>GACTGTCTTGCGCCGCCAGCGGCTTCACCTTCAGCAGCTACGCCATGAGCTGGGT<br>CCGCCAGGCCCCTGGCAAGGGACTGGAATGGGTGTCCGCCATCAACGCCCAGGGC<br>AAGAGCACCTACTACGCCGACAGCGTGAAGGGCCGGTTCACCATCAGCCGGGACA<br>ACAGCAAGAACACCCTGTACCTGCAGATGAACAGCCTGCGGGCCGAGGACACCGC<br>CGTGTACTACTGTGCCAGATGGGGCGACGAGGGCTTCGACATCTGGGGCCAGGGC<br>ACCCTGGTCACCGTCAGCTCA |
| SEQ ID NO: 252 | Light Kappa | DIQMTQSPSSLSASVGDRVTITCRASQGISNWLAWYQQKPGKAPKLLIYGASSLQ<br>SGVPSRFSGSGSGTDFTLTISSLQPEDFATYYCQQYSSFPTTFGQGTKVEIKRTV<br>AAPSVFIFPPSDEQLKSGTASVVCLLNNFYPREAKVQWKVDNALQSGNSQESVTE<br>QDSKDSTYSLSSTLTLSKADYEKHKVYACEVTHQGLSSPVTKSFNRGEC |

TABLE 1-continued

Examples of HER3 Antibodies of the Present Invention

| SEQ ID NUMBER | Ab region | |
|---|---|---|
| SEQ ID NO: 253 | Heavy IgG1 | EVQLLESGGGLVQPGGSLRLSCAASGFTFSSYAMSWVRQAPGKGLEWVSAINAQG KSTYYADSVKGRFTISRDNSKNTLYLQMNSLRAEDTAVYYCARWGDEGFDIWGQG TLVTVSSASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDKRVEPKSC DKTHTCPPCPAPELLGGPSVFLFPPKPKDTLMISRTPEVTCVVVDVSHEDPEVKF NWYVDGVEVHNAKTKPREEQYNSTYRVVSVLTVLHQDWLNGKEYKCKVSNKALPA PIEKTISKAKGQPREPQVYTLPPSREEMTKNQVSLTCLVKGFYPSDIAVEWESNG QPENNYKTTPPVLDSDGSFFLYSKLTVDKSRWQQGNVFSCSVMHEALHNHYTQKS LSLSPGK |
| MOR10703 S52aT | | |
| SEQ ID NO: 254 (Kabat) | HCDR1 | SYAMS |
| SEQ ID NO: 255 (Kabat) | HCDR2 | AINTQGKSTYYADSVKG |
| SEQ ID NO: 256 (Kabat) | HCDR3 | WGDEGFDI |
| SEQ ID NO: 257 (Kabat) | LCDR1 | RASQGISNWLA |
| SEQ ID NO: 258 (Kabat) | LCDR2 | GASSLQS |
| SEQ ID NO: 259 (Kabat) | LCDR3 | QQYSSFPTT |
| SEQ ID NO: 260 (Chothia) | HCDR1 | GFTFSSY |
| SEQ ID NO: 261 (Chothia) | HCDR2 | NTQGKS |
| SEQ ID NO: 262 (Chothia) | HCDR3 | WGDEGFDI |
| SEQ ID NO: 263 (Chothia) | LCDR1 | SQGISNW |
| SEQ ID NO: 264 (Chothia) | LCDR2 | GAS |
| SEQ ID NO: 265 (Chothia) | LCDR3 | YSSFPT |
| SEQ ID NO: 266 | VL | DIQMTQSPSSLSASVGDRVTITCRASQGISNWLAWYQQKPGKAPKLLIYGASSLQ SGVPSRFSGSGSGTDFTLTISSLQPEDFATYYCQQYSSFPTTFGQGTKVEIK |
| SEQ ID NO: 267 | VH | EVQLLESGGGLVQPGGSLRLSCAASGFTFSSYAMSWVRQAPGKGLEWVSAINTQG KSTYYADSVKGRFTISRDNSKNTLYLQMNSLRAEDTAVYYCARWGDEGFDIWGQG TLVTVSS |
| SEQ ID NO: 268 | DNA VL | GATATCCAGATGACCCAGAGCCCCAGCAGCCTGAGCGCCAGCGTGGGCGACAGAG TGACCATCACCTGTCGGGCCAGCCAGGGCATCAGCAACTGGCTGGCCTGGTATCA GCAGAAGCCCGGCAAGGCCCCCAAGCTGCTGATCTACGGCGCCAGCTCCCTGCAG AGCGGCGTGCCAAGCAGATTCAGCGGCAGCGGCTCCGGCACCGACTTCACCCTGA CCATCAGCAGCCTGCAGCCCGAGGACTTCGCCACCTACTACTGCCAGCAGTACAG CAGCTTCCCCACCACCTTCGGCCAGGGCACCAAGGTGGAAATCAAG |
| SEQ ID NO: 269 | DNA VH | GAGGTGCAATTGCTGGAAAGCGGCGGAGGCCTGGTGCAGCCTGGCGGCAGCCTGA GACTGTCTTGCGCCGCCAGCGGCTTCACCTTCAGCAGCTACGCCATGAGCTGGGT CCGCCAGGCCCCTGGCAAGGGACTGGAATGGGTGTCCGCCATCAACACCCAGGGC AAGAGCACCTACTACGCCGACAGCGTGAAGGGCCGGTTCACCATCAGCCGGGACA ACAGCAAGAACACCCTGTACCTGCAGATGAACAGCCTGCGGGCCGAGGACACCGC CGTGTACTACTGTGCCAGATGGGGCGACGAGGGCTTCGACATCTGGGGCCAGGGC ACCCTGGTCACCGTCAGCTCA |
| SEQ ID NO: 270 | Light Kappa | DIQMTQSPSSLSASVGDRVTITCRASQGISNWLAWYQQKPGKAPKLLIYGASSLQ SGVPSRFSGSGSGTDFTLTISSLQPEDFATYYCQQYSSFPTTFGQGTKVEIKRTV AAPSVFIFPPSDEQLKSGTASVVCLLNNFYPREAKVQWKVDNALQSGNSQESVTE QDSKDSTYSLSSTLTLSKADYEKHKVYACEVTHQGLSSPVTKSFNRGEC |
| SEQ ID NO: 271 | Heavy IgG1 | EVQLLESGGGLVQPGGSLRLSCAASGFTFSSYAMSWVRQAPGKGLEWVSAINTQG KSTYYADSVKGRFTISRDNSKNTLYLQMNSLRAEDTAVYYCARWGDEGFDIWGQG TLVTVSSASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDKRVEPKSC DKTHTCPPCPAPELLGGPSVFLFPPKPKDTLMISRTPEVTCVVVDVSHEDPEVKF NWYVDGVEVHNAKTKPREEQYNSTYRVVSVLTVLHQDWLNGKEYKCKVSNKALPA PIEKTISKAKGQPREPQVYTLPPSREEMTKNQVSLTCLVKGFYPSDIAVEWESNG QPENNYKTTPPVLDSDGSFFLYSKLTVDKSRWQQGNVFSCSVMHEALHNHYTQKS LSLDSPGK |

TABLE 1-continued

Examples of HER3 Antibodies of the Present Invention

| SEQ ID NUMBER | Ab region | |
|---|---|---|
| MOR10701 R55S | | |
| SEQ ID NO: 272 (Kabat) | HCDR1 | SYAMS |
| SEQ ID NO: 273 (Kabat) | HCDR2 | VTGAVGSSTYYPDSVKG |
| SEQ ID NO: 274 (Kabat) | HCDR3 | WGDEGFDI |
| SEQ ID NO: 275 (Kabat) | LCDR1 | RASQGISNWLA |
| SEQ ID NO: 276 (Kabat) | LCDR2 | GASSLQS |
| SEQ ID NO: 277 (Kabat) | LCDR3 | QQYSSFPTT |
| SEQ ID NO: 278 (Chothia) | HCDR1 | GFTFSSY |
| SEQ ID NO: 279 (Chothia) | HCDR2 | GAVGSS |
| SEQ ID NO: 280 (Chothia) | HCDR3 | WGDEGFDI |
| SEQ ID NO: 281 (Chothia) | LCDR1 | SQGISNW |
| SEQ ID NO: 282 (Chothia) | LCDR2 | GAS |
| SEQ ID NO: 283 (Chothia) | LCDR3 | YSSFPT |
| SEQ ID NO: 284 | VL | DIQMTQSPSSLSASVGDRVTITCRASQGISNWLAWYQQKPGKAPKLLIYGASSLQ<br>SGVPSRFSGSGSGTDFTLTISSLQPEDFATYYCQQYSSFPTTFGQGTKVEIK |
| SEQ ID NO: 285 | VH | EVQLLESGGGLVQPGGSLRLSCAASGFTFSSYAMSWVRQAPGKGLEWVSVTGAVG<br>SSTYYPDSVKGRFTISRDNSKNTLYLQMNSLRAEDTAVYYCARWGDEGFDIWGQG<br>TLVTVSS |
| SEQ ID NO: 286 | DNA VL | GATATCCAGATGACCCAGAGCCCCAGCAGCCTGAGCGCCAGCGTGGGCGACAGAG<br>TGACCATCACCTGTCGGGCCAGCCAGGGCATCAGCAACTGGCTGGCCTGGTATCA<br>GCAGAAGCCCGGCAAGGCCCCCAAGCTGCTGATCTACGGCGCCAGCTCCCTGCAG<br>AGCGGCGTGCCAAGCAGATTCAGCGGCAGCGGCTCCGGCACCGACTTCACCCTGA<br>CCATCAGCAGCCTGCAGCCCGAGGACTTCGCCACCTACTACTGCCAGCAGTACAG<br>CAGCTTCCCCACCACCTTCGGCCAGGGCACCAAGGTGGAAATCAAG |
| SEQ ID NO: 287 | DNA VH | GAGGTGCAATTGCTGGAAAGCGGCGGAGGCCTGGTGCAGCCTGGCGGCAGCCTGA<br>GACTGTCTTGCGCCGCCAGCGGCTTCACCTTCAGCAGCTACGCCATGAGCTGGGT<br>CCGCCAGGCCCCTGGCAAGGGACTGGAATGGGTGTCCGTGACAGGCGCCGTGGGC<br>AGCAGCACCTACTACCCCGACAGCGTGAAGGGCCGGTTCACCATCAGCCGGGACA<br>ACAGCAAGAACACCCTGTACCTGCAGATGAACAGCCTGCGGGCCGAGGACACCGC<br>CGTGTACTACTGTGCCAGATGGGGCGACGAGGGCTTCGACATCTGGGGCCAGGGC<br>ACCCTGGTCACCGTCAGCTCA |
| SEQ ID NO: 288 | Light Kappa | DIQMTQSPSSLSASVGDRVTITCRASQGISNWLAWYQQKPGKAPKLLIYGASSLQ<br>SGVPSRFSGSGSGTDFTLTISSLQPEDFATYYCQQYSSFPTTFGQGTKVEIKRTV<br>AAPSVFIFPPSDEQLKSGTASVVCLLNNFYPREAKVQWKVDNALQSGNSQESVTE<br>QDSKDSTYSLSSTLTLSKADYEKHKVYACEVTHQGLSSPVTKSFNRGEC |
| SEQ ID NO: 289 | Heavy IgG1 | EVQLLESGGGLVQPGGSLRLSCAASGFTFSSYAMSWVRQAPGKGLEWVSVTGAVG<br>SSTYYPDSVKGRFTISRDNSKNTLYLQMNSLRAEDTAVYYCARWGDEGFDIWGQG<br>TLVTVSSASTKGPSVFPLAPSSKSTSGGTAALGCLVKDYFPEPVTVSWNSGALTS<br>GVHTFPAVLQSSGLYSLSSVVTVPSSSLGTQTYICNVNHKPSNTKVDKRVEPKSC<br>DKTHTCPPCPAPELLGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALPA<br>PIEKTISKAKGQPREPQVYTLPPSREEMTKNQVSLTCLVKGFYPSDIAVEWESNG<br>QPENNYKTTPPVLDSDGSFFLYSKLTVDKSRWQQGNVFSCSVMHEALHNHYTQKS<br>LSLSPGK |
| MOR10701 R55G | | |
| SEQ ID NO: 290 (Kabat) | HCDR1 | SYAMS |
| SEQ ID NO: 291 (Kabat) | HCDR2 | VTGAVGGSTYYPDSVKG |
| SEQ ID NO: 292 (Kabat) | HCDR3 | WGDEGFDI |
| SEQ ID NO: 293 (Kabat) | LCDR1 | RASQGISNWLA |
| SEQ ID NO: 294 (Kabat) | LCDR2 | GASSLQS |
| SEQ ID NO: 295 (Kabat) | LCDR3 | QQYSSFPTT |

TABLE 1-continued

Examples of HER3 Antibodies of the Present Invention

| SEQ ID NUMBER | Ab region | |
|---|---|---|
| SEQ ID NO: 296 (Chothia) | HCDR1 | GFTFSSY |
| SEQ ID NO: 297 (Chothia) | HCDR2 | GAVGGS |
| SEQ ID NO: 298 (Chothia) | HCDR3 | WGDEGFDI |
| SEQ ID NO: 299 (Chothia) | LCDR1 | SQGISNW |
| SEQ ID NO: 300 (Chothia) | LCDR2 | GAS |
| SEQ ID NO: 301 (Chothia) | LCDR3 | YSSFPT |
| SEQ ID NO: 302 | VL | DIQMTQSPSSLSASVGDRVTITCRASQGISNWLAWYQQKPGKAPKLLIYGASSLQ SGVPSRFSGSGSGTDFTLTISSLQPEDFATYYCQQYSSFPTTFGQGTKVEIK |
| SEQ ID NO: 303 | VH | EVQLLESGGGLVQPGGSLRLSCAASGFTFSSYAMSWVRQAPGKGLEWVSVTGAVG GSTYYPDSVKGRFTISRDNSKNTLYLQMNSLRAEDTAVYYCARWGDEGFDIWGQG TLVTVSS |
| SEQ ID NO: 304 | DNA VL | GATATCCAGATGACCCAGAGCCCCAGCAGCCTGAGCGCCAGCGTGGGCGACAGAG TGACCATCACCTGTCGGGCCAGCCAGGGCATCAGCAACTGGCTGGCCTGGTATCA GCAGAAGCCCGGCAAGGCCCCCAAGCTGCTGATCTACGGCGCCAGCTCCCTGCAG AGCGGCGTGCCAAGCAGATTCAGCGGCAGCGGCTCCGGCACCGACTTCACCCTGA CCATCAGCAGCCTGCAGCCCGAGGACTTCGCCACCTACTACTGCCAGCAGTACAG CAGCTTCCCCACCACCTTCGGCCAGGGCACCAAGGTGGAAATCAAG |
| SEQ ID NO: 305 | DNA VH | GAGGTGCAATTGCTGGAAAGCGGCGGAGGCCTGGTGCAGCCTGGCGGCAGCCTGA GACTGTCTTGCGCCGCCAGCGGCTTCACCTTCAGCAGCTACGCCATGAGCTGGGT CCGCCAGGCCCCTGGCAAGGGACTGGAATGGGTGTCCGTGACAGGCGCCGTGGGC GGAAGCACCTACTACCCCGACAGCGTGAAGGGCCGGTTCACCATCAGCCGGGACA ACAGCAAGAACACCCTGTACCTGCAGATGAACAGCCTGCGGGCCGAGGACACCGC CGTGTACTACTGTGCCAGATGGGGCGACGAGGGCTTCGACATCTGGGGCCAGGGC ACCCTGGTCACCGTCAGCTCA |
| SEQ ID NO: 306 | Light Kappa | DIQMTQSPSSLSASVGDRVTITCRASQGISNWLAWYQQKPGKAPKLLIYGASSLQ SGVPSRFSGSGSGTDFTLTISSLQPEDFATYYCQQYSSFPTTFGQGTKVEIKRTV AAPSVFIFPPSDEQLKSGTASVVCLLNNFYPREAKVQWKVDNALQSGNSQESVTE QDSKDSTYSLSSTLTLSKADYEKHKVYACEVTHQGLSSPVTKSFNRGEC |
| SEQ ID NO: 307 | Heavy IgG1 | EVQLLESGGGLVQPGGSLRLSCAASGFTFSSYAMSWVRQAPGKGLEWVSVTGAVG GSTYYPDSVKGRFTISRDNSKNTLYLQMNSLRAEDTAVYYCARWGDEGFDIWGQG TLVTVSSASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDKRVEPKSC DKTHTCPPCPAPELLGGPSVFLFPPKPKDTLMISRTPEVTCVVVDVSHEDPEVKF NWYVDGVEVHNAKTKPREEQYNSTYRVVSVLTVLHQDWLNGKEYKCKVSNKALPA PIEKTISKAKGQPREPQVYTLPPSREEMTKNQVSLTCLVKGFYPSDIAVEWESNG QPENNYKTTPPVLDSDGSFFLYSKLTVDKSRWQQGNVFSCSVMHEALHNHYTQKS LSLSPGK |
| MOR10701 R55K | | |
| SEQ ID NO: 308 (Kabat) | HCDR1 | SYAMS |
| SEQ ID NO: 309 (Kabat) | HCDR2 | VTGAVGKSTYYPDSVKG |
| SEQ ID NO: 310 (Kabat) | HCDR3 | WGDEGFDI |
| SEQ ID NO: 311 (Kabat) | LCDR1 | RASQGISNWLA |
| SEQ ID NO: 312 (Kabat) | LCDR2 | GASSLQS |
| SEQ ID NO: 313 (Kabat) | LCDR3 | QQYSSFPTT |
| SEQ ID NO: 314 (Chothia) | HCDR1 | GFTFSSY |
| SEQ ID NO: 315 (Chothia) | HCDR2 | GAVGKS |
| SEQ ID NO: 316 (Chothia) | HCDR3 | WGDEGFDI |
| SEQ ID NO: 317 (Chothia) | LCDR1 | SQGISNW |
| SEQ ID NO: 318 (Chothia) | LCDR2 | GAS |
| SEQ ID NO: 319 (Chothia) | LCDR3 | YSSFPT |

TABLE 1-continued

Examples of HER Antibodies of the Present Invention

| SEQ ID NUMBER | Ab region | |
|---|---|---|
| SEQ ID NO: 320 | VL | DIQMTQSPSSLSASVGDRVTITCRASQGISNWLAWYQQKPGKAPKLLIYGASSLQ SGVPSRFSGSGSGTDFTLTISSLQPEDFATYYCQQYSSFPTTFGQGTKVEIK |
| SEQ ID NO: 321 | VH | EVQLLESGGGLVQPGGSLRLSCAASGFTFSSYAMSWVRQAPGKGLEWVSVTGAVG KSTYYPDSVKGRFTISRDNSKNTLYLQMNSLRAEDTAVYYCARWGDEGFDIWGQG TLVTVSS |
| SEQ ID NO: 322 | DNA VL | GATATCCAGATGACCCAGAGCCCCAGCAGCCTGAGCGCCAGCGTGGGCGACAGAG TGACCATCACCTGTCGGGCCAGCCAGGGCATCAGCAACTGGCTGGCCTGGTATCA GCAGAAGCCCGGCAAGGCCCCCAAGCTGCTGATCTACGGCGCCAGCTCCCTGCAG AGCGGCGTGCCAAGCAGATTCAGCGGCAGCGGCTCCGGCACCGACTTCACCCTGA CCATCAGCAGCCTGCAGCCCGAGGACTTCGCCACCTACTACTGCCAGCAGTACAG CAGCTTCCCCACCACCTTCGGCCAGGGCACCAAGGTGGAAATCAAG |
| SEQ ID NO: 323 | DNA VH | GAGGTGCAATTGCTGGAAAGCGGCGGAGGCCTGGTGCAGCCTGGCGGCAGCCTGA GACTGTCTTGCGCCGCCAGCGGCTTCACCTTCAGCAGCTACGCCATGAGCTGGGT CCGCCAGGCCCCTGGCAAGGGACTGGAATGGGTGTCCGTGACAGGCGCCGTGGGC AAAAGCACCTACTACCCCGACAGCGTGAAGGGCCGGTTCACCATCAGCCGGGACA ACAGCAAGAACACCCTGTACCTGCAGATGAACAGCCTGCGGGCCGAGGACACCGC CGTGTACTACTGTGCCAGATGGGGCGACGAGGGCTTCGACATCTGGGGCCAGGGC ACCCTGGTCACCGTCAGCTCA |
| SEQ ID NO: 324 | Light Kappa | DIQMTQSPSSLSASVGDRVTITCRASQGISNWLAWYQQKPGKAPKLLIYGASSLQ SGVPSRFSGSGSGTDFTLTISSLQPEDFATYYCQQYSSFPTTFGQGTKVEIKRTV AAPSVFIFPPSDEQLKSGTASVVCLLNNFYPREAKVQWKVDNALQSGNSQESVTE QDSKDSTYSLSSTLTLSKADYEKHKVYACEVTHQGLSSPVTKSFNRGEC |
| SEQ ID NO: 325 | Heavy IgG1 | EVQLLESGGGLVQPGGSLRLSCAASGFTFSSYAMSWVRQAPGKGLEWVSVTGAVG KSTYYPDSVKGRFTISRDNSKNTLYLQMNSLRAEDTAVYYCARWGDEGFDIWGQG TLVTVSSASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDKRVEPKSC DKTHTCPPCPAPELLGGPSVFLFPPKPKDTLMISRTPEVTCVVVDVSHEDPEVKF NWYVDGVEVHNAKTKPREEQYNSTYRVVSVLTVLHQDWLNGKEYKCKVSNKALPA PIEKTISKAKGQPREPQVYTLPPSREEMTKNQVSLTCLVKGFYPSDIAVEWESNG QPENNYKTTPPVLDSDGSFFLYSKLTVDKSRWQQGNVFSCSVMHEALHNHYTQKS LSLSPGK |
| MOR10701 deletion S56 | | |
| SEQ ID NO: 326 (Kabat) | HCDR1 | SYAMS |
| SEQ ID NO: 327 (Kabat) | HCDR2 | VTGAVGRTYYPDSVKG |
| SEQ ID NO: 328 (Kabat) | HCDR3 | WGDEGFDI |
| SEQ ID NO: 329 (Kabat) | LCDR1 | RASQGISNWLA |
| SEQ ID NO: 330 (Kabat) | LCDR2 | GASSLQS |
| SEQ ID NO: 331 (Kabat) | LCDR3 | QQYSSFPTT |
| SEQ ID NO: 332 (Chothia) | HCDR1 | GFTFSSY |
| SEQ ID NO: 333 (Chothia) | HCDR2 | GAVGRT |
| SEQ ID NO: 334 (Chothia) | HCDR3 | WGDEGFDI |
| SEQ ID NO: 335 (Chothia) | LCDR1 | SQGISNW |
| SEQ ID NO: 336 (Chothia) | LCDR2 | GAS |
| SEQ ID NO: 337 (Chothia) | LCDR3 | YSSFPT |
| SEQ ID NO: 338 | VL | DIQMTQSPSSLSASVGDRVTITCRASQGISNWLAWYQQKPGKAPKLLIYGASSLQ SGVPSRFSGSGSGTDFTLTISSLQPEDFATYYCQQYSSFPTTFGQGTKVEIK |
| SEQ ID NO: 339 | VH | EVQLLESGGGLVQPGGSLRLSCAASGFTFSSYAMSWVRQAPGKGLEWVSVTGAVG RTYYPDSVKGRFTISRDNSKNTLYLQMNSLRAEDTAVYYCARWGDEGFDIWGQGT LVTVSS |
| SEQ ID NO: 340 | DNA VL | GATATCCAGATGACCCAGAGCCCCAGCAGCCTGAGCGCCAGCGTGGGCGACAGAG TGACCATCACCTGTCGGGCCAGCCAGGGCATCAGCAACTGGCTGGCCTGGTATCA GCAGAAGCCCGGCAAGGCCCCCAAGCTGCTGATCTACGGCGCCAGCTCCCTGCAG AGCGGCGTGCCAAGCAGATTCAGCGGCAGCGGCTCCGGCACCGACTTCACCCTGA CCATCAGCAGCCTGCAGCCCGAGGACTTCGCCACCTACTACTGCCAGCAGTACAG CAGCTTCCCCACCACCTTCGGCCAGGGCACCAAGGTGGAAATCAAG |

TABLE 1-continued

Examples of HER3 Antibodies of the Present Invention

| SEQ ID NUMBER | Ab region | |
|---|---|---|
| SEQ ID NO: 341 | DNA VH | GAGGTGCAATTGCTGGAAAGCGGCGGAGGCCTGGTGCAGCCTGGCGGCAGCCTGA GACTGTCTTGCGCCGCCAGCGGCTTCACCTTCAGCAGCTACGCCATGAGCTGGGT CCGCCAGGCCCCTGGCAAGGGACTGGAATGGGTGTCCGTGACAGGCGCCGTGGGC AGAACCTACTACCCCGACAGCGTGAAGGGCCGGTTCACCATCAGCCGGGACAACA GCAAGAACACCCTGTACCTGCAGATGAACAGCCTGCGGGCCGAGGACACCGCCGT GTACTACTGTGCCAGATGGGGCGACGAGGGCTTCGACATCTGGGGCCAGGGCACC CTGGTCACCGTCAGCTCA |
| SEQ ID NO: 342 | Light Kappa | DIQMTQSPSSLSASVGDRVTITCRASQGISNWLAWYQQKPGKAPKLLIYGASSLQ SGVPSRFSGSGSGTDFTLTISSLQPEDFATYYCQQYSSFPTTFGQGTKVEIKRTV AAPSVFIFPPSDEQLKSGTASVVCLINNFYPREAKVQWKVDNALQSGNSQESVTE QDSKDSTYSLSSTLTLSKADYEKHKVYACEVTHQGLSSPVTKSFNRGEC |
| SEQ ID NO: 343 | Heavy IgG1 | EVQLLESGGGLVQPGGSLRLSCAASGFTFSSYAMSWVRQAPGKGLEWVSVTGAVG RTYYPDSVKGRFTISRDNSKNTLYLQMNSLRAEDTAVYYCARWGDEGFDIWGQGT LVTVSSASTKGPSVFPLAPSSKSTSGGTAALGCLVKDYFPEPVTVSWNSGALTSG VHTFPAVLQSSGLYSLSSVVTVPSSSLGTQTYICNVNHKPSNTKVDKRVEPKSCD KTHTCPPCPAPELLGGPSVFLFPPKPKDTLMISRTPEVTCVVVDVSHEDPEVKFN WYVDGVEVHNAKTKPREEQYNSTYRVVSVLTVLHQDWLNGKEYKCKVSNKALPAP IEKTISKAKGQPREPQVYTLPPSREEMTKNQVSLTCLVKGFYPSDIAVEWESNGQ PENNYKTTPPVLDSDGSFFLYSKLTVDKSRWQQGNVFSCSVMHEALHNHYTQKSL SLSPGK |
| MOR12609 | | |
| SEQ ID NO: 344 (Kabat) | HCDR1 | SYAMS |
| SEQ ID NO: 345 (Kabat) | HCDR2 | VINGLGYTTFYADSVKG |
| SEQ ID NO: 346 (Kabat) | HCDR3 | WGDEGFDI |
| SEQ ID NO: 347 (Kabat) | LCDR1 | RASQGISNWLA |
| SEQ ID NO: 348 (Kabat) | LCDR2 | GASSLQS |
| SEQ ID NO: 349 (Kabat) | LCDR3 | QQYSSFPTT |
| SEQ ID NO: 350 (Chothia) | HCDR1 | GFTFSSY |
| SEQ ID NO: 351 (Chothia) | HCDR2 | NGLGYT |
| SEQ ID NO: 352 (Chothia) | HCDR3 | WGDEGFDI |
| SEQ ID NO: 353 (Chothia) | LCDR1 | SQGISNW |
| SEQ ID NO: 354 (Chothia) | LCDR2 | GAS |
| SEQ ID NO: 355 (Chothia) | LCDR3 | YSSFPT |
| SEQ ID NO: 356 | VL | DIQMTQSPSSLSASVGDRVTITCRASQGISNWLAWYQQKPGKAPKLLIYGASSLQ SGVPSRFSGSGSGTDFTLTISSLQPEDFAVYYCQQYSSFPTTFGQGTKVEIK |
| SEQ ID NO: 357 | VH | QVQLVESGGGLVQPGGSLRLSCAASGFTFSSYAMSWVRQAPGKGLEWVSVINGLG YTTFYADSVKGRFTISRDNSKNTLYLQMNSLRAEDTAVYYCARWGDEGFDIWGQG TLVTVSS |
| SEQ ID NO: 358 | DNA VL | GATATCCAGATGACCCAGAGCCCGTCTAGCCTGAGCGCGAGCGTGGGTGATCGTG TGACCATTACCTGCAGAGCGAGCCAGGGTATTTCTAATTGGCTGGCTTGGTACCA GCAGAAACCAGGTAAAGCACCGAAACTATTAATTTATGGTGCTTCTTCTTTGCAA AGCGGGGTCCCGTCCCGTTTTAGCGGCTCTGGATCCGGCACTGATTTTACCCTGA CCATTAGCAGCCTGCAACCTGAAGACTTTGCGGTTTATTATTGCCAGCAGTATTC TTCTTTTCCTACTACCTTTGGCCAGGGTACGAAAGTTGAAATTAAA |
| SEQ ID NO: 359 | DNA VH | CAGGTGCAATTGGTGGAAAGCGGCGGCGGCCTGGTGCAACCGGGCGGCAGCCTGC GTCTGAGCTGCGCGGCCTCCGGATTTACCTTTAGCAGCTATGCGATGAGCTGGGT GCGCCAAGCCCCTGGGAAGGGTCTCGAGTGGGTGAGCGTTATTAATGGTCTTGGT TATACTACTTTTTATGCTGATTCTGTTAAGGGTCGTTTTACCATTTCACGTGATA ATTCGAAAAACACCCTGTATCTGCAAATGAACAGCCTGCGTGCGGAAGATACGGC CGTGTATTATTGCGCGCGTTGGGGTGATGAGGGTTTTGATATTTGGGGCCAAGGC ACCCTGGTGACGGTTAGCTCA |
| SEQ ID NO: 360 | Light Kappa | DIQMTQSPSSLSASVGDRVTITCRASQGISNWLAWYQQKPGKAPKLLIYGASSLQ SGVPSRFSGSGSGTDFTLTISSLQPEDFAVYYCQQYSSFPTTFGQGTKVEIKRTV AAPSVFIFPPSDEQLKSGTASVVCLLNNFYPREAKVQWKVDNALQSGNSQESVTE QDSKDSTYSLSSTLTLSKADYEKHKVYACEVTHQGLSSPVTKSFNRGEC |

TABLE 1-continued

Examples of HER3 Antibodies of the Present Invention

| SEQ ID NUMBER | Ab region | |
|---|---|---|
| SEQ ID NO: 361 | Heavy IgG1 | QVQLVESGGGLVQPGGSLRLSCAASGFTFSSYAMSWVRQAPGKGLEWVSVINGLG YTTFYADSVKGRFTISRDNSKNTLYLQMNSLRAEDTAVYYCARWGDEGFDIWGQG TLVTVSSASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDKRVEPKSC DKTHTCPPCPAPELLGGPSVFLFPPKPKDTLMISRTPEVTCVVVDVSHEDPEVKF NWYVDGVEVHNAKTKPREEQYNSTYRVVSVLTVLHQDWLNGKEYKCKVSNKALPA PIEKTISKAKGQPREPQVYTLPPSREEMTKNQVSLTCLVKGFYPSDIAVEWESNG QPENNYKTTPPVLDSDGSFFLYSKLTVDKSRWQQGNVFSCSVMHEALHNHYTQKS LSLSPGK |
| MOR12610 | | |
| SEQ ID NO: 362 (Kabat) | HCDR1 | SYAMS |
| SEQ ID NO: 363 (Kabat) | HCDR2 | GTGPYGGTYYPDSVKG |
| SEQ ID NO: 364 (Kabat) | HCDR3 | WGDEGFDI |
| SEQ ID NO: 365 (Kabat) | LCDR1 | RASQGISNWLA |
| SEQ ID NO: 366 (Kabat) | LCDR2 | GASSLQS |
| SEQ ID NO: 367 (Kabat) | LCDR3 | QQYSSFPTT |
| SEQ ID NO: 368 (Chothia) | HCDR1 | GFTFSSY |
| SEQ ID NO: 369 (Chothia) | HCDR2 | GPYGG |
| SEQ ID NO: 370 (Chothia) | HCDR3 | WGDEGFDI |
| SEQ ID NO: 371 (Chothia) | LCDR1 | SQGISNW |
| SEQ ID NO: 372 (Chothia) | LCDR2 | GAS |
| SEQ ID NO: 373 (Chothia) | LCDR3 | YSSFPT |
| SEQ ID NO: 374 | VL | DIQMTQSPSSLSASVGDRVTITCRASQGISNWLAWYQQKPGKAPKLLIYGASSLQ SGVPSRFSGSGSGTDFTLTISSLQPEDFAVYYCQQYSSFPTTFGQGTKVEIK |
| SEQ ID NO: 375 | VH | QVQLVESGGGLVQPGGSLRLSCAASGFTFSSYAMSWVRQAPGKGLEWVSGTGPYG GTYYPDSVKGRFTISRDNSKNTLYLQMNSLRAEDTAVYYCARWGDEGFDIWGQGT LVTVSS |
| SEQ ID NO: 376 | DNA VL | GATATCCAGATGACCCAGAGCCCGTCTAGCCTGAGCGCGAGCGTGGGTGATCGTG TGACCATTACCTGCAGAGCGAGCCAGGGTATTTCTAATTGGCTGGCTTGGTACCA GCAGAAACCAGGTAAAGCACCGAAACTATTAATTTATGGTGCTTCTTCTTTGCAA AGCGGGGTCCCGTCCCGTTTTAGCGGCTCTGGATCCGGCACTGATTTTACCCTGA CCATTAGCAGCCTGCAACCTGAAGACTTTGCGGTTTATTATTGCCAGCAGTATTC TTCTTTTCCTACTACCTTTGGCCAGGGTACGAAAGTTGAAATTAAA |
| SEQ ID NO: 377 | DNA VH | CAGGTGCAATTGGTGGAAAGCGGCGGCGGCCTGGTGCAACCGGGCGGCAGCCTGC GTCTGAGCTGCGCGGCCTCCGGATTTACCTTTAGCAGCTATGCGATGAGCTGGGT GCGCCAAGCCCCTGGGAAGGGTCTCGAGTGGGTGAGCGGTACTGGTCCTTATGGT GGTACTTATTATCCTGATTCTGTTAAGGGTCGTTTTACCATTTCACGTGATAATT CGAAAAACACCCTGTATCTGCAAATGAACAGCCTGCGTGCGGAAGATACGGCCGT GTATTATTGCGCGCGTTGGGGTGATGAGGGTTTTGATATTTGGGGCCAAGGCACC CTGGTGACGGTTAGCTCA |
| SEQ ID NO: 378 | Light Kappa | DIQMTQSPSSLSASVGDRVTITCRASQGISNWLAWYQQKPGKAPKLLIYGASSLQ SGVPSRFSGSGSGTDFTLTISSLQPEDFAVYYCQQYSSFPTTFGQGTKVEIKRTV AAPSVFIFPPSDEQLKSGTASVVCLLNNFYPREAKVQWKVDNALQSGNSQESVTE QDSKDSTYSLSSTLTLSKADYEKHKVYACEVTHQGLSSPVTKSFNRGEC |
| SEQ ID NO: 379 | Heavy IgG1 | QVQLVESGGGLVQPGGSLRLSCAASGFTFSSYAMSWVRQAPGKGLEWVSGTGPYG GTYYPDSVKGRFTISRDNSKNTLYLQMNSLRAEDTAVYYCARWGDEGFDIWGQGT LVTVSSASTKGPSVFPLAPSSKSTSGGTAALGCLVKDYFPEPVTVSWNSGALTSG VHTFPAVLQSSGLYSLSSVVTVPSSSLGTQTYICNVNHKPSNTKVDKRVEPKSCD KTHTCPPCPAPELLGGPSVFLFPPKPKDTLMISRTPEVTCVVVDVSHEDPEVKFN WYVDGVEVHNAKTKPREEQYNSTERVVSVLTVLHQDWLNGKEYKCKVSNKALPAP IEKTISKAKGQPREPQVYTLPPSREEMTKNQVSLTCLVKGFYPSDIAVEWESNGQ PENNYKTTPPVLDSDGSFFLYSKLTVDKSRWQQGNVFSCSVMHEALHNHYTQKSL SLSPGK |

Other antibodies of the invention include those where the amino acids or nucleic acids encoding the amino acids have been mutated, yet have at least 60, 70, 80, 90, 95, 96, 97, 98, and 99 percent identity to the sequences described in Table 1.

In some embodiments, it include mutant amino acid sequences wherein no more than 1, 2, 3, 4 or 5 amino acids have been mutated in the variable regions when compared with the variable regions depicted in the sequence described in Table 1, while retaining substantially the same therapeutic activity.

Since each of these antibodies or fragments thereof can bind to HER3, the VH, VL, full length light chain, and full length heavy chain sequences (amino acid sequences and the nucleotide sequences encoding the amino acid sequences) can be "mixed and matched" to create other HER3-binding antibodies of the invention. Such "mixed and matched" HER3-binding antibodies can be tested using the binding assays known in the art (e.g., ELISAs, and other assays described in the Example section). When these chains are mixed and matched, a VH sequence from a particular VH/VL pairing should be replaced with a structurally similar VH sequence. Likewise a full length heavy chain sequence from a particular full length heavy chain/full length light chain pairing should be replaced with a structurally similar full length heavy chain sequence. Likewise, a VL sequence from a particular VH/VL pairing should be replaced with a structurally similar VL sequence. Likewise a full length light chain sequence from a particular full length heavy chain/full length light chain pairing should be replaced with a structurally similar full length light chain sequence. Accordingly, in one aspect, the invention provides an isolated monoclonal antibody or fragment thereof having: a heavy chain variable region comprising an amino acid sequence selected from the group consisting of SEQ ID NO: 15, 33, 51, 69, 87, 105, 123, 141, 159, 177, 195, 213, 231, 249, 267, 285, 303, 321, 339, 357, and 375; and a light chain variable region comprising an amino acid sequence selected from the group consisting of SEQ ID NOs: 14, 32, 50, 68, 86, 104, 122, 140, 158, 176, 194, 212, 230, 248, 266, 284, 302, 320, 338, 356, and 374; wherein the antibody specifically binds to HER3 (e.g., human and/or cynomologus).

In another aspect, the present invention provides HER3-binding antibodies that comprise the heavy chain and light chain CDR1s, CDR2s and CDR3s as described in Table 1, or combinations thereof. The amino acid sequences of the VH CDR1s of the antibodies are shown in SEQ ID NOs: 2, 8, 20, 26, 38, 44, 56, 62, 74, 80, 92, 98, 110, 116, 128, 134, 146, 152, 164, 170, 182, 188, 200, 206, 218, 224, 236, 242, 254, 260, 272, 278, 290, 296, 308, 314, 326, 332, 344, 350, 362, and 368. The amino acid sequences of the VH CDR2s of the antibodies and are shown in SEQ ID NOs: 3, 9, 21, 27, 39, 45, 57, 63, 75, 81, 93, 99, 111, 117, 129, 135, 147, 153, 165, 171, 183, 189, 201, 207, 219, 225, 237, 243, 255, 261, 273, 279, 291, 297, 309, 315, 327, 333, 345, 351, 363, and 369. The amino acid sequences of the VH CDR3s of the antibodies are shown in SEQ ID NOs: 4, 10, 22, 28, 40, 46, 58, 64, 76, 82, 94, 100, 112, 118, 130, 136, 148, 154, 166, 172, 184, 190, 202, 208, 220, 226, 238, 244, 256, 262, 274, 280, 292, 298, 310, 316, 328, 334, 346, 352, 364, and 370. The amino acid sequences of the VL CDR1s of the antibodies are shown in SEQ ID NOs: 5, 11, 23, 29, 41, 47, 59, 65, 77, 83, 95, 101, 113, 119, 131, 137, 149, 155, 167, 173, 185, 191, 203, 209, 221, 227, 239, 245, 257, 263, 275, 281, 293, 299, 311, 317, 329, 335, 347, 353, 365, and 371. The amino acid sequences of the VL CDR2s of the antibodies are shown in SEQ ID NOs: 6, 12, 24, 30, 42, 48, 60, 66, 78, 84, 96, 102, 114, 120, 132, 138, 150, 156, 168, 174, 186, 192, 204, 210, 222, 228, 240, 246, 258, 264, 276, 282, 294, 300, 312, 318, 330, 336, 348, 354, 366, and 372. The amino acid sequences of the VL CDR3s of the antibodies are shown in SEQ ID NOs: 7, 13, 25, 31, 43, 49, 61, 67, 79, 85, 97, 103, 115, 121, 133, 139, 151, 157, 169, 175, 187, 193, 205, 211, 223, 229, 241, 247, 259, 265, 277, 283, 295, 301, 313, 319, 331, 337, 349, 355, 367, and 373. The CDR regions are delineated using the Kabat system (Kabat et al., (1991) Sequences of Proteins of Immunological Interest, Fifth Edition, U.S. Department of Health and Human Services, NIH Publication No. 91-3242; Chothia et al., (1987) J. Mol. Biol. 196:901-917; Chothia et al., (1989) Nature 342: 877-883; and Al-Lazikani et al., (1997) J. Mol. Biol. 273, 927-948).

In a specific embodiment, an antibody that binds to HER3 comprises a heavy chain variable region CDR1 of SEQ ID NO: 2; a CDR2 of SEQ ID NO: 3; a CDR3 of SEQ ID NO: 4; a light chain variable region CDR1 of SEQ ID NO: 5; a CDR2 of SEQ ID NO: 6; and a CDR3 of SEQ ID NO: 7.

In a specific embodiment, an antibody that binds to HER3 comprises a heavy chain variable region CDR1 of SEQ ID NO: 20; a CDR2 of SEQ ID NO: 21; a CDR3 of SEQ ID NO: 22; a light chain variable region CDR1 of SEQ ID NO: 23; a CDR2 of SEQ ID NO: 24; and a CDR3 of SEQ ID NO: 25.

In a specific embodiment, an antibody that binds to HER3 comprises a heavy chain variable region CDR1 of SEQ ID NO: 38; a CDR2 of SEQ ID NO: 39; a CDR3 of SEQ ID NO: 40; a light chain variable region CDR1 of SEQ ID NO: 41; a CDR2 of SEQ ID NO: 42; and a CDR3 of SEQ ID NO: 43.

In a specific embodiment, an antibody that binds to HER3 comprises a heavy chain variable region CDR1 of SEQ ID NO: 56; a CDR2 of SEQ ID NO: 57; a CDR3 of SEQ ID NO: 58; a light chain variable region CDR1 of SEQ ID NO: 59; a CDR2 of SEQ ID NO: 60; and a CDR3 of SEQ ID NO: 61.

In a specific embodiment, an antibody that binds to HER3 comprises a heavy chain variable region CDR1 of SEQ ID NO: 74; a CDR2 of SEQ ID NO: 75; a CDR3 of SEQ ID NO: 76; a light chain variable region CDR1 of SEQ ID NO: 77; a CDR2 of SEQ ID NO: 78; and a CDR3 of SEQ ID NO: 79.

In a specific embodiment, an antibody that binds to HER3 comprises a heavy chain variable region CDR1 of SEQ ID NO: 92; a CDR2 of SEQ ID NO: 93; a CDR3 of SEQ ID NO: 94; a light chain variable region CDR1 of SEQ ID NO: 95; a CDR2 of SEQ ID NO: 96; and a CDR3 of SEQ ID NO: 97.

In a specific embodiment, an antibody that binds to HER3 comprises a heavy chain variable region CDR1 of SEQ ID NO: 110; a CDR2 of SEQ ID NO: 111; a CDR3 of SEQ ID NO: 112; a light chain variable region CDR1 of SEQ ID NO: 113; a CDR2 of SEQ ID NO: 114; and a CDR3 of SEQ ID NO: 115.

In a specific embodiment, an antibody that binds to HER3 comprises a heavy chain variable region CDR1 of SEQ ID NO: 128; a CDR2 of SEQ ID NO: 129; a CDR3 of SEQ ID NO: 130; a light chain variable region CDR1 of SEQ ID NO: 131; a CDR2 of SEQ ID NO: 132; and a CDR3 of SEQ ID NO: 133.

In a specific embodiment, an antibody that binds to HER3 comprises a heavy chain variable region CDR1 of SEQ ID NO: 146; a CDR2 of SEQ ID NO: 147; a CDR3 of SEQ ID NO: 148; a light chain variable region CDR1 of SEQ ID NO: 149; a CDR2 of SEQ ID NO: 150; and a CDR3 of SEQ ID NO: 151.

In a specific embodiment, an antibody that binds to HER3 comprises a heavy chain variable region CDR1 of SEQ ID NO: 164; a CDR2 of SEQ ID NO: 165; a CDR3 of SEQ ID NO: 166; a light chain variable region CDR1 of SEQ ID NO: 167; a CDR2 of SEQ ID NO: 168; and a CDR3 of SEQ ID NO: 169.

In a specific embodiment, an antibody that binds to HER3 comprises a heavy chain variable region CDR1 of SEQ ID NO: 182; a CDR2 of SEQ ID NO: 183; a CDR3 of SEQ ID NO: 184; a light chain variable region CDR1 of SEQ ID NO: 185; a CDR2 of SEQ ID NO: 186; and a CDR3 of SEQ ID NO: 187.

In a specific embodiment, an antibody that binds to HER3 comprises a heavy chain variable region CDR1 of SEQ ID NO: 200; a CDR2 of SEQ ID NO: 201; a CDR3 of SEQ ID NO: 202; a light chain variable region CDR1 of SEQ ID NO: 203; a CDR2 of SEQ ID NO: 204; and a CDR3 of SEQ ID NO: 205.

In a specific embodiment, an antibody that binds to HER3 comprises a heavy chain variable region CDR1 of SEQ ID NO: 218; a CDR2 of SEQ ID NO: 219; a CDR3 of SEQ ID NO: 220; a light chain variable region CDR1 of SEQ ID NO: 221; a CDR2 of SEQ ID NO: 222; and a CDR3 of SEQ ID NO: 223.

In a specific embodiment, an antibody that binds to HER3 comprises a heavy chain variable region CDR1 of SEQ ID NO: 236; a CDR2 of SEQ ID NO: 237; a CDR3 of SEQ ID NO: 238; a light chain variable region CDR1 of SEQ ID NO: 239; a CDR2 of SEQ ID NO: 240; and a CDR3 of SEQ ID NO: 241.

In a specific embodiment, an antibody that binds to HER3 comprises a heavy chain variable region CDR1 of SEQ ID NO: 254; a CDR2 of SEQ ID NO: 255; a CDR3 of SEQ ID NO: 256; a light chain variable region CDR1 of SEQ ID NO: 257; a CDR2 of SEQ ID NO: 258; and a CDR3 of SEQ ID NO: 259.

In a specific embodiment, an antibody that binds to HER3 comprises a heavy chain variable region CDR1 of SEQ ID NO: 272; a CDR2 of SEQ ID NO: 273; a CDR3 of SEQ ID NO: 274; a light chain variable region CDR1 of SEQ ID NO: 275; a CDR2 of SEQ ID NO: 276; and a CDR3 of SEQ ID NO: 277.

In a specific embodiment, an antibody that binds to HER3 comprises a heavy chain variable region CDR1 of SEQ ID NO: 290; a CDR2 of SEQ ID NO: 291; a CDR3 of SEQ ID NO: 292; a light chain variable region CDR1 of SEQ ID NO: 293; a CDR2 of SEQ ID NO: 294; and a CDR3 of SEQ ID NO: 295.

In a specific embodiment, an antibody that binds to HER3 comprises a heavy chain variable region CDR1 of SEQ ID NO: 308; a CDR2 of SEQ ID NO: 309; a CDR3 of SEQ ID NO: 310; a light chain variable region CDR1 of SEQ ID NO: 311; a CDR2 of SEQ ID NO: 312; and a CDR3 of SEQ ID NO: 313.

In a specific embodiment, an antibody that binds to HER3 comprises a heavy chain variable region CDR1 of SEQ ID NO: 326; a CDR2 of SEQ ID NO: 327; a CDR3 of SEQ ID NO: 328; a light chain variable region CDR1 of SEQ ID NO: 329; a CDR2 of SEQ ID NO: 330; and a CDR3 of SEQ ID NO: 331.

In a specific embodiment, an antibody that binds to HER3 comprises a heavy chain variable region CDR1 of SEQ ID NO: 344; a CDR2 of SEQ ID NO: 345; a CDR3 of SEQ ID NO: 346; a light chain variable region CDR1 of SEQ ID NO: 347; a CDR2 of SEQ ID NO: 348; and a CDR3 of SEQ ID NO: 349.

In a specific embodiment, an antibody that binds to HER3 comprises a heavy chain variable region CDR1 of SEQ ID NO: 362; a CDR2 of SEQ ID NO: 363; a CDR3 of SEQ ID NO: 364; a light chain variable region CDR1 of SEQ ID NO: 365; a CDR2 of SEQ ID NO: 366; and a CDR3 of SEQ ID NO: 367.

In a specific embodiment, an antibody that binds to HER3 comprises a VH of SEQ ID NO. 15 and VL of SEQ ID NO: 14. In a specific embodiment, an antibody that binds to HER3 comprises a VH of SEQ ID NO: 33 and VL of SEQ ID NO: 32.

In a specific embodiment, an antibody that binds to HER3 comprises a VH of SEQ ID NO: 51 and VL of SEQ ID NO: 50. In a specific embodiment, an antibody that binds to HER3 comprises a SEQ ID NO: 69 and VL of SEQ ID NO: 68. In a specific embodiment, an antibody that binds to HER3 comprises a VH of SEQ ID NO: 87 and VL of SEQ ID NO: 86. In a specific embodiment, an antibody that binds to HER3 comprises a VH of SEQ ID NO: 105 and VL of SEQ ID NO: 104. In a specific embodiment, an antibody that binds to HER3 comprises a VH of SEQ ID NO: 123 and VL of SEQ ID NO: 122. In a specific embodiment, an antibody that binds to HER3 comprises a VH of SEQ ID NO: 141 and VL of SEQ ID NO: 140. In a specific embodiment, an antibody that binds to HER3 comprises a VH of SEQ ID NO: 159 and VL of SEQ ID NO: 158. In a specific embodiment, an antibody that binds to HER3 comprises a VH of SEQ ID NO: 177 and VL of SEQ ID NO: 176. In a specific embodiment, an antibody that binds to HER3 comprises a VH of SEQ ID NO: 195 and VL of SEQ ID NO: 194. In a specific embodiment, an antibody that binds to HER3 comprises a VH of SEQ ID NO: 213 and VL of SEQ ID NO: 212. In a specific embodiment, an antibody that binds to HER3 comprises a VH of SEQ ID NO: 231 and VL of SEQ ID NO: 230. In a specific embodiment, an antibody that binds to HER3 comprises a VH of SEQ ID NO: 249 and VL of SEQ ID NO: 248. In a specific embodiment, an antibody that binds to HER3 comprises a VH of SEQ ID NO: 267 and VL of SEQ ID NO: 266. In a specific embodiment, an antibody that binds to HER3 comprises a VH of SEQ ID NO: 285 and VL of SEQ ID NO: 284. In a specific embodiment, an antibody that binds to HER3 comprises a VH of SEQ ID NO: 303 and VL of SEQ ID NO: 302. In a specific embodiment, an antibody that binds to HER3 comprises a VH of SEQ ID NO: 321 and VL of SEQ ID NO: 320. In a specific embodiment, an antibody that binds to HER3 comprises a VH of SEQ ID NO: 339 and VL of SEQ ID NO: 338. In a specific embodiment, an antibody that binds to HER3 comprises a VH of SEQ ID NO: 357 and VL of SEQ ID NO: 356. In a specific embodiment, an antibody that binds to HER3 comprises a VH of SEQ ID NO: 375 and VL of SEQ ID NO: 374 In one embodiment, the HER3 antibodies are antagonist antibodies. In certain embodiments, an antibody that binds to HER3 is an antibody that is described in Table 1.

As used herein, a human antibody comprises heavy or light chain variable regions or full length heavy or light chains that are "the product of" or "derived from" a particular germline sequence if the variable regions or full length chains of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody that is "the product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody. A human antibody that is "the product of" or "derived from" a particular human germline immunoglobulin sequence may contain amino acid differences as compared to the germline sequence, due to, for example, naturally occurring somatic mutations or intentional introduction of site-directed mutations. However, in the VH or VL framework regions, a selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 60%, 70%, 80%, 90%, or at least 95%, or even at least 96%, 97%, 98%, or 99% identical in amino acid sequence to the amino acid sequence encoded by the germline immunoglobulin gene. Typically, a recombinant human antibody will display no more than 10 amino acid differences from the amino acid sequence encoded by the human germline immunoglobulin gene in the VH or VL framework regions. In certain cases, the human antibody may display no more than 5, or even no more than 4, 3, 2, or 1 amino acid difference from the amino acid sequence encoded by the germline immunoglobulin gene. Different germlined versions using the VH and VL germline sequences for a representative number of HER3 antibodies is shown in Table 2, using Kabat. The CDR positions are highlighted in boldface. The notation used in the Tables with germlined sequences is as follows: MOR10701-VH_3-07 means MOR10701 CDR loops in framework regions of VH germline sequence 3-07 (nomenclature is according to Vbase), MOR10703-VK_L1 means CDR from MOR10703 in germline framework regions from VK_L1, where VK is the kappa light chain.

TABLE 2

Different germlined versions of a selected number of representative antibodies

| SEQ ID NUMBER | Sequence Name | Amino Acid Sequence |
|---|---|---|
| | MOR10701 VH domain | |
| SEQ ID NO: 380 | MOR10701-VH_3-07 | EVQLVESGGGLVQPGGSLRLSCAASGFTFSSYAMSWVRQAPGKGLEWVATGAVGRSTYYPD SVKGRFTISRDNAKNSLYLQMNSLRAEDTAVYYCARWGDEGFDI |
| SEQ ID NO: 381 | MOR10701-VH_3-09 | EVQLVESGGGLVQPGRSLRLSCAASGFTFSSYAMSWVRQAPGKGLEWVSVTGAVGRSTYYPDS VKGRFTISRDNAKNSLYLQMNSLRAEDTALYYCAKWGDEGFDI |
| SEQ ID NO: 382 | MOR10701-VH_3-11 | QVQLVESGGGLVKPGGSLRLSCAASGFTFSSYAMSWIRQAPGKGLEWVSVTGAVGRSTYYPDS VKGRFTISRDNAKNSLYLQMNSLRAEDTAVYYCARWGDEGFDI |
| SEQ ID NO: 383 | MOR10701-VH_3-13 | EVQLVESGGGLVQPGGSLRLSCAASGFTFSSYAMSWVRQATGKGLEWVSVTGAVGRSTYYPDS VKGRFTISRENAKNSLYLQMNSLRAGDTAVYYCARWGDEGFDI |
| SEQ ID NO: 384 | MOR10701-VH_3-15 | EVQLVESGGGLVKPGGSLRLSCAASGFTFSSYAMSWVRQAPGKGLEWVSVTGAVGRSTYYPDS VKGRFTISRDDSKNTLYLQMNSLKTEDTAVYYCTTWGDEGFDI |
| SEQ ID NO: 385 | MOR10701-VH_3-20 | EVQLVESGGGVVRPGGSLRLSCAASGFTFSSYAMSWVRQAPGKGLEWVSVTGAVGRSTYYPDS VKGRFTISRDNAKNSLYLQMNSLRAEDTALYHCARWGDEGFDI |
| SEQ ID NO: 386 | MOR10701-VH_3-21 | EVQLVESGGGLVKPGGSLRLSCAASGFTFSSYAMSWVRQAPGKGLEWVSVTGAVGRSTYYPDS VKGRFTISRDNAKNSLYLQMNSLRAEDTAVYYCARWGDEGFDI |
| SEQ ID NO: 387 | MOR10701-VH_3-23 | EVQLLESGGGLVQPGGSLRLSCAASGFTFSSYAMSWVRQAPGKGLEWVSVTGAVGRSTYYPDS VKGRFTISRDNSKNTLYLQMNSLRAEDTAVYYCAKWGDEGFDI |
| SEQ ID NO: 388 | MOR10701-VH_3-30 | QVQLVESGGGVVQPGRSLRLSCAASGFTFSSYAMSWVRQAPGKGLEWVAVTGAVGRSTYYPD SVKGRFTISRDNSKNTLYLQMNSLRAEDTAVYYCAKWGDEGFDI |
| SEQ ID NO: 389 | MOR10701-VH_3-30.3 | QVQLVESGGGVVQPGRSLRLSCAASGFTFSSYAMSWVRQAPGKGLEWVAVTGAVGRSTYYPD SVKGRFTISRDNSKNTLYLQMNSLRAEDTAVYYCARWGDEGFDI |
| SEQ ID NO: 390 | MOR10701-VH_3-30.5 | QVQLVESGGGVVQPGRSLRLSCAASGFTFSSYAMSWVRQAPGKGLEWVAVTGAVGRSTYYPD SVKGRFTISRDNSKNTLYLQMNSLRAEDTAVYYCAKWGDEGFDI |
| SEQ ID NO: 391 | MOR10701-VH_3-33 | QVQLVESGGGVVQPGRSLRLSCAASGFTFSSYAMSWVRQAPGKGLEWVAVTGAVGRSTYYPD SVKGRFTISRDNSKNTLYLQMNSLRAEDTAVYYCARWGDEGFDI |
| SEQ ID NO: 392 | MOR10701-VH_3-43 | EVQLVESGGVVVQPGGSLRLSCAASGFTFSSYAMSWVRQAPGKGLEWVSVTGAVGRSTYYPDS VKGRFTISRDNSKNLYLQMNSLRTEDTALYYCAKWGDEGFDI |
| SEQ ID NO: 393 | MOR10701-VH_3-48 | EVQLVESGGGLVQPGGSLRLSCAASGFTFSSYAMSWVRQAPGKGLEWVSVTGAVGRSTYYPDS VKGRFTISRDNAKNSLYLQMNSLRDEDTAVYYCARWGDEGFDI |
| SEQ ID NO: 394 | MOR10701-VH_3-49 | EVQLVESGGGLVQPGRSLRLSCTASGFTFSSYAMSWFRQAPGKGLEWVGVTGAVGRSTYYPDS VKGRFTISRDGSKSIAYLQMNSLKTEDTAVYYCTRWGDEGFDI |
| SEQ ID NO: 395 | MOR10701-VH_3-53 | EVQLVETGGGLIQPGGSLRLSCAASGFTFSSYAMSWVRQAPGKGLEWVSVTGAVGRSTYYPDS VKGRFTISRDNSKNTLYLQMNSLRAEDTAVYYCARWGDEGFDI |
| SEQ ID NO: 396 | MOR10701-VH_3-64 | EVQLVESGGGLVQPGGSLRLSCAASGFTFSSYAMSWVRQAPGKGLEYVSVTGAVGRSTYYPDS VKGRFTISRDNSKNTLYLQMGSLRAEDMAVYYCARWGDEGFDI |
| SEQ ID NO: 397 | MOR10701-VH_3-66 | EVQLVESGGGLVQPGGSLRLSCAASGFTFSSYAMSWVRQAPGKGLEWVSVTGAVGRSTYYPDS VKGRFTISRDNSKNTLYLQMNSLRAEDTAVYYCARWGDEGFDI |
| SEQ ID NO: 398 | MOR10701-VH_3-72 | EVQLVESGGGLVQPGGSLRLSCAASGFTFSSYAMSWVRQAPGKGLEWVGVTGAVGRSTYYPD SVKGRFTISRDDSKNSLYLQMNSLKTEDTAVYYCARWGDEGFDI |

TABLE 2-continued

Different germlined versions of a selected number of representative antibodies

| SEQ ID NUMBER | Sequence Name | Amino Acid Sequence |
|---|---|---|
| SEQ ID NO: 399 | MOR10701-VH_3-73 | EVQLVESGGGLVQPGGSLKLSCAASGFTFSSYAMSWVRQASGKGLEWVGVTGAVGRSTYYPDS VKGRFTISRDDSKNTAYLQMNSLKTEDTAVYYCTRWGDEGFDI |
| SEQ ID NO: 400 | MOR10701-VH_3-74 | EVQLVESGGGLVQPGGSLRLSCAASGFTFSSYAMSWVRQAPGKGLVWVSVTGAVGRSTYYPDS VKGRFTISRDNAKNTLYLQMNSLRAEDTAVYYCARWGDEGFDI |
| SEQ ID NO: 401 | MOR10701-VH_3-d | EVQLVESRGVLVQPGGSLRLSCAASGFTFSSYAMSWVRQAPGKGLEWVSVTGAVGRSTYYPDS VKGRFTISRDNSKNTLHLQMNSLRAEDTAVYYCKKWGDEGFDI |
| | MOR10703 VH domain | |
| SEQ ID NO: 402 | MOR10703-VH_3-07 | EVQLVESGGGLVQPGGSLRLSCAASGFTFSSYAMSWVRQAPGKGLEWVAAINSQGKSTYYADS VKGRFTISRDNAKNSLYLQMNSLRAEDTAVYYCARWGDEGFDI |
| SEQ ID NO: 403 | MOR10703-VH_3-09 | EVQLVESGGGLVQPGRSLRLSCAASGFTFSSYAMSWVRQAPGKGLEWVSAINSQGKSTYYADS VKGRFTISRDNAKNSLYLQMNSLRAEDTALYYCAKWGDEGFDI |
| SEQ ID NO: 404 | MOR10703-VH_3-11 | QVQLVESGGGLVKPGGSLRLSCAASGFTFSSYAMSWIRQAPGKGLEWVSAINSQGKSTYYADS VKGRFTISRDNAKNSLYLQMNSLRAEDTAVYYCARWGDEGFDI |
| SEQ ID NO: 405 | MOR10703-VH_3-13 | EVQLVESGGGLVQPGGSLRLSCAASGFTFSSYAMSWVRQATGKGLEWVSAINSQGKSTYYADS VKGRFTISRENAKNSLYLQMNSLRAGDTAVYYCARWGDEGFDI |
| SEQ ID NO: 406 | MOR10703-VH_3-15 | EVQLVESGGGLVKPGGSLRLSCAASGFTFSSYAMSWVRQAPGKGLEWVGAINSQGKSTYYADS VKGRFTISRDDSKNTLYLQMNSLKTEDTAVYYCTTWGDEGFDI |
| SEQ ID NO: 407 | MOR10703-VH_3-20 | EVQLVESGGGVVRPGGSLRLSCAASGFTFSSYAMSWVRQAPGKGLEWVSAINSQGKSTYYADS VKGRFTISRDNAKNSLYLQMNSLRAEDTALYHCARWGDEGFDI |
| SEQ ID NO: 408 | MOR10703-VH_3-21 | EVQLVESGGGLVKPGGSLRLSCAASGFTFSSYAMSWVRQAPGKGLEWVSAINSQGKSTYYADS VKGRFTISRDNAKNSLYLQMNSLRAEDTAVYYCARWGDEGFDI |
| SEQ ID NO: 409 | MOR10703-VH_3-23 | EVQLLESGGGLVQPGGSLRLSCAASGFTFSSYAMSWVRQAPGKGLEWVSAINSQGKSTYYADS VKGRFTISRDNSKNTLYLQMNSLRAEDTAVYYCAKWGDEGFDI |
| SEQ ID NO: 410 | MOR10703-VH_3-30 | QVQLVESGGGVVQPGRSLRLSCAASGFTFSSYAMSWVRQAPGKGLEWVAAINSQGKSTYYAD SVKGRFTISRDNSKNTLYLQMNSLRAEDTAVYYCAKWGDEGFDI |
| SEQ ID NO: 411 | MOR10703-VH_3-30.3 | QVQLVESGGGVVQPGRSLRLSCAASGFTFSSYAMSWVRQAPGKGLEWVAAINSQGKSTYYAD SVKGRFTISRDNSKNTLYLQMNSLRAEDTAVYYCARWGDEGFDI |
| SEQ ID NO: 412 | MOR10703-VH_3-30.5 | QVQLVESGGGVVQPGRSLRLSCAASGFTFSSYAMSWVRQAPGKGLEWVAAINSQGKSTYYAD SVKGRFTISRDNSKNTLYLQMNSLRAEDTAVYYCAKWGDEGFDI |
| SEQ ID NO: 413 | MOR10703-VH_3-33 | QVQLVESGGGVVQPGRSLRLSCAASGFTFSSYAMSWVRQAPGKGLEWVAAINSQGKSTYYAD SVKGRFTISRDNSKNTLYLQMNSLRAEDTAVYYCARWGDEGFDI |
| SEQ ID NO: 414 | MOR10703-VH_3-43 | EVQLVESGGVVVQPGGSLRLSCAASGFTFSSYAMSWVRQAPGKGLEWVSAINSQGKSTYYADS VKGRFTISRDNSKNSLYLQMNSLRTEDTALYYCAKWGDEGFDI |
| SEQ ID NO: 415 | MOR10703-VH_3-48 | EVQLVESGGGLVQPGGSLRLSCAASGFTFSSYAMSWVRQAPGKGLEWVSAINSQGKSTYYADS VKGRFTISRDNAKNSLYLQMNSLRDEDTAVYYCARWGDEGFDI |
| SEQ ID NO: 416 | MOR10703-VH_3-49 | EVQLVESGGGLVQPGRSLRLSCTASGFTFSSYAMSWFRQAPGKGLEWVGAINSQGKSTYYADS VKGRFTISRDGSKSIAYLQMNSLKTEDTAVYYCTRWGDEGFDI |
| SEQ ID NO: 417 | MOR10703-VH_3-53 | EVQLVETGGGLIQPGGSLRLSCAASGFTFSSYAMSWVRQAPGKGLEWVSAINSQGKSTYYADS VKGRFTISRDNSKNTLYLQMNSLRAEDTAVYYCARWGDEGFDI |
| SEQ ID NO: 418 | MOR10703-VH_3-64 | EVQLVESGGGLVQPGGSLRLSCAASGFTFSSYAMSWVRQAPGKGLEYVSAINSQGKSTYYADSV KGRFTISRDNSKNTLYLQMGSLRAEDMAVYYCARWGDEGFDI |
| SEQ ID NO: 419 | MOR10703-VH_3-66 | EVQLVESGGGLVQPGGSLRLSCAASGFTFSSYAMSWVRQAPGKGLEWVSAINSQGKSTYYADS VKGRFTISRDNSKNTLYLQMNSLRAEDTAVYYCARWGDEGFDI |
| SEQ ID NO: 420 | MOR10703-VH_3-72 | EVQLVESGGGLVQPGGSLRLSCAASGFTFSSYAMSWVRQAPGKGLEWVGAINSQGKSTYYADS VKGRFTISRDDSKNSLYLQMNSLKTEDTAVYYCARWGDEGFDI |
| SEQ ID NO: 421 | MOR10703-VH_3-73 | EVQLVESGGGLVQPGGSLKLSCAASGFTFSSYAMSWVRQASGKGLEWVGAINSQGKSTYYADS VKGRFTISRDDSKNTAYLQMNSLKTEDTAVYYCTRWGDEGFDI |
| SEQ ID NO: 422 | MOR10703-VH_3-74 | EVQLVESGGGLVQPGGSLRLSCAASGFTFSSYAMSWVRQAPGKGLVWVSAINSQGKSTYYADS VKGRFTISRDNAKNTLYLQMNSLRAEDTAVYYCARWGDEGFDI |

TABLE 2-continued

Different germlined versions of a selected number of representative antibodies

| SEQ ID NUMBER | Sequence Name | Amino Acid Sequence |
|---|---|---|
| SEQ ID NO: 423 | MOR10703-VH_3-d | EVQLVESRGVLVQPGGSLRLSCAASGFTFSSYAMSWVRQAPGKGLEWVSAINSQGKSTYYADS VKGRFTISRDNSKNTLHLQMNSLRAEDTAVYYCKKWGDEGFDI |
| | MOR10701 VK domain | |
| SEQ ID NO: 424 | MOR10701-VKI_O12 (same as MOR10701 wt) | DIQMTQSPSSLSASVGDRVTITCRASQGISNWLAWYQQKPGKAPKLLIYGASSLQSGVPSRFSGS GSGTDFTLTISSLQPEDFATYYCQQYSSFPTT |
| SEQ ID NO: 425 | MOR10701-VKI_O2 | DIQMTQSPSSLSASVGDRVTITCRASQGISNWLAWYQQKPGKAPKLLIYGASSLQSGVPSRFSGS GSGTDFTLTISSLQPEDFATYYCQQYSSFPTT |
| SEQ ID NO: 426 | MOR10701-VKI_O18 | DIQMTQSPSSLSASVGDRVTITCRASQGISNWLAWYQQKPGKAPKLLIYGASSLQSGVPSRFSGS GSGTDFTFTISSLQPEDIATYYCQQYSSFPTT |
| SEQ ID NO: 427 | MOR10701-VKI_O8 | DIQMTQSPSSLSASVGDRVTITCRASQGISNWLAWYQQKPGKAPKLLIYGASSLQSGVPSRFSGS GSGTDFTFTISSLQPEDIATYYCQQYSSFPTT |
| SEQ ID NO: 428 | MOR10701-VKI_A20 | DIQMTQSPSSLSASVGDRVTITCRASQGISNWLAWYQQKPGKVPKLLIYGASSLQSGVPSRFSGS GSGTDFTLTISSLQPEDVATYYCQQYSSFPTT |
| SEQ ID NO: 429 | MOR10701-VKI_A30 | DIQMTQSPSSLSASVGDRVTITCRASQGISNWLAWYQQKPGKAPKRLIYGASSLQSGVPSRFSGS GSGTEFTLTISSLQPEDFATYYCQQYSSFPTT |
| SEQ ID NO: 430 | MOR10701-VKI_L14 | NIQMTQSPSAMSASVGDRVTITCRASQGISNWLAWFQQKPGKVPKHLIYGASSLQSGVPSRFS GSGSGTEFTLTISSLQPEDFATYYCQQYSSFPTT |
| SEQ ID NO: 431 | MOR10701-VKI_L1 | DIQMTQSPSSLSASVGDRVTITCRASQGISNWLAWFQQKPGKAPKSLIYGASSLQSGVPSRFSGS GSGTDFTLTISSLQPEDFATYYCQQYSSFPTT |
| SEQ ID NO: 432 | MOR10701-VKI_L15 | DIQMTQSPSSLSASVGDRVTITCRASQGISNWLAWYQQKPEKAPKSLIYGASSLQSGVPSRFSGS GSGTDFTLTISSLQPEDFATYYCQQYSSFPTT |
| SEQ ID NO: 433 | MOR10701-VKI_L4 | AIQLTQSPSSLSASVGDRVTITCRASQGISNWLAWYQQKPGKAPKLLIYGASSLQSGVPSRFSGSG SGTDFTLTISSLQPEDFATYYCQQYSSFPTT |
| SEQ ID NO: 434 | MOR10701-VKI_L18 | AIQLTQSPSSLSASVGDRVTITCRASQGISNWLAWYQQKPGKAPKLLIYGASSLQSGVPSRFSGSG SGTDFTLTISSLQPEDFATYYCQQYSSFPTT |
| SEQ ID NO: 435 | MOR10701-VKI_L5 | DIQMTQSPSSVSASVGDRVTITCRASQGISNWLAWYQQKPGKAPKLLIYGASSLQSGVPSRFSGS GSGTDFTLTISSLQPEDFATYYCQQYSSFPTT |
| SEQ ID NO: 436 | MOR10701-VKI_L19 | DIQMTQSPSSVSASVGDRVTITCRASQGISNWLAWYQQKPGKAPKLLIYGASSLQSGVPSRFSGS GSGTDFTLTISSLQPEDFATYYCQQYSSFPTT |
| SEQ ID NO: 437 | MOR10701-VKI_L8 | DIQLTQSPSFLSASVGDRVTITCRASQGISNWLAWYQQKPGKAPKLLIYGASSLQSGVPSRFSGS GSGTEFTLTISSLQPEDFATYYCQQYSSFPTT |
| SEQ ID NO: 438 | MOR10701-VKI_L23 | AIRMTQSPFSLSASVGDRVTITCRASQGISNWLAWYQQKPAKAPKLFIYGASSLQSGVPSRFSGS GSGTDYTLTISSLQPEDFATYYCQQYSSFPTT |
| SEQ ID NO: 439 | MOR10701-VKI_L9 | AIRMTQSPSSFSASTGDRVTITCRASQGISNWLAWYQQKPGKAPKLLIYGASSLQSGVPSRFSGS GSGTDFTLTISCLQSEDFATYYCQQYSSFPTT |
| SEQ ID NO: 440 | MOR10701-VKI_L24 | VIWMTQSPSLLSASTGDRVTISCRASQGISNWLAWYQQKPGKAPELLIYGASSLQSGVPSRFSGS GSGTDFTLTISCLQSEDFATYYCQQYSSFPTT |
| SEQ ID NO: 441 | MOR10701-VKI_L11 | AIQMTQSPSSLSASVGDRVTITCRASQGISNWLAWYQQKPGKAPKLIYGASSLQSGVPSRFSGS GSGTDFTLTISSLQPEDFATYYCQQYSSFPTT |
| SEQ ID NO: 442 | MOR10701-VKI_L12 | DIQMTQSPSTLSASVGDRVTITCRASQGISNWLAWYQQKPGKAPKLLIYGASSLQSGVPSRFSGS GSGTEFTLTISSLQPDDFATYYCQQYSSFPTT |
| | MOR10701 VK domain | |
| SEQ ID NO: 443 | MOR10703-VKI_O12 (same as MOR10703 wt) | DIQMTQSPSSLSASVGDRVTITCRASQGISNWLAWYQQKPGKAPKLLIYGASSLQSGVPSRFSGS GSGTDFTLTISSLQPEDFATYYCQQYSSFPTT |
| SEQ ID NO: 444 | MOR10703-VKI_O2 | DIQMTQSPSSLSASVGDRVTITCRASQGISNWLAWYQQKPGKAPKLLIYGASSLQSGVPSRFSGS GSGTDFTLTISSLQPEDFATYYCQQYSSFPTT |

TABLE 2-continued

Different germlined versions of a selected number of representative antibodies

| SEQ ID NUMBER | Sequence Name | Amino Acid Sequence |
|---|---|---|
| SEQ ID NO: 445 | MOR10703-VKI_O18 | DIQMTQSPSSLSASVGDRVTITCRASQGISNWLAWYQQKPGKAPKLLIYGASSLQSGVPSRFSGSGSGTDFTFTISSLQPEDIATYYCQQYSSFPTT |
| SEQ ID NO: 446 | MOR10703-VKI_O8 | DIQMTQSPSSLSASVGDRVTITCRASQGISNWLAWYQQKPGKAPKLLIYGASSLQSGVPSRFSGSGSGTDFTFTISSLQPEDIATYYCQQYSSFPTT |
| SEQ ID NO: 447 | MOR10703-VKI_A20 | DIQMTQSPSSLSASVGDRVTITCRASQGISNWLAWYQQKPGKVPKLLIYGASSLQSGVPSRFSGSGSGTDFTLTISSLQPEDVATYYCQQYSSFPTT |
| SEQ ID NO: 448 | MOR10703-VKI_A30 | DIQMTQSPSSLSASVGDRVTITCRASQGISNWLAWYQQKPGKAPKRLIYGASSLQSGVPSRFSGSGSGTEFTLTISSLQPEDFATYYCQQYSSFPTT |
| SEQ ID NO: 449 | MOR10703-VKI_L14 | NIQMTQSPSAMSASVGDRVTITCRASQGISNWLAWFQQKPGKVPKHLIYGASSLQSGVPSRFSGSGSGTEFTLTISSLQPEDFATYYCQQYSSFPTT |
| SEQ ID NO: 450 | MOR10703-VKI_L1 | DIQMTQSPSSLSASVGDRVTITCRASQGISNWLAWFQQKPGKAPKSLIYGASSLQSGVPSRFSGSGSGTDFTLTISSLQPEDFATYYCQQYSSFPTT |
| SEQ ID NO: 451 | MOR10703-VKI_L15 | DIQMTQSPSSLSASVGDRVTITCRASQGISNWLAWYQQKPEKAPKSLIYGASSLQSGVPSRFSGSGSGTDFTLTISSLQPEDFATYYCQQYSSFPTT |
| SEQ ID NO: 452 | MOR10703-VKI_L4 | AIQLTQSPSSLSASVGDRVTITCRASQGISNWLAWYQQKPGKAPKLLIYGASSLQSGVPSRFSGSGSGTDFTLTISSLQPEDFATYYCQQYSSFPTT |
| SEQ ID NO: 453 | MOR10703-VKI_L18 | AIQLTQSPSSLSASVGDRVTITCRASQGISNWLAWYQQKPGKAPKLLIYGASSLQSGVPSRFSGSGSGTDFTLTISSLQPEDFATYYCQQYSSFPTT |
| SEQ ID NO: 454 | MOR10703-VKI_L5 | DIQMTQSPSSVSASVGDRVTITCRASQGISNWLAWYQQKPGKAPKLLIYGASSLQSGVPSRFSGSGSGTDFTLTISSLQPEDFATYYCQQYSSFPTT |
| SEQ ID NO: 455 | MOR10703-VKI_L19 | DIQMTQSPSSVSASVGDRVTITCRASQGISNWLAWYQQKPGKAPKLLIYGASSLQSGVPSRFSGSGSGTDFTLTISSLQPEDFATYYCQQYSSFPTT |
| SEQ ID NO: 456 | MOR10703-VKI_L8 | DIQLTQSPSFLSASVGDRVTITCRASQGISNWLAWYQQKPGKAPKLLIYGASSLQSGVPSRFSGSGSGTEFTLTISSLQPEDFATYYCQQYSSFPTT |
| SEQ ID NO: 457 | MOR10703-VKI_L23 | AIRMTQSPFSLSASVGDRVTITCRASQGISNWLAWYQQKPAKAPKLFIYGASSLQSGVPSRFSGSGSGTDYTLTISSLQPEDFATYYCQQYSSFPTT |
| SEQ ID NO: 458 | MOR10703-VKI_L9 | AIRMTQSPSSFSASTGDRVTITCRASQGISNWLAWYQQKPGKAPKLLIYGASSLQSGVPSRFSGSGSGTDFTLTISCLQSEDFATYYCQQYSSFPTT |
| SEQ ID NO: 459 | MOR10703-VKI_L24 | VIWMTQSPSLLSASTGDRVTISCRASQGISNWLAWYQQKPGKAPELLIYGASSLQSGVPSRFSGSGSGTDFTLTISCLQSEDFATYYCQQYSSFPTT |
| SEQ ID NO: 460 | MOR10703-VKI_L11 | AIQMTQSPSSLSASVGDRVTITCRASQGISNWLAWYQQKPGKAPKLLIYGASSLQSGVPSRFSGSGSGTDFTLTISSLQPEDFATYYCQQYSSFPTT |
| SEQ ID NO: 461 | MOR10703-VKI_L12 | DIQMTQSPSTLSASVGDRVTITCRASQGISNWLAWYQQKPGKAPKLLIYGASSLQSGVPSRFSGSGSGTEFTLTISSLQPDDFATYYCQQYSSFPTT |

TABLE 3

JH segments

| SEQ ID NO: 462 | JH1 | WGQGTLVTVSS |
| SEQ ID NO: 463 | JH2 | WGRGTLVTVSS |
| SEQ ID NO: 464 | JH3 | WGQGTMVTVSS |
| SEQ ID NO: 465 | JH4 | WGQGTLVTVSS |
| SEQ ID NO: 466 | JH5 | WGQGTLVTVSS |
| SEQ ID NO: 467 | JH6 | WGQGTTVTVSS |

TABLE 4

JK segments

| SEQ ID NO: 468 | JK1 | FGQGTKVEIK |
| SEQ ID NO: 469 | JK2 | FGQGTKLEIK |
| SEQ ID NO: 470 | JK3 | FGPGTKVDIK |
| SEQ ID NO: 471 | JK4 | FGGGTKVEIK |
| SEQ ID NO: 472 | JK5 | FGQGTRLEIK |

Any combination of the VH-germlined sequences with a JH segments can be used. Representative examples of combinations are shown in Table 5.

TABLE 5

Representative examples of combinations of the VH-germlined sequences with a JH segments.

| | | |
|---|---|---|
| SEQ ID NO: 473 | MOR10701-VH_3-15_JH1 | EVQLVESGGGLVKPGGSLRLSCAASGFTFSSYAMSWVRQAPGKGLEWVGVTGAVGRST YYPDSVKGRFTISRDDSKNTLYLQMNSLKTEDTAVYYCTTWGDEGFDIWGQGTLVTVSS |
| SEQ ID NO: 474 | MOR10701-VH_3-151_JH3 | EVQLVESGGGLVKPGGSLRLSCAASGFTFSSYAMSWVRQAPGKGLEWVGVTGAVGRST YYPDSVKGRFTISRDDSKNTLYLQMNSLKTEDTAVYYCTTWGDEGFDI WGQGTMVTVSS |
| SEQ ID NO: 475 | MOR10703-VH_3-15_JH1 | EVQLVESGGGLVKPGGSLRLSCAASGFTFSSYAMSWVRQAPGKGLEWVGAINSQGKSTY YADSVKGRFTISRDDSKNTLYLQMNSLKTEDTAVYYCTTWGDEGFDIWGQGTLVTVSS |
| SEQ ID NO: 476 | MOR10703-VH_3-15_JH3 | EVQLVESGGGLVKPGGSLRLSCAASGFTFSSYAMSWVRQAPGKGLEWVGAINSQGKSTY YADSVKGRFTISRDDSKNTLYLQMNSLKTEDTAVYYCTTWGDEGFDI WGQGTMVTVSS |

Any combination of the VL-germlined sequences with a JK segments can be used. Representative examples of combinations are shown in Table 6.

TABLE 6

Representative examples of combinations of the VK-germlined sequences with a JK segments

| | | |
|---|---|---|
| SEQ ID NO: 477 | MOR10701-VKI_O2_JK1 | DIQMTQSPSSLSASVGDRVTITCRASQGISNWLAWYQQKPGKAPKLLIYGASSLQSGVPSR FSGSGSGTDFTLTISSLQPEDFATYYCQQYSSFPTTFGQGTKVEIK |
| SEQ ID NO: 478 | MOR10701-VKI_O2_JK4 | DIQMTQSPSSLSASVGDRVTITCRASQGISNWLAWYQQKPGKAPKLLIYGASSLQSGVPSR FSGSGSGTDFTLTISSLQPEDFATYYCQQYSSFPTTFGGGTKVEIK |
| SEQ ID NO: 479 | MOR10703-VKI_A20_JK4 | DIQMTQSPSSLSASVGDRVTITCRASQGISNWLAWYQQKPGKVPKLLIYGASSLQSGVPSR FSGSGSGTDFTLTISSLQPEDVATYYCQQYSSFPTTFGGGTKVEIK |
| SEQ ID NO: 480 | MOR10703-VKI_A20_JK1 | DIQMTQSPSSLSASVGDRVTITCRASQGISNWLAWYQQKPGKVPKLLIYGASSLQSGVPSR FSGSGSGTDFTLTISSLQPEDVATYYCQQYSSFPTTFGQGTKVEIK |

Once VH has been combined with JH and VK with JK, then any combination of VH or JH with VK or JK, can be used. In one embodiment, any of the VH germlined regions can be combined with any of the VK (VL) germlined regions for each antibody. A representative number of examples of combinations is shown in Table 7.

TABLE 7

Representative examples of combinations of germlined sequences

Combination 1

| | | |
|---|---|---|
| SEQ ID NO: 481 | MOR10701-VH 3-15_JH3 | EVQLVESGGGLVKPGGSLRLSCAASGFTFSSYAMSWVRQAPGKGLEWVGVTGAVGRSTY YPDSVKGRFTISRDDSKNTLYLQMNSLKTEDTAVYYCTTWGDEGFDIWGQGTMVTVSS |
| SEQ ID NO: 482 | MOR10701-VKI_A30_JK4 | DIQMTQSPSSLSASVGDRVTITCRASQGISNWLAWYQQKPGKAPKRLIYGASSLQSGVPSR FSGSGSGTEFTLTISSLQPEDFATYYCQQYSSFPTTFGGGTKVEIK |

Combination 2

| | | |
|---|---|---|
| SEQ ID NO: 483 | MOR10701-VH_3-30_JH1 | QVQLVESGGGVVQPGRSLRLSCAASGFTFSSYAMSWVRQAPGKGLEWVAVTGAVGRST YYPDSVKGRFTISRDNSKNTLYLQMNSLRAEDTAVYYCAKWGDEGFDIWGQGTLVTVSS |
| SEQ ID NO: 484 | MOR10701-VKI_L1_JK2 | DIQMTQSPSSLSASVGDRVTITCRASQGISNWLAWFQQKPGKAPKSLIYGASSLQSGVPSR FSGSGSGTDFTLTISSLQPEDFATYYCQQYSSFPTTFGQGTKLEIK |

Combination 3

| | | |
|---|---|---|
| SEQ ID NO: 485 | MOR10701-VH_3-30_JH2 | QVQLVESGGGVVQPGRSLRLSCAASGFTFSSYAMSWVRQAPGKGLEWVAVTGAVGRST YYPDSVKGRFTISRDNSKNTLYLQMNSLRAEDTAVYYCAKWGDEGFDIWGRGTLVTVSS |
| SEQ ID NO: 486 | MOR10701-VKI_L1_JK2 | DIQMTQSPSSLSASVGDRVTITCRASQGISNWLAWFQQKPGKAPKSLIYGASSLQSGVPSR FSGSGSGTDFTLTISSLQPEDFATYYCQQYSSFPTTFGQGTKLEIK |

Combination 4

| | | |
|---|---|---|
| SEQ ID NO: 487 | MOR10703-VH_3-20_JH5 | EVQLVESGGGVVRPGGSLRLSCAASGFTFSSYAMSWVRQAPGKGLEWVSAINSQGKSTY YADSVKGRFTISRDNAKNSLYLQMNSLRAEDTALYHCARWGDEGFDIWGQGTLVTVSS |

TABLE 7-continued

Representative examples of combinations of germlined sequences

| SEQ ID NO: 488 | MOR10703-VKI_L15_JK3 | DIQMTQSPSSLSASVGDRVTITCRASQGISNWLAWYQQKPEKAPKSLIYGASSLQSGVPSR<br>FSGSGSGTDFTLTISSLQPEDFATYYCQQYSSFPTTFGPGTKVDIK |
|---|---|---|

Combination 5

| SEQ ID NO: 489 | MOR10703-VH_3-33_JH2 | QVQLVESGGGVVQPGRSLRLSCAASGFTFSSYAMSWVRQAPGKGLEWVAAINSQGKSTY<br>YADSVKGRFTISRDNSKNTLYLQMNSLRAEDTAVYYCARWGDEGFDIWGRGTLVTVSS |
| SEQ ID NO: 490 | MOR10703-VKI_A20_JK1 | DIQMTQSPSSLSASVGDRVTITCRASQGISNWLAWYQQKPGKVPKLLIYGASSLQSGVPSR<br>FSGSGSGTDFTLTISSLQPEDVATYYCQQYSSFPTTFGQGTKVEIK |

Combination 6

| SEQ ID NO: 491 | MOR10703-VH_3-33_JH3 | QVQLVESGGGVVQPGRSLRLSCAASGFTFSSYAMSWVRQAPGKGLEWVAAINSQGKSTY<br>YADSVKGRFTISRDNSKNTLYLQMNSLRAEDTAVYYCARWGDEGFDIWGQGTMVTVSS |
| SEQ ID NO: 492 | MOR10703-VKI_A20_JK2 | DIQMTQSPSSLSASVGDRVTITCRASQGISNWLAWYQQKPGKVPKLLIYGASSLQSGVPSR<br>FSGSGSGTDFTLTISSLQPEDVATYYCQQYSSFPTTFGQGTKLEIK |

In one embodiment, the invention pertains to a heavy chain variable region comprising a sequence of $Xaa_1$-HCDR1-$Xaa_2$-HCDR2-$Xaa_3$-HCDR3-$Xaa_4$ where the heavy chain HCDR1, HCDR2, HCDR3 are any heavy chain CDRs selected from Tables 1 and 2. For illustrative purposes only, the sequence can be:

$Xaa_1$-SYAMS-$Xaa_2$-AINSQGKSTYYADSVKG-$Xaa_3$-WGDEGFDI-$Xaa_4$ (SEQ ID NO: 493), where, $Xaa_1$ is framework region of any 30 amino acids;
$Xaa_2$ is framework region of any 14 amino acids;
$Xaa_3$ is framework region of any 32 amino acids;
$Xaa_4$ is framework region of any 11 amino acids;

In one embodiment, the invention pertains to a light chain variable region comprising a sequence of $Xaa_1$-LCDR1-$Xaa_2$-LCDR2-$Xaa_3$-LCDR3-$Xaa_4$, where the light chain LCDR1, LCDR2, LCDR3 are any light chain CDRs selected from Tables 1 and 2. For illustrative purposes only, the sequence can be:

$Xaa_1$-RASQGISNWLA-$Xaa_2$-GASSLQS-$Xaa_3$-QQYSSF-PTT-$Xaa_4$ (SEQ ID NO: 494), where, $Xaa_1$ is a framework region of any 23 amino acids;
$Xaa_2$ is a framework region of any 15 amino acids;
$Xaa_3$ is a framework region of any 32 amino acids; and
$Xaa_4$ is a framework region of any 10 amino acids.

The antibodies disclosed herein can be derivatives of single chain antibodies, diabodies, domain antibodies, nanobodies, and unibodies. A "single-chain antibody" (scFv) consists of a single polypeptide chain comprising a VL domain linked to a VH domain, wherein VL domain and VH domain are paired to form a monovalent molecule. Single chain antibody can be prepared according to method known in the art (see, for example, Bird et al., (1988) Science 242:423-426 and Huston et al., (1988) Proc. Natl. Acad. Sci. USA 85:5879-5883). A "disbud" consists of two chains, each chain comprising a heavy chain variable region connected to a light chain variable region on the same polypeptide chain connected by a short peptide linker, wherein the two regions on the same chain do not pair with each other but with complementary domains on the other chain to form a bispecific molecule. Methods of preparing diabodies are known in the art (See, e.g., Holliger et al., (1993) Proc. Natl. Acad. Sci. USA 90:6444-6448, and Poljak et al., (1994) Structure 2:1121-1123). Domain antibodies (dAbs) are small functional binding units of antibodies, corresponding to the variable regions of either the heavy or light chains of antibodies. Domain antibodies are well expressed in bacterial, yeast, and mammalian cell systems. Further details of domain antibodies and methods of production thereof are known in the art (see, for example, U.S. Pat. Nos. 6,291,158; 6,582,915; 6,593,081; 6,172,197; 6,696,245; European Patents 0368684 & 0616640; WO05/035572, WO04/101790, WO04/081026, WO04/058821, WO04/003019 and WO03/002609. Nanobodies are derived from the heavy chains of an antibody. A nanobody typically comprises a single variable domain and two constant domains (CH2 and CH3) and retains antigen-binding capacity of the original antibody. Nanobodies can be prepared by methods known in the art (See e.g., U.S. Pat. No. 6,765,087, U.S. Pat. No. 6,838,254, WO 06/079372). Unibodies consist of one light chain and one heavy chain of a IgG4 antibody. Unibodies may be made by the removal of the hinge region of IgG4 antibodies. Further details of unibodies and methods of preparing them may be found in WO2007/059782.

Homologous Antibodies

In yet another embodiment, the present invention provides an antibody or fragment thereof comprising amino acid sequences that are homologous to the sequences described in Table 1, and said antibody binds to a HER3 protein (e.g., human and/or cynomologus HER3), and retains the desired functional properties of those antibodies described in Table 1.

For example, the invention provides an isolated monoclonal antibody (or a functional fragment thereof) comprising a heavy chain variable region and a light chain variable region, wherein the heavy chain variable region comprises an amino acid sequence that is at least 80%, at least 90%, or at least 95% identical to an amino acid sequence selected from the group consisting of SEQ ID NOs: 15, 33, 51, 69, 87, 105, 123, 141, 159, 177, 195, 213, 231, 249, 267, 285, 303, 321, 339, 357, and 375; the light chain variable region comprises an amino acid sequence that is at least 80%, at least 90%, or at least 95% identical to an amino acid sequence selected from the group consisting of SEQ ID NOs: 14, 32, 50, 68, 86, 104, 122, 140, 158, 176, 194, 212, 230, 248, 266, 284, 302, 320, 338, 356, and 374; the antibody binds to HER3 (e.g., human and/or cynomologus HER3) and neutralizes the signaling activity of HER3, which can be measured in a phosphorylation assay or other measure of HER signaling (e.g., phospho-HER3 assays, phospho-Akt assays, cell proliferation, and ligand blocking assays as described in the Examples). Also includes within the scope of the invention are variable heavy and light chain parental nucleotide sequences; and full length heavy and light chain sequences optimized for expression in a mammalian cell. Other antibodies of the invention include amino acids or nucleic acids that have been mutated, yet have at least 60, 70, 80, 90, 95, or 98% percent identity to the sequences described above. In some embodiments, it include mutant amino acid sequences wherein no more than 1, 2, 3, 4 or 5 amino acids have been mutated by amino acid deletion, insertion or substitution in the variable regions when compared with the variable regions depicted in the sequence described above.

In other embodiments, the VH and/or VL amino acid sequences may be 50%, 60%, 70%, 80%, 90%, 95%, 96%, 97%, 98% or 99% identical to the sequences set forth in Table 1. In other embodiments, the VH and/or VL amino acid sequences may be identical except an amino acid substitution in no more than 1, 2, 3, 4 or 5 amino acid position. An antibody having VH and VL regions having high (i.e., 80% or greater) identity to the VH and VL regions of the antibodies described in Table 1 can be obtained by mutagenesis (e.g., site-directed or PCR-mediated mutagenesis), followed by testing of the encoded altered antibody for retained function using the functional assays described herein.

In other embodiments, the variable regions of heavy chain and/or light chain nucleotide sequences may be 60%, 70%, 80%, 90%, 95%, 96%, 97%, 98% or 99% identical to the sequences set forth above.

As used herein, "percent identity" between the two sequences is a function of the number of identical positions shared by the sequences (i.e., % identity equals number of identical positions/total number of positions×100), taking into account the number of gaps, and the length of each gap, which needs to be introduced for optimal alignment of the two sequences. The comparison of sequences and determination of percent identity between two sequences can be accomplished using a mathematical algorithm, as described in the non-limiting examples below.

Additionally or alternatively, the protein sequences of the present invention can further be used as a "query sequence" to perform a search against public databases to, for example, identifies related sequences. For example, such searches can be performed using the BLAST program (version 2.0) of Altschul et al., (1990) J. Mol. Biol. 215:403-10.

Antibodies with Conservative Modifications

In certain embodiments, an antibody of the invention has a heavy chain variable region comprising CDR1, CDR2, and CDR3 sequences and a light chain variable region comprising CDR1, CDR2, and CDR3 sequences, wherein one or more of these CDR sequences have specified amino acid sequences based on the antibodies described herein or conservative modifications thereof, and wherein the antibodies retain the desired functional properties of the HER3-binding antibodies of the invention.

Accordingly, the invention provides an isolated HER3 monoclonal antibody, or a fragment thereof, consisting of a heavy chain variable region comprising CDR1, CDR2, and CDR3 sequences and a light chain variable region comprising CDR1, CDR2, and CDR3 sequences, wherein: the heavy chain variable region CDR1 amino acid sequences are selected from the group consisting of SEQ ID NOs: 2, 8, 20, 26, 38, 44, 56, 62, 74, 80, 92, 98, 110, 116, 128, 134, 146, 152, 164, 170, 182, 188, 200, 206, 218, 224, 236, 242, 254, 260, 272, 278, 290, 296, 308, 314, 326, 332, 344, 350, 362, and 368, and conservative modifications thereof; the heavy chain variable region CDR2 amino acid sequences are selected from the group consisting of SEQ ID NOs: 3, 9, 21, 27, 39, 45, 57, 63, 75, 81, 93, 99, 111, 117, 129, 135, 147, 153, 165, 171, 183, 189, 201, 207, 219, 225, 237, 243, 255, 261, 273, 279, 291, 297, 309, 315, 327, 333, 345, 351, 363, and 369 and conservative modifications thereof; the heavy chain variable region CDR3 amino acid sequences are selected from the group consisting of SEQ ID NOs: 4, 10, 22, 28, 40, 46, 58, 64, 76, 82, 94, 100, 112, 118, 130, 136, 148, 154, 166, 172, 184, 190, 202, 208, 220, 226, 238, 244, 256, 262, 274, 280, 292, 298, 310, 316, 328, 334, 346, 352, 364, and 370 and conservative modifications thereof; the light chain variable regions CDR1 amino acid sequences are selected from the group consisting of SEQ ID NOs: 5, 11, 23, 29, 41, 47, 59, 65, 77, 83, 95, 101, 113, 119, 131, 137, 149, 155, 167, 173, 185, 191, 203, 209, 221, 227, 239, 245, 257, 263, 275, 281, 293, 299, 311, 317, 329, 335, 347, 353, 365, and 371 and conservative modifications thereof; the light chain variable regions CDR2 amino acid sequences are selected from the group consisting of SEQ ID NOs: 6, 12, 24, 30, 42, 48, 60, 66, 78, 84, 96, 102, 114, 120, 132, 138, 150, 156, 168, 174, 186, 192, 204, 210, 222, 228, 240, 246, 258, 264, 276, 282, 294, 300, 312, 318, 330, 336, 348, 354, 366, and 372, and conservative modifications thereof; the light chain variable regions of CDR3 amino acid sequences are selected from the group consisting of SEQ ID NOs: 7, 13, 25, 31, 43, 49, 61, 67, 79, 85, 97, 103, 115, 121, 133, 139, 151, 157, 169, 175, 187, 193, 205, 211, 223, 229, 241, 247, 259, 265, 277, 283, 295, 301, 313, 319, 331, 337, 349, 355, 367, and 373, and conservative modifications thereof; the antibody or fragment thereof specifically binds to HER3, and neutralizes HER3 activity by inhibiting a HER signaling pathway, which can be measured in a phosphorylation assay or other measure of HER signaling (e.g., phospho-HER3 assays, phospho-Akt assays, cell proliferation, and ligand blocking assays as described in the Examples).

Antibodies that Bind to the Same Epitope

Figure 7A:
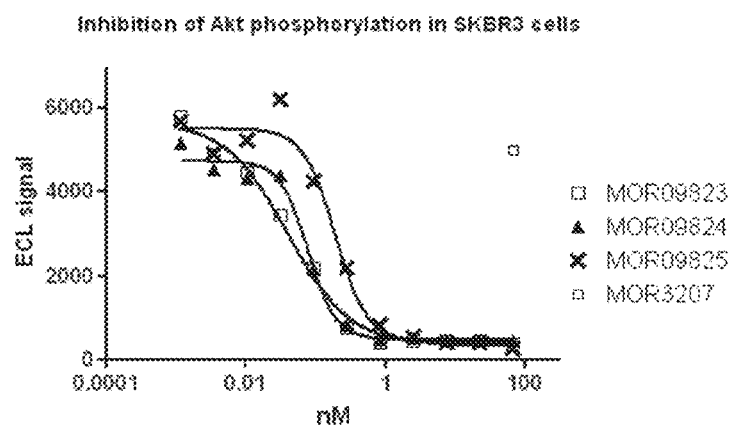
FIG. 7: Inhibition of HER3 dependent downstream signaling pathways in HER2 amplified cell lines in (A) SKBR3 cells; and (B) in BT-474 cells.
Figure 7B:
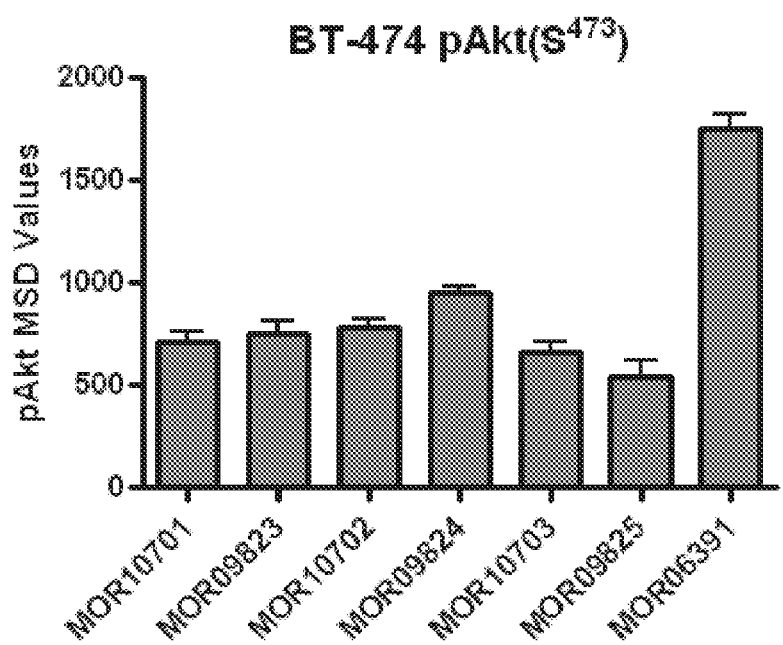

The present invention provides antibodies that interacts with (e.g., by binding, steric hindrance, stabilizing/destabilizing, spatial distribution) the same epitope as do the HER3-binding antibodies described in Table 1 and FIG. 7. Additional antibodies can therefore be identified based on their ability to cross-compete (e.g., to competitively inhibit the binding of, in a statistically significant manner) with other antibodies of the invention in HER3 binding assays. The ability of a test antibody to inhibit the binding of antibodies of the present invention to a HER3 protein (e.g., human and/or cynomologus HER3) demonstrates that the test antibody can compete with that antibody for binding to HER3; such an antibody may, according to non-limiting theory, bind to the same or a related (e.g., a structurally similar or spatially proximal) epitope on the HER3 protein as the antibody with which it competes. In a certain embodiment, the antibody that binds to the same epitope on HER3 as the antibodies of the present invention is a human monoclonal antibody. Such human monoclonal antibodies can be prepared and isolated as described herein.

In one embodiment, the antibody or fragments thereof binds to both domain 2 and domain 4 of HER3 to hold the HER3 in an inactive conformation which prevents exposure of an dimerization loop present within domain 2. This prevents heterodimerizaton with other family members, such as HER1, HER2, and HER4. The antibodies of fragments thereof inhibit both ligand dependent and ligand-independent HER3 signal transduction.

In another embodiment, the antibody or fragment thereof binds to both domain 2 and domain 4 of HER3 and without blocking the concurrent binding of a HER3 ligand such as neuregulin. While not required to provide a theory, it is feasible that the antibody or fragment thereof binding to both domain 2 and domain 4 of HER3, holds HER3 in an inactive conformation without blocking the ligand binding site on HER3. Thus a HER3 ligand (e.g., neuregulin) is able to bind to HER3 at the same time as the antibody or fragment thereof.

The antibodies of the invention or fragments thereof inhibit both ligand dependent and independent activation of HER3 without preventing ligand binding. This is considered advantageous for the following reasons:

(i) The therapeutic antibody would have clinical utility in a broad spectrum of tumors than an antibody which targeted a single mechanism of HER3 activation (i.e. ligand dependent or ligand independent) since distinct tumor types are driven by each mechanism.

(ii) The therapeutic antibody would be efficacious in tumor types where both mechanisms of HER3 activation are simultaneously involved. An antibody targeting a single mechanism of HER3 activation (i.e. ligand dependent or ligand independent) would display little or no efficacy in these tumor types (iii) The efficacy of an antibody which inhibits ligand dependent activation of HER3 without preventing ligand binding would be less likely to be adversely affected by increasing concentrations of ligand. This would translate to either increased efficacy in a tumor type driven by very high concentrations of HER3 ligand or a reduced drug resistance liability where resistance is mediated by up-regulation of HER3 ligands.

(iv) An antibody which inhibits HER3 activation by stabilizing the inactive form would be less prone to drug resistance driven by alternative mechanisms of HER3 activation.

Consequently, the antibodies of the invention may be used to treat conditions where existing therapeutic antibodies are clinically ineffective.

Engineered and Modified Antibodies

An antibody of the invention further can be prepared using an antibody having one or more of the VH and/or VL sequences shown herein as starting material to engineer a modified antibody, which modified antibody may have altered properties from the starting antibody. An antibody can be engineered by modifying one or more residues within one or both variable regions (i.e., VH and/or VL), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann et al., (1998) Nature 332:323-327; Jones et al., (1986) Nature 321:522-525; Queen et al., (1989) Proc. Natl. Acad., U.S.A. 86:10029-10033; U.S. Pat. No. 5,225,539 to Winter, and U.S. Pat. Nos. 5,530,101; 5,585,089; 5,693,762 and 6,180,370 to Queen et al.)

Accordingly, another embodiment of the invention pertains to an isolated HER3 binding monoclonal antibody, or fragment thereof, comprising a heavy chain variable region comprising CDR1 sequences having an amino acid sequence selected from the group consisting of SEQ ID NOs: 2, 8, 20, 26, 38, 44, 56, 62, 74, 80, 92, 98, 110, 116, 128, 134, 146, 152, 164, 170, 182, 188, 200, 206, 218, 224, 236, 242, 254, 260, 272, 278, 290, 296, 308, 314, 326, 332, 344, 350, 362, and 368; CDR2 sequences having an amino acid sequence selected from the group consisting of SEQ ID NOs: 3, 9, 21, 27, 39, 45, 57, 63, 75, 81, 93, 99, 111, 117, 129, 135, 147, 153, 165, 171, 183, 189, 201, 207, 219, 225, 237, 243, 255, 261, 273, 279, 291, 297, 309, 315, 327, 333, 345, 351, 363, and 369; CDR3 sequences having an amino acid sequence selected from the group consisting of SEQ ID NOs: 4, 10, 22, 28, 40, 46, 58, 64, 76, 82, 94, 100, 112, 118, 130, 136, 148, 154, 166, 172, 184, 190, 202, 208, 220, 226, 238, 244, 256, 262, 274, 280, 292, 298, 310, 316, 328, 334, 346, 352, 364, and 370, respectively; and a light chain variable region having CDR1 sequences having an amino acid sequence selected from the group consisting of SEQ ID NOs: 5, 11, 23, 29, 41, 47, 59, 65, 77, 83, 95, 101, 113, 119, 131, 137, 149, 155, 167, 173, 185, 191, 203, 209, 221, 227, 239, 245, 257, 263, 275, 281, 293, 299, 311, 317, 329, 335, 347, 353, 365, and 371; CDR2 sequences having an amino acid sequence selected from the group consisting of SEQ ID NOs: 6, 12, 24, 30, 42, 48, 60, 66, 78, 84, 96, 102, 114, 120, 132, 138, 150, 156, 168, 174, 186, 192, 204, 210, 222, 228, 240, 246, 258, 264, 276, 282, 294, 300, 312, 318, 330, 336, 348, 354, 366, and 372; and CDR3 sequences consisting of an amino acid sequence selected from the group consisting of SEQ ID NOs: 7, 13, 25, 31, 43, 49, 61, 67, 79, 85, 97, 103, 115, 121, 135, 139, 151, 157, 169, 175, 187, 193, 205, 211, 223, 229, 241, 247, 259, 265, 277, 283, 295, 301, 313, 319, 331, 337, 349, 355, 367, and 373, respectively. Thus, such antibodies contain the VH and VL CDR sequences of monoclonal antibodies, yet may contain different framework sequences from these antibodies. Such framework sequences can be obtained from public DNA databases or published references that include germline antibody gene sequences. For example, germline DNA sequences for human heavy and light chain variable region genes can be found in the "Vase" human germline sequence database (available on the Internet at www.mrc-cpe.cam.ac.uk/vbase), as well as in Kabat et al., (1991) Sequences of Proteins of Immunological Interest, Fifth Edition, U.S. Department of Health and Human Services, NIH Publication No. 91-3242; Chothia et al., (1987) J. Mol. Biol. 196:901-917; Chothia et al., (1989) Nature 342:877-883; and Al-Lazikani et al., (1997) J. Mol. Biol. 273:927-948; Tomlinson et al., (1992) J. fol. Biol. 227:776-798; and Cox et al., (1994) Eur. J. Immunol. 24:827-836; the contents of each of which are expressly incorporated herein by reference.

An example of framework sequences for use in the antibodies of the invention are those that are structurally similar to the framework sequences used by selected antibodies of the invention, e.g., consensus sequences and/or framework sequences used by monoclonal antibodies of the invention. The VH CDR1, 2 and 3 sequences, and the VL CDR1, 2 and 3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370 to Queen et al).

Another type of variable region modification is to mutate amino acid residues within the VH and/or VL CDR1, CDR2 and/or CDR3 regions to thereby improve one or more binding properties (e.g., affinity) of the antibody of interest, known as "affinity maturation." Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. Conservative modifications (as discussed above) can be introduced. The mutations may be amino acid substitutions, additions or deletions. Moreover, typically no more than one, two, three, four or five residues within a CDR region are altered.

Accordingly, in another embodiment, the invention provides isolated HER3 binding monoclonal antibodies, or fragment thereof, consisting of a heavy chain variable region having: a VH CDR1 region consisting of an amino acid sequence selected from the group having SEQ ID NOs: 2, 8, 20, 26, 38, 44, 56, 62, 74, 80, 92, 98, 110, 116, 128, 134, 146, 152, 164, 170, 182, 188, 200, 206, 218, 224, 236, 242, 254, 260, 272, 278, 290, 296, 308, 314, 326, 332, 344, 350, 362, and 368 or an amino acid sequence having one, two, three, four or five amino acid substitutions, deletions or additions as compared to SEQ ID NOs: 2, 8, 20, 26, 38, 44, 56, 62, 74, 80, 92, 98, 110, 116, 128, 134, 146, 152, 164, 170, 182, 188, 200, 206, 218, 224, 236, 242, 254, 260, 272, 278, 290, 296, 308, 314, 326, 332, 344, 350, 362, and 368; a VH CDR2 region having an amino acid sequence selected from the group consisting of SEQ ID NOs: 3, 9, 21, 27, 39, 45, 57, 63, 75, 81, 93, 99, 111, 117, 129, 135, 147, 153, 165, 171, 183, 189, 201, 207, 219, 225, 237, 243, 255, 261, 273, 279, 291, 297, 309, 315, 327, 333, 345, 351, 363, and 369 or an amino acid sequence having one, two, three, four or five amino acid substitutions, deletions or additions as compared to SEQ ID NOs: 3, 9, 21, 27, 39, 45, 57, 63, 75, 81, 93, 99, 111, 117, 129, 135, 147, 153, 165, 171, 183, 189, 201, 207, 219, 225, 237, 243, 255, 261, 273, 279, 291, 297, 309, 315, 327, 333, 345, 351, 363, and 369; a VH CDR3 region having an amino acid sequence selected from the group consisting of SEQ ID NOs: 4, 10, 22, 28, 40, 46, 58, 64, 76, 82, 94, 100, 112, 118, 130, 136, 148, 154, 166, 172, 184, 190, 202, 208, 220, 226, 238, 244, 256, 262, 274, 280, 292, 298, 310, 316, 328, 334, 346, 352, 364, and 370, or an amino acid sequence having one, two, three, four or five amino acid substitutions, deletions or additions as compared to SEQ ID NOs: 4, 10, 22, 28, 40, 46, 58, 64, 76, 82, 94, 100, 112, 118, 130, 136, 148, 154, 166, 172, 184, 190, 202, 208, 220, 226, 238, 244, 256, 262, 274, 280, 292, 298, 310, 316, 328, 334, 346, 352, 364, and 370; a VL CDR1 region having an amino acid sequence selected from the group consisting of SEQ ID NOs: 5, 11, 23, 29, 41, 47, 59, 65, 77, 83, 95, 101, 113, 119, 131, 137, 149, 155, 167, 173, 185, 191, 203, 209, 221, 227, 239, 245, 257, 263, 275, 281, 293, 299, 311, 317, 329, 335, 347, 353, 365, and 371, or an amino acid sequence having one, two, three, four or five amino acid substitutions, deletions or additions as compared to SEQ ID NOs: 5, 11, 23, 29, 41, 47, 59, 65, 77, 83, 95, 101, 113, 119, 131, 137, 149, 155, 167, 173, 185, 191, 203, 209, 221, 227, 239, 245, 257, 263, 275, 281, 293, 299, 311, 317, 329, 335, 347, 353, 365, and 371; a VL CDR2 region having an amino acid sequence selected from the group consisting of SEQ ID NOs: 6, 12, 24, 30, 42, 48, 60, 66, 78, 84, 96, 102, 114, 120, 132, 138, 150, 156, 168, 174, 186, 192, 204, 210, 222, 228, 240, 246, 258, 264, 276, 282, 294, 300, 312, 318, 330, 336, 348, 354, 366, and 372, or an amino acid sequence having one, two, three, four or five amino acid substitutions, deletions or additions as compared to SEQ ID NOs: 6, 12, 24, 30, 42, 48, 60, 66, 78, 84, 96, 102, 114, 120, 132, 138, 150, 156, 168, 174, 186, 192, 204, 210, 222, 228, 240, 246, 258, 264, 276, 282, 294, 300, 312, 318, 330, 336, 348, 354, 366, and 372; and a VL CDR3 region having an amino acid sequence selected from the group consisting of SEQ ID NOs: 7, 13, 25, 31, 43, 49, 61, 67, 79, 85, 97, 103, 115, 121, 135, 139, 139, 151, 157, 169, 175, 187, 193, 205, 211, 223, 229, 241, 247, 259, 265, 277, 283, 295, 301, 313, 319, 331, 337, 349, 355, 367, and 373, or an amino acid sequence having one, two, three, four or five amino acid substitutions, deletions or additions as compared to SEQ ID NOs: 7, 13, 25, 31, 43, 49, 61, 67, 79, 85, 97, 103, 115, 121, 135, 139, 139, 151, 157, 169, 175, 187, 193, 205, 211, 223, 229, 241, 247, 259, 265, 277, 283, 295, 301, 313, 319, 331, 337, 349, 355, 367, and 373.

Grafting Antibody Fragments into Alternative Frameworks or Scaffolds

A wide variety of antibody/immunoglobulin frameworks or scaffolds can be employed so long as the resulting polypeptide includes at least one binding region which specifically binds to HER3. Such frameworks or scaffolds include the 5 main idiotypes of human immunoglobulins, or fragments thereof, and include immunoglobulins of other animal species, preferably having humanized aspects. Novel frameworks, scaffolds and fragments continue to be discovered and developed by those skilled in the art.

In one aspect, the invention pertains to generating non-immunoglobulin based antibodies using non-immunoglobulin scaffolds onto which CDRs of the invention can be grafted. Known or future non-immunoglobulin frameworks and scaffolds may be employed, as long as they comprise a binding region specific for the target HER3 protein (e.g., human and/or cynomologus HER3). Known non-immunoglobulin frameworks or scaffolds include, but are not limited to, fibronectin (Compound Therapeutics, Inc., Waltham, Mass.), ankyrin (Molecular Partners AG, Zurich, Switzerland), domain antibodies (Domantis, Ltd., Cambridge, Mass., and Ablynx nv, Zwijnaarde, Belgium), lipocalin (Pieris Proteolab AG, Freising, Germany), small modular immuno-pharmaceuticals (Trubion Pharmaceuticals Inc., Seattle, Wash.), maxybodies (Avidia, Inc., Mountain View, Calif.), Protein A (Affibody AG, Sweden), and affilin (gamma-crystallin or ubiquitin) (Scil Proteins GmbH, Halle, Germany)

The fibronectin scaffolds are based on fibronectin type III domain (e.g., the tenth module of the fibronectin type III ($^{10}$Fn3 domain)). The fibronectin type III domain has 7 or 8 beta strands which are distributed between two beta sheets, which themselves pack against each other to form the core of the protein, and further containing loops (analogous to CDRs) which connect the beta strands to each other and are solvent exposed. There are at least three such loops at each edge of the beta sheet sandwich, where the edge is the boundary of the protein perpendicular to the direction of the beta strands (see U.S. Pat. No. 6,818,418). These fibronectin-based scaffolds are not an immunoglobulin, although the overall fold is closely related to that of the smallest functional antibody fragment, the variable region of the heavy chain, which comprises the entire antigen recognition unit in camel and llama IgG. Because of this structure, the non-immunoglobulin antibody mimics antigen binding properties that are similar in nature and affinity to those of antibodies. These scaffolds can be used in a loop randomization and shuffling strategy in vitro that is similar to the process of affinity maturation of antibodies in vivo. These fibronectin-based molecules can be used as scaffolds where the loop regions of the molecule can be replaced with CDRs of the invention using standard cloning techniques.

The ankyrin technology is based on using proteins with ankyrin derived repeat modules as scaffolds for bearing variable regions which can be used for binding to different targets. The ankyrin repeat module is a 33 amino acid polypeptide consisting of two anti-parallel α-helices and a β-turn. Binding of the variable regions is mostly optimized by using ribosome display.

Avimers are derived from natural A-domain containing protein such as HER3. These domains are used by nature for protein-protein interactions and in human over 250 proteins are structurally based on A-domains. Avimers consist of a number of different "A-domain" monomers (2-10) linked via amino acid linkers. Avimers can be created that can bind to the target antigen using the methodology described in, for example, U.S. Patent Application Publication Nos. 20040175756; 20050053973; 20050048512; and 20060008844.

Affibody affinity ligands are small, simple proteins composed of a three-helix bundle based on the scaffold of one of the IgG-binding domains of Protein A. Protein A is a surface protein from the bacterium *Staphylococcus aureus*. This scaffold domain consists of 58 amino acids, 13 of which are randomized to generate affibody libraries with a large number of ligand variants (See e.g., U.S. Pat. No. 5,831,012). Affibody molecules mimic antibodies, they have a molecular weight of 6 kDa, compared to the molecular weight of antibodies, which is 150 kDa. In spite of its small size, the binding site of affibody molecules is similar to that of an antibody.

Anticalins are products developed by the company Pieris ProteoLab AG. They are derived from lipocalins, a widespread group of small and robust proteins that are usually involved in the physiological transport or storage of chemically sensitive or insoluble compounds. Several natural lipocalins occur in human tissues or body liquids. The protein architecture is reminiscent of immunoglobulins, with hypervariable loops on top of a rigid framework. However, in contrast with antibodies or their recombinant fragments, lipocalins are composed of a single polypeptide chain with 160 to 180 amino acid residues, being just marginally bigger than a single immunoglobulin domain. The set of four loops, which makes up the binding pocket, shows pronounced structural plasticity and tolerates a variety of side chains. The binding site can thus be reshaped in a proprietary process in order to recognize prescribed target molecules of different shape with high affinity and specificity. One protein of lipocalin family, the bilin-binding protein (BBP) of Pieris Brassicae has been used to develop anticalins by mutagenizing the set of four loops. One example of a patent application describing anticalins is in PCT Publication No. WO 199916873.

Affilin molecules are small non-immunoglobulin proteins which are designed for specific affinities towards proteins and small molecules. New affilin molecules can be very quickly selected from two libraries, each of which is based on a different human derived scaffold protein. Affilin molecules do not show any structural homology to immunoglobulin proteins. Currently, two affilin scaffolds are employed, one of which is gamma crystalline, a human structural eye lens protein and the other is "ubiquitin" superfamily proteins. Both human scaffolds are very small, show high temperature stability and are almost resistant to pH changes and denaturing agents. This high stability is mainly due to the expanded beta sheet structure of the proteins. Examples of gamma crystalline derived proteins are described in WO200104144 and examples of "ubiquitin-like" proteins are described in WO2004106368.

Protein epitope mimetics (PEM) are medium-sized, cyclic, peptide-like molecules (MW 1-2 kDa) mimicking beta-hairpin secondary structures of proteins, the major secondary structure involved in protein-protein interactions.

In some embodiments, the Fabs are converted to silent IgG1 format by changing the Fc region. For example, antibodies in Table 1 can be converted to IgG format.

Human or Humanized Antibodies

The present invention provides fully human antibodies that specifically bind to a HER3 protein (e.g., human and/or cynomologus/mouse/rat HER3). Compared to the chimeric or humanized antibodies, the human HER3-binding antibodies of the invention have further reduced antigenicity when administered to human subjects.

The human HER3-binding antibodies can be generated using methods that are known in the art. For example, the humaneering technology used to converting non-human antibodies into engineered human antibodies. U.S. Patent Publication No. 20050008625 describes an in vivo method for replacing a nonhuman antibody variable region with a human variable region in an antibody while maintaining the same or providing better binding characteristics relative to that of the nonhuman antibody. The method relies on epitope guided replacement of variable regions of a non-human reference antibody with a fully human antibody. The resulting human antibody is generally unrelated structurally to the reference nonhuman antibody, but binds to the same epitope on the same antigen as the reference antibody. Briefly, the serial epitope-guided complementarity replacement approach is enabled by setting up a competition in cells between a "competitor" and a library of diverse hybrids of the reference antibody ("test antibodies") for binding to limiting amounts of antigen in the presence of a reporter system which responds to the binding of test antibody to antigen. The competitor can be the reference antibody or derivative thereof such as a single-chain Fv fragment. The competitor can also be a natural or artificial ligand of the antigen which binds to the same epitope as the reference antibody. The only requirements of the competitor are that it binds to the same epitope as the reference antibody, and that it competes with the reference antibody for antigen binding. The test antibodies have one antigen-binding V-region in common from the nonhuman reference antibody, and the other V-region selected at random from a diverse source such as a repertoire library of human antibodies. The common V-region from the reference antibody serves as a guide, positioning the test antibodies on the same epitope on the antigen, and in the same orientation, so that selection is biased toward the highest antigen-binding fidelity to the reference antibody.

Many types of reporter system can be used to detect desired interactions between test antibodies and antigen. For example, complementing reporter fragments may be linked to antigen and test antibody, respectively, so that reporter activation by fragment complementation only occurs when the test antibody binds to the antigen. When the test antibody- and antigen-reporter fragment fusions are co-expressed with a competitor, reporter activation becomes dependent on the ability of the test antibody to compete with the competitor, which is proportional to the affinity of the test antibody for the antigen. Other reporter systems that can be used include the reactivator of an auto-inhibited reporter reactivation system (RAIR) as disclosed in U.S. patent application Ser. No. 10/208,730 (Publication No. 20030198971), or competitive activation system disclosed in U.S. patent application Ser. No. 10/076,845 (Publication No. 20030157579).

With the serial epitope-guided complementarity replacement system, selection is made to identify cells expresses a single test antibody along with the competitor, antigen, and reporter components. In these cells, each test antibody competes one-on-one with the competitor for binding to a limiting amount of antigen. Activity of the reporter is proportional to the amount of antigen bound to the test antibody, which in turn is proportional to the affinity of the test antibody for the antigen and the stability of the test antibody. Test antibodies are initially selected on the basis of their activity relative to that of the reference antibody when expressed as the test antibody. The result of the first round of selection is a set of "hybrid" antibodies, each of which is comprised of the same non-human V-region from the reference antibody and a human V-region from the library, and each of which binds to the same epitope on the antigen as the reference antibody. One of more of the hybrid antibodies selected in the first round will have an affinity for the antigen comparable to or higher than that of the reference antibody.

In the second V-region replacement step, the human V-regions selected in the first step are used as guide for the selection of human replacements for the remaining non-human reference antibody V-region with a diverse library of cognate human V-regions. The hybrid antibodies selected in the first round may also be used as competitors for the second round of selection. The result of the second round of selection is a set of fully human antibodies which differ structurally from the reference antibody, but which compete with the reference antibody for binding to the same antigen. Some of the selected human antibodies bind to the same epitope on the same antigen as the reference antibody. Among these selected human antibodies, one or more binds to the same epitope with an affinity which is comparable to or higher than that of the reference antibody.

Using one of the mouse or chimeric HER3-binding antibodies described above as the reference antibody, this method can be readily employed to generate human antibodies that bind to human HER3 with the same binding specificity and the same or better binding affinity. In addition, such human HER3-binding antibodies can also be commercially obtained from companies which customarily produce human antibodies, e.g., KaloBios, Inc. (Mountain View, Calif.).

Camelid Antibodies

Antibody proteins obtained from members of the camel and dromedary (*Camelus bactrianus* and *Calelus dromaderius*) family including new world members such as llama species (Lama paccos, Lama glama and Lama vicugna) have been characterized with respect to size, structural complexity and antigenicity for human subjects. Certain IgG antibodies from this family of mammals as found in nature lack light chains, and are thus structurally distinct from the typical four chain quaternary structure having two heavy and two light chains, for antibodies from other animals. See PCT/EP93/02214 (WO 94/04678 published 3 Mar. 1994).

A region of the camelid antibody which is the small single variable domain identified as VHH can be obtained by genetic engineering to yield a small protein having high affinity for a target, resulting in a low molecular weight antibody-derived protein known as a "camelid nanobody". See U.S. Pat. No. 5,759,808 issued Jun. 2, 1998; see also Stijlemans et al., (2004) J Biol Chem 279:1256-1261; Dumoulin et al., (2003) Nature 424:783-788; Pleschberger et al., (2003) Bioconjugate Chem 14:440-448; Cortez-Retamozo et al., (2002) Int J Cancer 89:456-62; and Lauwereys et al., (1998) EMBO J. 17:3512-3520. Engineered libraries of camelid antibodies and antibody fragments are commercially available, for example, from Ablynx, Ghent, Belgium. (e.g., US20060115470; Domantis (US20070065440, US20090148434). As with other antibodies of non-human origin, an amino acid sequence of a camelid antibody can be altered recombinantly to obtain a sequence that more closely resembles a human sequence, i.e., the nanobody can be "humanized". Thus the natural low antigenicity of camelid antibodies to humans can be further reduced.

The camelid nanobody has a molecular weight approximately one-tenth that of a human IgG molecule, and the protein has a physical diameter of only a few nanometers. One consequence of the small size is the ability of camelid nanobodies to bind to antigenic sites that are functionally invisible to larger antibody proteins, i.e., camelid nanobodies are useful as reagents detect antigens that are otherwise cryptic using classical immunological techniques, and as possible therapeutic agents. Thus yet another consequence of small size is that a camelid nanobody can inhibit as a result of binding to a specific site in a groove or narrow cleft of a target protein, and hence can serve in a capacity that more closely resembles the function of a classical low molecular weight drug than that of a classical antibody.

The low molecular weight and compact size further result in camelid nanobodies being extremely thermostable, stable to extreme pH and to proteolytic digestion, and poorly antigenic. Another consequence is that camelid nanobodies readily move from the circulatory system into tissues, and even cross the blood-brain barrier and can treat disorders that affect nervous tissue. Nanobodies can further facilitated drug transport across the blood brain barrier. See U.S. patent application 20040161738 published Aug. 19, 2004. These features combined with the low antigenicity to humans indicate great therapeutic potential. Further, these molecules can be fully expressed in prokaryotic cells such as *E. coli* and are expressed as fusion proteins with bacteriophage and are functional.

Accordingly, a feature of the present invention is a camelid antibody or nanobody having high affinity for HER3. In certain embodiments herein, the camelid antibody or nanobody is naturally produced in the camelid animal, i.e., is produced by the camelid following immunization with HER3 or a peptide fragment thereof, using techniques described herein for other antibodies. Alternatively, the HER3-binding camelid nanobody is engineered, i.e., produced by selection for example from a library of phage displaying appropriately mutagenized camelid nanobody proteins using panning procedures with HER3 as a target as described in the examples herein. Engineered nanobodies can further be customized by genetic engineering to have a half life in a recipient subject of from 45 minutes to two weeks. In a specific embodiment, the camelid antibody or nanobody is obtained by grafting the CDRs sequences of the heavy or light chain of the human antibodies of the invention into nanobody or single domain antibody framework sequences, as described for example in PCT/EP93/02214. In one embodiment, the camelid antibody or nanobody binds to at least one of the following HER3 residues: Asn266, Lys267, Leu268, Thr269, Gln271, Glu273, Pro274, Asn275, Pro276, His277, Asn315, Asp571, Pro583, His584, Ala596, Lys597 (residues of SEQ ID NO: 1). In one embodiment, the camelid antibody or nanobody binds to at least one of the following HER3 residues: Tyr265, Lys267, Leu268, Phe270, Gly582, Pro583, Lys597, Ile600, Lys602, Glu609, Arg611, Pro612, Cys613, His614, Glu615 (residues of SEQ ID NO: 1).

Bispecific Molecules and Multivalent Antibodies

In another aspect, the present invention features biparatopic, bispecific or multispecific molecules comprising an HER3-binding antibody, or a fragment thereof, of the invention. An antibody of the invention, or fragments thereof, can be derivatized or linked to another functional molecule, e.g., another peptide or protein (e.g., another antibody or ligand for a receptor) to generate a bispecific molecule that binds to at least two different binding sites or target molecules. The antibody of the invention may in fact be derivatized or linked to more than one other functional molecule to generate biparatopic or multi-specific molecules that bind to more than two different binding sites and/or target molecules; such biparatopic or multi-specific molecules. To create a bispecific molecule of the invention, an antibody of the invention can be functionally linked (e.g., by chemical coupling, genetic fusion, non-covalent association or otherwise) to one or more other binding molecules, such as another antibody, antibody fragment, peptide or binding mimetic, such that a bispecific molecule results.

Further clinical benefits may be provided by the binding of two or more antigens within one antibody (Coloma et al., (1997); Merchant et al., (1998); Alt et al., (1999); Zuo et al., (2000); Lu et al., (2004); Lu et al., (2005); Marvin et al., (2005); Marvin et al., (2006); Shen et al., (2007); Wu et al., (2007); Dimasi et al., (2009); Michaelson et al., (2009)). (Morrison et al., (1997) Nature Biotech. 15:159-163; Alt et al. (1999) FEBS Letters 454:90-94; Zuo et al., (2000) Protein Engineering 13:361-367; Lu et al., (2004) JBC 279:2856-2865; Lu et al., (2005) JBC 280:19665-19672; Marvin et al., (2005) Acta Pharmacologica Sinica 26:649-658; Marvin et al., (2006) Curr Opin Drug Disc Develop 9:184-193; Shen et al., (2007) J Immun Methods 218:65-74; Wu et al., (2007) Nat. Biotechnol. 11:1290-1297; Dimasi et al., (2009) J Mol. Biol. 393:672-692; and Michaelson et al., (2009) mAbs 1:128-141.

The bispecific molecules of the present invention can be prepared by conjugating the constituent binding specificities, using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-5-acetyl-thioacetate (SATA), 5,5'-dithiobis(2-nitrobenzoic acid) (DTNB), o-phenylenedimaleimide (oPDM), N-succinimidyl-3-(2-pyridyldithio) propionate (SPDP), and sulfosuccinimidyl 4-(N-maleimidomethyl) cyclohaxane-1-carboxylate (sulfo-SMCC) (see e.g., Karpovsky et al., (1984) J. Exp. Med. 160:1686; Liu et al., (1985) Proc. Natl. Acad. Sci. USA 82:8648). Other methods include those described in Paulus (1985) Behring Ins. Mitt. No. 78:118-132; Brennan et al., (1985) Science 229:81-83), and Glennie et al., (1987) J. Immunol. 139: 2367-2375). Conjugating agents are SATA and sulfo-SMCC, both available from Pierce Chemical Co. (Rockford, Ill.).

When the binding specificities are antibodies, they can be conjugated by sulfhydryl bonding of the C-terminus hinge regions of the two heavy chains. In a particularly embodiment, the hinge region is modified to contain an odd number of sulfhydryl residues, for example one, prior to conjugation.

Alternatively, both binding specificities can be encoded in the same vector and expressed and assembled in the same host cell. This method is particularly useful where the bispecific molecule is a mAb×mAb, mAb×Fab, Fab×F(ab')$_2$ or ligand x Fab fusion protein. A bispecific molecule of the invention can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. No. 5,260,203; U.S. Pat. No. 5,455,030; U.S. Pat. No. 4,881,175; U.S. Pat. No. 5,132,405; U.S. Pat. No. 5,091,513; U.S. Pat. No. 5,476,786; U.S. Pat. No. 5,013,653; U.S. Pat. No. 5,258,498; and U.S. Pat. No. 5,482,858.

Binding of the bispecific molecules to their specific targets can be confirmed by, for example, enzyme-linked immunosorbent assay (ELISA), radioimmunoassay (REA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest.

In another aspect, the present invention provides multivalent compounds comprising at least two identical or different fragments of the antibodies of the invention binding to HER3. The antibody fragments can be linked together via protein fusion or covalent or non covalent linkage. Tetravalent compounds can be obtained for example by cross-linking antibodies of the antibodies of the invention with an antibody that binds to the constant regions of the antibodies of the invention, for example the Fc or hinge region. Trimerizing domain are described for example in Borean patent EP 1012280B1. Pentamerizing modules are described for example in PCT/EP97/05897.

In one embodiment, a biparatopic/bispecific binds to amino acid residues within domain 2 and domain 4 of HER3.

In another embodiment, the invention pertains to dual function antibodies in which a single monoclonal antibody has been modified such that the antigen binding site binds to more than one antigen, such as a dual function antibody which binds both HER3 and another antigen (e.g., HER1, HER2, and HER4). In another embodiment, the invention pertains to a dual function antibody that targets antigens having the same conformation, for example an antigen that has the same conformation of HER3 in the "closed" or "inactive" state. Examples of antigens with the same conformation of HER3 in the "closed" or "inactive" state include, but are not limited to, HER1 and HER4. Thus, a dual function antibody may bind to both HER3 and HER1; HER3 and HER4, or HER1 and HER4. The dual binding specificity of the dual function antibody may further translate into dual activity, or inhibition of activity. (See e.g., Jenny Bostrom et al., (2009) Science: 323; 1610-1614).

Antibodies with Extended Half Life

The present invention provides for antibodies that specifically bind to HER3 protein which have an extended half-life in vivo.

Many factors may affect a protein's half life in vivo. For examples, kidney filtration, metabolism in the liver, degradation by proteolytic enzymes (proteases), and immunogenic responses (e.g., protein neutralization by antibodies and uptake by macrophages and dentritic cells). A variety of strategies can be used to extend the half life of the antibodies of the present invention. For example, by chemical linkage to polyethyleneglycol (PEG), reCODE PEG, antibody scaffold, polysialic acid (PSA), hydroxyethyl starch (HES), albumin-binding ligands, and carbohydrate shields; by genetic fusion to proteins binding to serum proteins, such as albumin, IgG, FcRn, and transferring; by coupling (genetically or chemically) to other binding moieties that bind to serum proteins, such as nanobodies, Fabs, DARPins, avimers, antibodies, and anticalins; by genetic fusion to rPEG, albumin, domain of albumin, albumin-binding proteins, and Fc; or by incorporation into nanocarriers, slow release formulations, or medical devices.

To prolong the serum circulation of antibodies in vivo, inert polymer molecules such as high molecular weight PEG can be attached to the antibodies or a fragment thereof with or without a multifunctional linker either through site-specific conjugation of the PEG to the N- or C-terminus of the antibodies or via epsilon-amino groups present on lysine residues. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. The pegylation can be carried out by an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Linear or branched polymer derivatization that results in minimal loss of biological activity will be used. The degree of conjugation can be closely monitored by SDS-PAGE and mass spectrometry to ensure proper conjugation of PEG molecules to the antibodies. Unreacted PEG can be separated from antibody-PEG conjugates by size-exclusion or by ion-exchange chromatography. PEG-derivatized antibodies can be tested for binding activity as well as for in vivo efficacy using methods well-known to those of skill in the art, for example, by immunoassays described herein. Methods for pegylating proteins are known in the art and can be applied to the antibodies of the invention. See for example, EP 0 154 316 by Nishimura et al. and EP 0 401 384 by Ishikawa et al.

Other modified pegylation technologies include reconstituting chemically orthogonal directed engineering technology (ReCODE PEG), which incorporates chemically specified side chains into biosynthetic proteins via a reconstituted system that includes tRNA synthetase and tRNA. This technology enables incorporation of more than 30 new amino acids into biosynthetic proteins in E. coli, yeast, and mammalian cells. The tRNA incorporates a normative amino acid any place an amber codon is positioned, converting the amber from a stop codon to one that signals incorporation of the chemically specified amino acid.

Recombinant pegylation technology (rPEG) can also be used for serum half-life extension. This technology involves genetically fusing a 300-600 amino acid unstructured protein tail to an existing pharmaceutical protein. Because the apparent molecular weight of such an unstructured protein chain is about 15-fold larger than its actual molecular weight, the serum half-life of the protein is greatly increased. In contrast to traditional PEGylation, which requires chemical conjugation and repurification, the manufacturing process is greatly simplified and the product is homogeneous.

Polysialytion is another technology, which uses the natural polymer polysialic acid (PSA) to prolong the active life and improve the stability of therapeutic peptides and proteins. PSA is a polymer of sialic acid (a sugar). When used for protein and therapeutic peptide drug delivery, polysialic acid provides a protective microenvironment on conjugation. This increases the active life of the therapeutic protein in the circulation and prevents it from being recognized by the immune system. The PSA polymer is naturally found in the human body. It was adopted by certain bacteria which evolved over millions of years to coat their walls with it. These naturally polysialylated bacteria were then able, by virtue of molecular mimicry, to foil the body's defense system. PSA, nature's ultimate stealth technology, can be easily produced from such bacteria in large quantities and with predetermined physical characteristics. Bacterial PSA is completely non-immunogenic, even when coupled to proteins, as it is chemically identical to PSA in the human body.

Another technology include the use of hydroxyethyl starch ("HES") derivatives linked to antibodies. HES is a modified natural polymer derived from waxy maize starch and can be metabolized by the body's enzymes. HES solutions are usually administered to substitute deficient blood volume and to improve the rheological properties of the blood. Hesylation of an antibody enables the prolongation of the circulation half-life by increasing the stability of the molecule, as well as by reducing renal clearance, resulting in an increased biological activity. By varying different parameters, such as the molecular weight of HES, a wide range of HES antibody conjugates can be customized Antibodies having an increased half-life in vivo can also be generated introducing one or more amino acid modifications (i.e., substitutions, insertions or deletions) into an IgG constant domain, or FcRn binding fragment thereof (preferably a Fc or hinge Fc domain fragment). See, e.g., International Publication No. WO 98/23289; International Publication No. WO 97/34631; and U.S. Pat. No. 6,277,375.

Further, antibodies can be conjugated to albumin in order to make the antibody or antibody fragment more stable in vivo or have a longer half life in vivo. The techniques are well-known in the art, see, e.g., International Publication Nos. WO 93/15199, WO 93/15200, and WO 01/77137; and European Patent No. EP 413,622.

The HER3 antibody or a fragment thereof may also be fused to one or more human serum albumin (HSA) polypeptides, or a portion thereof. HSA, a protein of 585 amino acids in its mature form, is responsible for a significant proportion of the osmotic pressure of serum and also functions as a carrier of endogenous and exogenous ligands. The role of albumin as a carrier molecule and its inert nature are desirable properties for use as a carrier and transporter of polypeptides in vivo. The use of albumin as a component of an albumin fusion protein as a carrier for various proteins has been suggested in WO 93/15199, WO 93/15200, and EP 413 622. The use of N-terminal fragments of HSA for fusions to polypeptides has also been proposed (EP 399 666). Accordingly, by genetically or chemically fusing or conjugating the antibodies or fragments thereof to albumin, can stabilize or extend the shelf-life, and/or to retain the molecule's activity for extended periods of time in solution, in vitro and/or in vivo.

Fusion of albumin to another protein may be achieved by genetic manipulation, such that the DNA coding for HSA, or a fragment thereof, is joined to the DNA coding for the protein. A suitable host is then transformed or transfected with the fused nucleotide sequences, so arranged on a suitable plasmid as to express a fusion polypeptide. The expression may be effected in vitro from, for example, prokaryotic or eukaryotic cells, or in vivo e.g. from a transgenic organism. Additional methods pertaining to HSA fusions can be found, for example, in WO 2001077137 and WO 200306007, incorporated herein by reference. In a specific embodiment, the expression of the fusion protein is performed in mammalian cell lines, for example, CHO cell lines. Altered differential binding of an antibody to a receptor at low or high pHs is also contemplated to be within the scope of the invention. For example, the affinity of an antibody may be modified such that it remains bound to it's receptor at a low pH, e.g., the low pH within a lyzozome, by modifying the antibody to include additional amino acids such as a histine in a CDR of the antibody (See e.g., Tomoyuki Igawa et al. (2010) Nature Biotechnology; 28, 1203-1207).

Antibody Conjugates

The present invention provides antibodies or fragments thereof that specifically bind to a HER3 protein recombinantly fused or chemically conjugated (including both covalent and non-covalent conjugations) to a heterologous protein or polypeptide (or fragment thereof, preferably to a polypeptide of at least 10, at least 20, at least 30, at least 40, at least 50, at least 60, at least 70, at least 80, at least 90 or at least 100 amino acids) to generate fusion proteins. In particular, the invention provides fusion proteins comprising an antibody fragment described herein (e.g., a Fab fragment, Fd fragment, Fv fragment, F(ab)$_2$ fragment, a VH domain, a VH CDR, a VL domain or a VL CDR) and a heterologous protein, polypeptide, or peptide. Methods for fusing or conjugating proteins, polypeptides, or peptides to an antibody or an antibody fragment are known in the art. See, e.g., U.S. Pat. Nos. 5,336,603, 5,622,929, 5,359,046, 5,349,053, 5,447,851, and 5,112,946; European Patent Nos. EP 307,434 and EP 367,166; International Publication Nos. WO 96/04388 and WO 91/06570; Ashkenazi et al., (1991) Proc. Natl. Acad. Sci. USA 88:10535-10539; Zheng et al., (1995) J. Immunol. 154:5590-5600; and Vil et al., (1992) Proc. Natl. Acad. Sci. USA 89:11337-11341.

Additional fusion proteins may be generated through the techniques of gene-shuffling, motif-shuffling, exon-shuffling, and/or codon-shuffling (collectively referred to as "DNA shuffling"). DNA shuffling may be employed to alter the activities of antibodies of the invention or fragments thereof (e.g., antibodies or fragments thereof with higher affinities and lower dissociation rates). See, generally, U.S. Pat. Nos. 5,605,793, 5,811,238, 5,830,721, 5,834,252, and 5,837,458; Patten et al., (1997) Curr. Opinion Biotechnol. 8:724-33; Harayama, (1998) Trends Biotechnol. 16(2):76-82; Hansson et al., (1999) J. Mol. Biol. 287:265-76; and Lorenzo and Blasco, (1998) Biotechniques 24(2):308-313 (each of these patents and publications are hereby incorporated by reference in its entirety). Antibodies or fragments thereof, or the encoded antibodies or fragments thereof, may be altered by being subjected to random mutagenesis by error-prone PCR, random nucleotide insertion or other methods prior to recombination. A polynucleotide encoding an antibody or fragment thereof that specifically binds to a HER3 protein may be recombined with one or more components, motifs, sections, parts, domains, fragments, etc. of one or more heterologous molecules.

Moreover, the antibodies or fragments thereof can be fused to marker sequences, such as a peptide to facilitate purification. In preferred embodiments, the marker amino acid sequence is a hexa-histidine (SEQ ID NO: 495) peptide, such as the tag provided in a pQE vector (QIAGEN, Inc., 9259 Eton Avenue, Chatsworth, Calif., 91311), among others, many of which are commercially available. As described in Gentz et al., (1989) Proc. Natl. Acad. Sci. USA 86:821-824, for instance, hexa-histidine (SEQ ID NO: 495) provides for convenient purification of the fusion protein. Other peptide tags useful for purification include, but are not limited to, the hemagglutinin ("HA") tag, which corresponds to an epitope derived from the influenza hemagglutinin protein (Wilson et al., (1984) Cell 37:767), and the "flag" tag.

In other embodiments, antibodies of the present invention or fragments thereof conjugated to a diagnostic or detectable agent. Such antibodies can be useful for monitoring or prognosing the onset, development, progression and/or severity of a disease or disorder as part of a clinical testing procedure, such as determining the efficacy of a particular therapy. Such diagnosis and detection can accomplished by coupling the antibody to detectable substances including, but not limited to, various enzymes, such as, but not limited to, horseradish peroxidase, alkaline phosphatase, beta-galactosidase, or acetylcholinesterase; prosthetic groups, such as, but not limited to, streptavidin/biotin and avidin/biotin; fluorescent materials, such as, but not limited to, umbelliferone, fluorescein, fluorescein isothiocynate, rhodamine, dichlorotriaziny-lamine fluorescein, dansyl chloride or phycoerythrin; luminescent materials, such as, but not limited to, luminol; bioluminescent materials, such as but not limited to, luciferase, luciferin, and aequorin; radioactive materials, such as, but not limited to, iodine ($^{131}$I, $^{125}$I, $^{123}$I, and $^{121}$I) carbon ($^{14}$C), sulfur ($^{35}$S), tritium ($^{3}$H), indium ($^{115}$In, $^{113}$In, $^{112}$In, and $^{111}$In), technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, 47Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Tin; and positron emitting metals using various positron emission tomographies, and noradioactive paramagnetic metal ions.

The present invention further encompasses uses of antibodies or fragments thereof conjugated to a therapeutic moiety. An antibody or fragment thereof may be conjugated to a therapeutic moiety such as a cytotoxin, e.g., a cytostatic or cytocidal agent, a therapeutic agent or a radioactive metal ion, e.g., alpha-emitters. A cytotoxin or cytotoxic agent includes any agent that is detrimental to cells.

Further, an antibody or fragment thereof may be conjugated to a therapeutic moiety or drug moiety that modifies a given biological response. Therapeutic moieties or drug moieties are not to be construed as limited to classical chemical therapeutic agents. For example, the drug moiety may be a protein, peptide, or polypeptide possessing a desired biological activity. Such proteins may include, for example, a toxin such as abrin, ricin A, *pseudomonas* exotoxin, cholera toxin, or diphtheria toxin; a protein such as tumor necrosis factor, α-interferon, β-interferon, nerve growth factor, platelet derived growth factor, tissue plasminogen activator, an apoptotic agent, an anti-angiogenic agent; or, a biological response modifier such as, for example, a lymphokine. In one embodiment, the anti-HER3 antibody, or a fragment thereof, conjugated to a therapeutic moiety, such as a cytotoxin, a drug (e.g., an immunosuppressant) or a radiotoxin. Such conjugates are referred to herein as "immunoconjugates" Immunoconjugates that include one or more cytotoxins are referred to as "immunotoxins." A cytotoxin or cytotoxic agent includes any agent that is detrimental to (e.g., kills) cells. Examples include taxon, cytochalasin B, gramicidin D, ethidium bromide, emetine, mitomycin, etoposide, tenoposide, vincristine, vinblastine, t. colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, antimetabolites (e.g., methotrexate, 6-mercaptopurine, 6-thioguanine, cytarabine, 5-fluorouracil decarbazine), ablating agents (e.g., mechlorethamine, thioepa chloraxnbucil, meiphalan, carmustine (BSNU) and lomustine (CCNU), cyclothosphamide, busulfan, dibromomannitol, streptozotocin, mitomycin C, and cis-dichlorodiamine platinum (II) (DDP) cisplatin, anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). (See e.g., Seattle Genetics US20090304721).

Other examples of therapeutic cytotoxins that can be conjugated to an antibody of the invention include duocarmycins, calicheamicins, maytansines and auristatins, and derivatives thereof. An example of a calicheamicin antibody conjugate is commercially available (Mylotarg™; Wyeth-Ayerst).

Cytoxins can be conjugated to antibodies of the invention using linker technology available in the art. Examples of linker types that have been used to conjugate a cytotoxin to an antibody include, but are not limited to, hydrazones, thioethers, esters, disulfides and peptide-containing linkers. A linker can be chosen that is, for example, susceptible to cleavage by low pH within the lysosomal compartment or susceptible to cleavage by proteases, such as proteases preferentially expressed in tumor tissue such as cathepsins (e.g., cathepsins B, C, D).

For further discussion of types of cytotoxins, linkers and methods for conjugating therapeutic agents to antibodies, see also Saito et al., (2003) Adv. Drug Deliv. Rev. 55:199-215; Trail et al., (2003) Cancer Immunol. Immunother. 52:328-337; Payne, (2003) Cancer Cell 3:207-212; Allen, (2002) Nat. Rev. Cancer 2:750-763; Pastan and Kreitman, (2002) Curr. Opin. Investig. Drugs 3:1089-1091; Senter and Springer, (2001) Adv. Drug Deliv. Rev. 53:247-264.

Antibodies of the present invention also can be conjugated to a radioactive isotope to generate cytotoxic radiopharmaceuticals, also referred to as radioimmunoconjugates. Examples of radioactive isotopes that can be conjugated to antibodies for use diagnostically or therapeutically include, but are not limited to, iodine$^{131}$, indium$^{111}$, yttrium$^{90}$, and lutetium$^{177}$. Method for preparing radioimmunconjugates are established in the art. Examples of radioimmunoconjugates are commercially available, including Zevalin™ (DEC Pharmaceuticals) and Bexxar™ (Corixa Pharmaceuticals), and similar methods can be used to prepare radioimmunoconjugates using the antibodies of the invention. In certain embodiments, the macrocyclic chelator is 1,4,7,10-tetraazacyclododecane-N,N',N'',N'''-tetraacetic acid (DOTA) which can be attached to the antibody via a linker molecule. Such linker molecules are commonly known in the art and described in Denardo et al., (1998) Clin Cancer Res. 4(10):2483-90; Peterson et al., (1999) Bioconjug. Chem. 10(4):553-7; and Zimmerman et al., (1999) Nucl. Med. Biol. 26(8):943-50, each incorporated by reference in their entireties.

Techniques for conjugating therapeutic moieties to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies 84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., (1982) Immunol. Rev. 62:119-58.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Antibody Combinations

An another aspect, the invention pertains to HER3 antibodies, or fragments thereof of the invention used with other therapeutic agents such as another antibodies, small molecule inhibitors, mTOR inhibitors or PI3Kinase inhibitors. Examples include, but are not limited to, the following:

HER1 Inhibitors:

The HER3 antibodies or fragments thereof can be used with HER1 inhibitors which include, but are not limited to, Matuzumab (EMD72000), Erbitux®/Cetuximab (Imclone), Vectibix®/Panitumumab (Amgen), mAb 806, and Nimotuzumab (TheraCIM), Iressa®/Gefitinib (Astrazeneca); CI-1033 (PD183805) (Pfizer), Lapatinib (GW-572016) (GlaxoSmithKline), Tykerb®/Lapatinib Ditosylate (SmithKlineBeecham), Tarceva®/Erlotinib HCL (OSI-774) (OSI Pharma), and PKI-166 (Novartis), and N-[4-[(3-Chloro-4-fluorophenyl)amino]-7-[[(3"S")-tetrahydro-3-furanyl]oxy]-6-quinazolinyl]-4(dimethylamino)-2-butenamide, sold under the tradename Tovok® by Boehringer Ingelheim).

HER2 Inhibitors:

The HER3 antibodies or fragments thereof can be used with HER2 inhibitors which include, but are not limited to, Pertuzumab (sold under the trademark Omnitarg®, by Genentech), Trastuzumab (sold under the trademark Herceptin® by Genentech/Roche), MM-111, neratinib (also known as HKI-272, (2E)-N-[4-[[3-chloro-4-[(pyridin-2-yl)methoxy]phenyl]amino]-3-cyano-7-ethoxyquinolin-6-yl]-4-(dimethylamino)but-2-enamide, and described PCT Publication No. WO 05/028443), lapatinib or lapatinib ditosylate (sold under the trademark Tykerb® by GlaxoSmithKline.

HER3 Inhibitors:

The HER3 antibodies or fragments thereof can be used with HER3 inhibitors which include, but are not limited to, MM-121, MM-111, IB4C3, 2DID12 (U3 Pharma AG), AMG888 (Amgen), AV-203 (Aveo), MEHD7945A (Genentech), and small molecules that inhibit HER3.

HER4 Inhibitors:

The HER3 antibodies or fragments thereof can be used with HER4 inhibitors.

PI3K Inhibitors:

The HER3 antibodies or fragments thereof can be used with PI3 kinase inhibitors which include, but are not limited to, 4-[2-(1H-Indazol-4-yl)-6-[[4-(methylsulfonyl)piperazin-1-yl]methyl]thieno[3,2-d]pyrimidin-4-yl]morpholine (also known as GDC 0941 and described in PCT Publication Nos. WO 09/036,082 and WO 09/055,730), 2-Methyl-2-[4-[3-methyl-2-oxo-8-(quinolin-3-yl)-2,3-dihydroimidazo[4,5-c]quinolin-1-yl]phenyl]propionitrile (also known as BEZ 235 or NVP-BEZ 235, and described in PCT Publication No. WO 06/122806), BMK120 and BYL719.

mTOR Inhibitors:

The HER3 antibodies or fragments thereof can be used with mTOR inhibitors which include, but are not limited to, Temsirolimus (sold under the tradename Torisel® by Pfizer), ridaforolimus (formally known as deferolimus, (1R,2R,4S)-4-[(2R)-2[(1R,9S,12S,15R,16E,18R,19R,21R,23S,24E, 26E,28Z,30S,32S,35R)-1,18-dihydroxy-19,30-dimethoxy-15,17,21,23,29,35-hexamethyl-2,3,10,14,20-pentaoxo-11, 36-dioxa-4-azatricyclo[30.3.1.04,9]hexatriaconta-16,24,26, 28-tetraen-12-yl]propyl]-2-methoxycyclohexyl dimethylphosphinate, also known as Deforolimus, AP23573 and MK8669 (Ariad Pharm.), and described in PCT Publication No. WO 03/064383), everolimus (RAD001) (sold under the tradename Afinitor® by Novartis), One or more therapeutic agents may be administered either simultaneously or before or after administration of a HER3 antibody or fragment thereof of the present invention.

Methods of Producing Antibodies of the Invention (i) Nucleic Acids Encoding the Antibodies The invention provides substantially purified nucleic acid molecules which encode polypeptides comprising segments or domains of the HER3-binding antibody chains described above. Some of the nucleic acids of the invention comprise the nucleotide sequence encoding the HER3 antibody heavy chain variable region, and/or the nucleotide sequence encoding the light chain variable region. In a specific embodiment, the nucleic acid molecules are those identified in Table 1.

Some other nucleic acid molecules of the invention comprise nucleotide sequences that are substantially identical (e.g., at least 65, 80%, 95%, or 99%) to the nucleotide sequences of those identified in Table 1. When expressed from appropriate expression vectors, polypeptides encoded by these polynucleotides are capable of exhibiting HER3 antigen binding capacity.

Also provided in the invention are polynucleotides which encode at least one CDR region and usually all three CDR regions from the heavy or light chain of the HER3-binding antibody set forth above. Some other polynucleotides encode all or substantially all of the variable region sequence of the heavy chain and/or the light chain of the HER3-binding antibody set forth above. Because of the degeneracy of the code, a variety of nucleic acid sequences will encode each of the immunoglobulin amino acid sequences.

The nucleic acid molecules of the invention can encode both a variable region and a constant region of the antibody. Some of nucleic acid sequences of the invention comprise nucleotides encoding a mature heavy chain variable region sequence that is substantially identical (e.g., at least 80%, 90%, or 99%) to the mature heavy chain variable region sequence of a HER3 antibody set forth in Table 1. Some other nucleic acid sequences comprising nucleotide encoding a mature light chain variable region sequence that is substantially identical (e.g., at least 80%, 90%, or 99%) to the mature light chain variable region sequence of a HER3 antibody set forth in Table 1.

The polynucleotide sequences can be produced by de novo solid-phase DNA synthesis or by PCR mutagenesis of an existing sequence (e.g., sequences as described in the Examples below) encoding an HER3-binding antibody or its binding fragment. Direct chemical synthesis of nucleic acids can be accomplished by methods known in the art, such as the phosphotriester method of Narang et al., (1979) Meth. Enzymol. 68:90; the phosphodiester method of Brown et al., (1979) Meth. Enzymol. 68:109; the diethylphosphoramidite method of Beaucage et al., (1981) Tetra. Lett., 22:1859; and the solid support method of U.S. Pat. No. 4,458,066. Introducing mutations to a polynucleotide sequence by PCR can be performed as described in, e.g., PCR Technology: Principles and Applications for DNA Amplification, H. A. Erlich (Ed.), Freeman Press, NY, N.Y., 1992; PCR Protocols: A Guide to Methods and Applications, Innis et al. (Ed.), Academic Press, San Diego, Calif., 1990; Mattila et al., (1991) Nucleic Acids Res. 19:967; and Eckert et al., (1991) PCR Methods and Applications 1:17.

Also provided in the invention are expression vectors and host cells for producing the HER3-binding antibodies described above. Various expression vectors can be employed to express the polynucleotides encoding the HER3-binding antibody chains or binding fragments. Both viral-based and nonviral expression vectors can be used to produce the antibodies in a mammalian host cell. Nonviral vectors and systems include plasmids, episomal vectors, typically with an expression cassette for expressing a protein or RNA, and human artificial chromosomes (see, e.g., Harrington et al., (1997) Nat Genet. 15:345). For example, nonviral vectors useful for expression of the HER3-binding polynucleotides and polypeptides in mammalian (e.g., human) cells include pThioHis A, B & C, pcDNA3.1/His, pEBVHis A, B & C, (Invitrogen, San Diego, Calif.), MPSV vectors, and numerous other vectors known in the art for expressing other proteins. Useful viral vectors include vectors based on retroviruses, adenoviruses, adenoassociated viruses, herpes viruses, vectors based on SV40, papilloma virus, HBP Epstein Barr virus, vaccinia virus vectors and Semliki Forest virus (SFV). See, Brent et al., (1995) supra; Smith, Annu. Rev. Microbiol. 49:807; and Rosenfeld et al., (1992) Cell 68:143.

The choice of expression vector depends on the intended host cells in which the vector is to be expressed. Typically, the expression vectors contain a promoter and other regulatory sequences (e.g., enhancers) that are operably linked to the polynucleotides encoding an HER3-binding antibody chain or fragment. In some embodiments, an inducible promoter is employed to prevent expression of inserted sequences except under inducing conditions. Inducible promoters include, e.g., arabinose, lacZ, metallothionein promoter or a heat shock promoter. Cultures of transformed organisms can be expanded under noninducing conditions without biasing the population for coding sequences whose expression products are better tolerated by the host cells. In addition to promoters, other regulatory elements may also be required or desired for efficient expression of an HER3-binding antibody chain or fragment. These elements typically include an ATG initiation codon and adjacent ribosome binding site or other sequences. In addition, the efficiency of expression may be enhanced by the inclusion of enhancers appropriate to the cell system in use (see, e.g., Scharf et al., (1994) Results Probl. Cell Differ. 20:125; and Bittner et al., (1987) Meth. Enzymol., 153:516). For example, the SV40 enhancer or CMV enhancer may be used to increase expression in mammalian host cells.

The expression vectors may also provide a secretion signal sequence position to form a fusion protein with polypeptides encoded by inserted HER3-binding antibody sequences. More often, the inserted HER3-binding antibody sequences are linked to a signal sequences before inclusion in the vector. Vectors to be used to receive sequences encoding HER3-binding antibody light and heavy chain variable domains sometimes also encode constant regions or parts thereof. Such vectors allow expression of the variable regions as fusion proteins with the constant regions thereby leading to production of intact antibodies or fragments thereof. Typically, such constant regions are human.

The host cells for harboring and expressing the HER3-binding antibody chains can be either prokaryotic or eukaryotic. E. coli is one prokaryotic host useful for cloning and expressing the polynucleotides of the present invention. Other microbial hosts suitable for use include bacilli, such as Bacillus subtilis, and other enterobacteriaceae, such as Salmonella, Serratia, and various Pseudomonas species. In these prokaryotic hosts, one can also make expression vectors, which typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters typically control expression, optionally with an operator sequence, and have ribosome binding site sequences and the like, for initiating and completing transcription and translation. Other microbes, such as yeast, can also be employed to express HERS-binding polypeptides of the invention. Insect cells in combination with baculovirus vectors can also be used.

In some preferred embodiments, mammalian host cells are used to express and produce the HERS-binding polypeptides of the present invention. For example, they can be either a hybridoma cell line expressing endogenous immunoglobulin genes (e.g., the 1D6.C9 myeloma hybridoma clone as described in the Examples) or a mammalian cell line harboring an exogenous expression vector (e.g., the SP2/0 myeloma cells exemplified below). These include any normal mortal or normal or abnormal immortal animal or human cell. For example, a number of suitable host cell lines capable of secreting intact immunoglobulins have been developed including the CHO cell lines, various Cos cell lines, HeLa cells, myeloma cell lines, transformed B-cells and hybridomas. The use of mammalian tissue cell culture to express polypeptides is discussed generally in, e.g., Winnacker, FROM GENES TO CLONES, VCH Publishers, N.Y., N.Y., 1987. Expression vectors for mammalian host cells can include expression control sequences, such as an origin of replication, a promoter, and an enhancer (see, e.g., Queen et al., (1986) Immunol. Rev. 89:49-68), and necessary processing information sites, such as ribosome binding sites, RNA splice sites, polyadenylation sites, and transcriptional terminator sequences. These expression vectors usually contain promoters derived from mammalian genes or from mammalian viruses. Suitable promoters may be constitutive, cell type-specific, stage-specific, and/or modulatable or regulatable. Useful promoters include, but are not limited to, the metallothionein promoter, the constitutive adenovirus major late promoter, the dexamethasone-inducible MMTV promoter, the SV40 promoter, the MRP polIII promoter, the constitutive MPSV promoter, the tetracycline-inducible CMV promoter (such as the human immediate-early CMV promoter), the constitutive CMV promoter, and promoter-enhancer combinations known in the art.

Methods for introducing expression vectors containing the polynucleotide sequences of interest vary depending on the type of cellular host. For example, calcium chloride transfection is commonly utilized for prokaryotic cells, whereas calcium phosphate treatment or electroporation may be used for other cellular hosts. (See generally Sambrook, et al., supra). Other methods include, e.g., electroporation, calcium phosphate treatment, liposome-mediated transformation, injection and microinjection, ballistic methods, virosomes, immunoliposomes, polycation:nucleic acid conjugates, naked DNA, artificial virions, fusion to the herpes virus structural protein VP22 (Elliot and O'Hare, (1997) Cell 88:223), agent-enhanced uptake of DNA, and ex vivo transduction. For long-term, high-yield production of recombinant proteins, stable expression will often be desired. For example, cell lines which stably express HER3-binding antibody chains or binding fragments can be prepared using expression vectors of the invention which contain viral origins of replication or endogenous expression elements and a selectable marker gene. Following the introduction of the vector, cells may be allowed to grow for 1-2 days in an enriched media before they are switched to selective media. The purpose of the selectable marker is to confer resistance to selection, and its presence allows growth of cells which successfully express the introduced sequences in selective media. Resistant, stably transfected cells can be proliferated using tissue culture techniques appropriate to the cell type.

(ii) Generation of Monoclonal Antibodies of the Invention

Monoclonal antibodies (mAbs) can be produced by a variety of techniques, including conventional monoclonal antibody methodology e.g., the standard somatic cell hybridization technique of Kohler and Milstein, (1975) Nature 256: 495. Many techniques for producing monoclonal antibody can be employed e.g., viral or oncogenic transformation of B lymphocytes.

An animal system for preparing hybridomas is the murine system. Hybridoma production in the mouse is a well established procedure Immunization protocols and techniques for isolation of immunized splenocytes for fusion are known in the art. Fusion partners (e.g., murine myeloma cells) and fusion procedures are also known.

Chimeric or humanized antibodies of the present invention can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art. See e.g., U.S. Pat. No. 5,225,539 to Winter, and U.S. Pat. Nos. 5,530,101; 5,585,089; 5693762 and 6180370 to Queen et al.

In a certain embodiment, the antibodies of the invention are human monoclonal antibodies. Such human monoclonal antibodies directed against HER3 can be generated using transgenic or transchromosomic mice carrying parts of the human immune system rather than the mouse system. These transgenic and transchromosomic mice include mice referred to herein as HuMAb mice and KM mice, respectively, and are collectively referred to herein as "human Ig mice."

The HuMAb Mouse® (Medarex, Inc.) contains human immunoglobulin gene miniloci that encode un-rearranged human heavy (μ and γ) and κ light chain immunoglobulin sequences, together with targeted mutations that inactivate the endogenous μ and κ chain loci (see e.g., Lonberg et al., (1994) Nature 368(6474): 856-859). Accordingly, the mice exhibit reduced expression of mouse IgM or κ, and in response to immunization, the introduced human heavy and light chain transgenes undergo class switching and somatic mutation to generate high affinity human IgGκ monoclonal (Lonberg et al., (1994) supra; reviewed in Lonberg, (1994) Handbook of Experimental Pharmacology 113:49-101; Lonberg and Huszar, (1995) Intern. Rev. Immunol. 13:65-93, and Harding and Lonberg, (1995) Ann. N.Y. Acad. Sci. 764:536-546). The preparation and use of HuMAb mice, and the genomic modifications carried by such mice, is further described in Taylor et al., (1992) Nucleic Acids Research 20:6287-6295; Chen et al., (1993) International Immunology 5:647-656; Tuaillon et al., (1993) Proc. Natl. Acad. Sci. USA 94:3720-3724; Choi et al., (1993) Nature Genetics 4:117-123; Chen et al., (1993) EMBO J. 12:821-830; Tuaillon et al., (1994) J. Immunol. 152:2912-2920; Taylor et al., (1994) International Immunology 579-591; and Fishwild et al., (1996) Nature Biotechnology 14:845-851, the contents of all of which are hereby specifically incorporated by reference in their entirety. See further, U.S. Pat. Nos. 5,545,806; 5,569, 825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92103918, WO 93/12227, WO 94/25585, WO 97113852, WO 98/24884 and WO 99/45962, all to Lonberg and Kay; and PCT Publication No. WO 01/14424 to Korman et al.

In another embodiment, human antibodies of the invention can be raised using a mouse that carries human immunoglobulin sequences on transgenes and transchomosomes such as a mouse that carries a human heavy chain transgene and a human light chain transchromosome. Such mice, referred to herein as "KM mice", are described in detail in PCT Publication WO 02/43478 to Ishida et al.

Still further, alternative transgenic animal systems expressing human immunoglobulin genes are available in the art and can be used to raise HER3-binding antibodies of the invention. For example, an alternative transgenic system referred to as the Xenomouse (Abgenix, Inc.) can be used. Such mice are described in, e.g., U.S. Pat. Nos. 5,939,598; 6,075,181; 6,114,598; 6,150,584 and 6,162,963 to Kucherlapati et al.

Moreover, alternative transchromosomic animal systems expressing human immunoglobulin genes are available in the art and can be used to raise HER3-binding antibodies of the invention. For example, mice carrying both a human heavy chain transchromosome and a human light chain tranchromosome, referred to as "TC mice" can be used; such mice are described in Tomizuka et al., (2000) Proc. Natl. Acad. Sci. USA 97:722-727. Furthermore, cows carrying human heavy and light chain transchromosomes have been described in the art (Kuroiwa et al., (2002) Nature Biotechnology 20:889-894) and can be used to raise HER3-binding antibodies of the invention.

Human monoclonal antibodies of the invention can also be prepared using phage display methods for screening libraries of human immunoglobulin genes. Such phage display methods for isolating human antibodies are established in the art or described in the examples below. See for example: U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

Human monoclonal antibodies of the invention can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

(iii) Framework or Fc Engineering

Engineered antibodies of the invention include those in which modifications have been made to framework residues within VH and/or VL, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis. Such "backmutated" antibodies are also intended to be encompassed by the invention.

Another type of framework modification involves mutating one or more residues within the framework region, or even within one or more CDR regions, to remove T cell-epitopes to thereby reduce the potential immunogenicity of the antibody. This approach is also referred to as "deimmunization" and is described in further detail in U.S. Patent Publication No. 20030153043 by Carr et al.

In addition or alternative to modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention may be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In yet other embodiments, the Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In another embodiment, one or more amino acids selected from amino acid residues can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In another embodiment, one or more amino acid residues are altered to thereby alter the ability of the antibody to fix complement. This approach is described further in PCT Publication WO 94/29351 by Bodmer et al.

In yet another embodiment, the Fc region is modified to increase the ability of the antibody to mediate antibody dependent cellular cytotoxicity (ADCC) and/or to increase the affinity of the antibody for an Fcγ receptor by modifying one or more amino acids. This approach is described further in PCT Publication WO 00/42072 by Presta. Moreover, the binding sites on human IgG1 for FcγR1, FcγRII, FcγRIII and FcRn have been mapped and variants with improved binding have been described (see Shields et al., (2001) J. Biol. Chen. 276:6591-6604).

In still another embodiment, the glycosylation of an antibody is modified. For example, an aglycoslated antibody can be made (i.e., the antibody lacks glycosylation). Glycosylation can be altered to, for example, increase the affinity of the antibody for "antigen'. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such a glycosylation may increase the affinity of the antibody for antigen. Such an approach is described in further detail in U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, EP 1,176,195 by Hang et al. describes a cell line with a functionally disrupted FUT8 gene, which encodes a fucosyl transferase, such that antibodies expressed in such a cell line exhibit hypofucosylation. PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields et al., (2002) J. Biol. Chem. 277:26733-26740). PCT Publication WO 99/54342 by Umana et al. describes cell lines engineered to express glycoprotein-modifying glycosyl transferases (e.g., beta(1,4)-N acetylglucosaminyltransferase III (GnTIII)) such that antibodies expressed in the engineered cell lines exhibit increased bisecting GlcNac structures which results in increased ADCC activity of the antibodies (see also Umana et al., (1999) Nat. Biotech. 17:176-180).

In another embodiment, the antibody is modified to increase its biological half-life. Various approaches are possible. For example, one or more of the following mutations can be introduced: T252L, T254S, T256F, as described in U.S. Pat. No. 6,277,375 to Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

(iv) Methods of Engineering Altered Antibodies

As discussed above, the HER3-binding antibodies having VH and VL sequences or full length heavy and light chain sequences shown herein can be used to create new HER3-binding antibodies by modifying full length heavy chain and/or light chain sequences, VH and/or VL sequences, or the constant region(s) attached thereto. Thus, in another aspect of the invention, the structural features of a HER3-binding antibody of the invention are used to create structurally related HER3-binding antibodies that retain at least one functional property of the antibodies of the invention, such as binding to human HER3 and also inhibiting one or more functional properties of HER3 For example, one or more CDR regions of the antibodies of the present invention, or mutations thereof, can be combined recombinantly with known framework regions and/or other CDRs to create additional, recombinantly-engineered, HER3-binding antibodies of the invention, as discussed above. Other types of modifications include those described in the previous section. The starting material for the engineering method is one or more of the VH and/or VL sequences provided herein, or one or more CDR regions thereof. To create the engineered antibody, it is not necessary to actually prepare (i.e., express as a protein) an antibody having one or more of the VH and/or VL sequences provided herein, or one or more CDR regions thereof. Rather, the information contained in the sequence(s) is used as the starting material to create a "second generation" sequence(s) derived from the original sequence(s) and then the "second generation" sequence(s) is prepared and expressed as a protein.

Accordingly, in another embodiment, the invention provides a method for preparing a HER3-binding antibody consisting of: a heavy chain variable region antibody sequence having a CDR1 sequence selected from the group consisting of SEQ ID NOs: 2, 8, 20, 26, 38, 44, 56, 62, 74, 80, 92, 98, 110, 116, 128, 134, 146, 152, 164, 170, 182, 188, 200, 206, 218, 224, 236, 242, 254, 260, 272, 278, 290, 296, 308, 314, 326, 332, 344, 350, 362, and 368; a CDR2 sequence selected from the group consisting of SEQ ID NOs: 3, 9, 21, 27, 39, 45, 57, 63, 75, 81, 93, 99, 111, 117, 129, 135, 147, 153, 165, 171, 183, 189, 201, 207, 219, 225, 237, 243, 255, 261, 273, 279, 291, 297, 309, 315, 327, 333, 345, 351, 363, and 369; and/or a CDR3 sequence selected from the group consisting of SEQ ID NOs: 4, 10, 22, 28, 40, 46, 58, 64, 75, 82, 94, 100, 112, 118, 130, 136, 148, 154, 166, 172, 184, 190, 202, 208, 220, 226, 238, 244, 256, 262, 274, 280, 292, 298, 310, 316, 328, 334, 346, 352, 364, and 370; and a light chain variable region antibody sequence having a CDR1 sequence selected from the group consisting of SEQ ID NOs: 5, 11, 23, 29, 41, 47, 59, 65, 77, 83, 95, 101, 113, 119, 131, 137, 149, 155, 167, 173, 185, 191, 203, 209, 221, 227, 239, 245, 257, 263, 275, 281, 293, 299, 311, 317, 329, 335, 347, 353, 365, and 371; a CDR2 sequence selected from the group consisting of SEQ ID NOs: 6, 12, 24, 30, 42, 48, 60, 66, 78, 84, 96, 102, 114, 120, 132, 138, 150, 156, 168, 174, 186, 192, 204, 210, 222, 228, 240, 246, 258, 264, 276, 282, 294, 300, 312, 318, 330, 336, 348, 354, 366, and 372; and/or a CDR3 sequence selected from the group consisting of SEQ ID NOs: 7, 13, 25, 31, 43, 49, 61, 67, 79, 85, 97, 103, 115, 121, 133, 139, 151, 157, 169, 175, 187, 193, 205, 211, 223, 229, 241, 247, 259, 265, 277, 283, 295, 301, 313, 319, 331, 337, 349, 355, 367, and 373; altering at least one amino acid residue within the heavy chain variable region antibody sequence and/or the light chain variable region antibody sequence to create at least one altered antibody sequence; and expressing the altered antibody sequence as a protein. The altered antibody sequence can also be prepared by screening antibody libraries having fixed CDR3 sequences or minimal essential binding determinants as described in US20050255552 and diversity on CDR1 and CDR2 sequences. The screening can be performed according to any screening technology appropriate for screening antibodies from antibody libraries, such as phage display technology.

Standard molecular biology techniques can be used to prepare and express the altered antibody sequence. The antibody encoded by the altered antibody sequence(s) is one that retains one, some or all of the functional properties of the HER3-binding antibodies described herein, which functional properties include, but are not limited to, specifically binding to human and/or cynomologus HER3; the antibody binds to HER3 and neutralizes HER3 biological activity by inhibiting the HER signaling activity in a phospho-HER assay.

The functional properties of the altered antibodies can be assessed using standard assays available in the art and/or described herein, such as those set forth in the Examples (e.g., ELISAs).

In certain embodiments of the methods of engineering antibodies of the invention, mutations can be introduced randomly or selectively along all or part of an HER3-binding antibody coding sequence and the resulting modified HER3-binding antibodies can be screened for binding activity and/or other functional properties as described herein. Mutational methods have been described in the art. For example, PCT Publication WO 02/092780 by Short describes methods for creating and screening antibody mutations using saturation mutagenesis, synthetic ligation assembly, or a combination thereof. Alternatively, PCT Publication WO 03/074679 by Lazar et al. describes methods of using computational screening methods to optimize physiochemical properties of antibodies.

Characterization of the Antibodies of the Invention

The antibodies of the invention can be characterized by various functional assays. For example, they can be characterized by their ability to neutralize biological activity by inhibiting HER signaling in a phospho-HER assay as described herein, their affinity to a HER3 protein (e.g., human and/or cynomologus HER3), the epitope binning, their resistance to proteolysis, and their ability to block HER3 downstream signaling. Various methods can be used to measure HER3-mediated signaling. For example, the HER signaling pathway can be monitored by (i) measurement of phospho-HER3; (ii) measurement of phosphorylation of HER3 or other downstream signaling proteins (e.g. Akt), (iii) ligand blocking assays as described herein, (iv) heterodimer formation, (v) HER3 dependent gene expression signature, (vi) receptor internalization, and (vii) HER3 driven cell phenotypes (e.g. proliferation).

The ability of an antibody to bind to HER3 can be detected by labelling the antibody of interest directly, or the antibody may be unlabelled and binding detected indirectly using various sandwich assay formats known in the art.

In some embodiments, the HER3-binding antibodies of the invention block or compete with binding of a reference HER3-binding antibody to a HER3 polypeptide or protein. These can be fully human HER3-binding antibodies described above. They can also be other mouse, chimeric or humanized HER3-binding antibodies which bind to the same epitope as the reference antibody. The capacity to block or compete with the reference antibody binding indicates that a HER3-binding antibody under test binds to the same or similar epitope as that defined by the reference antibody, or to an epitope which is sufficiently proximal to the epitope bound by the reference HER3-binding antibody. Such antibodies are especially likely to share the advantageous properties identified for the reference antibody. The capacity to block or compete with the reference antibody may be determined by, e.g., a competition binding assay. With a competition binding assay, the antibody under test is examined for ability to inhibit specific binding of the reference antibody to a common antigen, such as a HER3 polypeptide or protein. A test antibody competes with the reference antibody for specific binding to the antigen if an excess of the test antibody substantially inhibits binding of the reference antibody. Substantial inhibition means that the test antibody reduces specific binding of the reference antibody usually by at least 10%, 25%, 50%, 75%, or 90%.

There are a number of known competition binding assays that can be used to assess competition of a HER3-binding antibody with the reference HER3-binding antibody for binding to a HER3 protein. These include, e.g., solid phase direct or indirect radioimmunoassay (RIA), solid phase direct or indirect enzyme immunoassay (EIA), sandwich competition assay (see Stahli et al., (1983) Methods in Enzymology 9:242-253); solid phase direct biotin-avidin EIA (see Kirkland et al., (1986) J. Immunol. 137:3614-3619); solid phase direct labeled assay, solid phase direct labeled sandwich assay (see Harlow & Lane, supra); solid phase direct label RIA using 1-125 label (see Morel et al., (1988) Molec. Immunol. 25:7-15); solid phase direct biotin-avidin EIA (Cheung et al., (1990) Virology 176:546-552); and direct labeled RIA (Moldenhauer et al., (1990) Scand. J. Immunol. 32:77-82). Typically, such an assay involves the use of purified antigen bound to a solid surface or cells bearing either of these, an unlabelled test HER3-binding antibody and a labelled reference antibody. Competitive inhibition is measured by determining the amount of label bound to the solid surface or cells in the presence of the test antibody. Usually the test antibody is present in excess. Antibodies identified by competition assay (competing antibodies) include antibodies binding to the same epitope as the reference antibody and antibodies binding to an adjacent epitope sufficiently proximal to the epitope bound by the reference antibody for steric hindrance to occur.

To determine if the selected HER3-binding monoclonal antibodies bind to unique epitopes, each antibody can be biotinylated using commercially available reagents (e.g., reagents from Pierce, Rockford, Ill.). Competition studies using unlabeled monoclonal antibodies and biotinylated monoclonal antibodies can be performed using a HER3 polypeptide coated-ELISA plates. Biotinylated MAb binding can be detected with a strep-avidin-alkaline phosphatase probe. To determine the isotype of a purified HER3-binding antibody, isotype ELISAs can be performed. For example, wells of microtiter plates can be coated with 1 µg/ml of anti-human IgG overnight at 4° C. After blocking with 1% BSA, the plates are reacted with 1 µg/ml or less of the monoclonal HER3-binding antibody or purified isotype controls, at ambient temperature for one to two hours. The wells can then be reacted with either human IgG1 or human IgM-specific alkaline phosphatase-conjugated probes. Plates are then developed and analyzed so that the isotype of the purified antibody can be determined To demonstrate binding of monoclonal HER3-binding antibodies to live cells expressing a HER3 polypeptide, flow cytometry can be used. Briefly, cell lines expressing HER3 (grown under standard growth conditions) can be mixed with various concentrations of a HER3-binding antibody in PBS containing 0.1% BSA and 10% fetal calf serum, and incubated at 4° C. for 1 hour. After washing, the cells are reacted with Fluorescein-labeled anti-human IgG antibody under the same conditions as the primary antibody staining. The samples can be analyzed by FACScan instrument using light and side scatter properties to gate on single cells. An alternative assay using fluorescence microscopy may be used (in addition to or instead of) the flow cytometry assay. Cells can be stained exactly as described above and examined by fluorescence microscopy. This method allows visualization of individual cells, but may have diminished sensitivity depending on the density of the antigen.

HER3-binding antibodies of the invention can be further tested for reactivity with a HER3 polypeptide or antigenic fragment by Western blotting. Briefly, purified HER3 polypeptides or fusion proteins, or cell extracts from cells expressing HER3 can be prepared and subjected to sodium dodecyl sulfate polyacrylamide gel electrophoresis. After electrophoresis, the separated antigens are transferred to nitrocellulose membranes, blocked with 10% fetal calf serum, and probed with the monoclonal antibodies to be tested. Human IgG binding can be detected using anti-human IgG alkaline phosphatase and developed with BCIP/NBT substrate tablets (Sigma Chem. Co., St. Louis, Mo.).

A number of readouts can be used to assess the efficacy, and specificity, of HER3 antibodies in cell-based assays of ligand-induced heterodimer formation. Activity can be assessed by one or more of the following:

(i) Inhibition of ligand-induced heterodimerisation of HER2 with other EGF family members in a target cell line, for example MCF-7 breast cancer cells Immunoprecipitation of HER2 complexes from cell lysates can be performed with a receptor-specific antibody, and the absence/presence of other EGF receptors and their biologically relevant ligands within the complex can be analysed following electrophoresis/Western transfer by probing with antibodies to other EGF receptors.

(ii) Inhibition of the activation of signaling pathways by ligand-activated heterodimers. Association with HER3 appears key for other members of the EGF family of receptors to elicit maximal cellular response following ligand binding. In the case of the kinase-defective HER3, HER2 provides a functional tyrosine kinase domain to enable signaling to occur following binding of growth factor ligands. Thus, cells co-expressing HER2 and HER3 can be treated with ligand, for example heregulin, in the absence and presence of inhibitor and the effect on HER3 tyrosine phosphorylation monitored by a number of ways including immunoprecipitation of HER3 from treated cell lysates and subsequent Western blotting using anti-phosphotyrosine antibodies (see Agus op. cit. for details). Alternatively, a high-throughput assay can be developed by trapping HER3 from solubilized lysates onto the wells of a 96-well plate coated with an anti-HER3 receptor antibody, and the level of tyrosine phosphorylation measured using, for example, europium-labelled anti-phosphotyrosine antibodies, as embodied by Waddleton et al., (2002) Anal. Biochem. 309:150-157.

In a broader extension of this approach, effector molecules known to be activated downstream of activated receptor heterodimers, such as mitogen-activated protein kinases (MAPK) and Akt, may be analysed directly, by immunoprecipitation from treated lysates and blotting with antibodies that detect the activated forms of these proteins, or by analysing the ability of these proteins to modify/activate specific substrates.

(iii) Inhibition of ligand-induced cellular proliferation. A variety of cell lines are known to co-express combinations of ErbB receptors, for example many breast and prostate cancer cell lines. Assays may be performed in 24/48/96-well formats with the readout based around DNA synthesis (tritiated thymidine incorporation), increase in cell number (crystal violet staining) etc.

A number of readouts can be used to assess the efficacy, and specificity, of HER3 antibodies in cell-based assays of ligand-independent homo- and heterodimer formation. For example, HER2 overexpression triggers ligand-independent activation of the kinase domain as a result of spontaneous dimer formation. Over expressed HER2 generates either homo- or heterodimers with other HER molecules such as HER1, HER3 and HER4.

Ability of antibodies or fragments thereof to block in vivo growth of tumour xenografts of human tumour cell lines whose tumorigenic phenotype is known to be at least partly dependent on ligand activation of HER3 heterodimer cell signaling e.g. BxPC3 pancreatic cancer cells etc. This can be assessed in immunocompromised mice either alone or in combination with an appropriate cytotoxic agent for the cell line in question. Examples of functional assays are also described in the Example section below.

Prophylactic and Therapeutic Uses

The present invention provides methods of treating a disease or disorder associated with the HER3 signaling pathway by administering to a subject in need thereof an effective amount of the antibodies of the invention. In a specific embodiment, the present invention provides a method of treating or preventing cancers (e.g., breast cancer, colorectal cancer, lung cancer, multiple myeloma, ovarian cancer, liver cancer, gastric cancer, pancreatic cancer, acute myeloid leukemia, chronic myeloid leukemia, osteosarcoma, squamous cell carcinoma, peripheral nerve sheath tumors, schwannoma, head and neck cancer, bladder cancer, esophageal cancer, Barretts esophageal cancer, glioblastoma, clear cell sarcoma of soft tissue, malignant mesothelioma, neurofibromatosis, renal cancer, melanoma, prostate cancer, benign prostatic hyperplasia (BPH), gynecomastia, and endometriosis) by administering to a subject in need thereof an effective amount of the antibodies of the invention. In some embodiments, the present invention provides methods of treating or preventing cancers associated with a HER signaling pathway by administering to a subject in need thereof an effective amount of the antibodies of the invention.

In a specific embodiment, the present invention provides methods of treating cancers associated with a HER signaling pathway that include, but are not limited to breast cancer, colorectal cancer, lung cancer, multiple myeloma, ovarian cancer, liver cancer, gastric cancer, pancreatic cancer, acute myeloid leukemia, chronic myeloid leukemia, osteosarcoma, squamous cell carcinoma, peripheral nerve sheath tumors, schwannoma, head and neck cancer, bladder cancer, esophageal cancer, Barretts esophageal cancer, glioblastoma, clear cell sarcoma of soft tissue, malignant mesothelioma, neurofibromatosis, renal cancer, melanoma, prostate cancer, benign prostatic hyperplasia (BPH), gynecomastia, and endometriosis.

In one embodiment, the invention pertains to treating esophageal cancer using the HER3 antibodies or fragments thereof.

In one embodiment, the invention pertains to treating benign prostatic hyperplasia (BPH) using the HER3 antibodies or fragments thereof. BHP is a common disease in aging males that is characterized by a non-neoplastic enlargement of the prostate leading to pressure on the urethra and resulting in urination and bladder problems (Mahapokail W, van Sluijs F J & Schalken J A. 2000 Prostate Cancer and Prostatic Diseases 3, 28-33). Anatomic or microscopic evidence of BPH is present at autopsy in approximately 55% of men aged 60-70 years. Transurethal resection of the prostate has been the treatment of choice for many years. Consequently, BPH is one of the most common reasons for surgical intervention among elderly men. Less invasive methods of treatment include:

(i) Alpha 1-blockers (doxazosin, prazosin, tamsulosin, terazosin, and alfuzosin) are a class of medications also used to treat high blood pressure. These medications relax the muscles of the bladder neck and prostate thus allowing easier urination.

(ii) Finasteride and dutasteride lower androgen levels thus reducing the size of the prostate gland, increasing urine flow rate, and decreasing symptoms of BPH. It may take 3 to 6 months before improvement in symptoms is observed. Potential side effects related to the use of finasteride and dutasteride include decreased sex drive and impotence The results in the Experiments section demonstrate for the first time that BPH is a neuregulin-dependent indication. The finding also show that MOR10703 significantly reduced prostate size in sexually mature rats without affecting hormone levels suggests that MOR10703 could be useful for the treatment of BPH.

To further test MOR10703 and other HER3 antibodies as therapeutics for BPH, primary human BPH surgical specimens can be transplanted into athymic mice or rats and effect of the Her3 antibodies studied using models (Otto U et al. Urol Int 1992; 48: 167-170). Alternatively, aspects of BPH can be induced in castrated dogs via the long-term administration of 5α-Androstane-3α,17β-diol plus estradiol and the HER3 antibodies tested in these canine models (Walsh P C, Wilson J D. J Clin Invest 1976; 57: 1093-1097).

In one embodiment, the invention pertains to treating gynecomastia using the HER3 antibodies or fragments thereof. The physical manifestation of gynecomastia is breast enlargement in males, it normally occurs in both breasts but can sometimes be in one only, known as asymmetrical or unilateral gynecosmastia. Gynecomastia is commonly caused by:

(i) Elevated estrogen levels resulting in the ratio of testosterone to oestrogen becoming unbalanced.

(ii) Androgen antagonists or anti-androgens used in the treatment of prostate cancer or BPH. These drugs suppress testosterone but by suppressing testosterone, oestrogen begins to rise.

Although a number of experimental drugs are currently being evaluated there are currently no approved treatments for gynecomastia. Consequently gynecomastia is treated via surgical removal of the breast tissue. The observation that MOR10703 induced irreversible atrophy of the male mammary gland indicates that it may be of benefit in the treatment of gynecomastia.

To further test MOR10703 and other HER3 antibodies for treating human gynecomastia, transgenic mouse models of gynecomastia can be used. These models have been developed by expressing human aromatase in the mouse mammary gland and recapitulate many aspects of human gynecomastia (Li et al., Endocrinology 2002; 143:4074-4083; Tekmal et al., Cancer Res 1996; 56:3180-318).

In one embodiment, the invention pertains to treating gynecomastia using the HER3 antibodies or fragments thereof. MOR10703 and other HER3 antibodies can also be examined for treating endometriosis, a gynecological condition in which cells from the lining of the uterus (endometrium) appear and flourish outside the uterine cavity. The main, but not universal, symptom of endometriosis is pelvic pain in various manifestations. Although the underlying causes of endometriosis are not well characterized is thought to be dependent on the presence of estrogen. Since MOR10703 induced endometrial atrophy in female mice resulting in a decrease in uterus weight, it may be used to treat endometriosis. To further study the effects of MOR10703 and other HER3 antibodies on endometriosis, human endometrium in the proliferative phase can be implanted into the peritoneal cavity of normal cycling and ovariectomized athymic mice or cycling non-obese diabetic (NOD)-severe combined immuno-deficiency (SCID) mice, and these SCID mice used as models (Grummer et al., 2001. Human Reproduction; 16; 1736-1743).

HER3 antibodies can also be used to treat or prevent other disorders associated with aberrant or defective HER signaling, including but are not limited to respiratory diseases, osteoporosis, osteoarthritis, polycystic kidney disease, diabetes, schizophrenia, vascular disease, cardiac disease, non-oncogenic proliferative diseases, fibrosis, and neurodegenerative diseases such as Alzheimer's disease.

Suitable agents for combination treatment with HER3-binding antibodies include standard of care agents known in the art that are able to modulate the ErbB signaling pathway. Suitable examples of standard of care agents for HER2 include, but are not limited to Herceptin and Tykerb. Suitable examples of standard of care agents for EGFR include, but are not limited to Iressa, Tarceva, Erbitux and Vectibix. Other agents that may be suitable for combination treatment with HER3-binding antibodies include, but are not limited to those that modulate receptor tyrosine kinases, G-protein coupled receptors, growth/survival signal transduction pathways, nuclear hormone receptors, apoptotic pathways, cell cycle and angiogenesis.

Diagnostic Uses

In one aspect, the invention encompasses diagnostic assays for determining HER3 protein and/or nucleic acid expression as well as HER3 protein function, in the context of a biological sample (e.g., blood, serum, cells, tissue) or from individual afflicted with cancer, or is at risk of developing cancer.

Diagnostic assays, such as competitive assays rely on the ability of a labelled analogue (the "tracer") to compete with the test sample analyte for a limited number of binding sites on a common binding partner. The binding partner generally is insolubilized before or after the competition and then the tracer and analyte bound to the binding partner are separated from the unbound tracer and analyte. This separation is accomplished by decanting (where the binding partner was preinsolubilized) or by centrifuging (where the binding partner was precipitated after the competitive reaction). The amount of test sample analyte is inversely proportional to the amount of bound tracer as measured by the amount of marker substance. Dose-response curves with known amounts of analyte are prepared and compared with the test results in order to quantitatively determine the amount of analyte present in the test sample. These assays are called ELISA systems when enzymes are used as the detectable markers. In an assay of this form, competitive binding between antibodies and HER3-binding antibodies results in the bound HER3 protein, preferably the HER3 epitopes of the invention, being a measure of antibodies in the serum sample, most particularly, neutralizing antibodies in the serum sample.

A significant advantage of the assay is that measurement is made of neutralizing antibodies directly (i.e., those which interfere with binding of HER3 protein, specifically, epitopes). Such an assay, particularly in the form of an ELISA test has considerable applications in the clinical environment and in routine blood screening.

Another aspect of the invention provides methods for determining HER3 nucleic acid expression or HER3 protein activity in an individual to thereby select appropriate therapeutic or prophylactic agents for that individual (referred to herein as "pharmacogenomics"). Pharmacogenomics allows for the selection of agents (e.g., drugs) for therapeutic or prophylactic treatment of an individual based on the genotype of the individual (e.g., the genotype of the individual examined to determine the ability of the individual to respond to a particular agent.)

Yet another aspect of the invention pertains to monitoring the influence of agents (e.g., drugs) on the expression or activity of HER3 protein in clinical trials.

Pharmaceutical Compositions

To prepare pharmaceutical or sterile compositions including a HER3-binding antibodies (intact or binding fragments), the HER3-binding antibodies (intact or binding fragments) is mixed with a pharmaceutically acceptable carrier or excipient. The compositions can additionally contain one or more other therapeutic agents that are suitable for treating or preventing cancer (breast cancer, colorectal cancer, lung cancer, multiple myeloma, ovarian cancer, liver cancer, gastric cancer, pancreatic cancer, acute myeloid leukemia, chronic myeloid leukemia, osteosarcoma, squamous cell carcinoma, peripheral nerve sheath tumors schwannoma, head and neck cancer, bladder cancer, esophageal cancer, Barretts esophageal cancer, glioblastoma, clear cell sarcoma of soft tissue, malignant mesothelioma, neurofibromatosis, renal cancer, melanoma, prostate cancer, benign prostatic hyperplasia (BPH), gynecomastia, and endometriosis).

Formulations of therapeutic and diagnostic agents can be prepared by mixing with physiologically acceptable carriers, excipients, or stabilizers in the form of, e.g., lyophilized powders, slurries, aqueous solutions, lotions, or suspensions (see, e.g., Hardman et al., (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N.Y.; Avis, et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY; Lieberman, et al. (eds.) (1990) Pharmaceutical Dosage Forms: Disperse Systems, Marcel Dekker, NY; Weiner and Kotkoskie (2000) Excipient Toxicity and Safety, Marcel Dekker, Inc., New York, N.Y.).

Selecting an administration regimen for a therapeutic depends on several factors, including the serum or tissue turnover rate of the entity, the level of symptoms, the immunogenicity of the entity, and the accessibility of the target cells in the biological matrix. In certain embodiments, an administration regimen maximizes the amount of therapeutic delivered to the patient consistent with an acceptable level of side effects. Accordingly, the amount of biologic delivered depends in part on the particular entity and the severity of the condition being treated. Guidance in selecting appropriate doses of antibodies, cytokines, and small molecules are available (see, e.g., Wawrzynczak (1996) Antibody Therapy, Bios Scientific Pub. Ltd, Oxfordshire, UK; Kresina (ed.) (1991) Monoclonal Antibodies, Cytokines and Arthritis, Marcel Dekker, New York, N.Y.; Bach (ed.) (1993) Monoclonal Antibodies and Peptide Therapy in Autoimmune Diseases, Marcel Dekker, New York, N.Y.; Baert et al., (2003) New Engl. J. Med. 348:601-608; Milgrom et al., (1999) New Engl. J. Med. 341:1966-1973; Slamon et al., (2001) New Engl. J. Med. 344:783-792; Beniaminovitz et al., (2000) New Engl. J. Med. 342:613-619; Ghosh et al., (2003) New Engl. J. Med. 348: 24-32; Lipsky et al., (2000) New Engl. J. Med. 343:1594-1602).

Determination of the appropriate dose is made by the clinician, e.g., using parameters or factors known or suspected in the art to affect treatment or predicted to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors known in the medical arts.

Compositions comprising antibodies or fragments thereof of the invention can be provided by continuous infusion, or by doses at intervals of, e.g., one day, one week, or 1-7 times per week. Doses may be provided intravenously, subcutaneously, topically, orally, nasally, rectally, intramuscular, intracerebrally, or by inhalation. A specific dose protocol is one involving the maximal dose or dose frequency that avoids significant undesirable side effects. A total weekly dose may be at least 0.05 µg/kg body weight, at least 0.2 µg/kg, at least 0.5 µg/kg, at least 1 µg/kg, at least 10 µg/kg, at least 100 µg/kg, at least 0.2 mg/kg, at least 1.0 mg/kg, at least 2.0 mg/kg, at least 10 mg/kg, at least 25 mg/kg, or at least 50 mg/kg (see, e.g., Yang et al., (2003) New Engl. J. Med. 349:427-434; Herold et al., (2002) New Engl. J. Med. 346:1692-1698; Liu et al., (1999) J. Neurol. Neurosurg. Psych. 67:451-456; Portielji et al., (2003) Cancer Immunol. Immunother. 52:133-144). The desired dose of antibodies or fragments thereof is about the same as for an antibody or polypeptide, on a moles/kg body weight basis. The desired plasma concentration of the antibodies or fragments thereof is about, on a moles/kg body weight basis. The dose may be at least 15 µg at least 20 µg, at least 25 µg, at least 30 µg, at least 35 µg, at least 40 µg, at least 45 µg, at least 50 µg, at least 55 µg, at least 60 µg, at least 65 µg, at least 70 µg, at least 75 µg, at least 80 µg, at least 85 µg, at least 90 µg, at least 95 µg, or at least 100 µg. The doses administered to a subject may number at least 1, 2, 3, 4, 5, 6, 7, 8, 9, 10, 11, or 12, or more.

For antibodies or fragments thereof of the invention, the dosage administered to a patient may be 0.0001 mg/kg to 100 mg/kg of the patient's body weight. The dosage may be between 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg to 0.25 mg/kg, 0.0001 to 0.15 mg/kg, 0.0001 to 0.10 mg/kg, 0.001 to 0.5 mg/kg, 0.01 to 0.25 mg/kg or 0.01 to 0.10 mg/kg of the patient's body weight.

The dosage of the antibodies or fragments thereof of the invention may be calculated using the patient's weight in kilograms (kg) multiplied by the dose to be administered in mg/kg. The dosage of the antibodies or fragments thereof of the invention may be 150 µg/kg or less, 125 µg/kg or less, 100 µg/kg or less, 95 µg/kg or less, 90 µg/kg or less, 85 µg/kg or less, 80 µg/kg or less, 75 µg/kg or less, 70 µg/kg or less, 65 µg/kg or less, 60 µg/kg or less, 55 µg/kg or less, 50 µg/kg or less, 45 µg/kg or less, 40 µg/kg or less, 35 µg/kg or less, 30 µg/kg or less, 25 µg/kg or less, 20 µg/kg or less, 15 µg/kg or less, 10 µg/kg or less, 5 µg/kg or less, 2.5 µg/kg or less, 2 µg/kg or less, 1.5 µg/kg or less, 1 µg/kg or less, 0.5 µg/kg or less, or 0.5 µg/kg or less of a patient's body weight.

Unit dose of the antibodies or fragments thereof of the invention may be 0.1 mg to 20 mg, 0.1 mg to 15 mg, 0.1 mg to 12 mg, 0.1 mg to 10 mg, 0.1 mg to 8 mg, 0.1 mg to 7 mg, 0.1 mg to 5 mg, 0.1 to 2.5 mg, 0.25 mg to 20 mg, 0.25 to 15 mg, 0.25 to 12 mg, 0.25 to 10 mg, 0.25 to 8 mg, 0.25 mg to 7 mg, 0.25 mg to 5 mg, 0.5 mg to 2.5 mg, 1 mg to 20 mg, 1 mg to 15 mg, 1 mg to 12 mg, 1 mg to 10 mg, 1 mg to 8 mg, 1 mg to 7 mg, 1 mg to 5 mg, or 1 mg to 2.5 mg.

The dosage of the antibodies or fragments thereof of the invention may achieve a serum titer of at least 0.1 µg/ml, at least 0.5 µg/ml, at least 1 µg/ml, at least 2 µg/ml, at least 5 µg/ml, at least 6 µg/ml, at least 10 µg/ml, at least 15 µg/ml, at least 20 µg/ml, at least 25 µg/ml, at least 50 µg/ml, at least 100 µg/ml, at least 125 µg/ml, at least 150 µg/ml, at least 175 µg/ml, at least 200 µg/ml, at least 225 µg/ml, at least 250 µg/ml, at least 275 µg/ml, at least 300 µg/ml, at least 325 µg/ml, at least 350 µg/ml, at least 375 µg/ml, or at least 400 µg/ml in a subject. Alternatively, the dosage of the antibodies or fragments thereof of the invention may achieve a serum titer of at least 0.1 µg/ml, at least 0.5 µg/ml, at least 1 µg/ml, at least, 2 µg/ml, at least 5 µg/ml, at least 6 µg/ml, at least 10 µg/ml, at least 15 µg/ml, at least 20 .mu.g/ml, at least 25 µg/ml, at least 50 µg/ml, at least 100 µg/ml, at least 125 µg/ml, at least 150 µg/ml, at least 175 µg/ml, at least 200 µg/ml, at least 225 µg/ml, at least 250 µg/ml, at least 275 µg/ml, at least 300 µg/ml, at least 325 µg/ml, at least 350 µg/ml, at least 375 µg/ml, or at least 400 µg/ml in the subject.

Doses of antibodies or fragments thereof of the invention may be repeated and the administrations may be separated by at least 1 day, 2 days, 3 days, 5 days, 10 days, 15 days, 30 days, 45 days, 2 months, 75 days, 3 months, or at least 6 months.

An effective amount for a particular patient may vary depending on factors such as the condition being treated, the overall health of the patient, the method route and dose of administration and the severity of side affects (see, e.g., Maynard et al., (1996) A Handbook of SOPs for Good Clinical Practice, Interpharm Press, Boca Raton, Fla.; Dent (2001) Good Laboratory and Good Clinical Practice, Urch Publ., London, UK).

The route of administration may be by, e.g., topical or cutaneous application, injection or infusion by intravenous, intraperitoneal, intracerebral, intramuscular, intraocular, intraarterial, intracerebrospinal, intralesional, or by sustained release systems or an implant (see, e.g., Sidman et al., (1983) Biopolymers 22:547-556; Langer et al., (1981) J. Biomed. Mater. Res. 15:167-277; Langer (1982) Chem. Tech. 12:98-105; Epstein et al., (1985) Proc. Natl. Acad. Sci. USA 82:3688-3692; Hwang et al., (1980) Proc. Natl. Acad. Sci. USA 77:4030-4034; U.S. Pat. Nos. 6,350,466 and 6,316, 024). Where necessary, the composition may also include a solubilizing agent and a local anesthetic such as lidocaine to ease pain at the site of the injection. In addition, pulmonary administration can also be employed, e.g., by use of an inhaler or nebulizer, and formulation with an aerosolizing agent. See, e.g., U.S. Pat. Nos. 6,019,968, 5,985,320, 5,985,309, 5,934, 272, 5,874,064, 5,855,913, 5,290,540, and 4,880,078; and PCT Publication Nos. WO 92/19244, WO 97/32572, WO 97/44013, WO 98/31346, and WO 99/66903, each of which is incorporated herein by reference their entirety.

A composition of the present invention may also be administered via one or more routes of administration using one or more of a variety of methods known in the art. As will be appreciated by the skilled artisan, the route and/or mode of administration will vary depending upon the desired results. Selected routes of administration for antibodies or fragments thereof of the invention include intravenous, intramuscular, intradermal, intraperitoneal, subcutaneous, spinal or other parenteral routes of administration, for example by injection or infusion. Parenteral administration may represent modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, a composition of the invention can be administered via a non-parenteral route, such as a topical, epidermal or mucosal route of administration, for example, intranasally, orally, vaginally, rectally, sublingually or topically. In one embodiment, the antibodies or fragments thereof of the invention is administered by infusion. In another embodiment, the multispecific epitope binding protein of the invention is administered subcutaneously.

If the antibodies or fragments thereof of the invention are administered in a controlled release or sustained release system, a pump may be used to achieve controlled or sustained release (see Langer, supra; Sefton, (1987) CRC Crit. Ref Biomed. Eng. 14:20; Buchwald et al., (1980), Surgery 88:507; Saudek et al., (1989) N. Engl. J. Med. 321:574). Polymeric materials can be used to achieve controlled or sustained release of the therapies of the invention (see e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, (1983) J. Macromol. Sci. Rev. Macromol. Chem. 23:61; see also Levy et al., (1985) Science 228:190; During et al., (1989) Ann. Neurol. 25:351; Howard et al., (1989) J. Neurosurg. 7 1:105); U.S. Pat. No. 5,679,377; U.S. Pat. No. 5,916,597; U.S. Pat. No. 5,912,015; U.S. Pat. No. 5,989,463; U.S. Pat. No. 5,128,326; PCT Publication No. WO 99/15154; and PCT Publication No. WO 99/20253. Examples of polymers used in sustained release formulations include, but are not limited to, poly(-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In one embodiment, the polymer used in a sustained release formulation is inert, free of leachable impurities, stable on storage, sterile, and biodegradable. A controlled or sustained release system can be placed in proximity of the prophylactic or therapeutic target, thus requiring only a fraction of the systemic dose (see, e.g., Goodson, in Medical Applications of Controlled Release, supra, vol. 2, pp. 115-138 (1984)).

Controlled release systems are discussed in the review by Langer, (1990), Science 249:1527-1533). Any technique known to one of skill in the art can be used to produce sustained release formulations comprising one or more antibodies or fragments thereof of the invention. See, e.g., U.S. Pat. No. 4,526,938, PCT publication WO 91/05548, PCT publication WO 96/20698, Ning et al., (1996), Radiotherapy & Oncology 39:179-189, Song et al., (1995) PDA Journal of Pharmaceutical Science & Technology 50:372-397, Cleek et al., (1997) Pro. Int'l. Symp. Control. Rel. Bioact. Mater. 24:853-854, and Lam et al., (1997) Proc. Int'l. Symp. Control Rel. Bioact. Mater. 24:759-760, each of which is incorporated herein by reference in their entirety.

If the antibodies or fragments thereof of the invention are administered topically, they can be formulated in the form of an ointment, cream, transdermal patch, lotion, gel, shampoo, spray, aerosol, solution, emulsion, or other form well-known to one of skill in the art. See, e.g., Remington's Pharmaceutical Sciences and Introduction to Pharmaceutical Dosage Forms, 19th ed., Mack Pub. Co., Easton, Pa. (1995). For non-sprayable topical dosage forms, viscous to semi-solid or solid forms comprising a carrier or one or more excipients compatible with topical application and having a dynamic viscosity, in some instances, greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, in some instances, in combination with a solid or liquid inert carrier, is packaged in a mixture with a pressurized volatile (e.g., a gaseous propellant, such as freon) or in a squeeze bottle. Moisturizers or humectants can also be added to pharmaceutical compositions and dosage forms if desired. Examples of such additional ingredients are well-known in the art.

If the compositions comprising antibodies or fragments thereof are administered intranasally, it can be formulated in an aerosol form, spray, mist or in the form of drops. In particular, prophylactic or therapeutic agents for use according to the present invention can be conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In the case of a pressurized aerosol the dosage unit may be determined by providing a valve to deliver a metered amount. Capsules and cartridges (composed of, e.g., gelatin) for use in an inhaler or insufflator may be formulated containing a powder mix of the compound and a suitable powder base such as lactose or starch.

Methods for co-administration or treatment with a second therapeutic agent, e.g., a cytokine, steroid, chemotherapeutic agent, antibiotic, or radiation, are known in the art (see, e.g., Hardman et al., (eds.) (2001) Goodman and Gilman's The Pharmacological Basis of Therapeutics, 10.sup.th ed., McGraw-Hill, New York, N.Y.; Poole and Peterson (eds.) (2001) Pharmacotherapeutics for Advanced Practice: A Practical Approach, Lippincott, Williams & Wilkins, Phila., Pa.; Chabner and Longo (eds.) (2001) Cancer Chemotherapy and Biotherapy, Lippincott, Williams & Wilkins, Phila., Pa.). An effective amount of therapeutic may decrease the symptoms by at least 10%; by at least 20%; at least about 30%; at least 40%, or at least 50%.

Additional therapies (e.g., prophylactic or therapeutic agents), which can be administered in combination with the antibodies or fragments thereof of the invention may be administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours apart from the antibodies or fragments thereof of the invention. The two or more therapies may be administered within one same patient visit.

The antibodies or fragments thereof of the invention and the other therapies may be cyclically administered. Cycling therapy involves the administration of a first therapy (e.g., a first prophylactic or therapeutic agent) for a period of time, followed by the administration of a second therapy (e.g., a second prophylactic or therapeutic agent) for a period of time, optionally, followed by the administration of a third therapy (e.g., prophylactic or therapeutic agent) for a period of time and so forth, and repeating this sequential administration, i.e., the cycle in order to reduce the development of resistance to one of the therapies, to avoid or reduce the side effects of one of the therapies, and/or to improve the efficacy of the therapies.

In certain embodiments, the antibodies or fragments thereof of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., Ranade, (1989) J. Clin. Pharmacol. 29:685). Exemplary targeting moieties include folate or biotin (see, e.g., U.S. Pat. No. 5,416,016 to Low et al); mannosides (Umezawa et al., (1988) Biochem. Biophys. Res. Commun 153:1038); antibodies (Bloeman et al., (1995) FEBS Lett. 357:140; Owais et al., (1995) Antimicrob. Agents Chemother. 39:180); surfactant protein A receptor (Briscoe et al., (1995) Am. J. Physiol. 1233:134); p 120 (Schreier et al, (1994) J. Biol. Chem. 269:9090); see also K. Keinanen; M. L. Laukkanen (1994) FEBS Lett. 346:123; J. J. Killion; I. J. Fidler (1994) Immunomethods 4:273.

The invention provides protocols for the administration of pharmaceutical composition comprising antibodies or fragments thereof of the invention alone or in combination with other therapies to a subject in need thereof. The therapies (e.g., prophylactic or therapeutic agents) of the combination therapies of the present invention can be administered concomitantly or sequentially to a subject. The therapy (e.g., prophylactic or therapeutic agents) of the combination therapies of the present invention can also be cyclically administered. Cycling therapy involves the administration of a first therapy (e.g., a first prophylactic or therapeutic agent) for a period of time, followed by the administration of a second therapy (e.g., a second prophylactic or therapeutic agent) for a period of time and repeating this sequential administration, i.e., the cycle, in order to reduce the development of resistance to one of the therapies (e.g., agents) to avoid or reduce the side effects of one of the therapies (e.g., agents), and/or to improve, the efficacy of the therapies.

The therapies (e.g., prophylactic or therapeutic agents) of the combination therapies of the invention can be administered to a subject concurrently. The term "concurrently" is not limited to the administration of therapies (e.g., prophylactic or therapeutic agents) at exactly the same time, but rather it is meant that a pharmaceutical composition comprising antibodies or fragments thereof of the invention are administered to a subject in a sequence and within a time interval such that the antibodies of the invention can act together with the other therapy(ies) to provide an increased benefit than if they were administered otherwise. For example, each therapy may be administered to a subject at the same time or sequentially in any order at different points in time; however, if not administered at the same time, they should be administered sufficiently close in time so as to provide the desired therapeutic or prophylactic effect. Each therapy can be administered to a subject separately, in any appropriate form and by any suitable route. In various embodiments, the therapies (e.g., prophylactic or therapeutic agents) are administered to a subject less than 15 minutes, less than 30 minutes, less than 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, 24 hours apart, 48 hours apart, 72 hours apart, or 1 week apart. In other embodiments, two or more therapies (e.g., prophylactic or therapeutic agents) are administered to a within the same patient visit.

The prophylactic or therapeutic agents of the combination therapies can be administered to a subject in the same pharmaceutical composition. Alternatively, the prophylactic or therapeutic agents of the combination therapies can be administered concurrently to a subject in separate pharmaceutical compositions. The prophylactic or therapeutic agents may be administered to a subject by the same or different routes of administration.

The invention having been fully described, it is further illustrated by the following examples and claims, which are illustrative and are not meant to be further limiting.

EXAMPLES

Example 1

Methods, Materials and Screening for Antibodies (i) Cell Lines

BXPC-3, SK-Br-3, BT-474, MDA-MB-453, FaDu and MCF-7 cell lines were purchased from ATCC and routinely maintained in growth media supplemented with 10% fetal bovine serum (FBS).

(ii) Generation of Recombinant Human, Cyno, Mouse and Rat HER3 Vectors

Murine HER3 extracellular domain was PCR amplified from mouse brain cDNA (Clontech) and sequence verified by comparison with Refseq NM_010153. Rat HER3 ECD was reverse transcribed from Rat-2 cell mRNA and sequence verified by comparison with NM_017218. Cynomolgus HER3 cDNA template was generated using RNA from various cyno tissues (Zyagen Laboratories), and the RT-PCR product cloned into pCR®-TOPO-XL (Invitrogen) prior to sequencing of both strands. Human HER3 was derived from a human fetal brain cDNA library (Source) and sequence verified by comparison with NM_001982.

To generate tagged recombinant proteins, human, mouse, rat and cyno HER3 was PCR amplified using Pwo Taq polymerase (Roche Diagnostics). Amplified PCR products were gel purified and cloned into a pDonR201 (Invitrogen) gateway entry vector that had previously been modified to include an in-frame N-terminal CD33 leader sequence and a C-terminal TAG, e.g., FLAG TAG. The TAG allows purification of monomeric proteins via an anti-TAG monoclonal antibody. The target genes were flanked with AttB1 and AttB2 allowing recombination into Gateway adapted proprietary destination vectors (e.g., pcDNA3.1) using the Gateway® cloning technology (Invitrogen). Recombination reactions were performed using a Gateway LR reaction with proprietary destination vectors containing a CMV promoter to create the TAG expression vectors, although any commercially available vector can be used.

Further recombinant HER3 proteins were generated that fused the HER3 ECD upstream of a C-terminal Factor X cleavage site and the human IgG hinge and Fc domain to create an Fc-tagged protein. To achieve this, the various HER3 ECD's were PCR amplified and cloned into a vector (e.g., pcDNA3.1) modified to contain an in-frame C-terminal fusion of Factor X site-Hinge-hFc. The generated open reading frame was flanked with AttB1 and AttB2 sites for further cloning with the Gateway® recombinant cloning technology (Invitrogen). An LR Gateway reaction was used to transfer HER3-Fc into a destination expression construct containing a CMV promoter. HER3 point mutation expression constructs were generated using standard site directed mutagenesis protocols and the resultant vectors sequence verified.

TABLE 8

Generation of HER3 expression vectors. HER3 amino acid numbering is based on NP_001973 (human), NP_034283 (mouse) and NP_058914 (rat).

| Name | Description |
| --- | --- |
| Hu HER3 | CD33-[Human HER3, residues 20-640]-TAG |
| Mu HER3 | CD33-[Murine HER3, residues 20-643]-TAG |
| Rat HER3 | CD33-[Rat HER3, residues 20-643]-TAG |
| Cyno HER3 | CD33-[Cyno HER3, residues 20-643]-TAG |
| HER3 D1-2 | CD33-[Human HER3, residues 20-329]-TAG |
| HER3 D2 | CD33-[Human HER3, residues 185-329]- TAG |
| HER3 D3-4 | CD33-[Human HER3, residues 330-643]- TAG |
| HER3 D4 | CD33-[Human HER3, residues 496-643]- TAG |
| Hu HER3-Fc | [Human HER3, residues 1-643]-Fc |
| Mu HER3-Fc | [Murine HER3, residues 1-643]-Fc |
| Cyno HER3-Fc | [Cyno HER3, residues 1-643]-Fc |
| Rat HER3-Fc | [Rat HER3, residues 1-643]-Fc |
| HER3 D2-Fc | [Human HER3 residues 207-329]-Fc |
| HER3 K267A | CD33-[Human HER3, residues 20-640, K267A]-TAG |
| HER3 L268A | CD33-[Human HER3, residues 20-640, L268A]-TAG |
| HER3 K267A/ L268A | CD33-[Human HER3, residues 20-640, K267A/ L268A]-TAG |

(iii) Expression of Recombinant HER3 Proteins

The desired HER3 recombinant proteins were expressed in HEK293 derived cell lines previously adapted to suspension culture and grown in a Novartis proprietary serum-free medium. Small scale expression verification was undertaken in transient 6-well-plate transfection assays on the basis of lipofection. Large-scale protein production via transient transfection and was performed at the 10-20 L scale in the Wave™ bioreactor system (Wave Biotech). DNA Polyethylenimine (Polysciences) was used as a plasmid carrier at a ratio of 1:3 (w:w). The cell culture supernatants were harvested 7-10 days post transfection and concentrated by cross-flow filtration and diafiltration prior to purification.

(iv) Tagged Protein Purification

Recombinant tagged HER3 proteins (e.g., TAG-HER3) were purified by collecting the cell culture supernatant and concentrating 10-fold by cross-flow filtration with a 10 kDa cut off filter (Fresenius). An anti-TAG column was prepared by coupling an anti-TAG monoclonal antibody to CNBr activated Sepharose 4B at a final ratio of 10 mg antibody per mL of resin. Concentrated supernatant was applied to a 35 ml anti-Tag column at a flow rate of 1-2 mL/minute. After baseline washing with PBS, bound material was eluted with 100 mM glycine (pH 2.7), neutralized and sterile filtered. Protein concentrations were determined by measuring the absorbance at 280 nm and converting using a theoretical factor of 0.66 AU/mg. The purified protein was finally characterized by SDS-PAGE, N-terminal sequencing and LC-MS.

(v) Fc Tag Purification

Concentrated cell culture supernatant was applied to a 50 ml Protein A Sepharose Fast Flow column at a flow rate of 1 ml/min. After baseline washing with PBS, the column was washed with 10 column volumes of 10 mM $NaH_2PO_4$/30% (v/v) Isopropanol, pH 7.3 followed by 5 column volumes of PBS. Finally, bound material was eluted with 50 mM Citrate/ 140 mM NaCl (pH 2.7), neutralized and sterile filtered.

(vi) Generation of Over-Expressing Cell Lines

To generate a cell line that expresses high levels of HER3 on the cell surface, a mammalian expression vector was constructed containing an insert coding for a CD33 leader sequence upstream of amino acid residues 20-667 of human HER3 fused in-frame to amino acid residues 669-1210 of human EGFR. When expressed in mammalian cells the resultant chimeric protein contains an N-terminal HER3 extracellular and transmembrane domain and a C-terminal EGFR cytoplasmic domain. The HER3/1 vector was transfected into CHO-S cells (Invitrogen) and stable pools generated following antibiotic selection. The resultant cell line (CHO HER3/1) expressed high levels of HER3 extracellular domain on its cell surface.

(vii) HuCAL GOLD® Pannings

For the selection of antibodies recognizing human HER3 multiple panning strategies were employed. Therapeutic antibodies against human HER3 protein were generated by selection of clones having high binding affinities, using as the source of antibody variant proteins a commercially available phage display library, the MorphoSys HuCAL GOLD® library. The phagemid library is based on the HuCAL® concept (Knappik et al., (2000) J Mol Biol 296:57-86) and employs the CysDisplay® technology for displaying the Fab on the phage surface (WO01/05950 to Lohning).

For the isolation of anti-HER3 antibodies, standard as well as RapMAT panning strategies were performed using solid phase, solution, whole cell and differential whole cell panning approaches.

(viii) Solid Phase Panning

To identify anti-HER3 antibodies a variety of solid phase panning strategies were performed using differing recombinant HER3 proteins. To perform each round of solid phase panning, Maxisorp plates (Nunc) were coated with HER3 protein. Tagged proteins were either captured using plates previously coated with anti-Fc (goat or mouse anti-human IgG, Jackson Immuno Research), anti-Tag antibody or via passive adsorption. The coated plates were washed with PBS and blocked. Coated plates were washed twice with PBS prior to the addition of HuCAL GOLD® phage-antibodies for 2 hours at room temperature on a shaker. Bound phages were eluted were added to *E. coli* TG-1 and incubated for phage infection. Subsequently infected bacteria were isolated and plated on agar plates. Colonies were scraped off the plates and phages were rescued and amplified. Each HER3 panning strategy comprised of individual rounds of panning and contained unique antigens, antigen concentrations and washing stringency.

(ix) Solution Phase Panning

Each round of solution phase panning was performed using various biotinylated recombinant HER3 proteins in the presence or absence of neuregulin 1-β1 (R&D Systems). Proteins were biotinylated using the EZ-link sulfo-NHS-LC biotinylation kit (Pierce) according to the manufacturers instructions. 800 µl of Streptavidin linked magnetic beads (Dynabeads, Dynal) were washed once with PBS and blocked overnight with Chemiblocker (Chemicon). HuCAL GOLD® phage-antibodies and the appropriate biotinylated HER3 were incubated in a reaction tube. Streptavidin magnetic beads were added for 20 minutes and were collected with a magnetic particle separator (Dynal). Bound phages were eluted from the Dynabeads by adding DTT containing buffer to each tube and added to *E. coli* TG-1. Phage infection was performed in an identical manner to that described in solid phase panning. Each HER3 panning strategy comprised of individual rounds of panning and contained unique antigens, antigen concentrations and washing stringency.

(x) Cell Based Panning

For cell pannings, HuCAL GOLD® phage-antibodies were incubated with approximately $10^7$ cells on a rotator for 2 hours at room temperature, followed by centrifugation. The cell pellet was isolated phages were eluted from the cells The supernatant was collected and added to *E. coli* TG-1 culture continued by the process described above. Two cell based strategies were employed to identify anti-HER3 antibodies:

a) Whole cell panning: In this strategy a variety of intact cell lines were used as the antigens.
b) Differential whole cell panning: In this strategy the antigens sequentially consisted of cells and recombinant HER3 proteins (see 1981.09 as an example). The cell based pannings were performed as described above whilst solid phase panning protocols were employed when recombinant proteins were utilized as antigens. The washes were conducted using PBS (2-3×) and PBST (2-3×).

(xi) RapMAT™ Library Generation and Pannings

In order to increase antibody binding affinity whilst maintaining library diversity the second round output of both solution and solid phase pannings were entered into the RapMAT™ process whilst the third round output of the whole cell and differential whole cell panning strategies were entered (Prassler et al., (2009) Immunotherapy; 1: 571-583. RapMAT™ libraries were generated by sub-cloning Fab-encoding inserts of phages selected via panning into the display vector pMORPH® 25_bla_LHCand were further digested to either generate H-CDR2RapMAT™ libraries and L-CDR3 RapMAT™ libraries by using specific restriction enzymes. The inserts were replaced with TRIM maturation cassettes (Virnekas et al., (1994) Nucleic Acids Research 22:5600-5607) for H-CDR2 or L-CDR3 according to pool composition. Library sizes were estimated to range between $8 \times 10^6$-$1 \times 10^8$ clones. RapMAT antibody-phage were produced and subjected to two further rounds of solution, solid phase or cell based panning using the experimental methods described previously.

Example 2

Transient Expression of Anti-HER3 IgG's

Suspension adapted HEK293-6E cells were cultivated in a BioWave20 to a density of approximately $2 \times 10^6$ viable cells/mL. The cells were transiently transfected with the relevant sterile DNA: PEI-MIX and further cultivated. Seven days after transfection, cells were removed by crossflow filtration using Fresenius filters (0.2 µm). The cell free material was concentrated with crossflow filtration using a 10 kDa cut off filter (Fresenius) and the concentrate was sterile filtered through a stericup filter (0.22 µm). The sterile supernatant was stored at 4° C.

Example 3

Purification of Anti-HER3 IgG

The purification of IgG was performed on a ÄKTA 100 explorer Air chromatography system at 6° C. in a cooling cabinet, using a XK16/20 column with 25 mL of self-packed MabSelect SuRe resin (all GE Healthcare). All flow rates were 3.5 mL/min, except for loading, at a pressure limit of 5 bar. The column was equilibrated with 3 column volumes of PBS prior to loading the filtered fermentation supernatant at 2.0 mL/min. The column was washed with 8 column volumes of PBS. IgG was eluted with a pH gradient, starting at 50 mM citrate/70 mM NaCl (pH 4.5), going linearly down in 12 Column volumes to 50 mM citrate/70 mM NaCl (pH 2.5), followed by a 2 column volume constant step of the same pH 2.5 buffer. The IgG containing fractions were pooled and immediately neutralized and sterile filtered (Millipore Steriflip, 0.22 um). $OD_{280}$ was measured and the protein concentration calculated based on the sequence data. The pools were separately tested for aggregation (SEC-MALS) and purity (SDS-PAGE and MS).

Example 4

Expression and Purification of HuCAL®-Fab Antibodies in *E. coli*

Expression of Fab fragments encoded by pMORPH®X9_Fab_MH in TG-1 cells was carried out in shaker flask cultures using 500 mL of 2×YT medium supplemented with 34 µg/mL chloramphenicol. Cultures were shaken at 30° C. until the OD600 nm reached 0.5. Expression was induced by addition of 0.75 mM IPTG (isopropyl-β-D-thiogalactopyranoside) for 20 hours at 30° C. Cells were disrupted using lysozyme. His$_6$-tagged ("His$_6$" disclosed as SEQ ID NO: 495) Fab fragments were isolated via IMAC (Bio-Rad). Buffer exchange to 1× Dulbecco's PBS (pH 7.2) was performed using PD10 columns. Samples were sterile filtered (0.2 µm). Protein concentrations were determined by UV-spectrophotometry. The purity of the samples was analyzed in denaturing, reducing 15% SDS-PAGE. The homogeneity of Fab preparations was determined in native state by size exclusion chromatography (HP-SEC) with calibration standards Example 5

HER3 Antibody Affinity ($K_D$) Measurements by Solution Equilibrium Titration (SET)

Affinity determination in solution was essentially performed as previously described (Friguet et al., (1985) J Immunol Methods 77:305-19). In order to improve the sensitivity and accuracy of the SET method, it was transferred from classical ELISA to ECL based technology (Haenel et al., (2005) Anal biochem 339:182-84).

Unlabeled HER3-Tag (human, rat, mouse or cyno) described previously was used for affinity determination by SET.

The data was evaluated with XLfit software (ID Business Solutions) applying customized fitting models. For $K_D$ determination of each IgG the following model was used (modified according to Piehler, et al (Piehler et al., (1997) J Immunol Methods 201:189-206).

$$y = \frac{2B_{max}}{[IgG]}\left([IgG]\over 2 - \frac{\left(\frac{x+[IgG]+K_D}{2} - \sqrt{\frac{(x+[IgG]+K_D)^2}{4} - x[IgG]}\right)^2}{2[IgG]}\right)$$

[IgG]: applied total IgG concentration
x: applied total soluble antigen concentration (binding sites)
$B_{max}$: maximal signal of IgG without antigen
$K_D$: affinity Example 6

Antibody Cell Binding Determination by FACS

The binding of antibodies to endogenous human antigen expressed on human cancer cells was accessed by FACS. In order to determine antibody $EC_{50}$ values SK-Br-3 cells were harvested with accutase and diluted to $1\times10^6$ cells/mL in FACS buffer (PBS/3% FBS/0.2% $NaN_3$). $1\times10^5$ cells/well were added to each well of a 96-well plate (Nunc) and centrifuged at 210 g for 5 minutes at 4° C. before removing the supernatant. Serial dilutions of test antibodies (diluted in 1:4 dilution steps with FACS buffer) were added to the pelleted cells and incubated for 1 hour on ice. The cells were washed and pelleted three times with 100 µL FACS buffer. PE conjugated goat anti-human IgG (Jackson ImmunoResearch) diluted 1/200 with FACS buffer were added to the cells and incubated on ice for 1 hour. Additional washing steps were performed three times with 100 µL FACS buffer followed by centrifugation steps at 210 g for 5 minutes at 4° C. Finally, cells were resuspended in 200 µL FACS buffer and fluorescence values were measured with a FACSArray (BD Biosciences). The amount of cell surface bound anti-HER3 antibody was assessed by measuring the mean channel fluorescence.

Example 7

HER3 Domain and Mutant Binding 96-well Maxisorp plates (Nunc) were coated overnight at 4° C. with 200 ng of the appropriate recombinant human protein (HER3-Tag, D1-2-Tag, D2-Tag, D3-4-Tag, D4-Tag, HER3 K267A-Tag, HER3 L268A-Tag, HER3 K267A/L268A and a tagged irrelevant control). All wells were then washed three times with PBS/0.1% Tween-20, blocked for one hour with PBS/1% BSA/0.1% Tween-20 and washed three times with PBS/0.1% Tween-20. Anti-HER3 antibodies were added to the relevant wells up to a final concentration of 10 µg/mL were added to the appropriate wells and incubated at room temperature for two hours. Plates were washed three times with PBS/0.1% Tween-20 prior to the addition of the appropriate peroxidase linked detection antibody diluted 1/10000 in PBS/1% BSA/0.1% Tween-20. The detection antibodies used were goat anti-mouse (Pierce, 31432), rabbit anti-goat (Pierce, 31402) and goat anti-human (Pierce, 31412). Plates were incubated at room temperature for one hour before washing three times with PBS/0.1% Tween-20. 100 µl TMB (3,3', 5,5' tetramethyl benzidine) substrate solution (BioFx) was added to all wells for 6 minutes before stopping the reaction with 50 µl 2.5% $H_2SO_4$. The extent of HER3 antibody binding to each recombinant protein was determined by measuring the $OD_{450}$ using a SpectraMax plate reader (Molecular Devices). Where appropriate, dose response curves were analyzed using Graphpad Prism.

Example 8

HER3 Epitope Mapping Using Hydrogen/Deuterium Exchange Mass Spectrometry

Materials $D_2O$ buffer was made by dissolving 25 mM TBS (pH 7.5)/500 mM NaCl in heavy water (Sigma). The reduction solution was 50 mM formate buffer (pH 4) 500 mM TCEP and the quenching solution 0.5% (v/v) trifluoroacetic acid (TFA) in water. Buffer A was 0.25% formic acid/10% methanol/10% ethylene glycol in water, and buffer B was 0.25% formic acid in acetonitrile. All chemicals were purchased from Sigma, and HPLC grade solvents were from Fisher Scientific.

Liquid Handling and Chromatography

Automated hydrogen-deuterium exchange mass spectrometry (HDX MS) experiments were designed based upon methods and equipment described by Wales et al., (2006) Anal. Chem. 78:1005-1014). In short, all liquid handling operations used a Pal HTS liquid-handler (LEAP Technologies) housed in a refrigerated enclosure maintained at 2° C. A 6-port injection valve and a wash station were mounted on the liquid-handler rail and facilitated sample injection into the chromatographic system and syringe washing. The chromatographic system, consisted of an additional 10-port valve, a 2.1 mm×30 mm Poroszyme pepsin column (Applied Biosystems), a reverse-phase 0.5 mm×2 mm Cap Trap cartridge (Michrom Bioresources), and a self-packed electrospray emitter as analytical column (100 µm×~60 mm, Kinetex 2.6 µm C18, Phenomenex). The 10-port valve head, the trap cartridge and the analytical column were housed in a separate enclosure constructed from aluminum and maintained at −5° C. by peltier stacks. Valves and columns were configured in such a way as to allow in-line protein digestion, peptide desalting, and reversed-phase chromatography prior to introduction of the sample into the electrospray ionization (ESI) source of the mass spectrometer (LTQ-Orbitrap, Thermo Scientific).

The fluid streams required for operation were provided by two separate HPLC pumps. The first HPLC (Surveyor MS pump, Thermo Scientific) delivered buffer A at a constant flow rate of 125 µL/min and was used to transfer sample through the immobilized pepsin cartridge onto the reversed-phase trap cartridge mounted across the 10-port valve. After the loading and desalting period, the 10-port valve was switched to elute the sample with the help of a gradient pump (AQUITY UPLC, Waters) from the reversed-phase trap cartridge, through the analytical column and into the ion source of the mass spectrometer. The immobilized enzyme cartridge was isolated to waste during gradient elution. The gradient pump delivered linear gradient segments of 0 to 40% mobile phase B over 35 minutes at 5 μL/min and 40 to 95% mobile phase B at 5 μL/min over 10 minutes. The gradient flow from the pump was split at the 10-port valve using a passive splitter so that the actual flow through the trap cartridge and analytical column for gradient elution was ~1 μL/min. The entire chromatographic run was 70 minutes long including washing and equilibration steps.

Mass Spectrometry

For the purpose of identification of proteolytic fragments resulting from online digestion several data-dependent MS/MS experiments were performed. For these acquisitions, tandem MS spectra were acquired with the LTQ analyzer of the LTQ-Orbitrap hybrid mass spectrometer. Precursor mass selection was based on MS scans acquired by the Orbitrap analyzer. Single stage MS acquisitions performed for the purpose of deuteration level determination were acquired at a resolution of 60,000 by the Orbitrap (over m/z 400-2000) analyzer.

Preparation of Protein and Protein: Fab Complexes

HER3 protein was prepared by diluting 50 μg HER3-Tag with 25 mM TBS (pH 7.5)/500 mM NaCl to yield a final volume of 50 μL. Protein:Fab complexes were prepared by mixing 50 μg HER3-Tag in a 1:1 molar ratio with the Fab's studied. Protein:Fab mixtures were then diluted to a final volume of 50 μL with 25 mM TBS (pH 7.5)/500 mM NaCl.

Protein:Fab complexes were prepared and allowed to incubate for at least 2 hours at 4° C. Four 96-well plates containing sample, diluent, quench, and reduction solutions were loaded into the liquid-handler before the start of each experimental. For on-exchange experiments 50 μL of HER3 or HER3:Fab complex was diluted with 150 μL D$_2$O buffer. The mixture was reduced by adding 200 μL reduction buffer for 1 minute before quenching with 600 μL of quench buffer. The total volume after all liquid handling steps was ~1 mL. Once mixed, the quenched solution was injected into the chromatographic system where it was automatically digested, separated and analyzed by LCMS. The average change in deuteration between sample and control was calculated as the difference between the deuterium uptake levels of the sample and control.

Data Processing

The Orbitrap RAW files were converted into mzXML files using an in-house program (RawXtract). Subsequently, tandem MS acquisitions were searched using SEQUEST (Yates Lab, Scripps Research Institute, La Jolla, Calif.) and search results were automatically filtered using DTASelect 2.0 (Yates Lab, Scripps Research Institute, La Jolla, Calif.). Using the peptide sequence identifications, an in-house written program was used to automatically extract single-ion chromatograms for each identified sequence and generate average spectra across the chromatographic peak. Average spectra were smoothed and centroided. The level of deuterium uptake was taken as the difference in mass between a deuterated sample and non-deuterated reference. Processed data was manually validated and adjusted to correct inaccuracies and errors from automated processing steps. Deuterium uptake levels were assigned to each residue of the protein sequence by delocalizing the deuterium content across each peptide (i.e., dividing the observed deuteration level by the number of amino acids in that peptide). If a residue was covered by more than one peptide, the normalized deuterium uptakes of all peptides covering that residue were averaged.

Example 9

X-Ray Crystallographic Structure Determination of the Human HER3/MOR09823 Fab and Human HER3/MOR09825 Fab Complexes The present example presents the crystal structure of full length HER3 bound to the Fab fragment of MOR09823 and the Fab fragment of MOR09825, determined at 3.2 Å and 3.4 Å resolution, respectively. Tagged human HER3 was further purified on a HiLoad 26/60 Superdex 200 PrepGrade column (GE Healthcare) equilibrated in PBS (pH 7.3). E. coli expressed MOR09823 and MOR09825 Fabs were isolated by lysing cells with lysozyme and His$_6$-tagged ("His$_6$" disclosed as SEQ ID NO: 495) Fab fragments were captured on a HisTrap_HP (GE Healthcare) column. MOR09823 Fab-fragments were further purified by gel filtration chromatography using a Superdex 75 16/60 column (GE Healthcare) equilibrated in 25 mM Tris (pH 7.5), 150 mM NaCl.

HER3 Fab complexes were prepared by mixing excess Fab with tagged HER3 in a molar ratios of 1.3-1.8:1 (concentration estimated by absorbance at 280 nm using calculated extinction coefficients of 0.9 and 1.4 (mg/ml)$^{-1}$ cm$^{-1}$ for HER3 and Fab, respectively) and purifying the complexes on a Superdex 200 10/300 column (GE Healthcare) equilibrated in 25 mM Tris (pH 7.5), 150 mM NaCl. Peak fractions were analyzed by SDS-PAGE and LCMS. For each complex, fractions containing both HER3 and Fab in an approximate equimolar ratio were pooled and concentrated. HER3/MOR09823 crystals were grown at 293K by sitting drop vapor diffusion from drops containing 150 nl HER3/MOR09823 complex and 150 nl of reservoir solution (100 mM sodium citrate pH 5.6, 20% PEG 4000 and 20% isopropanol). Crystals were transferred to reservoir solution containing additional 8% glycerol and flash cooled in liquid nitrogen. HER3/MOR09825 crystals were grown at 293K by sitting drop vapor diffusion from drops containing 150 nl HER3/MOR09825 complex and 150 nl of reservoir solution (100 mM bis-tris pH 6.5, 16% PEG 10,000). Crystals were transferred to 100 mM bis-tris pH 6.5, 18% PEG 10,000 and 22% glycerol and flash cooled in liquid nitrogen.

Data were collected at beamline 17-ID at the Advanced Photon Source (Argonne National Laboratory). HER3/MOR09823 Fab complex data were processed and scaled at 3.2 Å using HKL2000 (HKL Research Inc) in space group 1222 with cell dimensions a=124.16, b=19.44, c=180.25 Å, with good statistics. The HER3/MOR09823 Fab structure was solved by molecular replacement using Phaser (McCoy et al., (2007) J. Appl. Cryst. 40:658-674) with fragments of a Fab and the published HER3 ECD structure 1mb6 as search models. The final model, which contains 1 molecule of the HER3/MOR09823 Fab complex per asymmetric unit, was built in COOT (Emsley & Cowtan (2004) Acta Cryst. 60:2126-2132) and refined to R and R$_{free}$ values of 19.0 and 24.5%, respectively, with an rmsd of 0.010 Å and 1.37° for bond lengths and bond angles, respectively, using BUSTER (Global Phasing, LTD). Residues of HER3 that contain atoms within 5 Å of any atom in MOR09823 Fab as identified in PyMOL (Schrödinger, LLC) are listed in Tables 11 and 12. HER3/MOR09825 Fab complex data were processed and scaled at 3.4 Å using autoPROC (Global Phasing, LTD) in space group 1222 with cell dimensions a=124.23, b=140.94, c=180.25 Å, with good statistics. The HER3/MOR09825 Fab structure was solved by molecular replacement using Phaser (McCoy et al., (2007) J. Appl. Cryst. 40:658-674) with the HER3/MOR09823 Fab structure as a search model. The final model, which contains 1 molecule of the HER3/MOR09825 Fab complex per asymmetric unit, was built in COOT (Emsley & Cowtan (2004) Acta Cryst. 60:2126-2132) and refined to R and R$_{free}$ values of 18.8 and 24.9%, respectively, with an rmsd of 0.009 Å and 1.21° for bond lengths and bond angles, respectively, using BUSTER (Global Phasing, LTD). Residues of HER3 that contain atoms within 5 Å of any atom in MOR09825 Fab as identified in PyMOL (Schrödinger, LLC) are listed in Tables 13 and 14.

Example 10

Phospho-HER3 In Vitro Cell Assays

MCF-7 cells were routinely maintained in DMEM/F12, 15 mM HEPES, L-glutamine, 10%
FCS and SK-Br-3 in McCoy's 5a, 10% FCS, 1.5 mM L-glutamine. Sub-confluent MCF7 or SK-Br-3 cells grown in complete media were harvested with accutase (PAA Laboratories) and resuspended in the appropriate growth media at a final concentration of $5 \times 10^5$ cells/mL. 100 µL of cell suspension was then added to each well of a 96-well flat bottomed plate (Nunc) to give a final density of $5 \times 10^4$ cells/well. MCF7 cells were allowed to attach for approximately 3 hours before the media was exchanged for starvation media containing 0.5% FBS. All plates were then incubated overnight at 37° C. prior to treatment with the appropriate concentration of HER3 antibodies (diluted in the appropriate media) for 80 minutes at 37° C. MCF7 cells were treated with 50 ng/mL neuregulin 1-≈1 EGF domain (R&D Systems) for the final 20 minutes to stimulate HER3 phosphorylation. All media was gently aspirated and the cells washed with ice-cold PBS containing 1 mM $CaCl_2$ and 0.5 mM $MgCl_2$ (Gibco). The cells were lysed by adding 50 µL ice-cold lysis buffer (20 mM Tris (pH8.0)/137 mM NaCl/10% Glycerol/2 mM EDTA/1% NP-40/1 mM sodium orthovanadate/, Aprotinin (10 µg/mL)/Leupeptin (10 µg/mL)) and incubated on ice with shaking for 30 minutes. Lysates were then collected and spun at 1800 g for 15 minutes at 4° C. to remove cell debris. 20 µL of lysate was added to a pre-prepared capture plate.

HER3 capture plates were generated using a carbon plate (Mesoscale Discovery) coated overnight at 4° C. with 20 µL of 4 µg/mL MAB3481 capture antibody (R&D Systems) diluted in PBS and subsequently blocked with 3% bovine serum albumin in 1× Tris buffer (Mesoscale Discovery)/0.1% Tween-20. HER3 was captured from the lysate by incubating the plate at room temperature for one hour with shaking before the lysate was aspirated and the wells washed with 1× Tris buffer (Mesoscale Discovery)/0.1% Tween-20. Phosphorylated HER3 was detected using 0.75 µg/mL biotinylated anti-phosphotyrosine antibody (R&D Systems) prepared in 1% BSA/1× Tris/0.1% Tween-20 by incubating with shaking at room temperature for 1 hour. The wells were washed four times with 1× Tris/0.1% Tween-20 and biotinylated proteins were detected by incubating with S-Tag labelled Streptavidin (Mesoscale Discovery) diluted in 1% BSA/1× Tris/0.1% Tween-20 for one hour at room temperature. Each well was aspirated and washed four times with 1× Tris/0.1% Tween-20 before adding 20 µL of Read buffer T with surfactant (Mesoscale Discovery) and the signal quantified using a Mesoscale Sector Imager. Antibodies MOR06391 or MOR03207 were included in signalling experiments as isotype controls.

Example 11

Phospho-Akt (S473) In Vitro Cell Assays

Sub-confluent SK-Br-3 and BT-474 cells grown in complete media were harvested with accutase (PAA Laboratories) and resuspended in the appropriate growth media at a final concentration of $5 \times 10^5$ cells/mL. 100 µL of cell suspension was then added to each well of a 96-well flat bottomed plate (Nunc) to yield a final density of $5 \times 10^4$ cells/well. All plates were then incubated overnight at 37° C. prior to treatment with the appropriate concentration of HER3 antibodies (diluted in the appropriate media) for 80 minutes at 37° C. All media was gently aspirated and the cells washed with ice-cold PBS containing 1 mM $CaCl_2$ and 0.5 mM $MgCl_2$ (Gibco). The cells were lysed by adding 50 µL ice-cold lysis buffer (20 mM Tris (pH8.0)/137 mM NaCl/10% Glycerol/2 mM EDTA/1% NP-40/1 mM sodium orthovanadate/Aprotinin (10 µg/mL)/Leupeptin (10 µg/mL)) and incubated on ice with shaking for 30 minutes. Lysates were then collected and spun at 1800 g for 15 minutes at 4° C. to remove cell debris. 20 µL of lysate was added to a multi-spot 384-well Phospho-Akt carbon plate (Mesoscale Discovery) that had previously been blocked with 3% BSA/1× Tris/0.1% Tween-20. The plate was incubated at room temperature for two hours with shaking before the lysate was aspirated and the wells washed four times with 1× Tris buffer (Mesoscale Discovery)/0.1% Tween-20. Phosphorylated Akt was detected using 20 µL of SULFO-TAG anti-phospho-Akt (S473) antibody (Mesoscale Discovery) diluted 50-fold in 1% BSA/1× Tris/0.1% Tween-20 by incubating with shaking at room temperature for 2 hours. The wells were washed four times with 1× Tris/0.1% Tween-20 before adding 20 µL of Read buffer T with surfactant (Mesoscale Discovery) and the signal quantified using a Mesoscale Sector Imager. Antibodies MOR06391 or MOR03207 were included in signalling experiments as isotype controls.

Example 12

Cell-Line Proliferation Assays

SK-Br-3 cells were routinely cultured in McCoy's 5 Å medium modified, supplemented with 10% fetal bovine serum and BT-474 cells were cultured in DMEM supplemented with 10% FBS. Sub-confluent cells were trypsinized, washed with PBS, diluted to $5 \times 10^4$ cells/mL with growth media and plated in 96-well clear bottom black plates (Costar 3904) at a density of 5000 cells/well. The cells were incubated overnight at 37° C. before adding the appropriate concentration of HER3 antibody (typical final concentrations of 10 or 1 µg/mL). The plates were returned to the incubator for 6 days before assessing cell viability using CellTiter-Glo (Promega). 100 µL of CellTiter-Glo solution was added to each well and incubated at room temperature with gentle shaking for 10 minutes. The amount of luminescence was determined using a SpectraMax plate reader (Molecular Devices). The extent of growth inhibition obtained with each antibody was calculated by comparing the luminscence values obtained with each HER3 antibody to a standard isotype control antibody (MOR06391).

For proliferation assays MCF-7 cells were routinely cultured in DMEM/F12 (1:1) containing 4 mM L-Glutamine/15 mM HEPES/10% FBS. Sub-confluent cells were trypsinized, washed with PBS and diluted to $1 \times 10^5$ cells/mL with DMEM/F12 (1:1) containing 4 mM L-Glutamine/15 mM HEPES/10 µg/mL Human Transferrin/0.2% BSA. Cells were plated in 96-well clear bottom black plates (Costar) at a density of 5000 cells/well. The appropriate concentration of HER3 antibody (typical final concentrations of 10 or 1 µg/mL) was then added. 10 ng/mL of NRG1-β1 EGF domain (R&D Systems) was also added to the appropriate wells to stimulate cell growth. The plates were returned to the incubator for 6 days before assessing cell viability using CellTiter-Glo (Promega). The extent of growth inhibition obtained with each antibody was calculated by subtracting the background (no neuregulin) luminscence values and comparing the resulting values obtained with each anti-HER3 antibody to a standard isotype control antibody (MOR06391).

Example 13

Ligand Blocking Cell Assays

MCF-7 cells cultured in MEM supplemented with 10% FBS and 1 µg/mL insulin (Sigma) were rinsed and collected in a small volume of FACSmax cell dissociation buffer (Genlantis) prior to the addition of 5 mL of FACS buffer (PBS/1% FBS/0.1% sodium azide). The cell density was counted and adjusted to a final concentration of $1\times10^6$ cells/mL. 100 µl of cell suspension was added to each well of a 96-well plate and the cells pelleted via centrifugation (220 g, 3 minutes, 4° C.). Cell pellets were resuspended in 100 µL of the appropriate test antibodies diluted in FACS buffer (typical final antibody concentrations ranged from 100 to 0.1 nM) and the plate incubated on ice for 45 minutes. The ligand blocking antibody MAB3481 (R&D Systems) was included as a positive control. Cells were washed twice with staining buffer prior to adding 10 nM NRG1-β1 EGF domain (R&D Systems) diluted in FACS buffer and incubating on ice for 45 minutes. Cells were washed twice with staining buffer and bound neuregulin detected by incubating the cells with 10 nM anti-human NRG1-β1 EGF domain antibody (R&D Systems) on ice for 45 minutes. Cells were washed twice with staining buffer and incubated on ice for 45 minutes with PE-linked anti-goat antibody (Jackson ImmunoResearch) diluted 1/500 with FACS buffer. Cells were then pelleted via centrifugation and the pellet resuspended in 200 µL FACS buffer. To quantify each sample 10,000 live cells were counted on a LSR II Flow Cytometer (BD Biosciences) and the amount of cell surface bound neuregulin was assessed by measuring the mean channel fluorescence.

Example 14

Ligand Blocking Biochemical Assay

The present method includes utility of a Surface plasmon resonance (SPR)-based biosensor (Biacore™, GE Healthcare, Uppsala, Sweden) to examine the ability of HER3/antibody complexes to bind neuregulin.

Biacore™ utilizes the phenomenon of surface plasmon resonance (SPR) to detect and measure binding interactions. In a typical Biacore experiment, one of the interacting molecules (neuregulin) is immobilized on a matrix while the interacting partner (HER3) is flowed over the surface. A binding interaction results in an increase in mass on the sensor surface and a corresponding direct change in the refractive index of the medium in the vicinity of the sensor surface. Changes in refractive index or signal are recorded in resonance units (R.U.) Signal changes due to association and dissociation of complexes are monitored in a non-invasive manner, continuously and in real-time, the results of which are reported in the form of a sensorgram.

Biacore™ T100 (GE Healthcare, Uppsala, Sweden) was used to conduct all experiments reported herein. Sensor surface preparation and interaction analyses were performed at 25° C. Buffer and Biacore reagents were purchased from GE Healthcare. Running buffer containing 10 mM Hepes, pH7.4/150 mM NaCl, 0.05% P20, 0.5% BSA was utilized throughout the assay.

NRG-1β1 extracellular domain (R&D Systems) was incubated on ice for 45 minutes with EZ-link Sulfo-NHS-LC-LC-Biotin (Pierce) at a molar ratio of 5:1. The reaction was quenched via the addition excess ethanolamine and uncoupled biotin removed from the biotinylated-NRG using desalt spin columns (Zeba). Biotinylated-NRG was captured onto a sensor chip CAP pre-immobilized with approximately 3000 R.U. of ssDNA-streptavidin (Biotin CAPture kit) to yield neuregulin surface densities in the range 400-600 R.U. A reference flowcell was generated by omitting biotinylated-NRG from the injection steps such that only ssDNA-streptavidin was present on the flowcell surface.

HER3/antibody complexes were generated by incubating 10 nM human HER3-Fc with increasing concentrations (0-50 nM) of the appropriate test antibody for 15 minutes at room temperature prior to incubating in the Biacore™ at 10° C. Interaction analyses were performed by injecting HER3/antibody complexes over reference and neuregulin surfaces in series for 180 seconds at a flow-rate of 60 µL/min. Complex dissociation was monitored for 180 seconds at a flow rate of 60 µL/min. Surface regeneration was performed at the end of each analysis cycle using a 120 second injection of 8M guanidine: 1M NaOH (3:1) followed by a 120 second injection of 30% acetonitrile/0.25M NaOH at a flow rate of 30 µL/min.

Example 15

In Vivo PD Studies

BxPC3 and BT-474 cells were cultured and implanted in female athymic nu/nu Balb/C mice (Harlan Laboratories) as described in Examples 16 and 17.

Once tumors had reached an appropriate size, animals were examined for tumor quality. Animals with ulcerated tumors or animal with fluid-filled tumors were excluded from the study. The remaining animals were dosed intravenously with antibody via lateral tail vein injection. At the given time points, animals were euthanized via $CO_2$ asphyxiation and whole blood was collected via cardiac puncture and placed into a 1.5 mL Eppendorf collection tube. Tumor tissue was immediately dissected, placed into a screw-top polypropylene sample tube and snap frozen in liquid nitrogen. Tissue was stored at −80° C. until lysates were prepared.

Example 16

In Vivo BT-474 Efficacy Studies

BT-474 cells were cultured in DMEM containing 10% heat-inactivated fetal bovine serum without antibiotics until the time of implantation.

One day before cell inoculation, female athymic nu/nu Balb/C mice (Harlan Laboratories) were implanted subcutaneously with a sustained release 17β-estradiol pellet (Innovative Research of America) to maintain serum estrogen levels. One day after 17β-estradiol pellet implantation, $5\times10^6$ cells were injected orthotopically into the $4^{th}$ mammary fat-pad in a suspension containing 50% phenol red-free matrigel (BD Biosciences) in Hank's balanced salt solution. The total injection volume containing cells in suspension was 200 µL. 20 days following cell implantation animals with a tumor volume of approximately 200 $mm^3$ were enrolled in the efficacy study. In general, a total of 10 animals per group were enrolled in efficacy studies.

For single-agent studies, animals were dosed intravenously via lateral tail vein injection with either MOR10701 or MOR10703. An initial loading dose of 40 mg/kg was given for the first dose. After the initial dose, animals were on a 20 mg/kg, every other day schedule for the duration of the study. For combination studies, animals were dosed with either MOR10701 or MOR10703 (20 mg/kg, iv, q2d) and a suboptimal dose of trastuzumab (1 mg/kg, iv, 2qw).

For the duration of the studies, tumor volume was measured by calipering twice per week. Percent treatment/control (T/C) values were calculated using the following formula:

% $T/C = 100 \times \Delta T/\Delta C$ if $\Delta T > 0$ where:

T=mean tumor volume of the drug-treated group on the final day of the study;

$\Delta T$=mean tumor volume of the drug-treated group on the final day of the study—mean tumor volume of the drug-treated group on initial day of dosing;

C=mean tumor volume of the control group on the final day of the study; and $\Delta C$=mean tumor volume of the control group on the final day of the study—mean tumor volume of the control group on initial day of dosing.

Body weight was measured twice per week and dose was body weight adjusted. The % change in body weight was calculated as $(BW_{current} - BW_{initial})/(BW_{initial}) \times 100$. Data is presented as percent body weight change from the day of treatment initiation.

All data were expressed as mean±standard error of the mean (SEM). Delta tumor volume and body weight were used for statistical analysis. Between groups comparisons were carried out using a one-way ANOVA followed by a post hoc Tukey. For all statistical evaluations the level of significance was set at p<0.05. Significance compared to the vehicle control group is reported.

Example 17

In Vivo BxPC3 Efficacy Studies

BxPC3 cells were cultured in RPMI-1640 medium containing 10% heat-inactivated fetal bovine serum without antibiotics until the time of implantation.

Female athymic nu/nu Balb/C mice (Harlan Laboratories) were implanted subcutaneously with $10 \times 10^6$ cells in a mixture of 50% phosphate buffered saline with 50% matrigel. The total injection volume containing cells in suspension was 200 μL. Once tumors had reached approximately 200 mm³ in size, animals were enrolled in the efficacy study. In general, a total of 10 animals per group were enrolled in studies. Animals were excluded from enrollment if they exhibited unusual tumor growth characteristics prior to enrollment.

Animals were dosed intravenously via lateral tail vein injection. An initial loading dose of 40 mg/kg was given for the first dose. After the initial dose, animals were on a 20 mg/kg, every other day schedule for the duration of the study (25 days under treatment). Tumor volume and T/C values were calculated as previously detailed.

Example 18

Phospho-Akt (S473) In Vivo PD Assays

Approximately 50 mm³ frozen tumor (e.g. BT-474 or BXPC-3) tissue was thawed on ice and 100-300 μL of T-PER buffer (Pierce) containing phosphatase (Roche) and protease inhibitors (Roche) was added to each sample. The volume of lysis buffer added was dependent upon the size of the tumor sample. The tissue was broken down using a 1.5 mL pestle (Fisher Scientific) and the resultant suspensions were incubated on ice for 15 minutes before being frozen overnight at −80° C. Samples were thawed and spun for 15 minutes at 13000 g, 4° C. prior to quantifying the supernatant protein concentration by BCA assay (Thermo Scientific). Tissue supernatants were diluted with lysis buffer (Mesoscale Discovery) and 25 μg added to a multi-spot 96-well Phospho-Akt carbon plate (Mesoscale Discovery) that had previously been blocked with Blocking Solution-A (Mesoscale Discovery). The plate was incubated at room temperature for one hour with shaking before the lysate was aspirated and the wells washed four times with Tris Wash buffer (Mesoscale Discovery). Phosphorylated Akt was detected using 25 μL of SULFO-TAG anti-phospho-Akt (S473) antibody (Mesoscale Discovery) diluted in antibody dilution buffer by incubating with shaking at room temperature for one hour. The wells were washed four times with Tris Wash buffer before adding 150 μL of Read buffer T (with surfactant) (Mesoscale Discovery) and the signal quantified using a Mesoscale Sector Imager.

Example 19

Phospho HER3 (Y1197) In Vivo PD Assays

Approximately 50 mm³ frozen tumor (e.g. BXPC-3) tissue was thawed on ice and 100-300 μL of T-PER buffer (Pierce) containing phosphatase (Roche) and protease inhibitors (Roche) was added to each sample. The tissue was broken down using a 1.5 mL pestle (Fisher Scientific) and the resultant suspensions were incubated on ice for 15 minutes before being frozen overnight at −80° C. Samples were thawed and spun for 15 minutes at 13000 g, 4° C. prior to quantifying the supernatant protein concentration by BCA assay (Thermo Scientific). Tissue supernatants were diluted with lysis buffer and 150 μg added to a multi-spot 96-well carbon plate (Mesoscale Discovery) that had previously been coated overnight with 4 μg/mL MAB3481 (R&D Systems) and blocked with 3% milk. The plate was incubated at room temperature for two hours with shaking before the lysate was aspirated and the wells washed four times with Tris Wash buffer (Mesoscale Discovery). Phosphorylated HER3 was bound using anti-HER3 pY1197 diluted 1/8000 with blocking buffer. Following incubation at room temperature for one hour the wells were washed with Tris Wash buffer and the anti-pY1197 antibody detected using S-Tag labelled anti-rabbit antibody (Mesoscale Discovery) diluted 1/1000 in blocking buffer by incubating with shaking at room temperature for one hour. The wells were washed four times with Tris Wash buffer before adding 150 μl of ¼ diluted Read buffer T (with surfactant) (Mesoscale Discovery) and the signal quantified using a Mesoscale Sector Imager.

Example 20

In Vitro Drug Combination Studies

To assess the ability of HER3-targeted antibodies to combine with targeted therapies MOR09825 or MOR10703 were combined with trastuzumab, lapatinib, BEZ235, BKM120, BYL719, RAD001, erlotinib and cetuximab in cell viability assays. Approximately 1000-1500 SK-Br-3 (McCoy's), MDA-MB-453 (RPMI), FaDu (EMEM) or L3.3 (RPMI) cells were seeded into 384-well plates in the appropriate culture media supplemented with 2% FBS and allowed to adhere overnight at 37° C. The appropriate drug combinations (typical final drug concentrations for lapatinib, BKM120, and BYL719 ranged from 3 μM to 13 nM; for RAD001 ranged from 27 nM to 0.0041 nM; for erlotinib ranged from 1 μM to 0.0025 nM; for MOR1073 ranged from 100 nm to 0.01 nm;

for cetuximab ranged from 100 nM to 0.0015 nM; and for trastuzumab ranged from 300 nM to 0.046 nM)) were subsequently added to the wells such that each plate contained a dose response curve of each drug in a two-dimensional matrix. The plates were returned to the incubator for 3-6 days before assessing cell viability using CellTiter-Glo (Promega). CellTiter-Glo solution was added to each well and incubated at room temperature with gentle shaking for 10 minutes. The amount of luminescence was determined using a SpectraMax plate reader (Molecular Devices). The extent of growth inhibition obtained with each combination was calculated and combination activity highlighted using the Loewe additivity model.

Example 21

In Vivo Drug Combination Studies in L3.3 Cells

Pancreatic L3.3 cells were cultured in DMEM medium containing 10% heat-inactivated fetal bovine serum until the time of implantation. Female Foxn1 nude mice (Harlan Laboratories) were implanted subcutaneously with $3 \times 10^6$ cells in FBS free DMEM. The total injection volume containing cells in suspension was 100 µL. 12 days following cell implantation, animals were enrolled in the efficacy study with a mean tumor volume of approximately 100 mm$^3$ for all groups. In general, a total of 8 animals per group were enrolled in studies. Animals were excluded from enrollment if they exhibited unusual tumor growth characteristics prior to enrollment.

Animals were dosed intravenously with MOR10703 via lateral tail vein injection on a 20 mg/kg, every other day schedule for the duration of the study (14 days under treatment). Erlotinib was dosed at 50 mg/kg (PO) on a daily schedule either as a single-agent or in combination with MOR10703. Tumor volume and T/C values were calculated as previously detailed.

Results and Discussion

Collectively, these results show that a class of antibodies bind to amino acid residues within domain 2 and domain 4 of a conformational epitope of HER3 and stabilizes HER3 in an inactive or closed conformation. Binding of these antibodies inhibits both ligand-dependent and ligand-independent signaling. These antibodies are also able to bind concurrently with a HER3 ligand.

(i) Affinity Determination

Antibody affinity was determined by solution equilibrium titration (SET) as described above. The results are summarized in Table 9 and example titration curves for MOR10701 are contained in FIG. 1. The data indicate that a number of antibodies were identified that tightly bound human, cyno, rat and murine HER3.

TABLE 9

$K_D$ values of anti-HER3 IgGs as determined by solution equilibrium titration (SET). Hu (human), Cy (cynomolgus), Mu (murine) and ra (rat)

| MOR# | SET $K_D$ (pM) | | | |
|---|---|---|---|---|
| | hu HER3-Tag | cy HER3-Tag | mu HER3-Tag | ra HER3-Tag |
| 09823 | 9 | 4 | 2 | 11 |
| 09824 | 3 | 3 | 2 | 7 |
| 09825 | 25 | 56 | 24 | 96 |
| 09974 | 350 | 200 | 120 | n.d |
| 10701 | 4 | 4 | 6 | 10 |
| 10702 | 3 | 3 | 5 | 6 |

TABLE 9-continued $K_D$ values of anti-HER3 IgGs as determined by solution equilibrium titration (SET). Hu (human), Cy (cynomolgus), Mu (murine) and ra (rat)

| MOR# | SET $K_D$ (pM) | | | |
|---|---|---|---|---|
| | hu HER3-Tag | cy HER3-Tag | mu HER3-Tag | ra HER3-Tag |
| 10703 | 26 | 23 | 20 | 40 |
| 12609 | 10 | n.d | n.d | n.d |
| 12610 | 37 | n.d | n.d | n.d |
| 10703 N52S | 57 | n.d | n.d | n.d |
| 10703 N52G | 60 | n.d | n.d | n.d |
| 10703_A50V_N52S | 16 | n.d | n.d | n.d |
| 10703_A50V_N52G | 22 | n.d | n.d | n.d |
| 10701 R55G | 18 | n.d | n.d | n.d |
| 10701 R55K | 11 | n.d | n.d | n.d |

(ii) SK-Br-3 Cell $EC_{50}$ Determination

Figure 2:
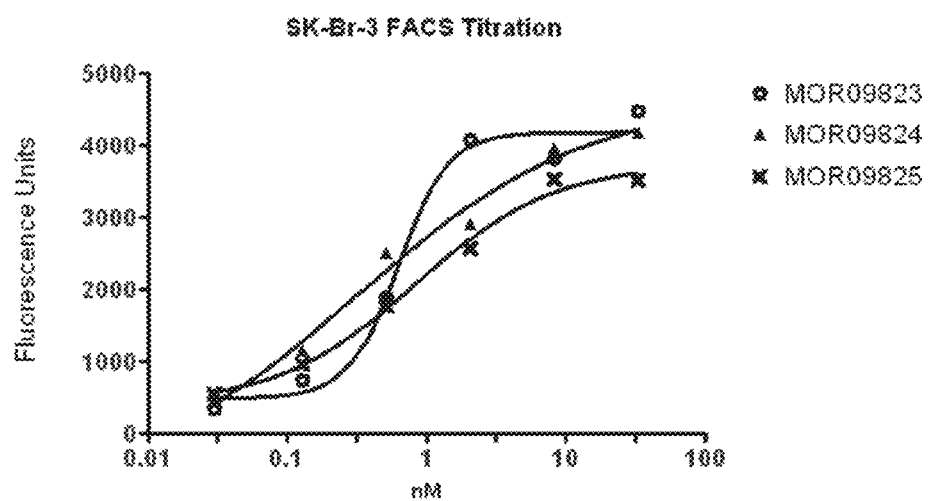
FIG. 2: SK-Br-3 cell binding determination by FACS titration

The ability of the identified antibodies to bind HER3 expressing cells was determined by calculating $EC_{50}$ values for their binding to the HER2 amplified cell line SK-Br-3 (see FIG. 2 and Table 10).

TABLE 10

FACS $EC_{50}$ values of anti-HER3 IgG on SK-Br-3 cells.

| MOR# | SK-Br-3 FACS $EC_{50}$ (pM) |
|---|---|
| 09823 | 630 |
| 09824 | 324 |
| 09825 | 839 |
| 09974 | n.d. |
| 10701 | n.d. |
| 10702 | n.d. |
| 10703 | 2454 | n.d. (not determined)

(iii) HER3 Domain Binding

A subset of anti-HER3 antibodies were characterized for their ability to bind the various extracellular domains of human HER3 in an ELISA assay. To achieve this, the extracellular domain of HER3 was divided into its four constitutive domains and various combinations of these domains were cloned, expressed and purified as independent proteins as described above. Using this strategy the following domains were successfully generated as soluble proteins: domains 1 and 2 (D1-2), domain 2 (D2), domains 3 and 4 (D3-4) and domain 4 (D4). A number of internally generated mouse anti-human HER3 antibodies (8D7, 1F5 and 8P2) were also tested as positive controls to demonstrate the integrity of each isolated domain.

Figure 3:
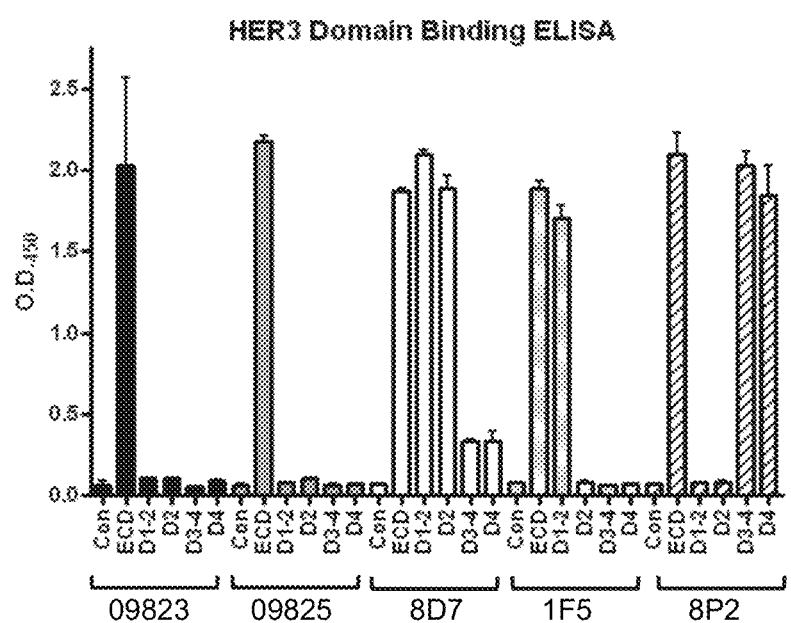
FIG. 3: HER3 domain binding ELISA

As shown in FIG. 3 MOR09823 and MOR09825 were both observed to successfully bind the HER3 extracellular domain, but little binding to the isolated domains was observed in this assay with these antibodies. There are several possible explanations for this binding pattern:

a) MOR09823 and MOR09825 may bind a linear epitope that spans a domain boundary thus part of the binding epitope would be lost when the domains were expressed as isolated proteins.

b) MOR09823 and MOR09825 may bind a non-linear epitope that bridges multiple domains. Consequently, separation of HER3 into its component units may destroy the binding site.

c) The shape/conformation of HER3 may be a component of the binding of MOR09823 and MOR09825 to HER3 such that only the full-length extracellular domain of HER3 is capable of adopting this shape/conformation whilst the isolated domains cannot fully assume this conformation.

(vi) HER3 Epitope Mapping Using Hydrogen/Deuterium Exchange Mass Spectrometry

Figure 4B:
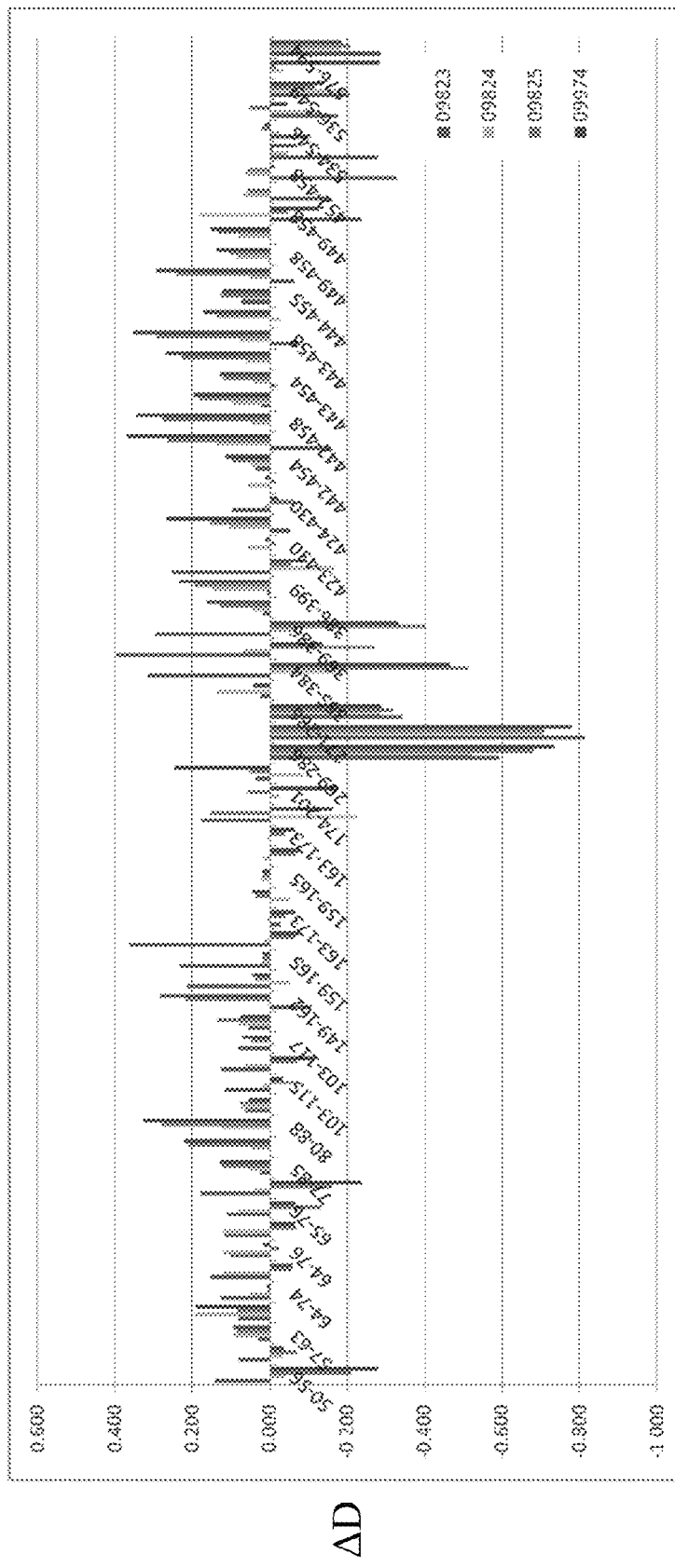
FIG. 4: Hydrogen deuterium exchange epitope mapping. A) HER3 ECD peptides recovered following HDX-MS analysis are indicated by dashed lines. Potential N-linked glycosylation sites are highlighted.
FIG. 4A discloses SEQ ID NO: 497. B) The relative degree of deuteration observed in peptides identified by MS. C) Protected residues mapped onto the published HER3 crystal structure.
Figure 4C:
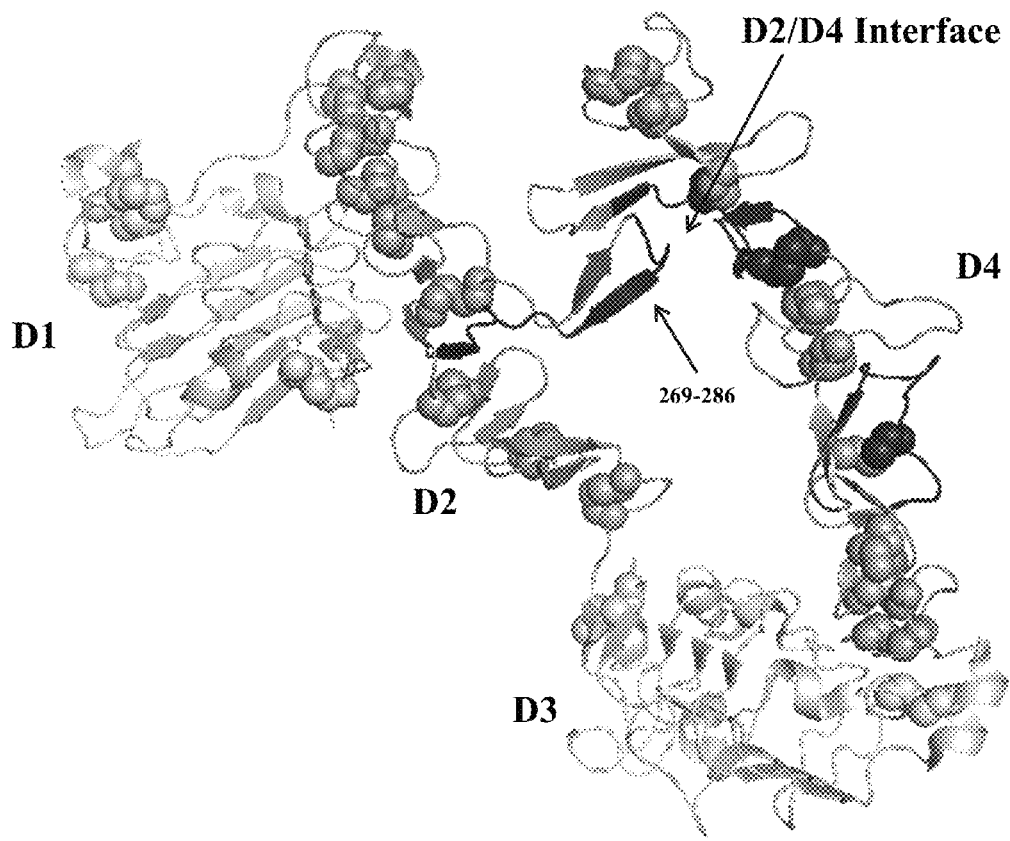

The HER3 epitope was further explored by HDX-MS analysis of HER3 ECD in the presence and absence of Fab versions of MOR09823, MOR09824, MOR09825 and MOR09974. FIG. 4A shows that in the absence of bound Fab, approximately 69% of the HER3 ECD sequence was covered by at least one peptide. Gaps in coverage may be due to glycosylation of residues within these regions or insufficient reduction of disulphide bonds in cysteine rich regions, which is particularly apparent in domain 2. Interestingly, although each Fab yielded individual protection patterns, one region of strong protection was consistently observed with MOR09823, MOR09824, MOR09825 and MOR09974 (see FIG. 4B) indicating that these highly related family of antibodies bind HER3 in an identical manner. The strongest protection was observed for domain 2 residues 269-286 (TFQLEPNPHTKYQYGGVC) (SEQ ID NO: 496) indicating that residues in this vicinity may be important for mAb binding. Mapping of the Fab protected residues onto the published HER3 crystal structure (Cho & Leahy, (2002) Science 297:1330-1333) highlights that residues 269-286 are within and proximal to a functionally important β-hairpin loop within domain 2 (see FIG. 4C).

(vii) HER3/MOR09823 Crystal Structure

Figure 5A:
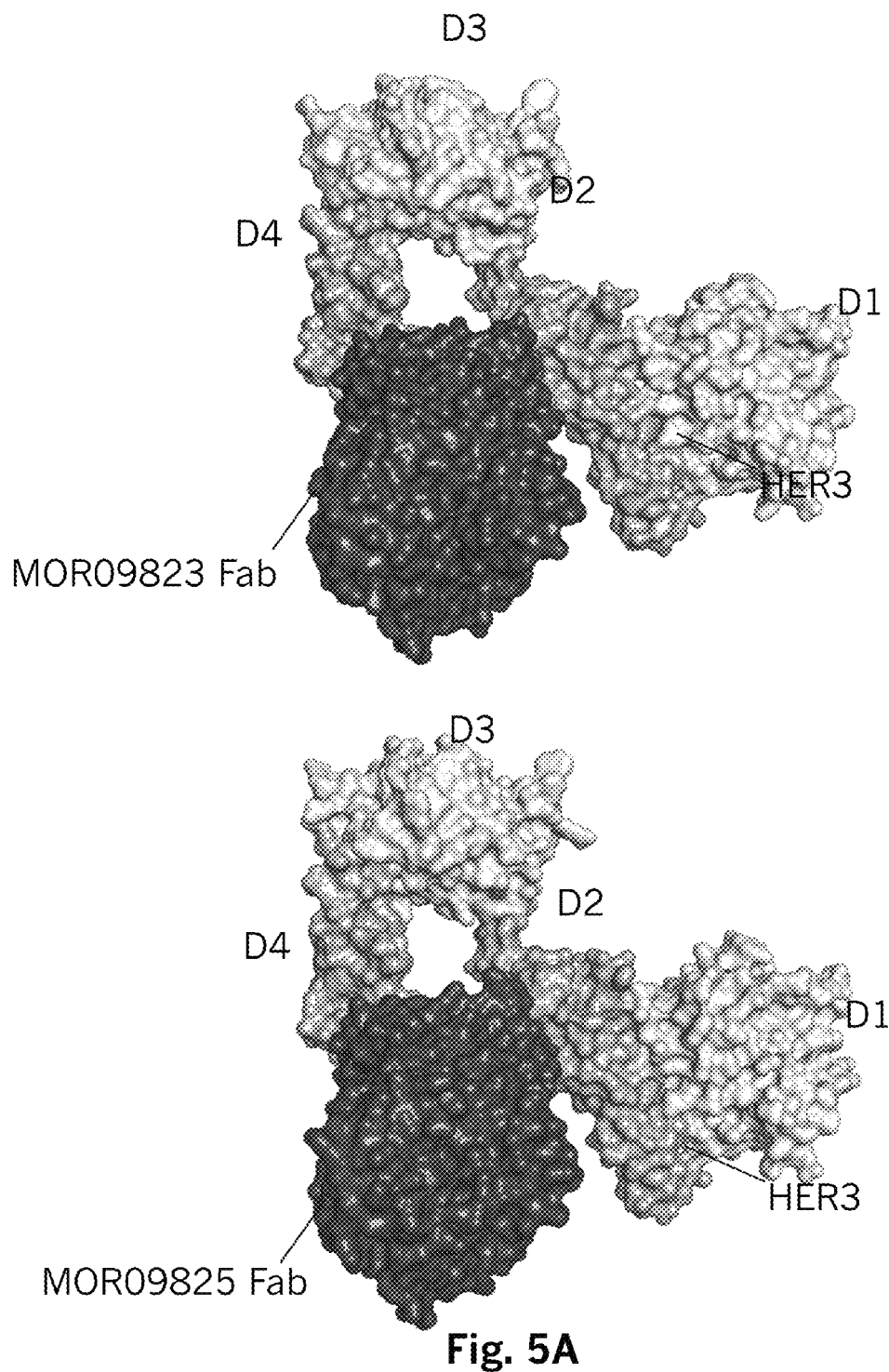
FIG. 5: A) Surface representation of the HER3/MOR09823 and HER3/MOR09825 x-ray crystal structures. HER3 (in lighter gray) is in the closed conformation, and MOR09823 or MOR09825 (in darkest gray) bind to both domains 2 and 4. B). Surface view of HER3 from the HER3/MOR09823 structure shown in a similar orientation as (A). MOR09823 was omitted for clarity. C) HER3/MOR09823 structure illustrated as a ribbon structure, viewed at a 90° rotation from panels (A), (B) and (D). D) A ribbon representation of the inactive HER3 conformation recognized by MOR09823 Fab with a close up view of the domain 2/domain 4 interface, highlighting the HER3 residues (all positions disclosed in FIG. 5C are residues of SEQ ID NO: 1) that are within 5 Å of the Fab. E) Mutant HER3/MOR10703 binding determination by ELISA titration.
Figure 5B:
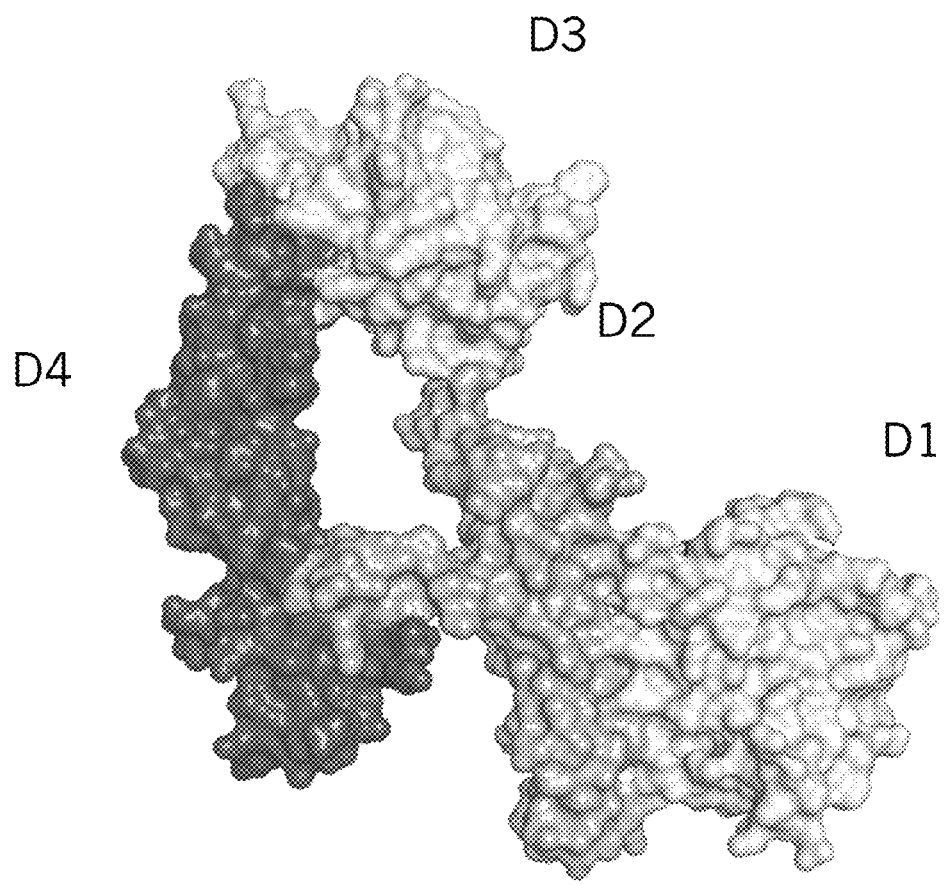

The 3.2 Å resolution x-ray crystal structure of MOR09823 Fab fragment bound to the HER3 extracellular domain was solved to further define the HER3 epitope that is recognized by this family of related antibodies (see FIG. 5A). In addition, the 3.4 Å structure of MOR09825 Fab fragment bound to human HER3 was resolved. In both the MOR09823/HER3 and MOR09825/HER3 crystal structures, HER3 is in the tethered (inactive) conformation (see FIGS. 5A, B, C and D). This conformation is characterized by a significant interaction interface between domains 2 and 4 mediated by a β-hairpin dimerization loop in domain 2. The observed conformation of HER3 is similar to that previously described by Cho et al. (Cho & Leahy, (2002), Science 297:1330-1333) who published the crystal structure of the HER3 extra-cellular domain in the absence of neuregulin. Since neuregulin can activate HER3, the tethered conformation of HER3 is presumed to be inactive. Similar tethered conformations have also been observed when the related EGFR family members HER4 (Bouyain et al., (2005) Proc. Natl. Acad. Sci. USA, 102: 15024-15029) and HER1 (Ferguson et al., (2003) Molec. Cell 11:507-517) have been crystallized.

The spatial relationships between domains 1 to 4 of HER3 in the inactive (tethered) state are significantly different from that of the extended (active) state. This finding is based upon the crystal structures of the related EGFR family members HER2 and ligand-bound HER1 (Cho et al., (2003) Nature 421:756-760; Ogiso et al., (2002) Cell 110:775-787; Garrett et al., (2002) Cell 110:763-773) both of which are in an extended (active) state. In the extended state, the domain 2 β-hairpin dimerization loop is released from its inhibitory interaction with 4 and is thus free to interact with its dimerization partner proteins. Thus, the domain 2 β-hairpin dimerization loop is functionally important both in maintaining the tethered (inactive) state and in mediating dimerization of EGF receptors in the extended state, leading to activation of the intracellular kinase domain. The MOR09823/HER3 and MOR09825/HER3 crystal structures (see FIG. 5) therefore suggest that both MOR09823 and MOR09825 function by stabilizing the inactive conformation of HER3.

Figure 5C:
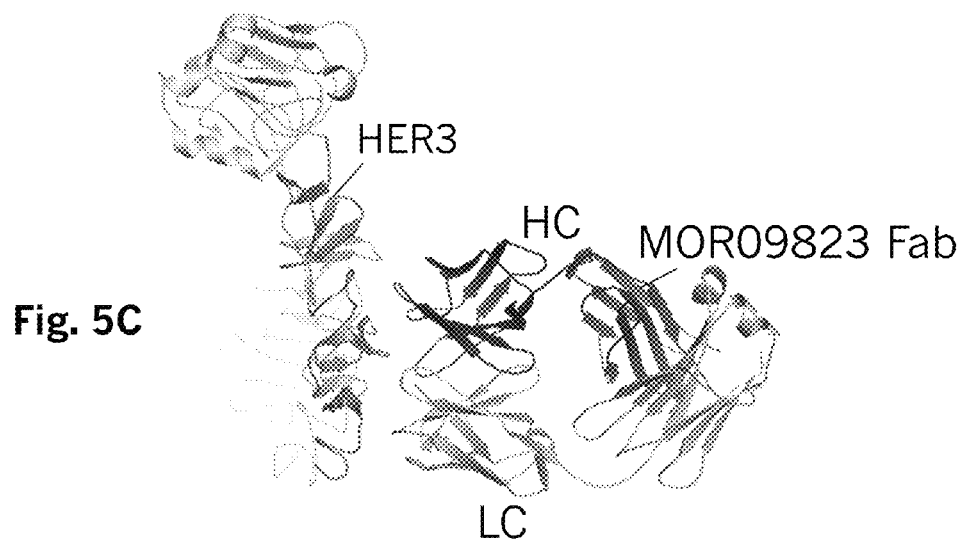
Figure 5D:
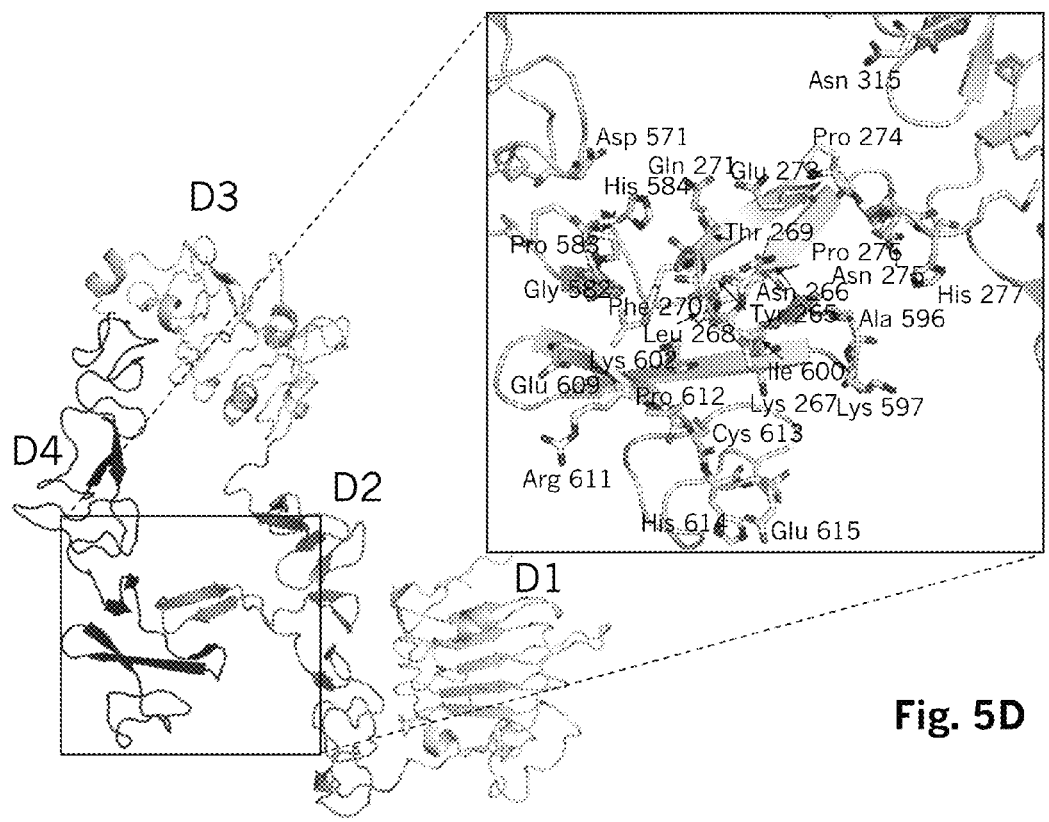
Figure 5E:
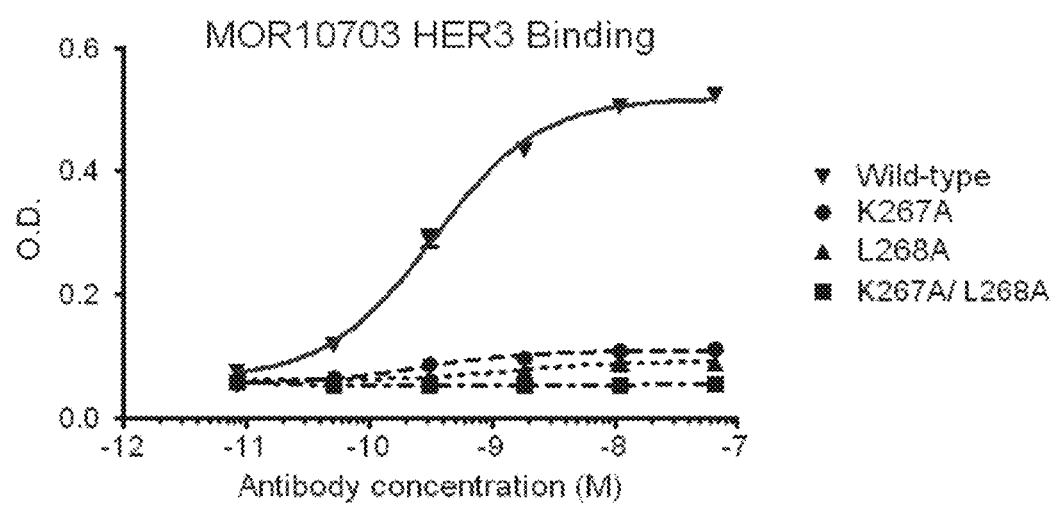

The crystal structure also revealed that the HER3 epitope recognized by both MOR09823 and MOR09825 is a non-linear epitope that includes residues from both domains 2 and 4 (see FIGS. 5C and D, Tables 11, 12, 13 and 14). The HER3 epitope recognized by this family of highly related antibodies can therefore be defined as:

Domain 2: residues 265-277, 315
Domain 4 residues: 571, 582-584, 596-597, 600-602, 609-615

Binding of both domains 2 and 4 by MOR09823 or MOR09825 would consequently stabilize the tethered conformation of HER3 thus antagonizing its ability to signal.

Figure 9:
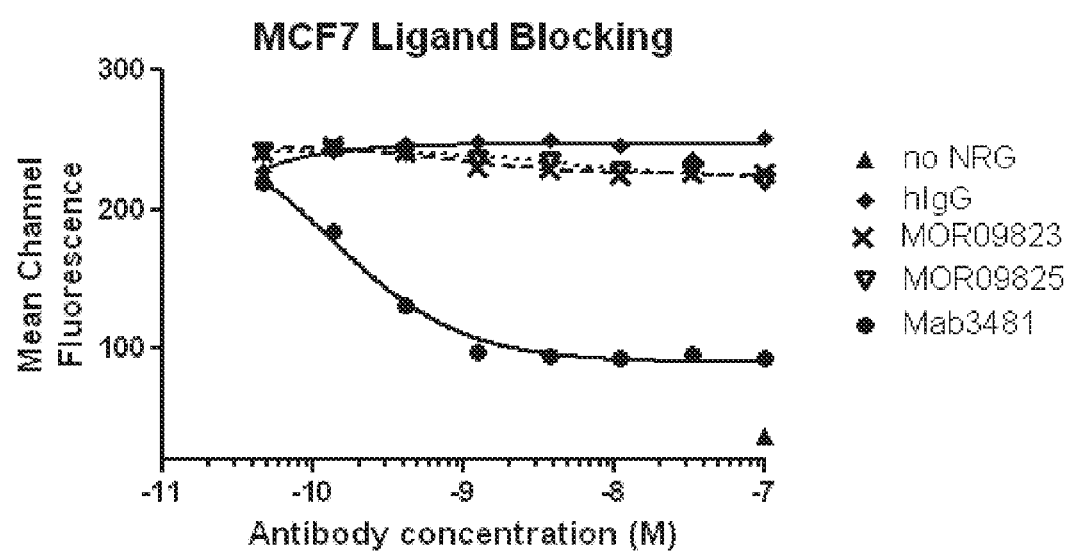
FIG. 9: The effect of MOR09823 and MOR09825 upon neuregulin binding to MCF7 cells.

The MOR09823/MOR09825 binding mode observed in the crystal structure is consistent with our other epitope mapping studies. Specifically, the ELISA domain binding experiments demonstrate that the affinity of MOR09823 and MOR09825 are significantly greater for the intact HER3 extracellular protein than for any isolated domains (e.g. D1, D1-D2, D3, or D3-D4 fragments) (see FIG. 3). There is also agreement with the HER3 HDX-MS data (see FIG. 4B), which identifies domain 2 β-hairpin as part of the antibody recognition epitope. Finally, both crystal structures indicate that the ligand-binding surface of HER3, which has been mapped by analogy to HER1 to domains 1 and 3 (Ogiso et al., (2002) Cell, 110:775-787; Garrett et al., (2002) Cell, 110: 763-773) is not occluded by either MOR09823 or MOR09825 binding (see FIG. 5B). This is consistent with our findings that neither MOR09823 nor MOR09825 block neuregulin binding to MCF7 cells (see FIG. 9) and that HER3/MOR09823 complexes can bind to immobilized neuregulin in biacore studies (see FIG. 10).

TABLE 11

Interactions between MOR09823 Fab heavy chain and human HER3. Fab VH residues are numbered based upon their linear amino acid sequence (SEQ ID NO: 15). HER3 residues are numbered based upon NP_001973. HER3 residues shown have at least one atom within 5 Å of an atom in the MOR09823 Fab.

| MOR09823 Fab | | | Human HER3 | | |
|---|---|---|---|---|---|
| Residue | Number | Chain | Residue | Number | Domain |
| Ser | 30 | VH | Pro | 276 | 2 |
| Ser | 31 | VH | Pro | 274 | 2 |
|  |  |  | Asn | 275 | 2 |
|  |  |  | Pro | 276 | 2 |
| Tyr | 32 | VH | Pro | 276 | 2 |
|  |  |  | His | 277 | 2 |
| Ala | 33 | VH | Asn | 266 | 2 |
|  |  |  | Leu | 268 | 2 |
| Ser | 35 | VH | Leu | 268 | 2 |
| Val | 50 | VH | Leu | 268 | 2 |
|  |  |  | Thr | 269 | 2 |
| Gly | 52 | VH | Glu | 273 | 2 |
|  |  |  | Thr | 269 | 2 |
| Ala | 53 | VH | Glu | 273 | 2 |
|  |  |  | Pro | 274 | 2 |
| Val | 54 | VH | Glu | 273 | 2 |
| Tyr | 58 | VH | Pro | 583 | 4 |
|  |  |  | Asp | 571 | 4 |
|  |  |  | His | 584 | 4 |
|  |  |  | Thr | 269 | 2 |
|  |  |  | Gln | 271 | 2 |
| Asn | 73 | VH | Asn | 315 | 2 |
| Ser | 74 | VH | Asn | 315 | 2 |
| Trp | 98 | VH | Leu | 268 | 2 |
|  |  |  | Lys | 267 | 2 |
|  |  |  | Asn | 266 | 2 |
| Asp | 100 | VH | Ala | 596 | 4 |
|  |  |  | Lys | 597 | 4 |
|  |  |  | Pro | 276 | 2 |
|  |  |  | His | 277 | 2 |
| Glu | 101 | VH | Lys | 267 | 2 |
|  |  |  | Lys | 597 | 4 |
| Phe | 103 | VH | Leu | 268 | 2 |

TABLE 12

Interactions between MOR09823 Fab light chain and human HER3. Fab VL residues are numbered based upon their linear amino acid sequence (SEQ ID NO: 14). HER3 residues are numbered based upon NP_001973. HER3 residues shown have at least one atom within 5 Å of an atom in the MOR09823 Fab.

| MOR09823 Fab | | | Human HER3 | | |
|---|---|---|---|---|---|
| Residue | Number | Chain | Residue | Number | Domain |
| Gln | 27 | VL | Arg | 611 | 4 |
| | | | Glu | 609 | 4 |
| Gly | 28 | VL | Arg | 611 | 4 |
| | | | Pro | 612 | 4 |
| Ile | 29 | VL | Pro | 612 | 4 |
| Ser | 30 | VL | Pro | 612 | 4 |
| | | | Cys | 613 | 4 |
| | | | His | 614 | 4 |
| | | | Glu | 615 | 4 |
| Asn | 31 | VL | Glu | 615 | 4 |
| | | | Cys | 613 | 4 |
| Trp | 32 | VL | Lys | 267 | 2 |
| | | | Tyr | 265 | 2 |
| | | | Pro | 612 | 4 |
| | | | Cys | 613 | 4 |
| | | | Ile | 600 | 4 |
| | | | Lys | 602 | 4 |
| Tyr | 49 | VL | Lys | 597 | 4 |
| Gly | 66 | VL | Glu | 615 | 4 |
| Ser | 67 | VL | His | 614 | 4 |
| | | | Glu | 615 | 4 |
| Gln | 89 | VL | Leu | 268 | 2 |
| Tyr | 91 | VL | Lys | 267 | 2 |
| | | | Leu | 268 | 2 |
| | | | Phe | 270 | 2 |
| Ser | 92 | VL | Phe | 270 | 2 |
| | | | Lys | 602 | 4 |
| | | | Pro | 612 | 4 |
| Ser | 93 | VL | Phe | 270 | 2 |
| | | | Glu | 609 | 4 |
| Phe | 94 | VL | Phe | 270 | 2 |
| | | | Leu | 268 | 2 |
| | | | Gly | 582 | 4 |
| | | | Pro | 583 | 4 |
| Thr | 96 | VL | Leu | 268 | 2 |

TABLE 13

Interactions between MOR09825 Fab heavy chain and human HER3. Fab VH residues are numbered based upon their linear amino acid sequence (SEQ ID NO: 51). HER3 residues are numbered based upon NP_001973. HER3 residues shown have at least one atom within 5 Å of an atom in the MOR09825 Fab.

| MOR09825 Fab | | | Human HER3 | | |
|---|---|---|---|---|---|
| Residue | Number | Chain | Residue | Number | Domain |
| Ser | 30 | VH | Asn | 315 | 2 |
| Ser | 31 | VH | Pro | 274 | 2 |
| | | | Pro | 276 | 2 |
| Tyr | 32 | VH | Pro | 276 | 2 |
| | | | His | 277 | 2 |
| Ala | 33 | VH | Asn | 266 | 2 |
| | | | Thr | 269 | 2 |
| Ser | 35 | VH | Leu | 268 | 2 |
| Trp | 47 | VH | Leu | 268 | 2 |
| Ala | 50 | VH | Leu | 268 | 2 |
| Asn | 52 | VH | Glu | 273 | 2 |
| | | | Gln | 271 | 2 |
| | | | Thr | 269 | 2 |
| Ser | 53 | VH | Glu | 273 | 2 |
| | | | Pro | 274 | 2 |
| Gln | 54 | VH | Glu | 273 | 2 |
| | | | Pro | 274 | 2 |
| Ser | 57 | VH | Gln | 271 | 2 |
| Tyr | 59 | VH | Pro | 583 | 4 |
| | | | Asp | 571 | 4 |
| | | | His | 584 | 4 |
| | | | Thr | 269 | 2 |
| | | | Gln | 271 | 2 |
| Asn | 74 | VH | Asn | 315 | 2 |
| Trp | 99 | VH | Leu | 268 | 2 |
| | | | Lys | 267 | 2 |
| | | | Asn | 266 | 2 |
| Asp | 101 | VH | Ala | 596 | 4 |
| | | | Lys | 597 | 4 |
| | | | Pro | 276 | 2 |
| | | | His | 277 | 2 |
| Glu | 102 | VH | Lys | 267 | 2 |
| | | | Lys | 597 | 4 |
| Phe | 104 | VH | Leu | 268 | 2 |

TABLE 14

Interactions between MOR09825 Fab light chain and human HER3. Fab VL residues are numbered based upon their linear amino acid sequence (SEQ ID NO: 50). HER3 residues are numbered based upon NP_001973. HER3 residues shown have at least one atom within 5 Å of an atom in the MOR09825 Fab.

| MOR09825 Fab | | | Human HER3 | | |
|---|---|---|---|---|---|
| Residue | Number | Chain | Residue | Number | Domain |
| Gln | 27 | VL | Arg | 611 | 4 |
| Gly | 28 | VL | Arg | 611 | 4 |
| | | | Pro | 612 | 4 |
| Ile | 29 | VL | Pro | 612 | 4 |
| Ser | 30 | VL | Pro | 612 | 4 |
| | | | Cys | 613 | 4 |
| | | | His | 614 | 4 |
| | | | Glu | 615 | 4 |
| Asn | 31 | VL | Glu | 615 | 4 |
| | | | His | 614 | 4 |
| | | | Cys | 613 | 4 |
| Trp | 32 | VL | Lys | 267 | 2 |
| | | | Tyr | 265 | 2 |
| | | | Pro | 612 | 4 |
| | | | Cys | 613 | 4 |
| | | | Ile | 600 | 4 |
| | | | Lys | 602 | 4 |
| Tyr | 49 | VL | Lys | 597 | 4 |
| Gly | 66 | VL | Glu | 615 | 4 |
| Ser | 67 | VL | His | 614 | 4 |
| | | | Glu | 615 | 4 |
| Gln | 89 | VL | Leu | 268 | 2 |
| Tyr | 91 | VL | Lys | 267 | 2 |
| | | | Leu | 268 | 2 |
| | | | Phe | 270 | 2 |
| Ser | 92 | VL | Phe | 270 | 2 |
| | | | Lys | 602 | 4 |
| | | | Pro | 612 | 4 |
| | | | Arg | 611 | 4 |
| Ser | 93 | VL | Phe | 270 | 2 |
| | | | Glu | 609 | 4 |
| Phe | 94 | VL | Phe | 270 | 2 |
| | | | Gly | 582 | 4 |
| | | | Pro | 583 | 4 |
| Thr | 96 | VL | Leu | 268 | 2 |

Visual inspection of the MOR09823/MOR09825 crystal structures highlighted that HER3 residues Lys267 and Leu268 formed multiple interactions with various antibody CDR's suggesting that they may be important for antibody binding. Consequently, Lys267 and/or Leu268 were mutated to alanine, expressed and the resultant recombinant proteins purified in order to assess their impact upon antibody binding. ELISA binding assays indicated that mutation of either Lys267 or Leu268 abolished MOR10703 binding to HER3 (FIG. 5F) suggesting that both residues are an integral part of the HER3 epitope and thus supporting the proposed interactions between MOR09823/MOR09825 and HER3.

(viii) Inhibition of Cell Signaling

Figure 6A:
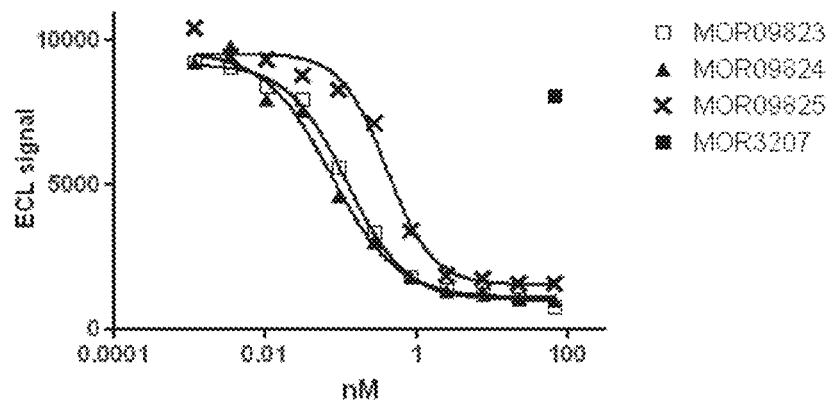
FIG. 6: Inhibition of ligand induced (A) or ligand-independent (B) HER3 phosphorylation.
Figure 6B:
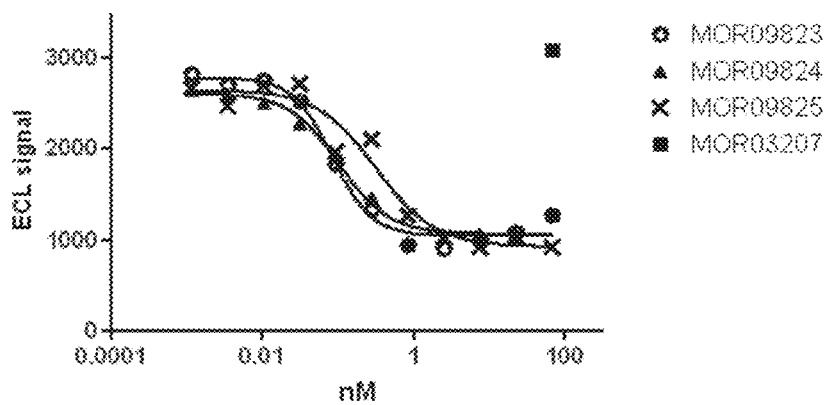

To ascertain the effect of anti-HER3 antibodies upon ligand dependent HER3 activity MCF7 cells were incubated with IgG prior to stimulation with neuregulin. Example inhibition curves are illustrated in FIG. 6A and summarized in Table 15. The effect of anti-HER3 antibodies upon HER2-mediated HER3 activation was also studied using the HER2 amplified cell line SK-Br-3 (FIG. 6B and Table 15).

TABLE 15 pHER3 $IC_{50}$ and extent of inhibition values of anti-HER3 IgG in MCF7, and SK-Br-3 cells.

| | MCF7 pHER3 | | SK-Br-3 pHER3 | |
|---|---|---|---|---|
| MOR# | $IC_{50}$ (pM) | % inhibition | $IC_{50}$ (pM) | % inhibition |
| 09823 | 181 | 89 | 56 | 59 |
| 09824 | 103 | 91 | 110 | 64 |
| 09825 | 399 | 80 | 169 | 66 |
| 09974 | 3066 | 69 | 1928 | 67 |
| 10701 | n.d. | n.d. | 370 | 74 |
| 10702 | n.d. | n.d. | n.d. | n.d. |
| 10703 | 333 | 80 | 167 | 69 |
| 12609 | 5 | 86 | 241 | 71 |
| 12610 | 126 | 84 | 192 | 75 |

To determine whether inhibition of HER3 activity impacted downstream cell signaling Aid, phosphorylation was also measured in HER2 amplified cells following treatment with anti-HER3 antibodies (see FIG. 7 and Table 16).

TABLE 16 pAkt ($S^{473}$) $IC_{50}$ and extent of inhibition values of anti-HER3 IgG in SK-Br-3 BT-474 and MCF7 cells.

| | SK-Br-3 pAkt | | | MCF7 pAkt | |
|---|---|---|---|---|---|
| MOR# | $IC_{50}$ (pM) | % inhibition | BT-474 pAkt % inhibition | $IC_{50}$ (pM) | % inhibition |
| 09823 | 55 | 92 | 57 | n.d. | n.d. |
| 09824 | 62 | 93 | 46 | n.d. | n.d. |
| 09825 | 156 | 91 | 69 | 294 | 79 |
| 09974 | 814 | 85 | n.d. | n.d. | n.d. |
| 10701 | n.d. | n.d. | 59 | n.d. | n.d. |
| 10702 | n.d. | n.d. | 55 | n.d. | n.d. |
| 10703 | 70 | 89 | 62 | 449 | 79 |

In summary MOR09823, MOR09824, MOR09825, MOR09974, MOR10701, MOR10702 MOR10703, MOR12609 and MOR12610 are each capable of inhibiting cellular HER3 activity in both a ligand-dependent and ligand-independent manner.

(ix) Inhibition of Proliferation

Figure 8A:
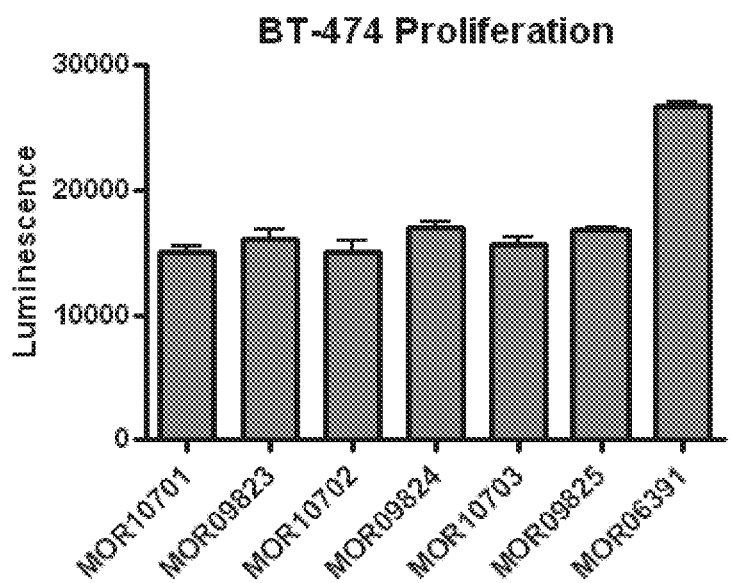
FIG. 8: The impact of HER3 inhibition upon cell growth in A) BT-474 and B) neuregulin stimulated MCF7 cells.
Figure 8B:
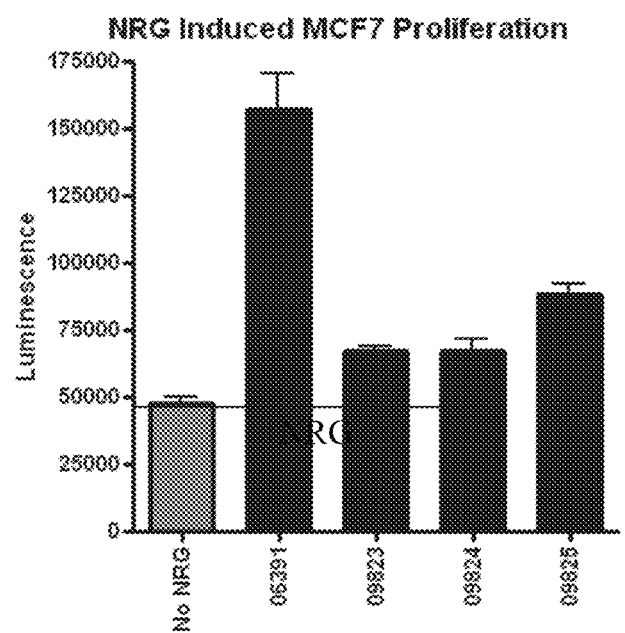

Since MOR09823, MOR09824, MOR09825, MOR09974, MOR10701, MOR10702 and MOR10703 all inhibited HER3 activity and downstream signaling they were tested for their ability to block ligand dependent and independent in vitro cell growth (Example data is shown in FIG. 8 and summarized in Table 17). The anti-HER3 antibodies tested were all effective inhibitors of cell proliferation.

TABLE 17

Inhibition of proliferation following treatment with 10 μg/ml anti-HER3 IgG in SK-Br-3, BT-474 and MCF7 cells.

| | % Inhibition | | |
|---|---|---|---|
| MOR# | SK-Br-3 | BT-474 | MCF7 |
| 09823 | 39 | 39.8 | 82 |
| 09824 | 33 | 36.8 | 82 |
| 09825 | 41 | 37.2 | 63 |
| 09974 | 35 | n.d. | 20 |
| 10701 | n.d. | 43.6 | n.d. |
| 10702 | n.d. | 43.8 | n.d. |
| 10703 | 35 | 41.6 | 81 |

(x) Ligand Blocking Assessment

The ability of the described anti-HER3 antibodies to block ligand binding was assessed by examining the binding of neuregulin to MCF7 cells previously treated with either MOR09823 or MOR09825. The presence of either MOR09823 or MOR09825 had no significant effect upon the ability of neuregulin to bind MCF7 cells whilst the positive control used in the experiment (Mab3481) was capable of profoundly interfering with neuregulin binding (see FIG. 9). These results are consistent with the crystal structure since MOR09823 interacts with domains 2 and 4 whilst the major contact points for HER3's interaction with neuregulin are hypothesized to be primarily clustered within domains 1 and 3. Given that neuregulin is capable of binding the inactive conformation of HER3 (Kani et al., (2005) Biochemistry 44: 15842-15857) it is probable that MOR09823 and MOR09825 function by preventing the HER3 domain rearrangements necessary for signaling or by interfering with receptor dimerization.

(xi) Ligand Blocking Assessment (Biochemical)

To explore whether MOR09823 and neuregulin can bind HER3 concurrently a biochemical assay was established using Biacore™ technology. Interaction analyses were performed by capturing biotinylated neuregulin on the surface of a Biacore™ sensor chip CAP (GE Healthcare) utilizing a Biotin CAPture kit (GE Healthcare). HER3 complexes were generated by incubating human HER3-Fc with increasing concentrations of either MOR09823, 105.5 (Thermo Scientific) or human IgG. Preformed HER3/antibody complexes were injected over reference and active surfaces and the interaction of HER3 with neuregulin observed.

Figure 10:
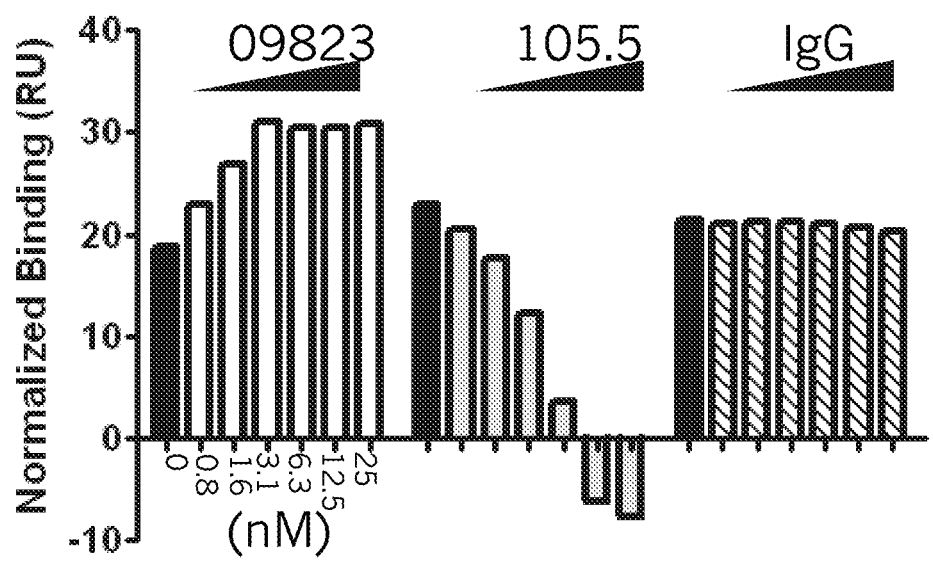
FIG. 10: Impact of MOR09823 binding upon HER3/neuregulin complex formation as assessed by Biacore™. No antibody (black bars), MOR09823 (white bars), 105.5 (grey) & control IgG (striped bars).

Control IgG had no effect upon HER3/neuregulin complex formation whilst 105.5 was observed to significantly inhibit the ability of HER3 to bind neuregulin confirming its description as a ligand blocking antibody (FIG. 10). In contrast HER3/MOR09823 complexes were capable of binding neuregulin demonstrating that MOR09823 does not prevent ligand binding. Interestingly, a dose-dependent increase in RU values was uniquely observed when MOR09823/HER3 complexes were injected. This data indicates that a trimeric complex containing neuregulin, HER3 and MOR09823 is generated on the chip surface. The ability of this trimeric complex to form is predicted by the HER3/MOR09823 crystal structure since MOR09823 binding does not occlude the ligand binding site of HER3 suggesting that binding of neuregulin and MOR09823 are not mutually exclusive.

In another embodiment, the antibody or fragment thereof binds to both domain 2 and domain 4 of HER3 and without blocking the concurrent binding of a HER3 ligand such as neuregulin. While not required to provide a theory, it is feasible that the antibody or fragment thereof binding to both domain 2 and domain 4 of HER3, holds HER3 in an inactive conformation without blocking the ligand binding site on HER3. Thus a HER3 ligand (e.g., neuregulin) is able to bind to HER3 at the same time as the antibody.

The antibodies of the invention or fragments thereof inhibit both ligand dependent and independent activation of HER3 without preventing ligand binding. This is considered advantageous for the following reasons:

(i) The therapeutic antibody would have clinical utility in a broad spectrum of tumors than an antibody which targeted a single mechanism of HER3 activation (i.e. ligand dependent or ligand independent) since distinct tumor types are driven by each mechanism.

(ii) The therapeutic antibody would be efficacious in tumor types where both mechanisms of HER3 activation are simultaneously involved. An antibody targeting a single mechanism of HER3 activation (i.e. ligand dependent or ligand independent) would display little or no efficacy in these tumor types (iii) The efficacy of an antibody which inhibits ligand dependent activation of HER3 without preventing ligand binding would be less likely to be adversely affected by increasing concentrations of ligand. This would translate to either increased efficacy in a tumor type driven by very high concentrations of HER3 ligand or a reduced drug resistance liability where resistance is mediated by up-regulation of HER3 ligands.

(iv) An antibody which inhibits HER3 activation by stabilizing the inactive form would be less prone to drug resistance driven by alternative mechanisms of HER3 activation.

Consequently, the antibodies of the invention may be used to treat conditions where existing therapeutic antibodies are clinically ineffective.

(xii) In Vivo Inhibition of HER3 Activity and Effect Upon Tumor Growth

Figure 11A:
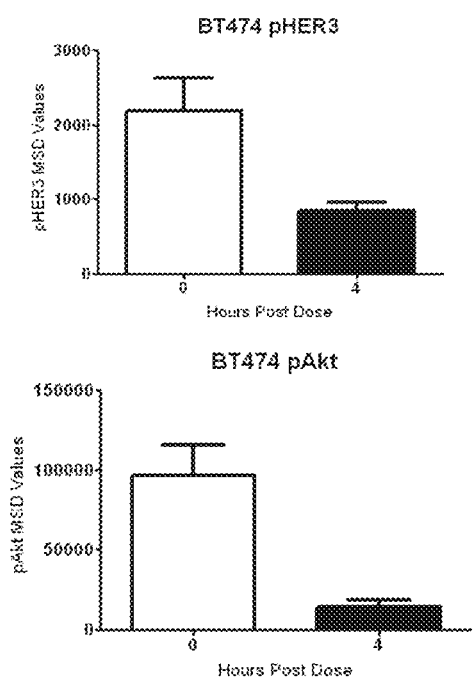
FIG. 11: MOR09823 mediated inhibition of (A) ligand independent (BT-474) and (B) ligand dependent (BxPC3) HER3 signaling in vivo.
Figure 11B:
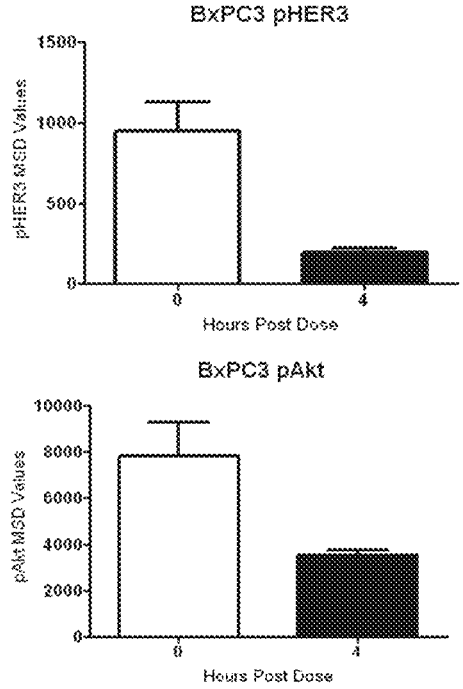
Figure 12A:
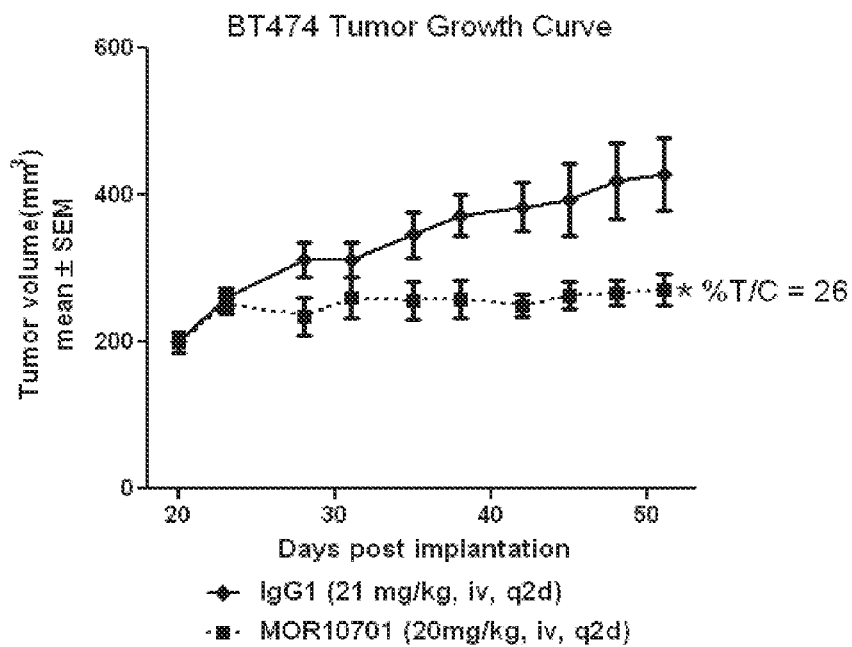
FIG. 12: The impact of (A) MOR10701 and (B) MOR10703 upon BT-474 tumor growth.
Figure 12B:
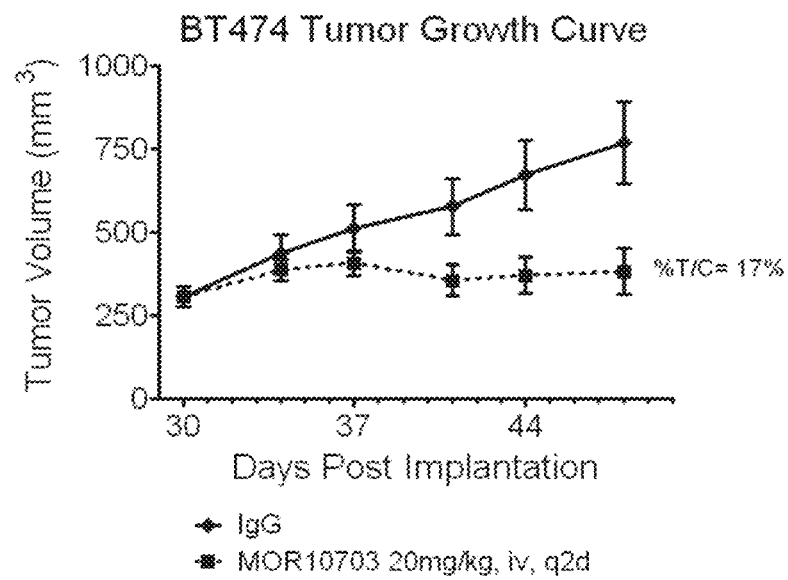
Figure 13:
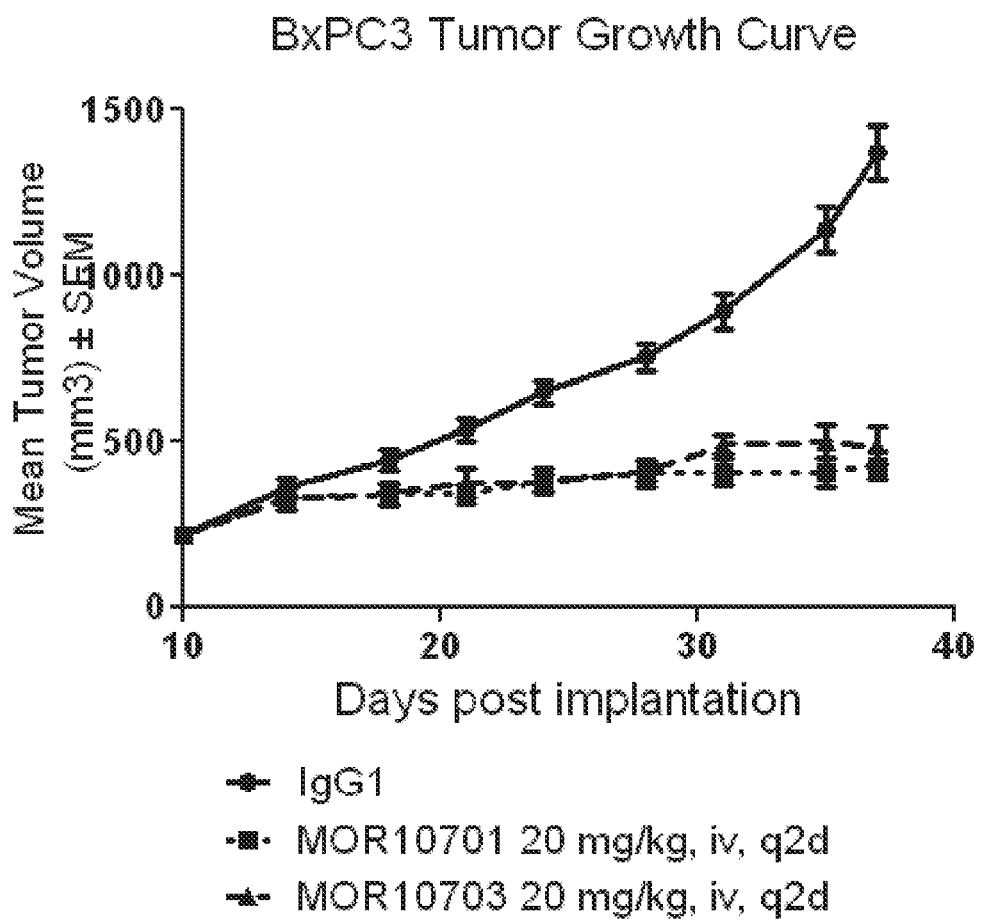
FIG. 13: The impact of MOR10701 and MOR10703 upon BxPC3 tumor growth.

To determine the in vivo activity of the described anti-HER3 antibodies, MOR09823 was tested in both BxPC-3 and BT-474 tumor models. MOR09823 was demonstrated to inhibit HER3 activity as evidenced by a significant reduction in tumor pHER3 levels (FIG. 11). Signaling downstream of HER3 was similarly inhibited as demonstrated by reduced pAkt levels in both BxPC-3 and BT-474 (FIG. 11). In a HER2 driven BT-474 efficacy study, repeated MOR10701 treatment yielded a 74% inhibition of tumor growth (see FIG. 12A) whilst MOR10703 yielded 83% inhibition. In the BxPC3 tumor growth model, both MOR10701 and MOR10703 very effectively inhibited ligand driven tumor growth (see FIG. 13).

(xiii) In Vitro Drug Combinations and Impact Upon Cell Growth.

Figure 14:
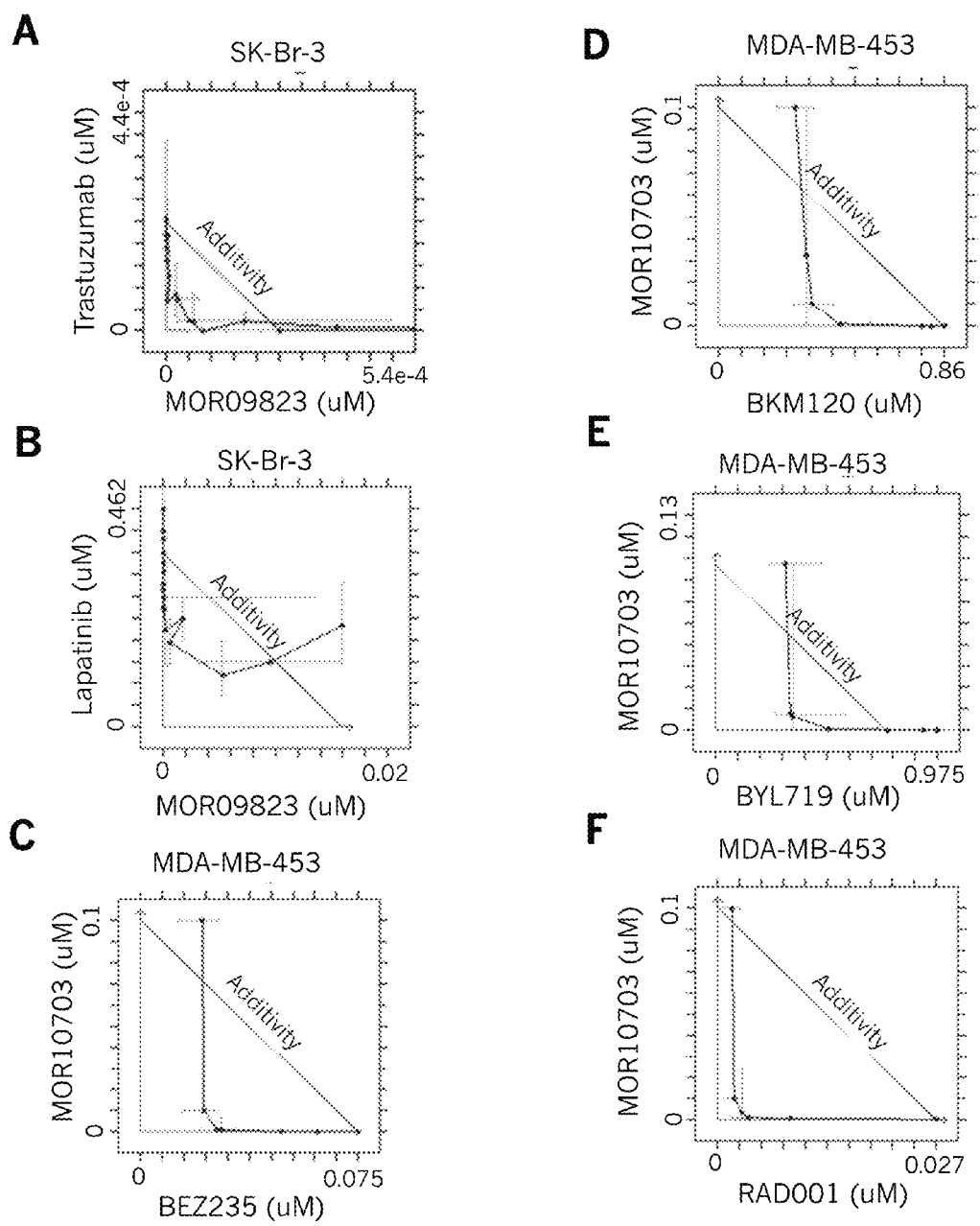
FIG. 14: MOR10703 in vitro drug combination isobolograms (A) MOR09823/trastuzumab, (B) MOR09823/lapatinib, (C) MOR10703/BEZ235, (D) MOR10703/BKM120, (E) MOR10703/BYL719, (F) MOR10703/RAD001, (G) MOR10703/cetuximab and (H) MOR10703/erlotinib.
Figure 14:
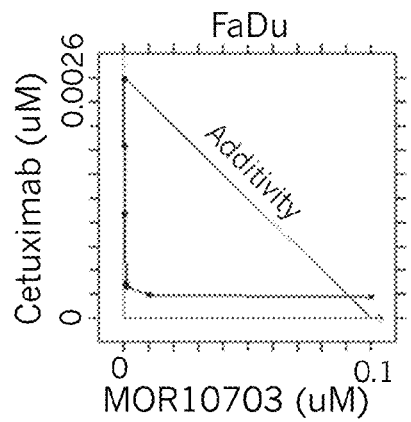
Figure 14:
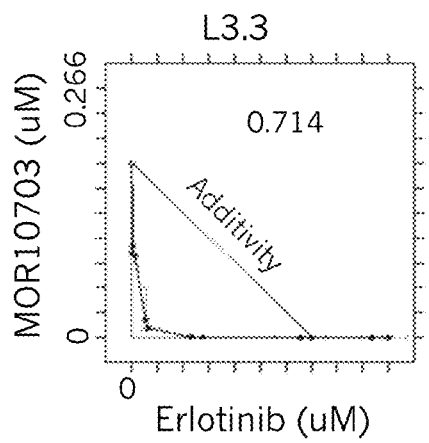

Since tumor cell growth is frequently driven by multiple signaling pathways we assessed whether combinations of MOR09823 or MOR10703 with various targeted agents would be of benefit in blocking cell proliferation. The targeted agents chosen primarily inhibited HER2 (trastuzumab, lapatinib) EGFR (cetuximab, erlotinib), PI3K/mTOR (BEZ235), PI3K (BKM120), PIK3CA (BYL719) and mTOR (RAD001) since these targets are commonly activated in human tumors. Isobologram analysis (see FIG. 14) indicated that MOR09823 and MOR10703 displayed synergistic drug combinations with trastuzumab, lapatinib, erlotinib, cetuximab, BEZ235, BKM120, BYL719 and RAD001. This data suggests that inhibition of HER3 signaling is of particular benefit to inhibitors that target receptor tyrosine kinases or the PI3K signaling pathway.

(xiv) In Vivo MOR10703 Drug Combinations

Figure 15A:
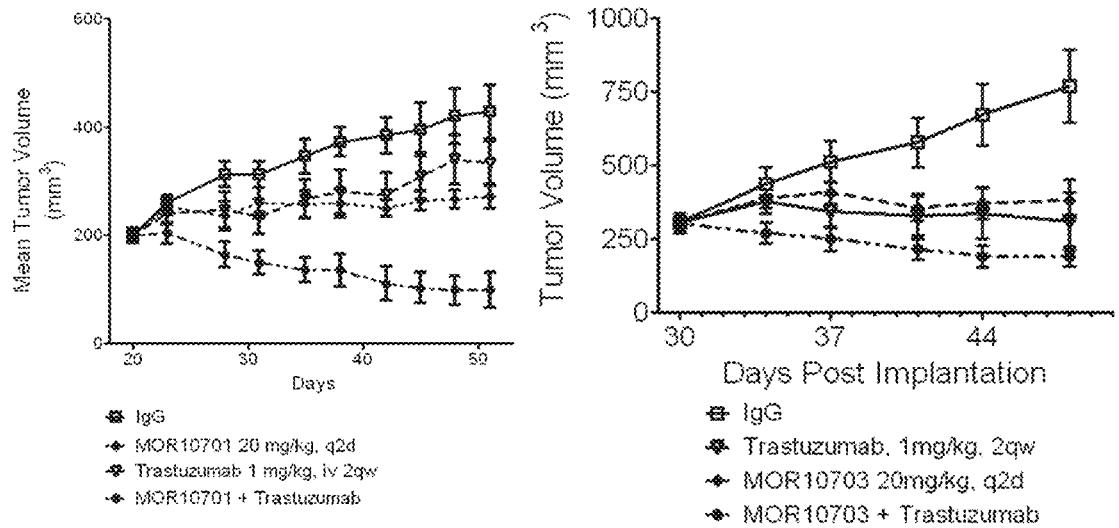
FIG. 15: MOR10701 or MOR10703 in vivo combinations with (A) trastuzumab and (B) erlotinib in BT-474 and L3.3.
Figure 15B:
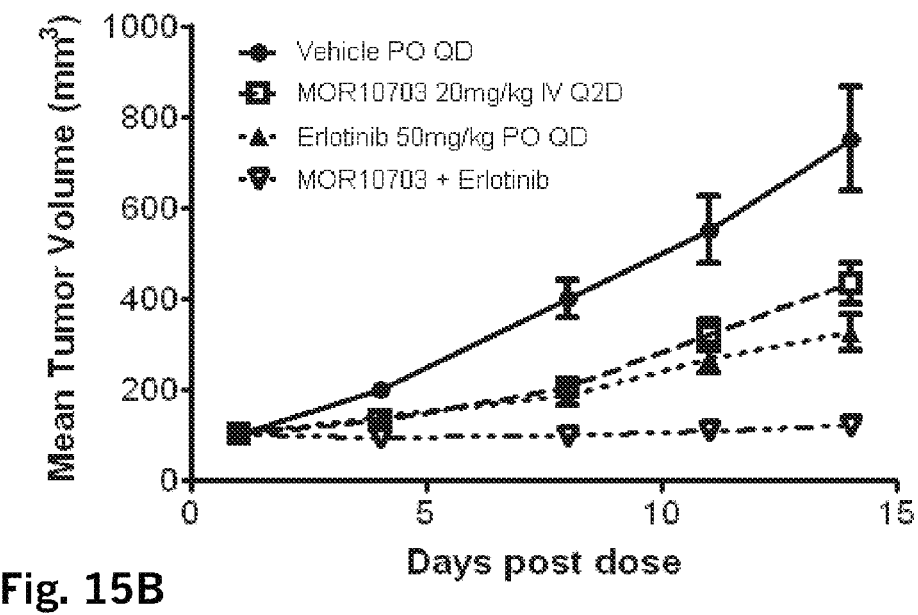
Figure 16:
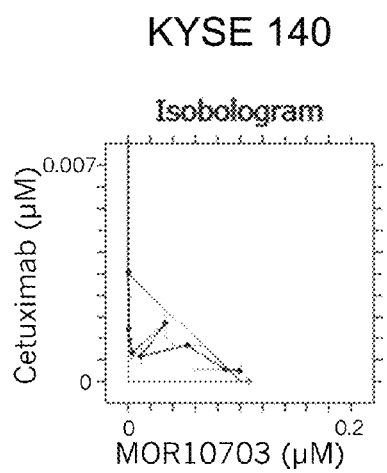
FIG. 16: MOR10703 alone or MOR10703 in an in vitro combination with cetuximab and BYL719 on esophageal cells

Since HER3 inhibition combined with receptor tyrosine kinase targeted agents in vitro we assessed the impact of either MOR10701 or MOR10703 in combination with trastuzumab and erlotinib in vivo. In BT-474 xenografts (see FIG. 15A), combination of either MOR10701 or MOR10703 (20 mg/kg) with a sub-optimal dose of trastuzumab (1 mg/kg) was sufficient to induce tumor regressions (% T/C=−50 and −37 respectively). In L3.3 pancreatic xenografts, combination of MOR10703 (20 mg/kg) with daily erlotinib (50 mg/kg) resulted in tumor stasis (% T/C=3, see FIG. 15B). In both models, the combination of two drugs was significantly more efficacious than either drug alone thus supporting our earlier in vitro finding of the benefit of combining HER3-targeted antibodies with ErbB-targeted agents.

In summary, the unique ability of this family of antibodies to stabilize the inactive conformation of HER3 results in significant in vivo efficacy in models where HER3 is activated in either a ligand dependent or independent manner. Furthermore, HER3 inhibition by this family of antibodies appears beneficial in combination with a wide variety of targeted therapies.

Example 22

HER3 Antibodies for Benign Prostatic Hyperplasia (BPH), Gynecomastia, and Endometriosis Experimental Procedure Sexually mature IGS Wistar Hannover rats of approximately 9 weeks of age were dosed via intravenous injection on a twice weekly schedule with 30, 75 and 200 mg/kg MOR10703. Following completion of the 13 week dosing period, 10 rats from each dose group were sacrificed and major organs collected for further analysis. In addition, 6 rats from the 200 mg/kg dose group were allowed to recover from MOR10703 for 10 weeks prior to sacrifice in order to determine the reversibility of any observed changes. Post animal sacrifice, organ weights were recorded prior to fixation in 10% neutral-buffered formalin. Tissue sections were prepared and assessed by microscopic examination.

Results

In male rats, decreased prostate weight was observed at all doses, which correlated with reduced secretion in the prostate and seminal vesicles (Table 18). These effects were reversible after 10 weeks of recovery. Differences in absolute mean vs. control were as follows: 30 mg/kg: −31%, 75 mg/kg: −40%, and 200 mg/kg: −35%. Mammary gland atrophy, mostly moderate or marked, was present in all dosed males and was not reversible after 10 weeks recovery. This change was characterized by the absence of the normally abundant acinar and lobular development seen in the male mammary gland. By contrast to the controls, sparse ductular elements were present in the mammary glands of all treated males.

TABLE 18

| MOR10703-related differences in organ weights in male rats | | | | |
| --- | --- | --- | --- | --- |
| Sex | | Male | | |
| Dose (mg/kg) | 0 | 30 | 75 | 200 |
| Number examined | 10 | 10 | 10 | 10 |
| Body weight mean (g) | 412 | 390 | 392 | 397 |
| (% diff) | (—) | −5 | −4 | −4 |
| Brain weight mean (g) | 2.1 | 2.1 | 2.1 | 2.1 |
| (% diff) | (—) | −3 | −3 | −1 |

TABLE 18-continued

MOR10703-related differences in organ weights in male rats

Prostate

| | | | | |
|---|---|---|---|---|
| Absolute mean (g) | 0.9 | 0.6 [c] | 0.6 [c] | 0.6 [c] |
| (% diff) | (—) | −31 | −40 | −35 |
| Rel.[b] to body weight (%) | 0.22 | 0.16 [c] | 0.14 [c] | 0.15 [c] |
| (% diff) | (—) | −28 | −38 | −33 |
| Rel. to brain weight | 43 | 31 | 27 [c] | 28 [c] |
| (% diff) | (—) | −29 | −38 | −35 |

[a] Expressed as percent difference of group means (% diff).
[b] Relative.
[c] Based upon statistical analysis of group means, values are significantly different from control group.

In females, decreased uterus weight was observed at all doses, which was reversible after 10 weeks of recovery (Table 19). Absolute mean vs. control differences were 30 mg/kg: −24%, 75 mg/kg: −27%, and 200 mg/kg: −19%. Endometrial atrophy, observed as a profound decrease in glandular epithelium in the uterus at all doses ≥30 mg/kg/day correlated with the decrease in uterus weights observed at the end of treatment. This was slightly reversible after 10 weeks of recovery in that an increased amount of glandular epithelium was present although not as much as in control animals. Other reproductive organs: ovaries, oviducts, cervix and vagina appeared to be within normal limits, considering the different stages of the cycle that can be observed.

TABLE 19

MOR10703-related differences in organ weights in female rats

| Sex | Female | | | |
|---|---|---|---|---|
| Dose (mg/kg) | 0 | 30 | 75 | 200 |
| Number examined | 10 | 10 | 10 | 10 |
| Body weight mean (g) | 237 | 246 | 239 | 241 |
| (% diff) | (—) | −4 | −1 | −2 |
| Brain weight mean (g) | 1.9 | 2.0 | 1.9 | 2.0 |
| (% diff) | (—) | −1 | −1 | −2 |
| Uterus | | | | |
| Absolute mean (g) | 0.48 | 0.36 [c] | 0.35 [c] | 0.39 |
| (% diff) | (—) | −24 | −27 | −19 |
| Rel.[b] to body weight (%) | 0.20 | 0.15 [c] | 0.15 [c] | 0.16 |
| (% diff) | (—) | −26 | −27 | −21 |
| Rel. to brain weight | 25 | 18 [c] | 18 [c] | 20 [c] |
| (% diff) | (—) | −29 | −38 | −35 |

[a] Expressed as percent difference of group means (% diff).
[b] Relative.
[c] Based upon statistical analysis of group means, values are significantly different from control group. Refer to data tables for actual significance levels and tests used.

Discussion

Benign prostatic hyperplasia (BPH) is a common disease in aging males that is characterized by a non-neoplastic enlargement of the prostate leading to pressure on the urethra and resulting in urination and bladder problems {Mahapokail W, van Sluijs F J & Schalken J A. 2000 Prostate Cancer and Prostatic Diseases 3, 28-33}. Anatomic or microscopic evidence of BPH is present at autopsy in approximately 55% of men aged 60-70 years. Transurethal resection of the prostate has been the treatment of choice for many years. Consequently, BPH is one of the most common reasons for surgical intervention among elderly men. Less invasive methods of treatment include:

(i) Alpha 1-blockers (doxazosin, prazosin, tamsulosin, terazosin, and alfuzosin) are a class of medications also used to treat high blood pressure. These medications relax the muscles of the bladder neck and prostate thus allowing easier urination.

(ii) Finasteride and dutasteride lower androgen levels thus reducing the size of the prostate gland, increasing urine flow rate, and decreasing symptoms of BPH. It may take 3 to 6 months before improvement in symptoms is observed. Potential side effects related to the use of finasteride and dutasteride include decreased sex drive and impotence The results in the Experiments section demonstrate for the first time that BPH is a neuregulin-dependent indication. The finding that MOR10703 significantly reduced prostate size in sexually mature rats without affecting hormone levels suggests that MOR10703 could be useful for the treatment of BPH.

To further test MOR10703 and other HER3 antibodies as therapeutics for BPH, primary human BPH surgical specimens can be transplanted into athymic mice or rats and effect of the Her3 antibodies studied using models (Otto U et al. Urol Int 1992; 48: 167-170).

Alternatively, aspects of BPH can be induced in castrated dogs via the long-term administration of 5α-Androstane-3α, 17β-diol plus estradiol and the HER3 antibodies tested in these canine models (Walsh P C, Wilson J D. J Clin Invest 1976; 57: 1093-1097).

The physical manifestation of gynecomastia is breast enlargement in males, it normally occurs in both breasts but can sometimes be in one only, known as asymmetrical or unilateral gynecosmastia. Gynecomastia is commonly caused by:

(i) Elevated estrogen levels resulting in the ratio of testosterone to oestrogen becoming unbalanced.

(ii) Androgen antagonists or anti-androgens used in the treatment of prostate cancer or BPH. These drugs suppress testosterone but by suppressing testosterone, oestrogen begins to rise.

Although a number of experimental drugs are currently being evaluated there are currently no approved treatments for gynecomastia. Consequently gynecomastia is treated via surgical removal of the breast tissue. The observation that MOR10703 induced irreversible atrophy of the male mammary gland indicates that it may be of benefit in the treatment of gynecomastia.

To further test MOR10703 and other HER3 antibodies for treating human gynecomastia, transgenic mouse models of gynecomastia can be used. These models have been developed by expressing human aromatase in the mouse mammary gland and recapitulate many aspects of human gynecomastia (Li et al., Endocrinology 2002; 143:4074-4083; Tekmal et al., Cancer Res 1996; 56:3180-318).

MOR10703 and other HER3 antibodies can also be examined for treating endometriosis, a gynecological condition in which cells from the lining of the uterus (endometrium) appear and flourish outside the uterine cavity. The main, but not universal, symptom of endometriosis is pelvic pain in various manifestations. Although the underlying causes of endometriosis are not well characterized is thought to be dependent on the presence of estrogen. Since MOR10703 induced endometrial atrophy in female mice resulting in a decrease in uterus weight, it may be used to treat endometriosis. To further study the effects of MOR10703 and other HER3 antibodies on endometriosis, human endometrium in the proliferative phase can be implanted into the peritoneal cavity of normal cycling and ovariectomized athymic mice or cycling non-obese diabetic (NOD)-severe combined immuno-deficiency (SCID) mice, and these SCID mice used as models (Grummer et al., 2001. Human Reproduction; 16; 1736-1743).

Example 23

In Vitro Studies to Assess HER3 Antibodies for Esophageal Cancer

In Vitro Esophageal Drug Combination Studies

To assess the ability of HER3-targeted antibodies to combine with targeted therapies MOR10703 was combined with cetuximab or BYL719 in cell viability assays. Approximately 1000-1200 KYSE140 and KYSE180 cells were seeded into 384-well plates in the appropriate culture media supplemented with 2% FBS and allowed to adhere overnight at 37° C. The appropriate drug combinations (typical final drug concentrations for BYL719 ranged from 2.8 μM to 3.8 nM; for cetuximab ranged from 93 nM to 0.13 nM; for MOR10703 100 nM to 4.1 nM) were subsequently added to the wells such that each plate contained a dose response curve of each drug in a two-dimensional matrix. Treated cells were subsequently incubated for 96-120 hours. At the end of the drug treatment, CellTiter-Glo regent were added to each well to lyse the cells, and luminescence signals were recorded using an Envision plate reader. The extent of growth inhibition obtained with each combination was calculated and combination activity highlighted using the Loewe additivity model.

Esophageal In Vitro Drug Combinations and Impact Upon Cell Growth

Since tumor cell growth is frequently driven by multiple signaling pathways, combinations of MOR10703 with cetuximab or BYL719 were assessed to determine whether they would be of benefit in blocking proliferation of esophageal cancer cell lines. The targeted agents chosen primarily inhibited EGFR (cetuximab) and PIK3CA (BYL719) since these targets are commonly activated in human tumors. Isobologram analysis indicated that MOR10703 displayed synergistic drug combinations with cetuximab and BYL719. This data shows that inhibition of HER3 signaling is of particular benefit to inhibitors that target receptor tyrosine kinases or the PI3K signaling pathway.

Example 24

In Vivo Studies to Assess HER3 Antibodies for Esophageal Cancer

To assess the in vivo ability of HER3-targeted antibodies to combine with targeted therapies MOR10703 was combined with cetuximab or BYL719 and tested in two in vivo xenograft models.

(i) In Vivo KYSE140 Xenografts

KYSE140 cells were cultured in RPMI 1640 medium containing 10% heat-inactivated fetal bovine serum without antibiotics until the time of implantation. KYSE140 cells were harvested in exponential growth. Ten million cells were mixed with PBS/Matrigel (50:50) were subcutaneously implanted into the upper right flank of SCID-Beige mice. On Day 28, tumors were measured and animals with a tumor volume of approximately 200 mm$^3$ were enrolled in the efficacy study. In general, a total of 10 animals per group were enrolled in efficacy studies. For single-agent and combination studies, animals were dosed intravenously via lateral tail vein injection with MOR10703 or cetuximab. BYL719 was formulated in 0.5% methylcellulose and dosed via oral gavage.

(ii) In Vivo KYSE180 Xenografts

KYSE180 cells were cultured in RPMI 1640 medium containing 10% heat-inactivated fetal bovine serum without antibiotics until the time of implantation. KYSE180 cells were harvested in exponential growth. Five million cells were subcutaneously implanted into the upper right flank of nude mice. On Day 18, tumors were measured and animals with a tumor volume of approximately 200 mm$^3$ were enrolled in the efficacy study. In general, a total of 10 animals per group were enrolled in efficacy studies. For single-agent and combination studies, animals were dosed intravenously via lateral tail vein injection with MOR10703 or cetuximab. BYL719 was formulated in 0.5% methylcellulose and dosed via oral gavage.

(iii) In Vivo Primary Esophageal Xenografts

Human esophageal primary tumors were passaged in mice. When tumor size reached approximately 150 mm$^3$ in size, animals were enrolled in the efficacy study. For single-agent and combination studies, animals were dosed intravenously via lateral tail vein injection with MOR10703 or cetuximab. BYL719 was formulated in 0.5% methylcellulose and dosed via oral gavage.

In Vivo Inhibition of HER3 and Effect Upon Esophageal Tumor Growth

Figure 17:
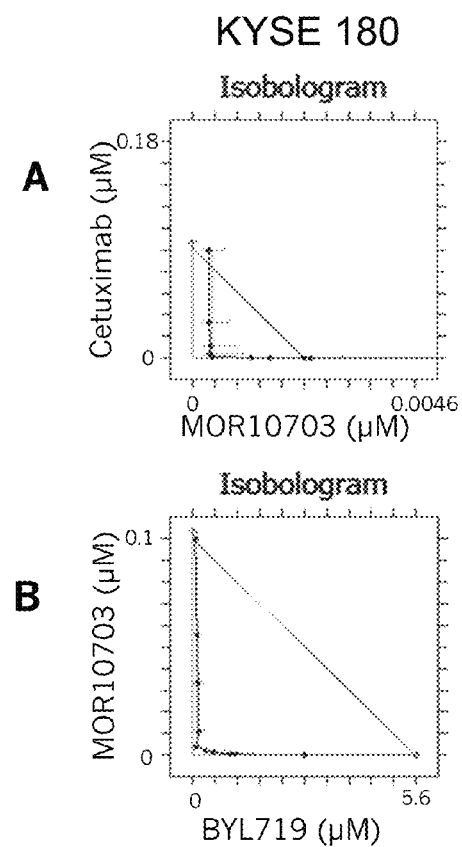
FIG. 17: MOR10703 alone or MOR10703 in vivo combinations with (A) cetuximab and (B) BYL719 in KYSE140 and KYSE180 esophageal tumor models.
Figure 18:
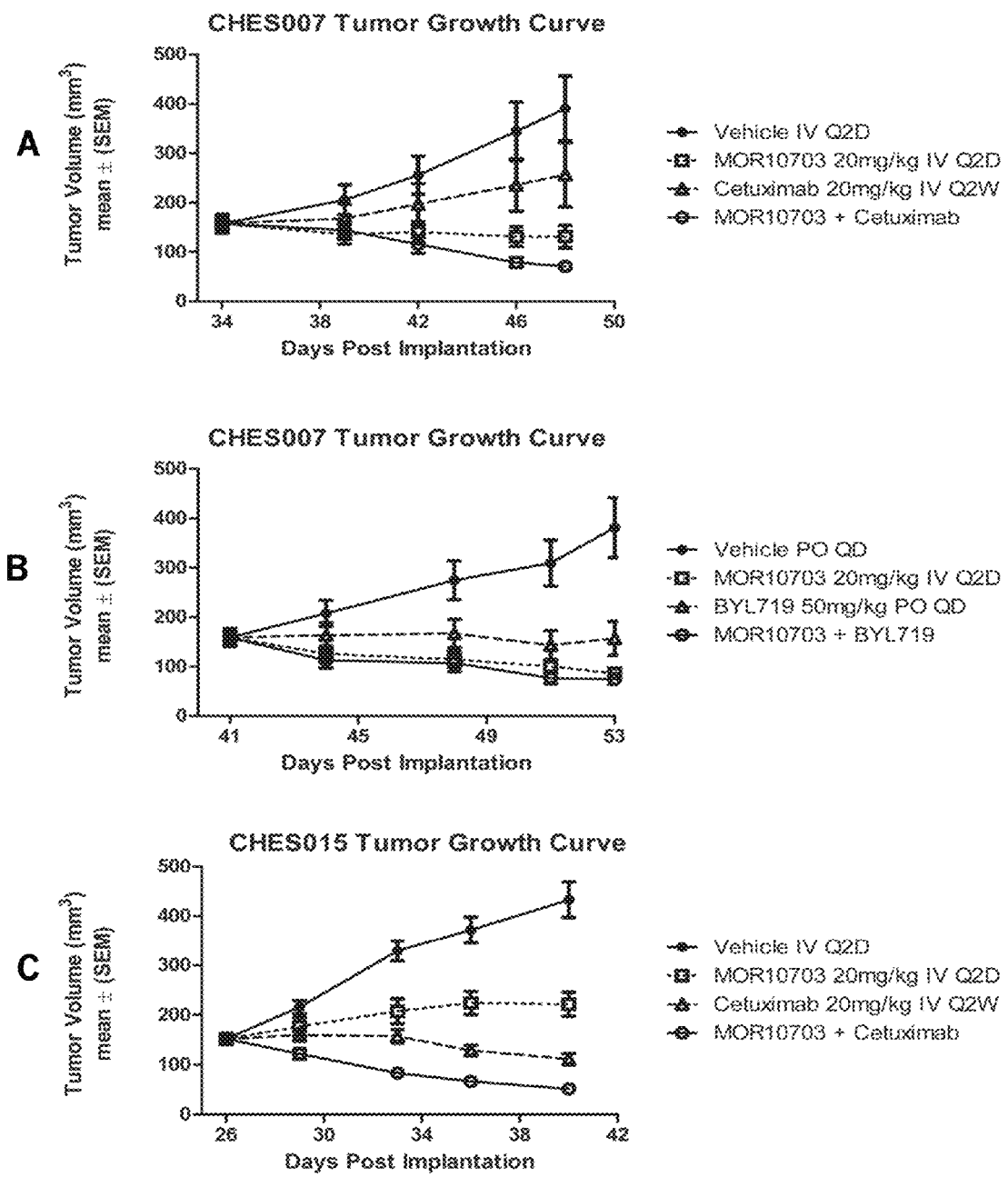
FIG. 18: MOR10703 alone or MOR10703 in vivo combinations with (A) cetuximab and (B) BYL719 in CHE007 esophageal tumor models, and (C) MOR10703 alone or MOR10703 in vivo combinations with cetuximab in CHES015 esophageal tumor model.

To determine the in vivo activity of the described anti-HER3 antibodies, MOR10703 was tested in both KYSE140 and KYSE180 esophageal tumor models, as well as two primary esophageal tumor models, CHES007 and CHES015. In both KYSE140 and KYSE180 in vivo models, treatment with single-agent MOR10703 was demonstrated to effectively inhibit tumor growth (FIG. 17). In KYSE180, the combination of MOR10703 and BYL719 was sufficient to induce significant tumor regressions. These findings were extended to the primary esophageal tumor models, where a combination of MOR10703 with either cetuximab or BYL719 also induced potent tumor regressions (FIG. 18). Together, these data further support our earlier in vitro finding of the benefit of combining HER3-targeted antibodies with wither EGFR or PI3K-targeted agents.

Example 25

In Vivo Studies to Assess HER3 Combinations with BYL719 in Gastric Cancer

To assess the in vivo ability of HER3-targeted antibodies to combine with targeted therapies in gastric cancer, MOR10703 was combined with BYL719 and tested in an in vivo xenograft model.

(i). In Vivo NCI-N87 Xenograft

NCI-N87 cells were grown in DMEM culture medium containing 4.5 g/l glucose supplemented with 10% heat-inactivated FCS, 2 mM L-glutamine, 1 mM sodium pyruvate until the point of implantation. NC1-N87 tumors were established by injecting 8×106 to 1×107 cells (in HBSS containing 50% v/v Matrigel) subcutaneously. On Day 10, tumors were measured and animals with a tumor volume of approximately 250 mm$^3$ were enrolled in the efficacy study. For single-agent and combination arms, animals were dosed intravenously via lateral tail vein injection with MOR10703. BYL719 was formulated in 0.5% methylcellulose and dosed via oral gavage.

Effect of Combination Treatment on N87 Gastric Tumor Growth

Figure 19:
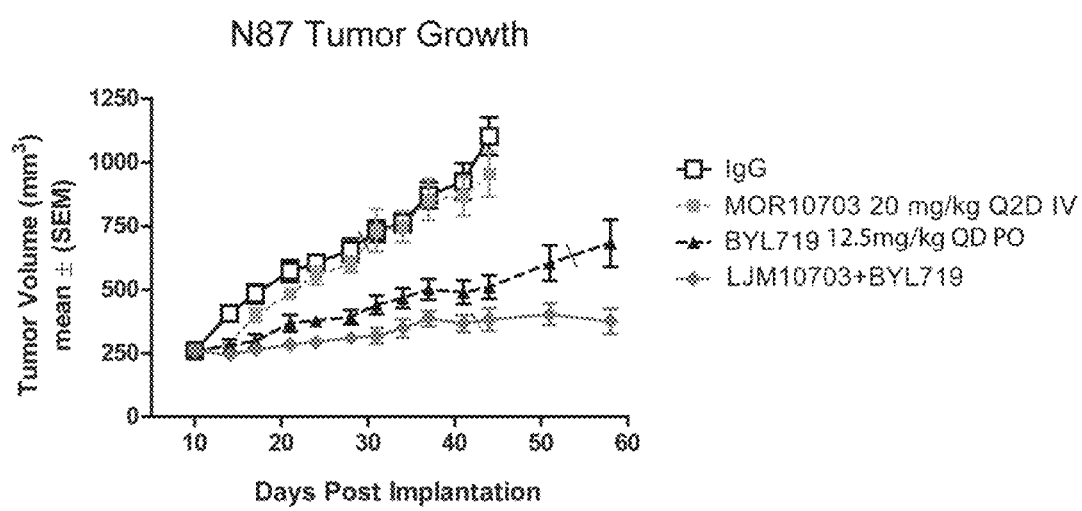
FIG. 19: MOR10703 alone or MOR10703 in vivo combinations with BYL719 in N87 gastric tumor model showing prolonged tumor regression.

As seen was seen for esophageal tumors, the combination of MOR10703 and BYL719 was sufficient to induce significant, prolonged tumor regressions in the N87 gastric tumor model thus further supporting the benefit of combining HER3-targeted antibodies with PI3K-targeted agents (see FIG. 19).

Example 26

In Vivo Studies to Assess HER3 Combinations with Cetuximab in Squamous Cell Cancer of the Head and Neck (SCCHN)

To assess the in vivo ability of HER3-targeted antibodies to combine with targeted therapies in SCCHN, MOR10703 was combined with cetuximab and tested in an in vivo xenograft model.

(i). In Vivo A253 Xenograft

A253 cells were cultured in DMEM containing 10% heat-inactivated fetal bovine serum without antibiotics until the time of implantation. A253 cells were harvested in exponential growth. Five million cells in 200 µl PBS were subcutaneously implanted into the upper right flank of nude mice. On Day 25, tumors were measured and animals with a tumor volume of approximately 200 mm3 were enrolled in the efficacy study. In general, a total of 9 animals per group were enrolled in efficacy studies. For single-agent and combination studies, animals were dosed intravenously via lateral tail vein injection with MOR10703 or cetuximab.

Effect of Combination Treatment on A253 SCCHN Tumor Growth

Figure 20:
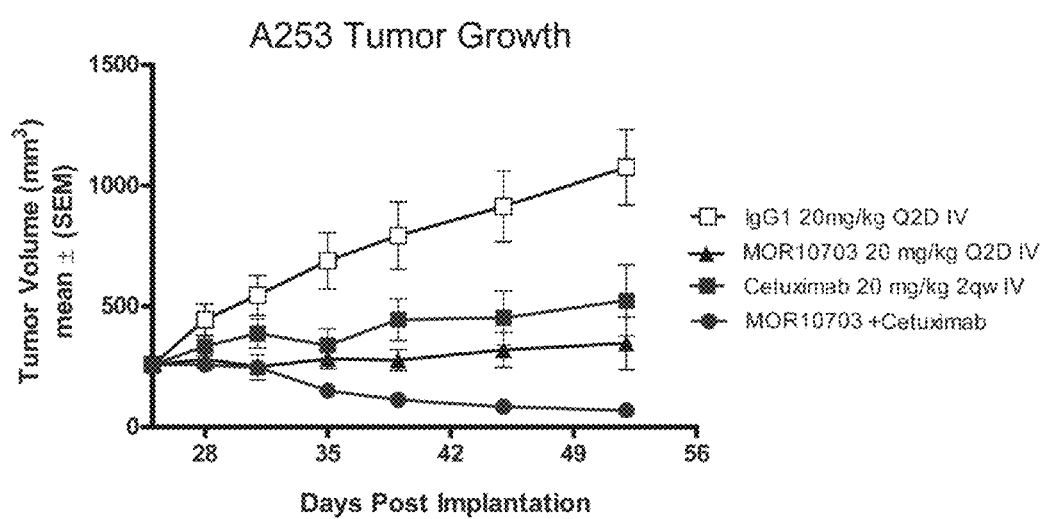
FIG. 20: MOR10703 alone or MOR10703 in vivo combinations with cetuximab in the A253 SCCHN model, treatment with either MOR10703 or cetuximab as a single agent resulted in tumor stasis. Combination of MOR10703 with cetuximab resulted in tumor regression.

In the A253 SCCHN model, treatment with either MOR10703 or cetuximab as a single agent resulted in tumor stasis. Combination of MOR10703 with cetuximab was significantly more active and resulted in tumor regression (see FIG. 20).

Collectively, these results show MOR10703 as a single agent can inhibit tumor growth. The results also show there is a synergistic effect on tumor regression when MOR10703 is combined with inhibitors that target other receptor tyrosine kinases or the PI3K signaling pathway.

INCORPORATION BY REFERENCE

All references cited herein, including patents, patent applications, papers, text books, and the like, and the references cited therein, to the extent that they are not already, are hereby incorporated herein by reference in their entirety.

EQUIVALENTS

The foregoing written specification is considered to be sufficient to enable one skilled in the art to practice the invention. The foregoing description and examples detail certain preferred embodiments of the invention and describe the best mode contemplated by the inventors. It will be appreciated, however, that no matter how detailed the foregoing may appear in text, the invention may be practiced in many ways and the invention should be construed in accordance with the appended claims and any equivalents thereof.

We claim:

1. A method of treating benign prostate hyperplasia comprising:

selecting a patient suffering from benign prostate hyperplasia; and administering an antibody or fragment thereof that specifically binds to a HER3 receptor, such that the antibody or fragment thereof binds to a conformational epitope comprising amino acid residues within domain 2 and domain 4 of the HER3 receptor and blocks both ligand-dependent and ligand-independent signal transduction, wherein the antibody or fragment thereof comprises:

(a) a heavy chain variable region CDR1 of SEQ ID NO: 38; a heavy chain variable region CDR2 of SEQ ID NO: 39; a heavy chain variable region CDR3 of SEQ ID NO: 40; a light chain variable region CDRI of SEQ ID NO: 41; a light chain variable region CDR2 of SEQ ID NO: 42; and a light chain variable region CDR3 of SEQ ID NO: 43;

(b) a heavy chain variable region CDR1 of SEQ ID NO: 44; a heavy chain variable region CDR2 of SEQ ID NO: 45; a heavy chain variable region CDR3 of SEQ ID NO: 46; a light chain variable region CDR1 of SEQ ID NO: 47; a light chain variable region CDR2 of SEQ ID NO: 48; and a light chain variable region CDR3 of SEQ ID NO: 49;

(c) a variable heavy chain (VH) sequence of SEQ ID NO: 51 and a variable light chain (VL) sequence of SEQ ID NO: 50;

(d) a variable heavy chain (VH) sequence having SEQ ID NO: 141 and a variable light chain (VL) sequence having of SEQ ID NO: 140;

(e) a variable heavy chain (VH) sequence selected from the group consisting of SEQ ID NOs.: 402-423;

(f) a variable light kappa chain (VK) sequence selected from the group consisting of SEQ ID NOs.: 443-461 and SEQ ID NOs.: 479-480; or (g) a sequence selected from the group consisting of SEQ ID NOs.: 487-492;

thereby treating benign prostate hyperplasia.

2. The method of claim 1, wherein the antibody or fragment thereof is administered by a route selected from the group consisting of oral, subcutaneous, intraperitoneal, intramuscular, intracerebroventricular, intraparenchymal, intrathecal, intracranial, buccal, mucosal, nasal, and rectal administration.

3. The method of claim 1, wherein the antibody or fragment is formulated into a pharmaceutical composition comprising a physiologically acceptable carrier, excipient, or diluent.

4. The method of claim 3, further comprising an additional therapeutic agent.

5. The method of claim 4, wherein the additional therapeutic agent is selected from the group consisting of an HER1 inhibitor, a HER2 inhibitor, a HER3 inhibitor, a HER4 inhibitor, an mTOR inhibitor and a PI3 Kinase inhibitor.

6. The method of claim 5, wherein the additional therapeutic agent is a HER1 inhibitor selected from the group consisting of Matuzumab (EMD72000), Cetuximab, Panitumumab, mAb 806, Nimotuzumab, Gefitinib, CI-1033 (PD183805), Lapatinib (GW-572016), Lapatinib Ditosylate, Erlotinib HCL (OSI-774), PKI-166, and N-[4-[(3-Chloro-4-fluorophenyl)amino]-7-[[(3"S")-tetrahydro-3-furanyl]oxy]-6-quinazolinyl]-4(dimethylamino)-2-butenamidea HER2 inhibitor selected from the group consisting of Pertuzumab, Trastuzumab, MM-111, neratinib, lapatinib or lapatinib ditosylate/Tykerb®; a HER3 inhibitor selected from the group consisting of, MM-121, MM-111, IB4C3, 2DID12 (U3 Pharma AG), AMG888 (Amgen), AV-203(Aveo), MEHD7945A (Genentech), MOR10703 (Novartis) and small molecules that inhibit HER3; and a HER4 inhibitor.

7. The method of claim 5, wherein the additional therapeutic agent is an mTOR inhibitor selected from the group consisting of Temsirolimus, ridaforolimus/Deforolimus, AP23573, MK8669, and everolimus.

8. The method of claim 5, wherein the additional therapeutic agent is a PI3 Kinase inhibitor selected from the group consisting of GDC 0941, BEZ235, BMK120 and BYL719.

* * * * *